(12) United States Patent
Perez-Pinera et al.

(10) Patent No.: US 12,215,345 B2
(45) Date of Patent: *Feb. 4, 2025

(54) COMPOSITIONS AND METHODS FOR THE INDUCTION AND TUNING OF GENE EXPRESSION

(71) Applicant: Duke University, Durham, NC (US)

(72) Inventors: Pablo Perez-Pinera, Urbana, IL (US); Charles A. Gersbach, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,348

(22) Filed: Oct. 20, 2017

(65) Prior Publication Data

US 2018/0094238 A1 Apr. 5, 2018

Related U.S. Application Data

(63) Continuation of application No. 14/220,116, filed on Mar. 19, 2014, now Pat. No. 9,828,582.

(60) Provisional application No. 61/803,254, filed on Mar. 19, 2013.

(51) Int. Cl.
| | |
|---|---|
| *C12N 15/63* | (2006.01) |
| *A61K 38/17* | (2006.01) |
| *C12N 5/071* | (2010.01) |

(52) U.S. Cl.
CPC ........ *C12N 5/0602* (2013.01); *A61K 38/1709* (2013.01); *C12N 15/635* (2013.01); *C12N 2501/60* (2013.01)

(58) Field of Classification Search
CPC .............. C07K 2319/71; C07K 14/415; C07K 2319/09; C07K 14/195; C12N 2501/60; C12N 15/635; C12N 15/85–15/8695; C12N 15/63
See application file for complete search history.

(56) References Cited

U.S. PATENT DOCUMENTS

| | | | |
|---|---|---|---|
| 3,687,808 A | 8/1972 | Merigan, Jr. | |
| 4,469,863 A | 9/1984 | Ts'o et al. | |
| 4,476,301 A | 10/1984 | Imbach et al. | |
| 4,501,729 A | 2/1985 | Boucher et al. | |
| 4,554,101 A | 11/1985 | Hopp | |
| 4,587,044 A | 5/1986 | Miller et al. | |
| 4,605,735 A | 8/1986 | Miyoshi et al. | |
| 4,667,025 A | 5/1987 | Miyoshi et al. | |
| 4,737,323 A | 4/1988 | Martin et al. | |
| 4,762,779 A | 8/1988 | Snitman | |
| 4,789,737 A | 12/1988 | Miyoshi et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,845,205 A | 7/1989 | Huynh et al. | |
| 4,876,335 A | 10/1989 | Yamane et al. | |
| 4,904,582 A | 2/1990 | Tullis | |
| 4,948,882 A | 8/1990 | Ruth | |
| 4,958,013 A | 9/1990 | Letsinger | |
| 5,013,830 A | 5/1991 | Ohsuka et al. | |
| 5,023,243 A | 6/1991 | Tullis | |
| 5,034,506 A | 7/1991 | Summerton et al. | |
| 5,082,830 A | 1/1992 | Brakel et al. | |
| 5,109,124 A | 4/1992 | Ramachandran et al. | |
| 5,112,963 A | 5/1992 | Pieles et al. | |
| 5,118,802 A | 6/1992 | Smith et al. | |
| 5,130,302 A | 7/1992 | Spielvogel et al. | |
| 5,134,066 A | 7/1992 | Rogers et al. | |
| 5,138,045 A | 8/1992 | Cook et al. | |
| 5,149,797 A | 9/1992 | Pederson et al. | |
| 5,166,315 A | 11/1992 | Summerton et al. | |
| 5,175,273 A | 12/1992 | Bischofberger et al. | |
| 5,177,196 A | 1/1993 | Meyer et al. | |
| 5,185,444 A | 2/1993 | Summerton et al. | |
| 5,188,897 A | 2/1993 | Suhadolnik et al. | |
| 5,214,134 A | 5/1993 | Weis et al. | |
| 5,214,136 A | 5/1993 | Lin et al. | |
| 5,216,141 A | 6/1993 | Benner | |
| 5,218,105 A | 6/1993 | Cook et al. | |
| 5,219,740 A | 6/1993 | Miller et al. | |
| 5,220,007 A | 6/1993 | Pederson et al. | |
| 5,235,033 A | 8/1993 | Summerton et al. | |
| 5,245,022 A | 9/1993 | Weis et al. | |
| 5,254,469 A | 10/1993 | Warren, III | |
| 5,256,775 A | 10/1993 | Froehler | |
| 5,258,506 A | 11/1993 | Urdea et al. | |
| 5,262,536 A | 11/1993 | Hobbs, Jr. | |
| 5,264,423 A | 11/1993 | Cohen et al. | |

(Continued)

FOREIGN PATENT DOCUMENTS

| | | |
|---|---|---|
| AU | 2022318664 A1 | 2/2024 |
| CA | 2749305 | 7/2010 |

(Continued)

OTHER PUBLICATIONS

US 11,898,176 B2, 02/2024, Gersbach et al. (withdrawn)
Kwa et al. Chromatin modifying agents—the cutting edge of anticancer therapy. Drug Discovery Today, vol. 16. No. 13/14, pp. 543-547, Jul. 2011. (Year: 2011).*
Zenser et al. A new TAP system for isolation of plant protein complexes and subsequent mass-spec analysis. https://www.sigmaaldrich.com/deepweb/assets/sigmaaldrich/product/documents/388/028/flag_ha_tap_poster.pdf, published 2008, printed as pp. 1/4-4/4. (Year: 2008).*

(Continued)

*Primary Examiner* — Jennifer Dunston
(74) *Attorney, Agent, or Firm* — Michael Best & Friedrich LLP

(57) ABSTRACT

Disclosed herein are compositions of transcription activator-like effectors transcription factors and methods of using the compositions for inducing gene expression of mammalian genes.

8 Claims, 10 Drawing Sheets

Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,478,745 A | 12/1995 | Samulski et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,773,700 A | 6/1998 | Van Grinsven et al. |
| 5,962,428 A | 10/1999 | Carrano et al. |
| 6,140,081 A | 10/2000 | Barbas |
| 6,207,453 B1 | 3/2001 | Maass et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 * | 10/2002 | Vernachio ............ C07K 14/005 435/320.1 |
| 6,534,261 B1 | 3/2003 | Cox, III et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,449,561 B1 | 11/2008 | Sommer et al. |
| 7,572,582 B2 | 8/2009 | Wengel et al. |
| 7,728,118 B2 | 6/2010 | Wood et al. |
| 7,745,651 B2 | 6/2010 | Heyes et al. |
| 7,799,565 B2 | 9/2010 | Maclachlan et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,697,359 B1 | 4/2014 | Zhang et al. |
| 8,889,356 B2 | 11/2014 | Zhang |
| 8,993,233 B2 | 3/2015 | Zhang et al. |
| 9,139,554 B2 | 9/2015 | Hope et al. |
| 9,458,205 B2 | 10/2016 | Gregory et al. |
| 9,738,879 B2 | 8/2017 | Gersbach et al. |
| 9,834,791 B2 | 12/2017 | Zhang et al. |
| 9,890,364 B2 * | 2/2018 | Joung .................. C12N 9/0071 |
| 10,190,106 B2 | 1/2019 | Wolfe et al. |
| 10,266,850 B2 | 4/2019 | Doudna et al. |
| 10,676,735 B2 | 6/2020 | Gersbach et al. |
| 10,704,060 B2 | 7/2020 | Gersbach et al. |
| 10,711,256 B2 | 7/2020 | Gersbach et al. |
| 10,745,714 B2 | 8/2020 | Gersbach et al. |
| 11,155,796 B2 | 10/2021 | Gersbach et al. |
| 11,421,251 B2 | 8/2022 | Gersbach et al. |
| 11,427,817 B2 | 8/2022 | Josephs et al. |
| 11,970,710 B2 | 4/2024 | Gersbach et al. |
| 11,976,307 B2 | 5/2024 | Gersbach et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2008/0200409 A1 | 8/2008 | Wilson et al. |
| 2009/0018031 A1 | 1/2009 | Trinklein et al. |

(56) References Cited

U.S. PATENT DOCUMENTS

| | | |
|---|---|---|
| 2010/0035968 A1 | 2/2010 | Rasmussen et al. |
| 2010/0076057 A1 | 3/2010 | Sontheimer et al. |
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |
| 2011/0263682 A1 | 10/2011 | De Kimpe et al. |
| 2011/0301073 A1 | 12/2011 | Gregory et al. |
| 2011/0301218 A1 | 12/2011 | Bozzoni et al. |
| 2012/0207744 A1 | 8/2012 | Mendlein et al. |
| 2013/0274129 A1 | 10/2013 | Katzen et al. |
| 2014/0140969 A1 | 5/2014 | Beausejour et al. |
| 2014/0170753 A1 | 6/2014 | Zhang |
| 2014/0179006 A1 | 6/2014 | Zhang |
| 2014/0186958 A1 | 7/2014 | Zhang et al. |
| 2014/0234975 A1 | 8/2014 | Silva et al. |
| 2014/0295557 A1 | 10/2014 | Joung et al. |
| 2014/0309177 A1 | 10/2014 | Perez-Pinera et al. |
| 2014/0315862 A1 | 10/2014 | Kaye |
| 2014/0356956 A1 | 12/2014 | Church et al. |
| 2014/0357530 A1 | 12/2014 | Zhang et al. |
| 2015/0024499 A1 | 1/2015 | Brouns et al. |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2015/0225717 A1 | 8/2015 | Lee et al. |
| 2015/0252358 A1 | 9/2015 | Maeder et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0199419 A1 | 7/2016 | Miura |
| 2016/0281166 A1 | 9/2016 | Bhattacharjee et al. |
| 2016/0354487 A1 | 12/2016 | Zhang et al. |
| 2017/0002316 A1 | 1/2017 | Gascón Jiménez et al. |
| 2017/0198308 A1 | 7/2017 | Qi et al. |
| 2017/0204407 A1 | 7/2017 | Gilbert et al. |
| 2017/0283831 A1 | 10/2017 | Zhang et al. |
| 2017/0298331 A1 | 10/2017 | Gersbach et al. |
| 2017/0327806 A1 | 11/2017 | Joung et al. |
| 2017/0362635 A1 | 12/2017 | Chamberlain et al. |
| 2018/0023064 A1 | 1/2018 | Gersbach et al. |
| 2018/0073012 A1 | 3/2018 | Liu et al. |
| 2018/0127780 A1 | 5/2018 | Liu et al. |
| 2018/0135109 A1 | 5/2018 | Jayaram et al. |
| 2018/0201951 A1 | 7/2018 | Guilak et al. |
| 2018/0237771 A1 | 8/2018 | Kim et al. |
| 2018/0251735 A1 | 9/2018 | Ko |
| 2018/0271069 A1 | 9/2018 | Min et al. |
| 2018/0280539 A1 | 10/2018 | Debs et al. |
| 2018/0291370 A1 | 10/2018 | Gersbach et al. |
| 2018/0305689 A1 | 10/2018 | Sætrom et al. |
| 2018/0305704 A1 | 10/2018 | Zhang |
| 2018/0305719 A1 | 10/2018 | Perez-Pinera et al. |
| 2018/0319850 A1 | 11/2018 | Payne et al. |
| 2018/0320197 A1 | 11/2018 | Gersbach et al. |
| 2018/0327740 A1 | 11/2018 | Gifford et al. |
| 2018/0334685 A1 | 11/2018 | Yeo et al. |
| 2018/0334688 A1 | 11/2018 | Gersbach et al. |
| 2018/0353615 A1 | 12/2018 | Gersbach et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0127713 A1 | 5/2019 | Gersbach et al. |
| 2019/0134221 A1 | 5/2019 | Bumcrot et al. |
| 2019/0136229 A1 | 5/2019 | Josephs et al. |
| 2019/0151476 A1 | 5/2019 | Gersbach et al. |
| 2019/0183932 A1 | 6/2019 | Mackall et al. |
| 2019/0194633 A1 | 6/2019 | Gersbach et al. |
| 2019/0201402 A1 | 7/2019 | Jiang et al. |
| 2019/0248854 A1 | 8/2019 | Tremblay et al. |
| 2019/0264232 A1 | 8/2019 | Hou et al. |
| 2019/0351074 A1 | 11/2019 | Ahituv et al. |
| 2019/0359959 A1 | 11/2019 | Jaenisch et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0080108 A1 | 3/2020 | Jaskula-Ranga et al. |
| 2020/0109406 A1 | 4/2020 | Miller et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0260698 A1 | 8/2020 | Kyrychenko et al. |
| 2020/0275641 A1 | 9/2020 | Min et al. |
| 2020/0318139 A1 | 10/2020 | Gersbach et al. |
| 2020/0332307 A1 | 10/2020 | Hummel et al. |
| 2020/0347105 A1 | 11/2020 | Gersbach et al. |
| 2021/0002665 A1 | 1/2021 | Gersbach et al. |
| 2021/0032654 A1 | 2/2021 | Gersbach et al. |
| 2021/0040460 A1 | 2/2021 | Gersbach et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0201375 A1 | 6/2023 | Gersbach et al. |
| 2023/0348870 A1 | 11/2023 | Gersbach et al. |
| 2023/0349888 A1 | 11/2023 | Gersbach et al. |
| 2023/0383270 A1 | 11/2023 | Gersbach et al. |
| 2023/0383297 A1 | 11/2023 | Gersbach et al. |
| 2024/0026352 A1 | 1/2024 | Gersbach et al. |
| 2024/0052328 A1 | 2/2024 | Kwon et al. |
| 2024/0058425 A1 | 2/2024 | Gersbach et al. |
| 2024/0067968 A1 | 2/2024 | Cosgrove et al. |
| 2024/0141341 A1 | 5/2024 | Gersbach et al. |
| 2024/0279628 A1 | 8/2024 | Gersbach et al. |

FOREIGN PATENT DOCUMENTS

| | | |
|---|---|---|
| CA | 2981508 A1 | 10/2016 |
| CA | 3086885 A1 | 7/2019 |
| CA | 3101477 A1 | 12/2019 |
| EP | 3009511 A2 | 4/2016 |
| EP | 3199632 A1 | 8/2017 |
| EP | 3712272 A1 | 9/2020 |
| EP | 3209783 B1 | 11/2021 |
| EP | 3995584 A1 | 5/2022 |
| JP | 2013-509159 A | 3/2013 |
| JP | 2015-534817 A | 12/2015 |
| JP | 2016-521452 A2 | 7/2016 |
| JP | 2016-521975 A | 7/2016 |
| JP | 2016-523082 A | 8/2016 |
| KR | 20190134673 A | 12/2019 |
| WO | WO 1991/18114 A1 | 11/1991 |
| WO | WO 1992/000387 A1 | 1/1992 |
| WO | WO 1993/007883 A1 | 4/1993 |
| WO | WO 93/024640 | 12/1993 |
| WO | WO 94/016737 | 8/1994 |
| WO | WO 1998/053058 A1 | 11/1998 |
| WO | WO 1998/053059 A1 | 11/1998 |
| WO | WO 1998/053060 A1 | 11/1998 |
| WO | WO 2000/028004 A1 | 5/2000 |
| WO | WO 01/83793 | 11/2001 |
| WO | WO 2001/092551 A2 | 12/2001 |
| WO | WO 2002/016536 A1 | 2/2002 |
| WO | WO 2003/016496 A2 | 2/2003 |
| WO | WO2003/072788 A1 | 9/2003 |
| WO | WO 2007/019301 A2 | 2/2007 |
| WO | WO 2008/006028 | 1/2008 |
| WO | WO 2008/070859 A2 | 6/2008 |
| WO | WO 2010/075424 A2 | 7/2010 |
| WO | WO2010/144740 A1 | 12/2010 |
| WO | WO 2011/036640 | 3/2011 |
| WO | 2011/141820 A1 | 11/2011 |

(56) References Cited

FOREIGN PATENT DOCUMENTS

| | | | |
|---|---|---|---|
| WO | WO 2011/154427 | 12/2011 | |
| WO | WO-2012136476 A1 * | 10/2012 | ............ C12N 15/85 |
| WO | WO 2013/098244 A1 | 7/2013 | |
| WO | WO 2013/163628 | 10/2013 | |
| WO | WO 2013/176772 A1 | 11/2013 | |
| WO | WO 2014/018423 A2 | 1/2014 | |
| WO | WO 2014/059255 A1 | 4/2014 | |
| WO | 2014/081855 A1 | 5/2014 | |
| WO | WO 2014/065596 A1 | 5/2014 | |
| WO | 2014/093595 A1 | 6/2014 | |
| WO | 2014/093622 A2 | 6/2014 | |
| WO | 2014/093712 A1 | 6/2014 | |
| WO | 2014/099744 A1 | 6/2014 | |
| WO | WO 2014/089290 A1 | 6/2014 | |
| WO | WO 2014/093479 A1 | 6/2014 | |
| WO | WO 2014/093655 A2 | 6/2014 | |
| WO | WO 2014/093661 A2 | 6/2014 | |
| WO | WO 2014/093709 A1 | 6/2014 | |
| WO | WO 2014/144288 A1 | 9/2014 | |
| WO | WO 2014/144592 A2 | 9/2014 | |
| WO | WO 2014/186585 A2 | 11/2014 | |
| WO | 2014/197568 A2 | 12/2014 | |
| WO | WO 2014/204726 A1 | 12/2014 | |
| WO | WO 2015/006747 A2 | 1/2015 | |
| WO | 2015/021457 A2 | 2/2015 | |
| WO | 2015/035139 A2 | 3/2015 | |
| WO | WO2015/035136 A2 | 3/2015 | |
| WO | WO 2015/048690 A1 | 4/2015 | |
| WO | WO 2015/070083 A1 | 5/2015 | |
| WO | 2015/089462 A1 | 6/2015 | |
| WO | WO2015/089427 A1 | 6/2015 | |
| WO | WO 2015/155686 A2 | 10/2015 | |
| WO | WO2015/161276 A2 | 10/2015 | |
| WO | 2015/195621 A1 | 12/2015 | |
| WO | 2016/011080 A2 | 1/2016 | |
| WO | WO2016/011070 A2 | 1/2016 | |
| WO | WO2016/049258 A2 | 3/2016 | |
| WO | WO 2016/063264 A1 | 4/2016 | |
| WO | WO 2016/070070 A1 | 5/2016 | |
| WO | WO 2016/081924 A1 | 5/2016 | |
| WO | WO2016/114972 A1 | 7/2016 | |
| WO | WO2016/123578 A1 | 8/2016 | |
| WO | WO 2016/161380 A1 | 10/2016 | |
| WO | 2016/205613 A1 | 12/2016 | |
| WO | WO 2016/187717 A1 | 12/2016 | |
| WO | WO 2017/015637 A1 | 1/2017 | |
| WO | 2017/016915 A1 | 2/2017 | |
| WO | 2017/049407 A1 | 3/2017 | |
| WO | WO 2017/035416 A2 | 3/2017 | |
| WO | WO 2017/049266 A2 | 3/2017 | |
| WO | WO 2017/066497 A2 | 4/2017 | |
| WO | WO 2017/070632 A2 | 4/2017 | |
| WO | WO 2017/072590 A1 | 5/2017 | |
| WO | WO 2017/075478 A2 | 5/2017 | |
| WO | WO 2017/095967 A2 | 6/2017 | |
| WO | WO 2017/139505 A2 | 8/2017 | |
| WO | WO 2017/165859 A1 | 9/2017 | |
| WO | 2017/180976 A1 | 10/2017 | |
| WO | WO 2017/180805 A2 | 10/2017 | |
| WO | WO 2017/193029 A2 | 11/2017 | |
| WO | 2018/002812 A1 | 1/2018 | |
| WO | 2018/005805 A1 | 1/2018 | |
| WO | 2018/017483 A1 | 1/2018 | |
| WO | WO 2018/013932 A1 | 1/2018 | |
| WO | WO 2018/017751 A1 | 1/2018 | |
| WO | WO 2018/017754 A1 | 1/2018 | |
| WO | WO 2018/031762 A1 | 2/2018 | |
| WO | WO 2018/035388 A1 | 2/2018 | |
| WO | WO 2018/035495 A1 | 2/2018 | |
| WO | 2018/039145 A1 | 3/2018 | |
| WO | WO 2018/081504 A1 | 5/2018 | |
| WO | WO 2018/098480 A1 | 5/2018 | |
| WO | 2018/107003 A1 | 6/2018 | |
| WO | WO 2018/129296 A1 | 7/2018 | |
| WO | 2018/162702 A1 | 9/2018 | |
| WO | 2018/179578 A1 | 10/2018 | |
| WO | WO 2018/191388 A1 | 10/2018 | |
| WO | 2019/009682 A2 | 1/2019 | |
| WO | 2019/023291 A2 | 1/2019 | |
| WO | WO 2019/002590 A1 | 1/2019 | |
| WO | WO 2019/036599 A1 | 2/2019 | |
| WO | 2019/046755 A1 | 3/2019 | |
| WO | WO 2019/067786 A1 | 4/2019 | |
| WO | WO 2019/077001 A1 | 4/2019 | |
| WO | WO 2019/079514 A1 | 4/2019 | |
| WO | 2019/084050 A1 | 5/2019 | |
| WO | WO 2019/092505 A1 | 5/2019 | |
| WO | 2019/113472 A1 | 6/2019 | |
| WO | 2019/123014 A1 | 6/2019 | |
| WO | 2019/136216 A1 | 7/2019 | |
| WO | WO 2019/144061 A1 | 7/2019 | |
| WO | 2019/204750 A1 | 10/2019 | |
| WO | 2019/213626 A1 | 11/2019 | |
| WO | WO 2019/232069 A1 | 12/2019 | |
| WO | 2020/018918 A1 | 1/2020 | |
| WO | WO 2020/124257 A1 | 6/2020 | |
| WO | WO 2020/132226 A1 | 6/2020 | |
| WO | 2020/168133 A1 | 8/2020 | |
| WO | WO 2020/163396 A1 | 8/2020 | |
| WO | WO 2020/210776 A1 | 10/2020 | |
| WO | WO 2020/214609 A1 | 10/2020 | |
| WO | WO 2020/214613 A1 | 10/2020 | |
| WO | WO 2020/257665 A1 | 12/2020 | |
| WO | WO 2021/026516 A1 | 2/2021 | |
| WO | WO 2021/034984 A2 | 2/2021 | |
| WO | WO 2021/034987 A1 | 2/2021 | |
| WO | WO 2021/055956 A1 | 3/2021 | |
| WO | WO 2021/067878 A1 | 4/2021 | |
| WO | WO 2021/113536 A1 | 6/2021 | |
| WO | PCT/US2021/054292 | 10/2021 | |
| WO | PCT/US2021/054636 | 10/2021 | |
| WO | PCT/US2021/056122 | 10/2021 | |
| WO | PCT/US2021/059270 | 11/2021 | |
| WO | WO 2021/222268 A1 | 11/2021 | |
| WO | WO 20217222314 A1 | 11/2021 | |
| WO | WO 20217222327 A1 | 11/2021 | |
| WO | WO 20217222328 A1 | 11/2021 | |
| WO | WO 20217226555 A2 | 11/2021 | |
| WO | 2022/038264 A1 | 2/2022 | |
| WO | PCT/US2022/018400 | 3/2022 | |
| WO | 2022/087321 A1 | 4/2022 | |
| WO | 2022/104159 A1 | 5/2022 | |
| WO | WO 2022/103935 A1 | 5/2022 | |
| WO | 2022/133062 A1 | 6/2022 | |
| WO | WO 2022/187288 A2 | 9/2022 | |
| WO | WO 2023/010133 A2 | 2/2023 | |
| WO | WO 2023/137471 A1 | 7/2023 | |
| WO | WO 2023/137472 A2 | 7/2023 | |
| WO | WO2023/200998 A2 | 10/2023 | |
| WO | WO 2024/015881 A2 | 1/2024 | |
| WO | 2024/040253 A1 | 2/2024 | |
| WO | WO 2024/064642 A2 | 3/2024 | |
| WO | 2024/081937 A1 | 4/2024 | |
| WO | 2024/092258 A2 | 5/2024 | |
| WO | WO 2024/040254 A3 | 5/2024 | |

OTHER PUBLICATIONS

Maeder et al. Robust, synergistic regulations of human gene expression using TALE activators. Nature Methods, vol. 10, No. 3, pp. 243-245, p. 1/1 of Online Methods, and pp. Jan. 1-14-14/14 of Supplementary Material, Feb. 10, 2013. (Year: 2013).*

Aartsma-Rus, A. et al., "Antisense-mediated exon skipping: a versatile tool with therapeutic and research applications," RNA 13, 2007, 1609-1624.

Aartsma-Rus, A. et al., "Exploring the frontiers of therapeutic exon skipping for Duchenne muscular dystrophy by double targeting within one or multiple exons," Mol Ther, 2006, 14:401-407.

Aartsma-Rus, A. et al., "Theoretic applicability of antisense-mediated exon skipping for Duchenne muscular dystrophy mutations," Hum Mutat, 2009, 30:293-299.

Adler, A.F. et al., "Nonviral direct conversion of primary mouse embryonic fibroblasts to neuronal cells," Molecular therapy, 2012 Nucleic acids 1, e32.

(56) References Cited

OTHER PUBLICATIONS

Aiuti, A. et al., "Lentiviral hematopoietic stem cell gene therapy in patients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bartsevich, V.V. et al., "Engineered zinc finger proteins for controlling stem cell fate," Stem Cells 21, 2003, 632-637.
Beerli, R. R. et al., "Chemically regulated zinc finger transcription factors," J Biol CheM, 2000, 275(42): p. 32617-27.
Beerli, R.R. et al., "Engineering polydactyl zinc-finger transcription factors," Nat Biotechnol 20, 2002, 135-141.
Beerli, R.R. et al., "Positive and negative regulation of endogenous genes by designed transcription factors," Proc Natl Acad Sci U S A 97, 2000, 1495-1500.
Beerli, R.R. et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogen 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred oncogene," Human gene therapy 10, 1999, 1607-1617.
Bhakta, M. S. et al., "Highly active zinc-finger nucleases by extended modular assembly," Genome Res, 2013, 530-538.
Bidou, L. et al., "Sense from nonsense: therapies for premature stop codon diseases," Trends in Molecular Medicine 18, 2012, 679-688.
Blancafort, P. et al., "Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," MolecularTerapy 20, 2012, 443-455.
Brunet, E. et al., "Chromosomal translocations induced at specific loci in human stem cells," Proc Natl Acad Sci USA, 2009, 106:10620-10625.
Buler et al. Energy-sensing factors coactivator peroxisome proliferator-activated receptor gamma coactivator 1-alpha (PGC-1 alpha) and AMP-activated protein kinase control expression of inflammatory mediators in liver. The Journal of Biological Chemistry, vol. 287, No. 3, pp. 1847-1860, Jan. 13, 2012.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Cerletti, M. et al., "Highly efficient, functional engraftment of skeletal muscle stem cells in dystrophic muscles," Cell 134, 2008, 37-47.
Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by CRISPR-on, an RNA-guided transcriptional activator system," Cell Res, 2013, 23(10): p. 1163-1171.

Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration inpatients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantificationof zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-92.
Darabi, R. et al., "Human ES-and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding, Q. et al., "A TALEN Genome-Editing System for Generating Human Stem Cell-Based Disease Models," 2013, Cell Stem Cell 12, 238-251.
Ding, Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Edelstein et al. Gene therapy clinical trials worldwide 1989-2004—an overview. J. Gene Med. vol. 6, pp. 597-602, 2004.
Esvelt et al., "Orthogonal Cas9 proteins for RNA-guided gene regulation and editing," Nature Methods 2013, 10(11): p. 1116-21.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines functional exchangeability of dual-RNA and Cas9 among orthologous type II CRISPR-Cas systems," Nucleic Acids Res, 2013.
Fu, Y., et al., "High-frequency off-target mutagenesis induced by CRISPR-Cas nucleases in human cells," Nat Biotechnol, 2013, 31(9): p. 822-6.
Fu, Y., et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
Gertz, J. et al., "Transposase mediated construction of RNA-seq libraries," Genome Res 22, 2012, 134-141.
Goemans, N. M. et al., "Systemic administration of PRO051 in Duchenne's muscular dystrophy," The New England journal of medicine 364, 2011, 1513-1522.
Gou, D. et al., "A novel approach for the construction of multiple shRNA expression vectors," J Gene Med, 2007, 9(9): p. 751-63.

(56) References Cited

OTHER PUBLICATIONS

Graslund, T. et al., "Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic, P. et al., "Systemic delivery of genes to striated muscles using adeno-associated viral vectors," Nat Med, 2004, 10:828-834.
Guschin, D. Y. et al., "A rapid and general assay for monitoring endogenous gene modification," Methods Mol Biol 649, 2010, 247-256.
Hockemeyer, D. et al., "Efficient targeting of expressed and silent genes in human ESCs and iPSCs using zinc-finger nucleases," Nat Biotechnol, 2009, 27(9): p. 851-7.
Hockemeyer, D. et al., "Genetic engineering of human pluripotent cells using TALE nucleases," Nat Biotechnol 29, 2011, 731-734.
Hoffman, E. P. et al., "Dystrophin: the protein product of the Duchenne muscular dystrophy locus," Cell, 1987, 51:919.
Hou, Z. et al., "Efficient genome engineering in human pluripotent stem cells using Cas9 from Neisseria meningitidis," Proc Natl Acad Sci USA, 2013, 110:15644-15649.
Hsu et al. (2012) "Dissecting Neural Function Using Targeted Genome Engineering Technologies", ACS Chem. Neurosci., pp. 603-610.
Hsu et al., "DNA targeting specificity of RNA-guided Cas9 nucleases," Nature Biotechnology 31, 2013, 827-832 doi:10.1038/nbt2647.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang, W. Y. et al., "Efficient genome editing in zebrafish using CRISPR-Cas system," Nat Biotechnol, 2013, 31(3):p. 227-9.
Jinek, M. et al., "A programmable dual-RNA-guided DNA endonuclease in adaptive bacterial immunity," Science 337, 2012, 816-821.
Jinek, M. et al., "RNA-programmed genome editing in human cells. eLife 2," e00471, 2013.
Jinek, M. et al., "Structures of Cas9 endonucleases reveal RNA-mediated conformational activation," Science, 2014, 343(6176): p. 1247997.
Joung, J. K. et al., "TALENs: a widely applicable technology for targeted genome editing," Nature Reviews Molecular Cell Biology 14, 2013, 49-55.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns, N. A. et al., "Cas9 effector-mediated regulation of transcription and differentiation in human pluripotent stem cells," Development, 2014, 141(1): p. 219-23.
Kim, H. et al., "Surrogate reporters for enrichment of cells with nuclease-induced mutations," Nat Methods, 2011, 8:941-943.
Kim, Y. et al., "TALENs and ZFNs are associated with different mutation signatures," Nat Methods, 2013.
Kimura, E. et al., "Cell-lineage regulated myogenesis for dystrophin replacement: a novel therapeutic approach for treatment of muscular dystrophy," Hum Mol Genet 17, 2008, 2507-2517.
Konermann, S. et al., "Optical control of mammalian endogenous transcription and epigenetic states," Nature, 2013, 500(7463): p. 472-6.
Konieczny, P. et al., "Gene and cell-mediated therapies for muscular dystrophy," Muscle Nerve, 2013, 47:649-663.
Kubokawa, I. et al., "Molecular characterization of the 5'-UTR of retinal dystrophin reveals a cryptic intron that regulates translational activity," Molecular Vision, vol. 16, pp. 2590-2597.
Kyte et al., "A Simple Method for Displaying the Hydropathic Character of a Protein," J. Mol. Biol., 1982, 157:105-132.
Langmead, B. et al., "Ultrafast and memory-efficient alignment of short DNA sequences to the human genome," Genome biology 10, 2009, R25.
Larson, M. H. et al., "CRISPR interference (CRISPRi) for sequence-editing control of gene expression," Nat Protoc, 2013, 8(11): p. 2180-96.

Latta-Mahieu et al. Gene transfer of a chimeric trans-activator is immunogenic and results in short-lived transgene expression. Human Gene Therapy, vol. 13, No. 13, pp. 1611-1620, Sep. 2002.
Lattanzi, L. et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee, H. J. et al., "Targeted chromosomal deletions in human cells using zinc finger nucleases," Genome research 20, 2010, 81-89.
Li, D. et al., "Marginal level dystrophin expression improves clinical outcome in a strain of dystrophin/utrophin double knockout mice," PLoS One, 2010, 5:e15286.
Li, H. etal, "In vivo genome editing restores haemostasis in a mouse model of haemophilia," Nature 475, 2011, 217-221.
Li, T. et al., "Modularly asseirbled designer TAL effector nucleases for targeted gene knockout and gene replacement in eukaryotes," Nucleic Acids Research, 2011, vol. 39, No. 14, pp. 6315-6325.
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu, Q. L. et al., "The status of exon skipping as a therapeutic approach to duchenne muscular dystrophy," Molecular Therapy 19, 2011, 9-15.
Lund et al. "Promoter-targeted phage display selections with preassembled synthetic zinc finger libraries for endogenous gene regulation." Journal of Molecular Biology, vol. 340, pp. 599-613, 2004.
Luo et al. Synthetic DNA delivery systems. Nature Biotechnology, vol. 18, pp. 33-37, 2000.
Maeder et al. Robust, synergistic regulation of human gene expression using TALE activators. Nature Methods, vol. 10, No. 3, pp. 243-246, Feb. 10, 2013, including pp. 1/14-14/14 of Supplementary Material.
Maeder, M. L., "Targeted DNA demethylation and activation of endogenous genes using programmable TALE-TET1 fusion proteins," Nat Biotechnol, 2013, 31(12): p. 1137-42.
Mali, P. et al., "Cas9 as a versatile tool for engineering biology," Nat Methods, 2013, 10(10): p. 957-63.
Mali, P. et al., "CAS9 transcriptional activators for target specificity screening and paired nickases for cooperative genome engineering," Nat Biotechnol, 2013, 31(9): p. 833-8.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-6.
Mercer, A. C. et al., "Regulation of Endogenous Human Gene Expression by Ligand-Inducible TALE Transcription Factors," ACS Synth Biol, 2013.
Miller, J.C. et al., "A TALE nuclease architecture for efficient genome editing," Nat Biotechnol 29, 2011, 143-148.
Moscou, M. J. et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.

(56) References Cited

OTHER PUBLICATIONS

Myslinski et al., "An unusually compact external promoter for RNA polymerase III transcription of the human H1RNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nishimasu, H. et al., "Crystal structure of cas9 incomplex with guide RNA and target DNA Cell," 2014, 156(5): p. 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Reading frame correction by targeted genome editing restores dystrophin expression in cells from Duchenne muscular dystrophy patients," Mol Ther, 2013, 21:1718-1726.
Palu et al. In pursuit of new developments for gene therapy of human diseases. J. Biotechnol. vol. 68, pp. 1-13, 1999.
Papayannakos, C. et al., "Understanding lentiviral vector chromatin targeting: working to reduce insertional mutagenic potential for gene therapy," Gene Ther, 2013, 20(6): p. 581-8.
Park, K.S. et al., "Phenotypic alteration of eukaryotic cells using randomized libraries of artificial transcription factors," Nat Biotechnol 21, 2003, 1208-1214.
Pattanayak, V. et al., "High-throughput profiling of off-target DNA cleavage reveals RNA-programmed Cas9 nuclease specificity," Nat Biotechnol, 2013, 31(9): p. 839-43.
Peault, B. et al., "Stem and progenitor cells in skeletal muscle development, maintenance, and therapy," Molecular Therapy 15, 2007, 867-877.
Perez, E. et al., "Establishment of HIV-1 resistance in CD4+ T cells by genome editing using zinc-finger nucleases," Nature biotechnology 26, 2008, 808-816.
Perez-Pinera et al. Abstract 855. "Synergistic Transcriptional Activationby Combinations of Engineered TALEs" was publicly presented at the American Society of Gene & Cell Therapy's 15th Annual Meeting in Philadelphia, Pennsylvania during the Late Abstracts Poster Session Ill: Saturday, May 19, 2012.
Perez-Pinera et al. Synergistic and tunable human gene activation by combinations of synthetic transcription factors. Nature Methods, vol. 10, No. 3, p. 239-244, Feb. 3, 2013, including pp. 1/12-12-12 of Supplementary Material.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activationby CRISPR-Cas9-based transcription factors," Nat Methods, 2013, 10:973-976.
Perez-Pinera, P. et al., "Advances in targeted genome editing" Current Opinion in Chemical Biology 16, 2012, 268-277.
Persons, D. A., "Lentiviral vector gene therapy: effective and safe?" Mol Ther, 2010, 18(5): p. 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activationby customizable zinc finger transcription factors," J Am Chem Soc, 2012, 134(40): p. 16480-3.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran, F. A. et al., "Double nicking by RNA-guided CRISPR Cas9 for enhanced genome editing specificity," Cell, 2013, 154(6): p. 1380-9.

Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.
Rousseau, J. et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon, P. and Trono. D., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor (1989).
Schmid-Burgk, J. L. et al., "A ligation-independent cloning technique for high-throughput of transcription activator-like effector genes," Nat Biotechnol 31, 2012, 76-81.
Scholze et al. TAL effectors are remote controls for gene activation. Current Opinion in Microbiology, vol. 14, pp. 47-53, Jan. 2011.
Schultz, B. R. & Chamberlain, J. S., "Recombinant adeno-associated virus transduction and integration," Molecular Therapy 16, 2008, 1189-1199.
Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifyginagents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA and joining varies among somatic tissues, despite similarity in mechanism," Cellular and Molecular Life Science 68, 2011, 661-676.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized TAL effector nucleases (TALENs) for use in treatment of sickle cell disease," Molecular bioSystems 8, 2012, 1255-1263.
Szyf, M., "Epigenetics, DNA methylation, and chromatin modifying drugs," Annual Review of Pharmacology and Toxicology, 2009, vol. 49, pp. 243-263.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV,"N Engl J Med, 2014, 370:901-910.
Tedesco, F. S. et al., "Repairing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Musculat Dystrophy," Science Translational Medicine 3, 96ra78-96ra78, 2011.
Tedesco, F. S. et al., "Transplantation of Genetically Corrected Human iPSC-Derived Progenitors in Mice with Limb-Girdle Muscular Dystrophy," Science Translational Medicine 4, 140ra189, 2012.
Urnov, F. et al., "Highly efficient endogenous human gene correction using designed zinc-finger nucleases," Nature 435, 2005, 646-651.
Van Putten, M. et al., "Low dystrophin levels in heart can delay heart failure in mdx mice," J Mol Cell Cardiol, 2014, 69C:17-23.

(56) References Cited

OTHER PUBLICATIONS

Van Putten, M. et al., "Low dystrophin levels increase survival and inprove muscle pathology and function in dystrophin/utrophin double-knockout mice," FASEB J, 2013, 27:2484-2495.
Verma and Weitzman. Gene Therapy: Twenty-first century medicine. Annual Review of Biochemistry, vol. 74, pp. 711-738, 2005.
Verma et al. Gene therapy—promises, problems and prospects. Nature, vol. 389, pp. 239-242, 1997.
Vierbuchen, T. et al., "Direct conversion of fibroblasts to functional neurons by defined factors," Nature 463, 2010, 1035-1041.
Wang et al., "Adeno-associated virus vector carrying human minidystrophin genes effectively ameliorates muscular dystrophy in mdx mouse model," Proc Natl Acad Sci USA. (2000) 97(25):13714-13719.
Wang H. et al., "One-Step Generation of Mice Carrying Mutations in Multiple Genes by CRISPR-Cas-Mediated Genome Engineering," Cell, 2013, 153(4): p. 910-8.
Wein, N. et al., "Efficient bypass of mutations in dysferlin deficient patient cells by antisense-induced exon skipping," Hum Mutat 31, 2010, 136-142.
Welch, E. M. et al., "PTC124 targets genetic disorders caused by nonsense mutations," Nature 447, 2007, 87-91.
Yan et al. Biochimica et Biophysica Acta, vol. 1835, No. 1, pp. 76-85, Jan. 2013.
Yang, L., "Optimization of scarless human stem cell genome editing," Nucleic Acids Res, 2013, 41:9049-9061.
Yusa, K. et al., "Targeted gene correction of α1-antitrypsin deficiency in induced pluripotent stem cells," Nature 478, 2011, 391-394.
Zhang, F. et al. "Efficient construction of sequence-specific TAL effectors for modulating mammalian transcription," Nat Biotechnol 29, 2011, 149-153.
Zhu, C. H. et al., "Cellular senescence in human telomerase reverse transcriptase and cyclin-dependent kinase 4: consequences in aging muscle and therapeutic strategies for muscular dystrophies," Aging cell 6, 2007, 515-523.
Zou, J. et al., "Site-specific gene correction ofa point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
United States Patent Office Action for U.S. Appl. No. 14/220,116 dated Jul. 22, 2015 (26 pages).
United States Patent Office Final Action for U.S. Appl. No. 14/220,116 dated May 4, 2016 (29 pages).
United States Patent Office Action for U.S. Appl. No. 14/397,420 dated Jun. 2, 2016 (8 pages).
United States Patent Office Action for U.S. Appl. No. 14/397,420 dated Oct. 5, 2016 (10 pages).
International Search Report and Written Opinion for Application No. PCT/US13/38536 dated Nov. 29, 2013 (27 pages).
United States Patent Office Action for U.S. Appl. No. 14/220,116 dated Dec. 2, 2016 (16 pages).
United States Patent Office Action for U.S. Appl. No. 14/895,316 dated Dec. 15, 2016 (13 pages).
United States Patent Office Action for U.S. Appl. No. 14/220,116 dated Jul. 19, 2017 (15 pages).
United States Patent Office Notice of Allowance for U.S. Appl. No. 14/220,116 dated Sep. 19, 2017 (8 pages).
United States Patent Office Action for U.S. Appl. No. 14/895,316 dated Mar. 21, 2018 (8 pages).
United States Patent Office Action for U.S. Appl. No. 14/895,316 dated Oct. 22, 2018 (11 pages).
United States Patent Office Action for U.S. Appl. No. 14/895,316 dated Apr. 19, 2019 (11 pages).
United States Patent Office Action for U.S. Appl. No. 15/991,333 dated Apr. 19, 2019 (12 pages).
United States Patent Office Action for U.S. Appl. No. 15/634,425 dated Aug. 8, 2019 (10 pages).
United States Patent Office Notice of Allowance for U.S. Appl. No. 14/895,316 dated Sep. 30, 2019 (9 pages).
United States Patent Office Action for U.S. Appl. No. 15/991,333 dated Oct. 4, 2019 (6 pages).
United States Patent Office Notice of Allowance for U.S. Appl. No. 14/895,316 dated Jan. 27, 2020 (7 pages).
United States Patent Office Notice of Allowance for U.S. Appl. No. 15/634,425 dated Mar. 9, 2020 (8 pages).
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
Yang et al., "Gene Reactivation by 5-Aza-2'-Deoxycytidine-Induced Demethylation Requires SRCAP-Mediated H2A.Z Insertion to Establish Nucleosome Depleted Regions", PLoS Genetics, 2012, vol. 8, Issue 3, e1002604, 12 pages.
Takeshima et al., "Mutation spectrum of the dystrophin gene in 442 Duchene/Becker muscular dystrophy cases from one Japanese referral center," Journal of Human Genetics, 2010, 55: 379-388.
Wang et al., "Efficient delivery of genome-editing proteins using bioreducible lipid nanoparticles," Proc Natl Acad USA, 2016, 113(11): 2868-2873.
United States Patent Office Action for U.S. Appl. No. 16/858,689 dated Nov. 16, 2021 (14 pages).
U.S. Appl. No. 17/636,750, filed Feb. 18, 2022.
U.S. Appl. No. 17/636,754, filed Feb. 18, 2022.
U.S. Appl. No. 17/766,003, filed Apr. 1, 2022.
U.S. Appl. No. 63/314,183, filed Feb. 25, 2022.
U.S. Appl. No. 63/314,256, filed Feb. 25, 2022.
U.S. Appl. No. 63/317,847, filed Mar. 8, 2022.
U.S. Appl. No. 63/325,037, filed Mar. 29, 2022.
U.S. Appl. No. 63/325,039, filed Mar. 29, 2022.
U.S. Appl. No. 63/330,679, filed Apr. 13, 2022.
U.S. Appl. No. 63/372,373, filed Mar. 8, 2022.
U.S. Appl. No. 63/330,691, filed Apr. 13, 2022.
U.S. Appl. No. 17/471,935, filed Sep. 10, 2021.
U.S. Appl. No. 17/633,467, filed Feb. 7, 2022.
U.S. Appl. No. 63/335,122, filed Apr. 26, 2022.
U.S. Appl. No. 63/342,027, filed May 13, 2022.
Ousterout et al., "Genetic Correction of Duchenne Muscular Dystrophy Using Zinc Finger Nucleases," Mol. Ther., 2013, vol. 21, Supplement 1, 292, p. S111-S112.
Rousseau et al., "New TALENs To Correct the Reading Frame of Exon 54 of the Dystrophin Gene," Mol. Ther., 2013, vol. 21, Supplement 1, 293, p. S112.
United States Patent Office Action for U.S. Appl. No. 16/858,689 dated Mar. 4, 2022 (8 pages).
United States Patent Office Action for U.S. Appl. No. 16/927,679 dated Jun. 14, 2022 (11 pages).
'T Hoen et al., "Generation and characterization of transgenic mice with the full-length human DMD gene," J. Biol. Chem., 2008, 283: 5899-5907.
Acosta et al., "Use of two gRNAs for CRISPR/Cas9 improves bi-allelic homologous recombination efficiency in mouse embryonic stem cells," Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.
Adamson et al., "A Multiplexed Single-Cell CRISPR Screening Platform Enables Systematic Dissection of the Unfolded Protein Response," Cell, 2016, 167: 1867-1882.e21.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.
Albuquerque et al., "Mammalian nicotinic acetylcholine receptors: from structure to function," Physiol Rev, 2009, 89: 73-120.
Aloia, "Epigenetic Regulation of Cell-Fate Changes That Determine Adult Liver Regeneration After Injury," Front. Cell Dev. Biol., 2021, 9: 643055.

(56) References Cited

OTHER PUBLICATIONS

Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Andersen et al., "Dual role of delta-like 1 homolog (DLK1) in skeletal muscle development and adult muscle regeneration," Development, 2013, 140: 3743-3753.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Arnett et al., "Adeno-associated viral vectors do not efficiently target muscle satellite cells," Molecular Therapy Methods & Clinical Development, 2014, 1: 14038.
Asokan et al., "Reengineering a receptor footprint of adeno-associated virus enables selective and systemic gene transfer to muscle," Nat Biotechnol, 2010, 28: 79-82.
Asrani et al., "Burden of liver diseases in the world," J Hepatol, 2019, 70(1): 151-171.
Bae et al., "Cas-OFFinder: a fast and versatile algorithm that searches for potential off-target sites of Cas9 RNA-guided endonucleases," Bioinformatics, 2014, 30: 1473-1475.
Balboa et al., "Conditionally Stabilized dCas9 Activator for Controlling Gene Expression in Human Cell Reprogramming and Differentiation," Stem Cell Rep, 2015, 5: 448-459.
Baratta et al., "Cellular organization of normal mouse liver: a histological, quantitative immunocytochemical, and fine structural analysis," Histochem Cell Biol, 2009, 131(6): 713-726.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Bauer et al., "An erythroid enhancer of BCL11A subject to genetic variation determines fetal hemoglobin level," Science 342, 2013, 253-257.
Beaudry et al., "Directed evolution of an RNA enzyme," Science, 1992, 257(5070): 635-641.
Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Bernstein et al., "An integrated encyclopedia of DNA elements in the human genome," Nature, 2012, 489: 57-74.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Bladen et al., "The Treat-NMD DMD Global Database: analysis of more than 7,000 Duchenne muscular dystrophy mutations," Human Mutation, 2015, 36(4):395-402.

Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Blancafort et al., "Writing and rewriting the epigenetic code of cancer cells: from engineered proteins to small molecules," Mol. Pharmacol., 2013, 83(3): 563-576.
Boldrin et al., "Donor satellite cell engraftment is significantly augmented when the host niche is preserved and endogenous satellite cells are incapacitated," Stem Cells, 2012, 30: 1971-1984.
Bolger et al., "Trimmomatic: a flexible trimmer for Illumina sequence data," Bioinformatics, 2014, 30: 2114-2120.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context-dependent manner," Nat Commun, 2016, 7: 12284.
Canver et al., "BCL11A enhancer dissection by Cas9-mediated in situ saturating mutagenesis," Nature, 2015, 527: 192-197.
Carroll, "A CRISPR approach to gene targeting," Molecular Therapy, 2012, 20: 1658-1660.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL1," Stem Cell Reports, 2014, 3: 282-296.
Chang et al., "Integrating Combinatorial Lipid Nanoparticle and Chemically Modified Protein for Intracellular Delivery and Genome Editing," Acc. Chem. Res., 2019, 52: 665-675.

(56) References Cited

OTHER PUBLICATIONS

Cheloufi et al., "The histone chaperone CAF-1 safeguards somatic cell identity," Nature, 2015, 528: 218-224.
Chen et al., "Acetylation of RelA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "Genome-wide CRISPR screen in a mouse model of tumor growth and metastasis," Cell, 2015, 160: 1246-1260.
Chen et al., "microRNA-1 and microRNA-206 regulate skeletal muscle satellite cell proliferation and differentiation by repressing Pax7," J Cell Biol, 2010, 190: 867-879.
Chen et al., "Targeted activation of diverse CRISPR-Cas systems for mammalian genome editing via proximal CRISPR targeting," Nature Communications, 2017, 8: 14958.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Childers et al., "Gene therapy prolongs survival and restores function in murine and canine models of myotubular myopathy," Sci Transl Med, 2014, 6: 220ra210.
Christoffersen et al., "Ribozymes as human therapeutic agents," J. Med. Chem., 1995, 38(12): 2023-2037.
Chronis et al., "Cooperative Binding of Transcription Factors Orchestrates Reprogramming," Cell, 2017, 168: 442-459 e420.
Concise Encyclopedia of Polymer Science And Engineering, 1990, pp. 858-859.
Cooper et al., "Improved induction of immune tolerance to factor IX by hepatic AAV-8 gene transfer," Hum Gene Ther, 2009, 20: 767-776.
Corces et al., "The chromatin accessibility landscape of primary human cancers," Science, 2018, 362(6413): eaav1898.
Cordier et al., "Muscle-specific promoters may be necessary for adeno-associated virus-mediated gene transfer in the treatment of muscular dystrophies," Hum. Gene Ther., 2001, 12: 205-215.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Deconinck et al., "Utrophin-Dystrophin-Deficient Mice as a Model for Duchenne Muscular Dystrophy," Cell, 1997, 90(4): 717-727.
Dempster et al., "Extracting Biological Insights from the Project Achilles Genome-Scale CRISPR Screens in Cancer Cell Lines," Cold Spring Harbor Laboratory, 2019, 35 pages.
Diao et al., "A new class of temporarily phenotypic enhancers identified by CRISPR/Cas9-mediated genetic screening," Genome Res, 2016, 26: 397-405.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Dobin et al., "STAR: ultrafast universal RNA-seq aligner," Bioinformatics, 2013, 29: 15-21.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
Eguchi et al., "Reprogramming cell fate with a genome-scale library of artificial transcription factors," Proc Natl Acad Sci U S A, 2016, 113: E8257-E8266.
ENCODE Project Consortium, "Expanded encyclopaedias of DNA elements in the human and mouse genomes," Nature, 2020, 583: 699-710.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Ernst et al., "ChromHMM: automating chromatin-state discovery and characterization," Nat. Methods, 2012, 9: 215-216.
Erwin et al., "Synthetic transcription elongation factors license transcription across repressive chromatin," Science, 2017, 358: 1617-1622.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).

(56) References Cited

OTHER PUBLICATIONS

FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1):S224.
Friedland et al., "*Staphyloccocus aureus* Cas9: An Alternative Cas9 for Genome Editing Applications," Retrieved from the Internet: <http://www.editasmedicine.com/data/documents/ASGCT%20poster 2015 Ari.pdf> Retrieved on Feb. 28, 2018.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.
Gao et al., "Complex transcriptional modulation with orthogonal and inducible dCas9 regulators," Nat Methods, 2016, 13: 1043-1049.
Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.

Gebeyehu et al., "Novel biotinylated nucleotide-analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession AF214528.1 (2000).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
GenBank P38036.2 (2013).
Gersbach et al., "Targeted plasmid integration into the human genome by an engineered zinc-finger recombinase," Nucleic Acids Res, 2011, 39: 7868-7878.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Goldstein et al., "In Situ Modification of Tissue Stem and Progenitor Cell Genomes," Cell Reports, 2019, 27: 1254-1264.e7.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46):16359-64.
Gray et al., "G quadruplexes are genomewide targets of transcriptional helicases XPB and XPD," Nat. Chem. Biol, 2014, 10: 313-318.
Gregorevic et al., "Systemic microdystrophin gene delivery improves skeletal muscle structure and function in old dystrophic mdx mice," Mol Ther, 2008, 16: 657-664.
Grissa et al., "CRISPRFinder: a web tool to identify clustered regularly interspaced short palindromic repeats," Nucleic Acids Res., 2007, 35(Web Server issue):W52-57.
Guo et al., "Harnessing accurate non-homologous end joining for efficient prease deletion in CRISPR/Cas9-mediated genome editing," Genome Biology, 2018, 19: 170, 20 pages.
Guo, J. et al., "Directed evolution of an enhanced and highly efficient FokI cleavage domain for zinc finger nucleases," J Mol Biol, 2010.
Hacein-Bey-Abina et al., "LMO2-associated clonal T cell proliferation in two patients after gene therapy for SCID-X1," Science, 2003, 302: 415-419.
Hakim et al., "Evaluation of Muscle Function of the Extensor Digitorum Longus Muscle Ex vivo and Tibialis Anterior Muscle In situ in Mice," J. Vis. Exp., 2013, 1-8.

(56) References Cited

OTHER PUBLICATIONS

Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PLoS ONE, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1774.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Henikoff et al., "Amino acid substitution matrices from protein blocks," Proc. Natl. Acad. Sci. USA, 1992, 89: 10915-9.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hori et al., "Simple and reproducible hepatectomy in the mouse using the clip technique," World J Gastroenterol, 2012, 18(22): 2767-2774.
Horlbeck et al., "Compact and highly active next-generation libraries for CRISPR-mediated gene repression and activation," eLife, 2016, 5: e19760.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157: 1262-1278.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/- mice," Muscle & Nerve, 2011, 43(2): 263-267.
Huntriss et al., "Imprinted expression of SNRPN in human preimplantation embryos," Am J Hum Genet, 1998, 63: 1009-1014.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jansen et al., "Identification of genes that are associated with DNA repeats in prokaryotes," Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Jiang et al., "A Cas9-guide RNA complex preorganized for target DNA recognition," Science, 2015, 348, 1477-1481.
Jiang et al., "Notch signaling deficiency underlies age-dependent depletion of satellite cells in muscular dystrophy," Disease Models & Mechanisms, 2014, 7: 997-1004.
Jiang et al., "RNA-guided editing of bacterial genomes using CRISPR-Cas systems," Nat. Biotechnol., 2013, 31:233-239.
Jimenez et al., "Activation of the beta-globin locus control region precedes commitment to the erythroid lineage," Proceedings of the National Academy of Sciences, 1992, 89: 10618-10622.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Jobling et al., "Chitayat-Hall and Schaaf-Yang syndromes:a common aetiology: expanding the phenotype of MAGEL2-related disorders," J Med Genet, 2018, 55: 316-321.
Jooss et al., "Transduction of dendritic cells by DNA viral vectors directs the immune response to transgene products in muscle fibers," J. Virol., 1998, 72: 4212-4223.
Josephs et al., "Structure and specificity of the RNA-guided endonuclease Cas9 during DNA interrogation, target binding and cleavage," Nucleic Acids Research, 2015, 43(18): 8924-8941.
Joyce, "Amplification, mutation and selection of catalytic RNA," Gene, 1989, 82(1): 83-87.
Joyce, "Directed molecular evolution," Scientific American, 1992, 267(6): 90-97.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virusspecific proteins in MDCK cells," FEBS Lett., 1990, 259: 327-330.
Karlin et al., "Applications and statistics for multiple high-scoring segments in molecular sequences," Proc. Natl. Acad. Sci. USA, 1993, 90: 5873-77.
Kauppinen et al., "Locked nucleic acid (LNA): High affinity targeting of RNA for diagnostics and therapeutics," Drug Discov Today Technol, 2005, 2(3): 287-290.
Keefe et al., "Muscle stem cells contribute to myofibers in sedentary adult mice," Nat Commun, 2015, 6: 7087.
Keil et al., "Brain transcriptome databases: a user's guide," J Neurosci, 2018, 38(10): 2399-2412.
Kempfer et al., "Methods for mapping 3D chromosome architecture," Nat. Rev. Genet., 2020, 21: 207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "A Histone acetylation contributes to chromatin looping between the locus control region and globin gene by influencing hypersensitive site formation," Biochim Biophys Acta, 2013, 1829: 963-969.
Kim et al., "Epigenetic therapy of Prader-Willi Syndrome," Transl Res, 2019, 208: 105-118.
Kim et al., "Expansion and Purification Are Critical for the Therapeutic Application of Pluripotent Stem Cell-Derived Myogenic Progenitors," Stem Cell Rep, 2017, 9: 12-22.
Kim et al., "Targeting the histone methyltransferase G9a activates imprinted genes and improves survival of a mouse model of Prader-Willi syndrome," Nat Med, 2017, 23: 213-222.

(56) References Cited

OTHER PUBLICATIONS

Kim et al., "Engineering and Application of Zinc Finger Proteins and TALEs for Biomedical Research," Mol Cells, 2017, 40(8): 533-541.
Klann et al., "CRISPR-based methods for high-throughput annotation of regulatory DNA," Curr Opin Biotechnol, 2018, 52: 32-41.
Klann et al., "CRISPR-Cas9 epigenome editing enables high-throughput screening for functional regulatory elements in the human genome," Nat Biotechnol, 2017, 35: 561-568.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Broadening the targeting range of *Staphylococcus aureus* CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523(7561): 481-485.
Kleinstiver et al., "Genome-wide specificities of CRISPR-Cas Cpf1 nucleases in human cells," Nature Biotechnology, 2016, 34(8):869-874.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.
Kodaka et al., "Skeletal Muscle Cell Induction from Pluripotent Stem Cells," Stem Cells Int, Apr. 2017, Article ID 1376151, 16 pages.
Koerber et al., "DNA shuffling of adeno-associated virus yields functionally diverse viral progeny," Mol Ther, 2008, 16: 1703-1709.
Komor et al., "Programmable editing of a target base in genomic DNA without double-stranded DNA cleavage," Nature, 2016, 533(7603): 420-424.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther, 2010, 17: 1355-1362.
Korkmaz et al., "Functional genetic screens for enhancer elements in the human genome using CRISPR-Cas9," Nat Biotechnol, 2016, 34: 192-198.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kreis et al., "The Multifaceted p21 (Cip1/Waf1/CDKN1A) in Cell Differentiation, Migration and Cancer Therapy," Cancers (Basel), 2019, 11(9): 1220.
Kuhnel et al., "Tumor-specific adenoviral gene therapy: Transcriptional repression of gene expression by utilizing p53-signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwon et al., "Myogenic Progenitor Cell Lineage Specification by CRISPR/Cas9-Based Transcriptional Activators," Stem cell reports, 2020, 14: 755-769.
Lacerra et al., "Restoration of hemoglobin A synthesis in erythroid cells from peripheral blood of thalassemic patients," Proc. Natl. Acad. Sci., 2000, 97(17): 9591-9596.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.
Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lambert et al., "The Human Transcription Factors," Cell, 2018, 172: 650-665.
Lamey et al., "Pax genes in myogenesis: alternate transcripts add complexity," Histol Histopathol, 2004, 19: 1289-1300.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langouet et al., "Zinc finger protein 274 regulates imprinted expression of transcripts in Prader-Willi syndrome neurons," Hum Mol Genet, 2018, 27: 505-515.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Nanoparticle delivery of Cas9 ribonucleoprotein and donor DNA in vivo induces homology-directed DNA repair," Nat Biomed Eng, 2017, 1: 889-901.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Levskaya et al., "Synthetic biology: engineering *Escherichia coli* to see light," Nature, 2005, 438:441-442.
Li et al., "Chimeric DNA methyltransferases target DNA methylation to specific DNA sequences and repress expression of target genes," Nucleic Acids Res., 2007, 35(1): 100-112.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.

(56) References Cited

OTHER PUBLICATIONS

Li et al., "The autism-related gene SNRPN regulates cortical and spine development via controlling nuclear receptor Nr4a1," Sci Rep, 2016, 6: 29878.
Lian et al., "Robust cardiomyocyte differentiation from human pluripotent stem cells via temporal modulation of canonical Wnt signaling," Proc Natl Acad Sci, 2012, 109: E1848-E1857.
Liao et al., "In Vivo Target Gene Activation via CRISPR/Cas9-Mediated Trans-epigenetic Modulation," Cell, 2017, 171: 1495-1507.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Long et al., "Postnatal genome editing partially restores dystrophin expression in a mouse model of muscular dystrophy," Science, 2016, 351(6271): 400-403.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
MacPherson et al., "Flexible guide-RNA design for CRISPR applications using Protospacer Workbench," Nature biotechnology, 2015, 33(8): 2 pages.
Mader et al., "CRISPR RNA-guided activation of endogenous human genes," Nature Methods, 2013, 10(10): 977-979.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "Robust, synergistic regulation of human gene expression using TALE activators," Nat Methods, 2013, 10(3): 243-245.
Magli et al., "PAX7 Targets, CD54, Integrin α9β1, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Majzner et al., "Clinical lessons learned from the first leg of the CAR T cell journey," Nature Medicine, 2019, 25(9): 1341-1355.

Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease? ," Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
McFadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Meyers et al., "Computational correction of copy number effect improves specificity of CRISPR-Cas9 essentiality screens in cancer cells," Nat. Genet., 2017, 49: 1779-1784.
Miller et al., "Transcriptional landscape of the prenatal human brain," Nature, 2014, 508: 199-206.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3' overhangs efficiently suppress targeted gene expression in mammalian cells," Nature Biotechnol, 2002, 20(5): 497-500.

(56) References Cited

OTHER PUBLICATIONS

Mojica et al., "Intervening sequences of regularly spaced prokaryotic repeats derive from foreign genetic elements," J Molec Evolution, 2005, 60(2): 174-182.
Mojica et al., "Short motif sequences determine the targets of the prokaryotic CRISPR defence system," Microbiology, 2009, 155: 733-740.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murray et al., "Codon usage in plant genes," Nucl. Acids Res., 1989, 17:477-498.
Naguibneva et al., "An LNA-based loss-of-function assay for micro-RNAs," Biomed Pharmacother, 2006, 60: 633-638.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574-1584.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Local and Systemic Gene Editing in a Mouse Model of Duchenne Muscular Dystrophy," Molecular Therapy, 2016, 24(Supp 1):S191.
Nelson et al., "Long-term evaluation of AAV-CRISPR genome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673-2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Olguin et al., "Pax-7 up-regulation inhibits myogenesis and cell cycle progression in satellite cells: a potential mechanism for self-renewal," Dev Biol, 2004, 275: 375-388.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Streptococcus thermophilus*," mBio, 2015, 6(2): e00262-15.
Pang et al., "Induction of human neuronal cells by defined transcription factors," Nature, 2011, 476: 220-223.
Papapetrou, "Induced pluripotent stem cells, past and future," Science, 2016, 353: 991-992.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Multi-Parametric MRI at 14T for Muscular Dystrophy Mice Treated with AAV Vector-Mediated Gene Therapy," PLoS ONE, 2015, 10(4): e0124914.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.
Penczek et al., "Three-dimensional reconstruction of single particles embedded in ice," Ultramicroscopy, 1992, 40, 33-53.
Perez-Pinera et al., "Synergistic and tunable human gene activation by combinations of synthetic transcription factors," Nat Methods, 2013, 10: 239-242.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Ponting et al., "Evolution and functions of long noncoding RNAs," Cell, 2009, 136(4): 629-641.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus lncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.

(56) References Cited

OTHER PUBLICATIONS

Puccini et al., "Colorectal cancer: epigenetic alterations and their clinical implications", Biochim Biophys Acta, 2017, vol. 1868, No. 2, pp. 439-448.
Rackham et al., "A predictive computational framework for direct reprogramming between human cell types," Nature Genetics, 2016, 48: 331-335.
Raeburn et al., "Techniques for drug delivery to the airways, and the assessment of lung function in animal models," J. Pharmacol. Toxicol. Meth., 1992, 27:143-159.
Rajagopal et al., "High-throughput mapping of regulatory DNA," Nat. Biotechnol, 2016, 34: 167-174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Genome engineering using the CRISPR-Cas9 system," Nature Protocols, 2013, 8(11): 2281-2308.
Rao et al., "Engineering human pluripotent stem cells into a functional skeletal muscle tissue," Nat Commun, 2018, 9: 126.
Ratcliff et al., "A novel single-molecule study to determine protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity," Nat Biotechnol, Jul. 2020, 38(7): 883-891.
Riordan et al., "Application of CRISPR/Cas9 for biomedical discoveries," Cell & Bioscience, 2015, 5(1):11 pages.
Rmilah et al., "Understanding the marvels behind liver regeneration," Wiley Interdiscip Rev Dev Biol., 2019, 8(3):e340.
Roadmap Epigenomics Consortium, "Integrative analysis of 111 reference human epigenomes," Nature, 2015, 518: 317-330.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Russa et al. "The New State of the Art: Cas9 for Gene Activation and Repression," Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atohl drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Hum Genet, 2007, Chapter 12, Unit 12.10, Supplement 54, 24 pages.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
Santalucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Schultz et al., "SETDB1: a novel KAP-I-associated histone H3, lysine 9-specific methyltransferase that contributes to HPI-mediated silencing of euchromatic genes by KRAB zinc-finger proteins," Genes & Development, 2002, 16: 919-932.
Segal and Meckler, "Genome Engineering at the Dawn of the Golden Age," Annu. Rev. Genomics Hum. Genet., 2013, 14: 135-158.
Semenova et al., "The Cas6e ribonuclease is not required for interference and adaptation by the E. coli type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019).
Sequence alignment: SEQ ID No. 102921 (2019).
Sequence alignment: SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Sharma et al., "In vivo genome editing of the albumin locus as a platform for protein replacement therapy," Blood, 2015, 126: 1777-1784.
Shea et al., "Synthesis, hybridization properties and antiviral activity of lipid-oligodeoxynucleotide conjugates," Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chern, 2013, 288(40): 28814-28823.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.

(56) References Cited

OTHER PUBLICATIONS

Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Skene et al., "Genetic identification of brain cell types underlying schizophrenia," Nat Genet, 2018, 50: 825-833.
Soejima et al., "Imprinting centers, chromatin structure, and disease," J Cell Biochem, 2005, 95(2): 226-233.
Song et al., "Non-immunogenic utrophin gene therapy for the treatment of muscular dystrophy animal models," Nature Medicine, 2019, 25(10): 1505-1511.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlas of the Mouse Diaphragm: Myogenicity, Vascularity, and the Pax3 Connection" J Histochem Cytochem, 2012, 60(9): 638-657.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szymczak et al., "Correction of multi-gene deficiency in vivo using a single 'self-cleaving' 2A peptide-based retroviral vector," Nature Biotechnology, 2004, 22(5): 589-594.
Takahashi et al., "A decade of transcription factor-mediated reprograming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Tam et al., "Benefits and limitations of genome-wide association studies," Nat. Rev. Genet., 2019, 20: 467-484.
Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered *Staphylococcus aureus* Cas9 nucleases with high genome-wide specificity," Proc. Nat. Acad. Sci. USA, 2019, 116(46): 20969-20976.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening *S. aureus* CRISPR-Cas9 Paired Guide RNAs for Efficient Targeted Deletion in Duchenne Muscular Dystrophy," Editas, Poster presented on May 5, 2016.
Tyle, "Iontophoretic Devices for Drug Delivery," Pharm. Res., 1986, 3: 318-326.
U.S. Appl. No. 17/471,935, filed Sep. 10, 2021, by Gersbach et al.
U.S. Appl. No. 17/636,750, filed Feb. 18, 2022, by Gersbach et al.
U.S. Appl. No. 17/636,754, filed Feb. 18, 2022, by Gersbach et al.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Van Arensbergen et al., "Genome-wide mapping autonomous promoter activity in human cells," Nature Biotechnology, 2017, 35(2): 145-153.
Van der Oost et al., "Unravelling the structural and mechanistic basis of CRISPR-Cas systems," Nature Reviews Microbiology, 2014, 12: 479-492.
Van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class *Anthozoa*," Protein Structures: Kaleidoscope of Structural Properties and Functions, 2003, 405-439.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827-838.
Vorobyov et al., "Expression of two protein isoforms of PAX7 is controlled by competing cleavage-polyadenylation and splicing," Gene, 2004, 342: 107-112.
Wada et al., "Codon usage tabulated from the GenBank genetic sequence data," Nucl. Acids Res., 1990, 18: 2367-2411.
Waddell et al., "Dlk1 Is Necessary for Proper Skeletal Muscle Development and Regeneration," PLoS ONE, 2010, 5(11): e15055.

(56) References Cited

OTHER PUBLICATIONS

Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "Potential of Epigenetic Therapy for Pader-Willi Syndrome," Trends in Pharmacological Sciences, 2019, 40(9): 605-608.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9 mediated genome editing and guide RNA design," Mammalian Genome, 2015, 26(9): 501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11(4):184.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Wu et al., "Genome-wide binding of the CRISPR endonuclease Cas9 in mammalian cells," Nat Biotechnol, 2014, 32: 670-676.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039. e6.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299. e5.
Xie et al., "sgRNAcas9: a software package for designing CRISPR sgRNA and evaluating potential off-target cleavage sites," PLoS One, 2014, 9(6): e100448.
Xu et al., "CRISPR-mediated Genome Editing Restores Dystrophin Expression and Function in mdx Mice," Molecular Therapy: The Journal of the American Society of Gene Therapy, 2016, 24(3):564-569.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Determination of protein-DNA binding constants and specificities from statistical analyses of single molecules: MutS-DNA interactions," Nucleic acids research, 2005, 33(13): 4322-4334.
Yang et al., "Generation of pure GABAergic neurons by transcription factor programming," Nat Methods, 2017, 14: 621-628.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Zetsche et al., "Cpf1 Is a Single RNA-Guided Endonuclease of a Class 2 CRISPR-Cas System," Cell, 2015, 163(3):759-71.
Zhang et al., "Comprehensive Structure-Function Study of NeurogeninS Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9-mediated double-stranded DNA cleavage," Genome Biol, 2017 18(35): 18 pages.
Zhang et al., "Gene activation in human cells using CRISPR/Cpf1-p300 and CRISPR/Cpf1-SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhang et al., "Rapid single-step induction of functional neurons from human pluripotent stem cells," Neuron, 2013, 78: 785-798.
Zhao et al., "High-efficiency transfection of primary human and mouse T lymphocytes using RNA electroporation," Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zhao et al., "The LIM-homeoboxgene Lhx8 is required for the development of many cholinergic neurons in the mouse forebrain," Proc Natl Acad Sci U S A, 2003, 100: 9005-9010.

(56) References Cited

OTHER PUBLICATIONS

Zhou et al., "Haploinsufficiency of utrophin gene worsens skeletal muscle inflammation and fibrosis in mdx mice," Journal of the Neurological Sciences, 2008, 264(1): 106-111.
Zhu et al., "The role of histone deacetylase 7 (HDAC7) in cancer cell proliferation: regulation on c-Myc," J. Mol. Med, 2011, 89: 279-289.
United States Patent Office Notice of Allowance for U.S. Appl. No. 16/890,232 dated Sep. 28, 2022 (8 pages).
United States Patent Office Action for U.S. Appl. No. 16/858,689 dated Oct. 19, 2022 (11 pages).
NCBI Reference Sequence XM011532698.1 (2015).
NCBI Reference Sequence NM_004020.2 (2010).
NCBI Reference Sequence NG_028016.2 (2013).
United States Patent Office Action for U.S. Appl. No. 16/927,679 dated Nov. 22, 2022 (8 pages).
United States Patent Office Notice of Allowance for U.S. Appl. No. 16/890,232 dated Feb. 2, 2023 (8 pages).
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Min et al., "CRISPR Correction of Duchene Muscular Dystrophy Exon 44 Deletion Mutations in Mice and Human Cells," Science Advances, 2019, 5: eaav4324.
Robinson-Hamm et al., "Gene therapies that restore dystrophin expression for the treatment of Duchenne muscular dystrophy," Human Genetics, 2016, 135(9): 1029-1040.
United States Patent Office Action for U.S. Appl. No. 16/858,689 dated Mar. 23, 2023 (10 pages).
Yu et al., "Dystrophin-deficient large animal models: translational research and exon skipping," Am J Transl Res, 2015, 7(8): 1314-1331.
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Trinklein et al., "Identification and functional analysis of human transcriptional promoters," Genome Research, 2003, 13(2): 308-312.
United States Patent Office Action for U.S. Appl. No. 16/927,679 dated Jun. 2, 2023 (12 pages).
United States Patent Office Notice of Allowance for U.S. Appl. No. 16/890,232 dated Jun. 22, 2023 (7 pages).
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
United States Patent Office Action for U.S. Appl. No. 16/927,679 dated Sep. 21, 2023 (6 pages).
Buckingham, M. et al. "The role of Pax genes in the development of tissues and organs: Pax3 and Pax7 regulate muscle progenitor cell functions." Annu. Rev. Cell Dev. Biol. 23 (2007): 645-673.
Abaandou et al., "Affecting HEK293 Cell Growth and Production Performance by Modifying the Expression of Specific Genes," Cells, 2021, 10: 1667, 21 pages.

Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al. "553. AAV-fMediated Delivery of HSV-Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes," Plos One, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortés-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene regulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dnmt3b DNA methyltransferases," J. Biol. Chem., 2002, 277(23): 20409-20414.

(56) References Cited

OTHER PUBLICATIONS

Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation, " Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy—Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PloS One, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges, " Theranostics, 2016, 6(3): 369-391.
Poirier et al., "The proprotein convertase PCSK9 induces the degradation of low density lipoprotein receptor (LDLR) and its closest family members VLDLR and ApoER2" J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
United States Patent Office Action for U.S. Appl. No. 16/858,689 dated Feb. 2, 2024 (16 pages).
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).

(56) References Cited

OTHER PUBLICATIONS

GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209- 229.e26.
Jung et al. "BLIMP1 and NR4A3 transcription factors reciprocally regulate antitumor Car T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Mori et al., "Two novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165- 1169.
Vojta et al., "Repurposing the CRISPR-Cas9 system for targeted DNA methylation," Nucleic Acids Research, 2016, 44(12): 5615-5628.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for ChIP peak annotation, comparison and visualization," Bioinformatics, 2015, 31(14): 2382-2383.
Yuan et al., "Genetic Modulation of RNA Splicing with a CRISPR-Guided Cytidine Deaminase," Molecular Cell, 2018, 72(2): 380-394.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
United States Patent Office Action for U.S. Appl. No. 16/927,679 dated May 29, 2024 (13 pages).
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells," Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.
Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
United States Patent Office Notice of Allowance for U.S. Appl. No. 16/890,232 dated Mar. 1, 2024 (7 pages).
Bulcha et al., "Viral vector platforms within the gene therapy landscape," Signal Transduction and Targeted Therapy, 2021, 6: 53.
Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.
Thule et al., "Engineered Insulin Secretion in Human Primary Thyroid Cells," Molecular Therapy, 2012, 20 (Supplement 1): S164, Article 421.
Swiech et al., "In vivo interrogation of gene function in the mammalian brain using CRISPR-Cas9," Nature Biotechnology, 2014, 33(1): 102-106 (Supplementary Information included).
Shim et al., "Nonviral Delivery Systems for Cancer Gene Therapy: Strategies and Challenges," Current Gene Therapy, 2017, 17(5): 1-18.
Maggio et al., "Adenoviral vectors encoding CRISPR/Cas9 multiplexes rescue dystrophin synthesis in unselected populations of DMD muscle cells," Scientific Reports, 2016, 6: 37051.
Long et al., "Correction of Diverse Muscular Dystrohpy Mutations in Human Engineered Heart Muscle by Single-Site Genome Editing," Sci Adv, 2018, 4(1): eaap9004.
Hideki et al., Geneseq Accession No. BFK30060, 2018. Reference cited by examiner in U.S. Appl. No. 16/963,034, U. S. Patent Office Action dated Jun. 27, 2024.
Kotterman et al., "Engineering adeno-associated viruses for clinical gene therapy," Nature Reviews, 2014, 15(7): 445-451.
Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.

(56) References Cited

OTHER PUBLICATIONS

Liao, "Targeted disruption of DNMT1, DNMT3A and DNMT3B in human embryonic stem cells," Nature Genetics, 2015, 47(5): 469-478.

Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.

Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.

Razzouk, "CRISPR-Cas9: A cornerstone for the evolution of precision medicine," Annal of Human Genetics, 2018, 82 (6): 331-357.

Simeonov et al., "Discovery of stimulation-responsive immune enhancers with CRISPR activation," Nature, 2017, 549 (7670): 111-115.

United States Patent Office Notice of Allowance for Application No. 1/858,689 dated Nov. 12, 2024 (10 pages).

\* cited by examiner

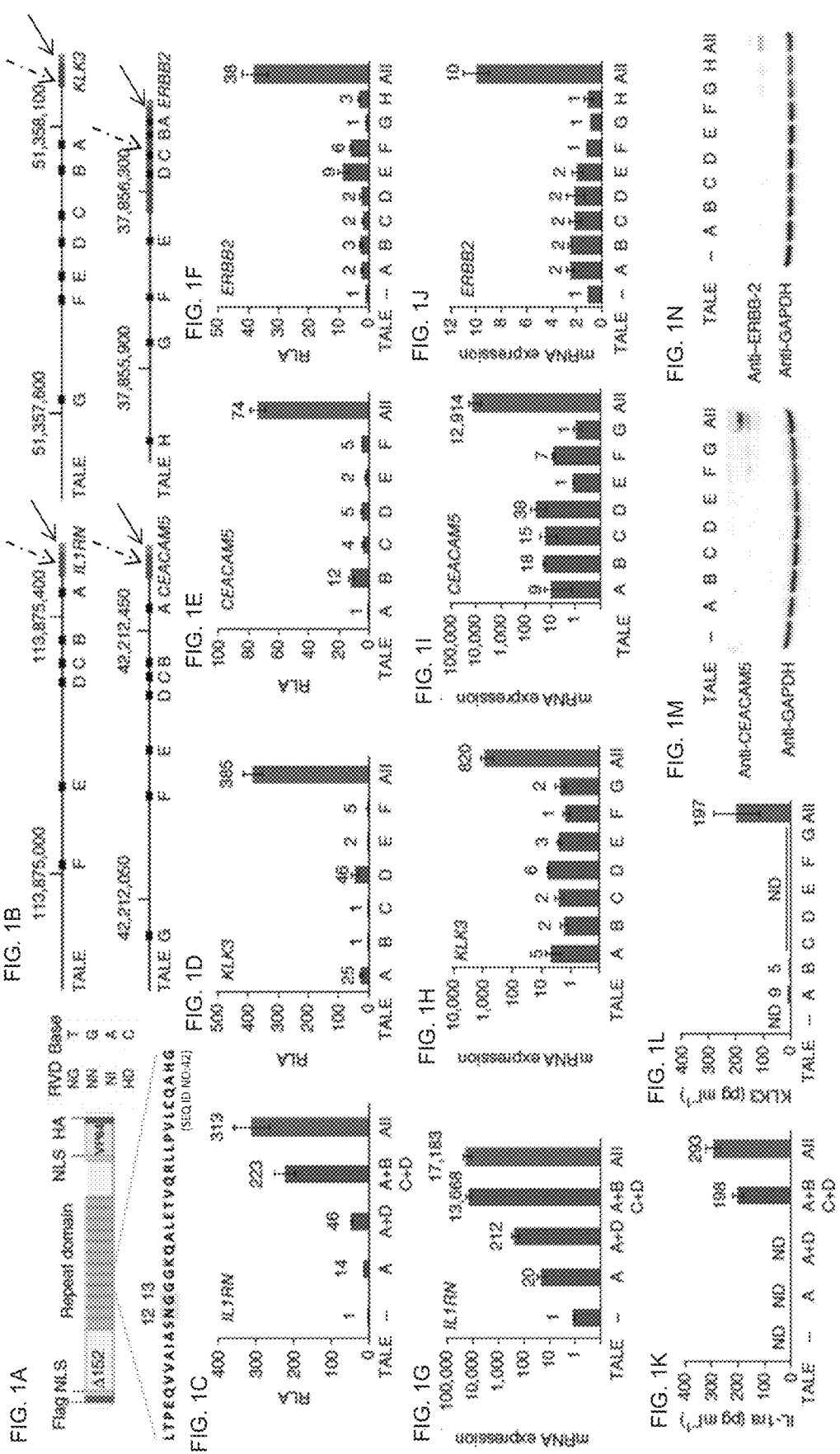

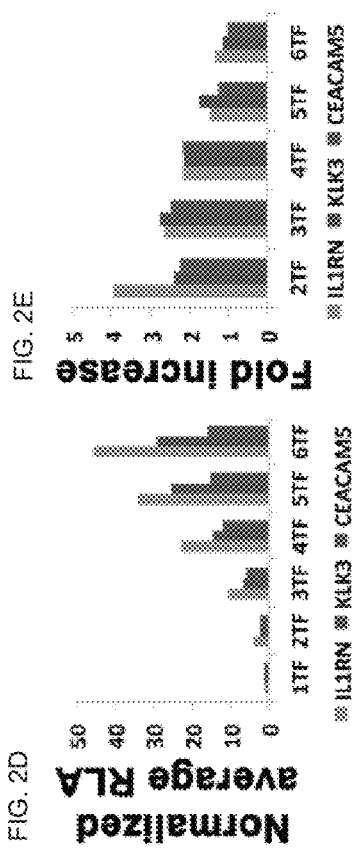
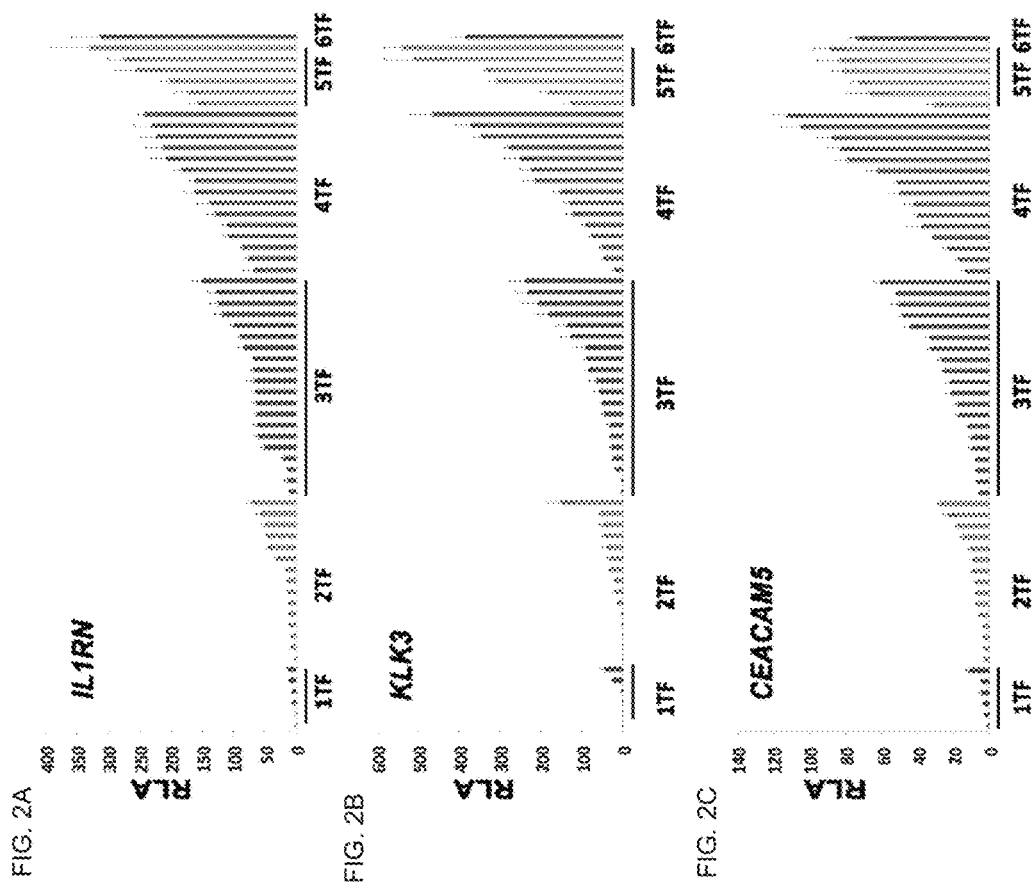

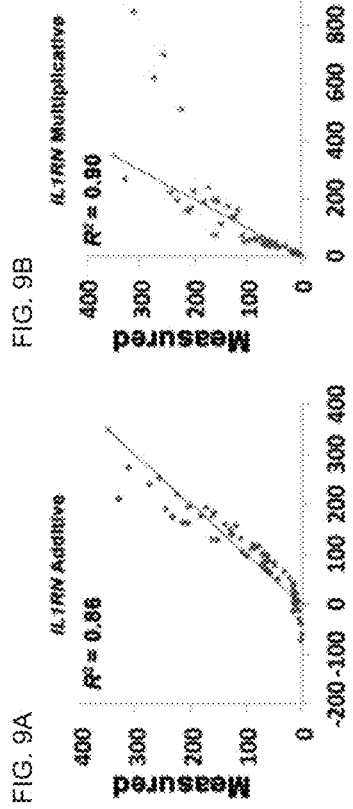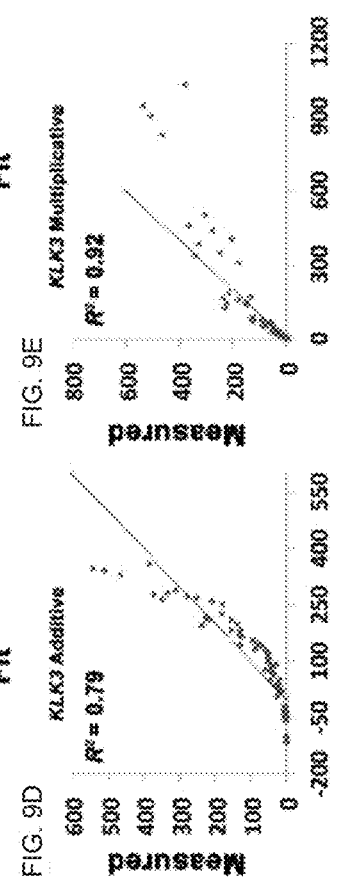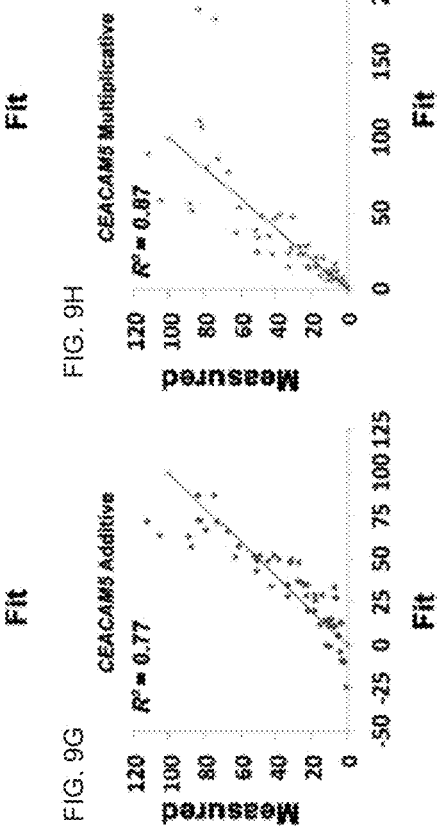

SEQUENCE LISTING

<160> NUMBER OF SEQ ID NOS: 99

<210> SEQ ID NO 1
<211> LENGTH: 17
<212> TYPE: DNA
<213> ORGANISM: Homo sapiens

<400> SEQUENCE: 1
gggctcctcc ttgtact                                                  17

<210> SEQ ID NO 2
<211> LENGTH: 17
<212> TYPE: DNA
<213> ORGANISM: Homo sapiens

<400> SEQUENCE: 2
ggcatcaagt cagccat                                                  17

<210> SEQ ID NO 3
<211> LENGTH: 18
<212> TYPE: DNA
<213> ORGANISM: Homo sapiens

<400> SEQUENCE: 3
agcctgagtc accctcct                                                 18

<210> SEQ ID NO 4
<211> LENGTH: 18
<212> TYPE: DNA
<213> ORGANISM: Homo sapiens

<400> SEQUENCE: 4
acgcagataa gaaccagt                                                 18

<210> SEQ ID NO 5
<211> LENGTH: 18
<212> TYPE: DNA
<213> ORGANISM: Homo sapiens

<400> SEQUENCE: 5
gtctggcttg ttcccaat                                                 18

<210> SEQ ID NO 6
<211> LENGTH: 20
<212> TYPE: DNA
<213> ORGANISM: Homo sapiens

<400> SEQUENCE: 6
cctaggtccc tcaaaagcat                                              20

<210> SEQ ID NO 7
<211> LENGTH: 17
<212> TYPE: DNA
<213> ORGANISM: Homo sapiens

<400> SEQUENCE: 7
ccagcctcca gcagcat                                                 17

<210> SEQ ID NO 8
<211> LENGTH: 16
<212> TYPE: DNA
<213> ORGANISM: Homo sapiens

<400> SEQUENCE: 8
agctctccct cccctt                                                  16

<210> SEQ ID NO 9
<211> LENGTH: 16
<212> TYPE: DNA
<213> ORGANISM: Homo sapiens

<400> SEQUENCE: 9
cccctagatg aagtct                                                  16

<210> SEQ ID NO 10
<211> LENGTH: 19
<212> TYPE: DNA
<213> ORGANISM: Homo sapiens

<400> SEQUENCE: 10
acccaccccc tgtttctgt                                               19

<210> SEQ ID NO 11
<211> LENGTH: 16
<212> TYPE: DNA
<213> ORGANISM: Homo sapiens

<400> SEQUENCE: 11
cttggagtgc aaagga                                                  16

<210> SEQ ID NO 12
<211> LENGTH: 17
<212> TYPE: DNA
<213> ORGANISM: Homo sapiens

<400> SEQUENCE: 12
ctcacaatct cctgagt                                                 17

<210> SEQ ID NO 13
<211> LENGTH: 16
<212> TYPE: DNA
<213> ORGANISM: Homo sapiens

<400> SEQUENCE: 13
ctgtggacca caagat                                                  16

<210> SEQ ID NO 14
<211> LENGTH: 18
<212> TYPE: DNA
<213> ORGANISM: Homo sapiens

```
<400> SEQUENCE: 14
aaagaccaca cccatgac                                          18

<210> SEQ ID NO 15
<211> LENGTH: 16
<212> TYPE: DNA
<213> ORGANISM: Homo sapiens

<400> SEQUENCE: 15
ctgaggaact gaaaat                                            16

<210> SEQ ID NO 16
<211> LENGTH: 18
<212> TYPE: DNA
<213> ORGANISM: Homo sapiens

<400> SEQUENCE: 16
ccaccttgcc gaaaagat                                          18

<210> SEQ ID NO 17
<211> LENGTH: 17
<212> TYPE: DNA
<213> ORGANISM: Homo sapiens

<400> SEQUENCE: 17
tgtcctccca ggggatg                                           17

<210> SEQ ID NO 18
<211> LENGTH: 16
<212> TYPE: DNA
<213> ORGANISM: Homo sapiens

<400> SEQUENCE: 18
ctgtcacaaa ggaaaa                                            16

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
gttgggcatc atcccacct                                         19

<210> SEQ ID NO 20
<211> LENGTH: 17
<212> TYPE: DNA
<213> ORGANISM: Artificial sequence
<220> FEATURE:
<223> OTHER INFORMATION: Synthetic

<400> SEQUENCE: 20
ccctccacca cagtcct                                           17

<210> SEQ ID NO 21
<211> LENGTH: 16
<212> TYPE: DNA
<213> ORGANISM: Artificial sequence
<220> FEATURE:
<223> OTHER INFORMATION: Synthetic

<400> SEQUENCE: 21
ccggctggac ccggct                                            16
```

<210> SEQ ID NO 22
<211> LENGTH: 17
<212> TYPE: DNA
<213> ORGANISM: Artificial sequence
<220> FEATURE:
<223> OTHER INFORMATION: Synthetic

<400> SEQUENCE: 22
cgcagcaccc cgcgccc                                                17

<210> SEQ ID NO 23
<211> LENGTH: 18
<212> TYPE: DNA
<213> ORGANISM: Artificial sequence
<220> FEATURE:
<223> OTHER INFORMATION: Synthetic

<400> SEQUENCE: 23
cccacggggc cctttact                                               18

<210> SEQ ID NO 24
<211> LENGTH: 17
<212> TYPE: DNA
<213> ORGANISM: Artificial sequence
<220> FEATURE:
<223> OTHER INFORMATION: Synthetic

<400> SEQUENCE: 24
cccctggttt ctccggt                                                17

<210> SEQ ID NO 25
<211> LENGTH: 18
<212> TYPE: DNA
<213> ORGANISM: Artificial sequence
<220> FEATURE:
<223> OTHER INFORMATION: Synthetic

<400> SEQUENCE: 25
gccactccca gacttgtt                                               18

<210> SEQ ID NO 26
<211> LENGTH: 17
<212> TYPE: DNA
<213> ORGANISM: Artificial sequence
<220> FEATURE:
<223> OTHER INFORMATION: Synthetic

<400> SEQUENCE: 26
ctgcatttag ggattct                                                17

<210> SEQ ID NO 27
<211> LENGTH: 19
<212> TYPE: DNA
<213> ORGANISM: Artificial sequence
<220> FEATURE:
<223> OTHER INFORMATION: Synthetic

<400> SEQUENCE: 27
ccccaggaaa gtttaagat                                              19

<210> SEQ ID NO 28
<211> LENGTH: 17
<212> TYPE: DNA
<213> ORGANISM: Artificial sequence
<220> FEATURE:

<223> OTHER INFORMATION: Synthetic

<400> SEQUENCE: 28
cgatgtgact gtctcct                                                              17

<210> SEQ ID NO 29
<211> LENGTH: 18
<212> TYPE: DNA
<213> ORGANISM: Artificial sequence
<220> FEATURE:
<223> OTHER INFORMATION: Synthetic

<400> SEQUENCE: 29
agccgcgagc acccaagt                                                             18

<210> SEQ ID NO 30
<211> LENGTH: 22
<212> TYPE: DNA
<213> ORGANISM: Artificial sequence
<220> FEATURE:
<223> OTHER INFORMATION: Synthetic

<400> SEQUENCE: 30
ttggtgggca ggtaggtgag tt                                                        22

<210> SEQ ID NO 31
<211> LENGTH: 18
<212> TYPE: DNA
<213> ORGANISM: Artificial sequence
<220> FEATURE:
<223> OTHER INFORMATION: Synthetic

<400> SEQUENCE: 31
tccccacaga tggtgcat                                                             18

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
gaacggcgtg gattcaatag                                                           20

<210> SEQ ID NO 33
<211> LENGTH: 18
<212> TYPE: DNA
<213> ORGANISM: Artificial sequence
<220> FEATURE:
<223> OTHER INFORMATION: Synthetic

<400> SEQUENCE: 33
ctcgtggcag ggcagtct                                                             18

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
agctgtggct gacctgaaat                                                           20

```
<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
gaccctctgg gagaaaatcc                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
gtccttgcaa gtatccagca                                              20

<210> SEQ ID NO 37
<211> LENGTH: 18
<212> TYPE: DNA
<213> ORGANISM: Artificial sequence
<220> FEATURE:
<223> OTHER INFORMATION: Synthetic

<400> SEQUENCE: 37
gcagcacctc ctggtcac                                                18

<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
atccgacaca tcctgattcc                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39 cctcccatg gcaagatact                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
agcagttgtc tgcaacagga                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic
```

```
<400> SEQUENCE: 41
caatgacccc ttcattgacc                                                20

<210> SEQ ID NO 42
<211> LENGTH: 20
<212> TYPE: DNA
<213> ORGANISM: Artificial sequence
<220> FEATURE:
<223> OTHER INFORMATION: Synthetic

<400> SEQUENCE: 42
ttgattttgg agggatctcg                                                20

<210> SEQ ID NO 43
<211> LENGTH: 2634
<212> TYPE: DNA
<213> ORGANISM: Artificial sequence
<220> FEATURE:
<223> OTHER INFORMATION: Synthetic Oligonucleotide

<400> SEQUENCE: 43
atggactaca aagaccatga cggtgattat aaagatcatg acatcgatta caaggatgac       60
gatgacaaga tggcccccaa gaagaagagg aaggtgggcc gcggatctgt ggatctacgc      120
acgctcggct acagtcagca gcagcaagag aagatcaaac cgaaggtgcg ttcgacagtg      180
gcgcagcacc acgaggcact ggtgggccat gggtttacac acgcgcacat cgttgcgctc      240
agccaacacc cggcagcgtt agggaccgtc gctgtcacgt atcagcacat aatcacggcg      300
ttgccagagg cgacacacga agacatcgtt ggcgtcggca aacagtggtc cggcgcacgc      360
gccctggagg ccttgctcac ggatgcgggg gagttgagag gtccgccgtt acagttggac      420
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagca caatggcgg caagcaagcg ctcgaaacgg tgcagcggct gttgccggtg      600
ctgtgccagg accatggcct gaccccggac caagtggtgg ctatcgccag caacaatggc      660
ggcaagcaag cgctcgaaac ggtgcagcgg ctgttgccgg tgctgtgcca ggaccatggc      720
ctgaccccgg accaagtggt ggctatcgcc agcaacaatg gcggcaagca agcgctcgaa      780
acggtgcagc ggctgttgcc ggtgctgtgc caggaccatg gcctgacccc ggaccaagtg      840
gtggctatcg ccagccacga tggcggcaag caagcgctcg aaacggtgca gcggctgttg      900
ccggtgctgt gccaggacca tggcctgacc ccggaccaag tggtggctat cgccagcaac      960
ggtggcggca agcaagcgct cgaaacggtg cagcggctgt tgccggtgct gtgccaggac     1020
catggcctga ccccggacca agtggtggct atcgccagcc acgatggcgg caagcaagcg     1080
ctcgaaacgg tgcagcggct gttgccggtg ctgtgccagg accatggcct gaccccggac     1140
caagtggtgg ctatcgccag ccacgatggc ggcaagcaag cgctcgaaac ggtgcagcgg     1200
ctgttgccgg tgctgtgcca ggaccatggc ctgaccccgg accaagtggt ggctatcgcc     1260
agcaacggtg gcggcaagca agcgctcgaa acggtgcagc ggctgttgcc ggtgctgtgc     1320
caggaccatg gcctgacccc ggaccaagtg gtggctatcg ccagccacga tggcggcaag     1380
caagcgctcg aaacggtgca gcggctgttg ccggtgctgt gccaggacca tggcctgacc     1440
ccggaccaag tggtggctat cgccagccac gatggcggca agcaagcgct cgaaacggtg     1500
cagcggctgt tgccggtgct gtgccaggac catggcctga ctccggacca gtggtggct      1560 atcgccagca acggtggcgg caagcaagcg ctcgaaacgg tgcagcggct gttgccggtg     1620
```

```
ctgtgccagg accatggcct gaccccggac caagtggtgg ctatcgccag caacggtggc    1680
ggcaagcaag cgctcgaaac ggtgcagcgg ctgttgccgg tgctgtgcca ggaccatggc    1740
ctgaccccgg accaagtggt ggctatcgcc agcaacaatg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
attggcggca agcaagcgct cgaaacggtg cagcggctgt gccggtgct gtgccaggac    2040 catggcctga ccccggacca agtggtggct atcgccagcc acgatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aaagaaacgc aaagttgggc gcgccgacgc gctggacgat    2460
ttcgatctcg acatgctggg ttctgatgcc ctcgatgact ttgacctgga tatgttggga    2520
agcgacgcat ggatgacttt gatctggac atgctcggct ccgatgctct ggacgatttc    2580
gatctcgata tgttaattaa ctacccgtac gacgttccgg actacgcttc ttga          2634
```

<210> SEQ ID NO 44
<211> LENGTH: 877
<212> TYPE: PRT
<213> ORGANISM: Unknown
<220> FEATURE:
<223> OTHER INFORMATION: Synthetic peptide

<400> SEQUENCE: 44

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
```

```
                180                 185                 190
Thr Val Gln Arg Leu Leu Pro Val Leu Cys Gln Asp His Gly Leu Thr
            195                 200                 205
Pro Asp Gln Val Val Ala Ile Ala Ser Asn Asn Gly Gly Lys Gln Ala
        210                 215                 220
Leu Glu Thr Val Gln Arg Leu Leu Pro Val Leu Cys Gln Asp His Gly
225                 230                 235                 240
Leu Thr Pro Asp Gln Val Val Ala Ile Ala Ser Asn Asn Gly Gly Lys
                245                 250                 255
Gln Ala Leu Glu Thr Val Gln Arg Leu Leu Pro Val Leu Cys Gln Asp
            260                 265                 270
His Gly Leu Thr Pro Asp Gln Val Val Ala Ile Ala Ser His Asp Gly
        275                 280                 285
Gly Lys Gln Ala Leu Glu Thr Val Gln Arg Leu Leu Pro Val Leu Cys
        290                 295                 300
Gln Asp His Gly Leu Thr Pro Asp Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
            340                 345                 350
Ser His Asp Gly Gly Lys Gln Ala Leu Glu Thr Val Gln Arg Leu Leu
        355                 360                 365
Pro Val Leu Cys Gln Asp His Gly Leu Thr Pro Asp Gln Val Val Ala
    370                 375                 380
Ile Ala Ser His Asp Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Gly Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser His Asp Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser Asn Gly Gly Gly Lys
        515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser Asn Gly Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Asn Gly Gly Lys Gln Ala Leu Glu Thr Val Gln Arg Leu Leu Pro Val
        595                 600                 605
```

Leu Cys Gln Asp His Gly Leu Thr Pro Asp Gln Val Ala Ile Ala
    610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
                660                 665                 670

Leu Leu Pro Val Leu Cys Gln Asp His Gly Leu Thr Pro Asp Gln Val
            675                 680                 685

Val Ala Ile Ala Ser His Asp Gly Gly Lys Gln Ala Leu Glu Thr Val
        690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
                725                 730                 735

Ser Ile Val Ala Gln Leu Ser Arg Pro Asp Pro Ala Leu Ala Ala Leu
                740                 745                 750

Thr Asn Asp His Leu Val Ala Leu Ala Cys Leu Gly Gly Arg Pro
                755                 760                 765

Ala Met Asp Ala Val Lys Lys Gly Leu Pro His Ala Pro Glu Leu Ile
770                 775                 780

Arg Arg Val Asn Arg Arg Ile Gly Glu Arg Thr Ser His Arg Val Ala
785                 790                 795                 800

Gly Ser Lys Ala Ser Pro Lys Lys Lys Arg Lys Val Gly Arg Ala Asp
                805                 810                 815

Ala Leu Asp Asp Phe Asp Leu Asp Met Leu Gly Ser Asp Ala Leu Asp
                820                 825                 830

Asp Phe Asp Leu Asp Met Leu Gly Ser Asp Ala Leu Asp Phe Asp
            835                 840                 845

Leu Asp Met Leu Gly Ser Asp Ala Leu Asp Asp Phe Asp Leu Asp Met
850                 855                 860

Leu Ile Asn Tyr Pro Tyr Asp Val Pro Asp Tyr Ala Ser
865                 870                 875

<210> SEQ ID NO 45
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 45
atggactaca aagaccatga cggtgattat aaagatcatg acatcgatta caaggatgac     60
gatgacaaga tggccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc    360 gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540

```
atcgccagca acaatggcgg caagcaagcg ctcgaaacgg tgcagcggct gttgccggtg    600
ctgtgccagg accatggcct gaccccggac caagtggtgg ctatcgccag caacaatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagcaacat tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca agtggtggct atcgccagcc acgatggcgg caagcaagcg   1080
ctcgaaacgg tgcagcggct gttgccggtg ctgtgccagg accatggcct gaccccggac   1140
caagtggtgg ctatcgccag caacattggc ggcaagcaag cgctcgaaac ggtgcagcgg   1200
ctgttgccgg tgctgtgcca ggaccatggc ctgaccccgg accaagtggt ggctatcgcc   1260
agcaacattg gcggcaagca agcgctcgaa acggtgcagc ggctgttgcc ggtgctgtgc   1320
caggaccatg gcctgacccc ggaccaagtg gtggctatcg ccagcaacaa tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ctccggacca agtggtggct   1560
atcgccagcc acgatggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacaatg gcggcaagca agcgctcgaa   1800
acggtgcagc ggctgttgcc ggtgctgtgc caggaccatg gcctgacccc ggaccaagtg   1860
gtggctatcg ccagccacga tggcggcaag caagcgctcg aaacggtgca gcggctgttg   1920
ccggtgctgt gccaggacca tggcctgacc ccggaccaag tggtggctat cgccagccac   1980
gatggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcg gcctgatcc ggcgttggcc gcgttgacca cgacgacca cctcgtcgcc   2280 ttggcctgcc tcggcggacg tcctgccatg gatgcagtga aaagggatt gccgcacgcg   2340 ccggaattga tcagaagagt caatcgccgt attggcgaac gcacgtccca tcgcgttgcc   2400
ggatccaagg ctagcccgaa aaagaaacgc aaagttgggc gcgccgacgc gctggacgat   2460
ttcgatctcg acatgctggg ttctgatgcc ctcgatgact tgacctgga tatgttggga   2520 agcgacgcat ggatgactt tgatctggac atgctcggct ccgatgctct ggacgatttc   2580
gatctcgata tgttaattaa ctacccgtac gacgttccgg actacgcttc ttga         2634
```

<210> SEQ ID NO 46
<211> LENGTH: 877
<212> TYPE: PRT
<213> ORGANISM: Unknown
<220> FEATURE:
<223> OTHER INFORMATION: Synthetic peptide

<400> SEQUENCE: 46

```
Met Asp Tyr Lys Asp His Asp Gly Asp Tyr Lys Asp His Asp Ile Asp
1               5                   10                  15
Tyr Lys Asp Asp Asp Asp Lys Met Ala Pro Lys Lys Lys Arg Lys Val
                20                  25                  30
Gly Arg Gly Ser Val Asp Leu Arg Thr Leu Gly Tyr Ser Gln Gln Gln
            35                  40                  45
Gln Glu Lys Ile Lys Pro Lys Val Arg Ser Thr Val Ala Gln His His
    50                  55                  60
Glu Ala Leu Val Gly His Gly Phe Thr His Ala His Ile Val Ala Leu
65                  70                  75                  80
Ser Gln His Pro Ala Ala Leu Gly Thr Val Ala Val Thr Tyr Gln His
                85                  90                  95
Ile Ile Thr Ala Leu Pro Glu Ala Thr His Glu Asp Ile Val Gly Val
            100                 105                 110
Gly Lys Gln Trp Ser Gly Ala Arg Ala Leu Glu Ala Leu Leu Thr Asp
        115                 120                 125
Ala Gly Glu Leu Arg Gly Pro Pro Leu Gln Leu Asp Thr Gly Gln Leu
130                 135                 140
Val Lys Ile Ala Lys Arg Gly Gly Val Thr Ala Met Glu Ala Val His
145                 150                 155                 160
Ala Ser Arg Asn Ala Leu Thr Gly Ala Pro Leu Asn Leu Thr Pro Asp
                165                 170                 175
Gln Val Val Ala Ile Ala Ser Asn Asn Gly Gly Lys Gln Ala Leu Glu
            180                 185                 190
Thr Val Gln Arg Leu Leu Pro Val Leu Cys Gln Asp His Gly Leu Thr
        195                 200                 205
Pro Asp Gln Val Val Ala Ile Ala Ser Asn Asn Gly Gly Lys Gln Ala
210                 215                 220
Leu Glu Thr Val Gln Arg Leu Leu Pro Val Leu Cys Gln Asp His Gly
225                 230                 235                 240
Leu Thr Pro Asp Gln Val Val Ala Ile Ala Ser His Asp Gly Gly Lys
                245                 250                 255
Gln Ala Leu Glu Thr Val Gln Arg Leu Leu Pro Val Leu Cys Gln Asp
            260                 265                 270
His Gly Leu Thr Pro Asp Gln Val Val Ala Ile Ala Ser Asn Ile Gly
        275                 280                 285
Gly Lys Gln Ala Leu Glu Thr Val Gln Arg Leu Leu Pro Val Leu Cys
290                 295                 300
Gln Asp His Gly Leu Thr Pro Asp Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
            340                 345                 350
Ser His Asp Gly Gly Lys Gln Ala Leu Glu Thr Val Gln Arg Leu Leu
        355                 360                 365
Pro Val Leu Cys Gln Asp His Gly Leu Thr Pro Asp Gln Val Val Ala
370                 375                 380
Ile Ala Ser Asn Ile Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
```

```
Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser Asn Asn Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                    485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                    565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                    645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Lys Gln Ala Leu Glu
                    725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
            755                 760                 765

Ala Met Asp Ala Val Lys Lys Gly Leu Pro His Ala Pro Glu Leu Ile
            770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                    805                 810                 815

Ala Leu Asp Asp Phe Asp Leu Asp Met Leu Gly Ser Asp Ala Leu Asp
            820                 825                 830
```

Asp Phe Asp Leu Asp Met Leu Gly Ser Asp Ala Leu Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 47
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 47

| | | | | | |
|---|---|---|---|---|---|
| atggactaca | aagaccatga | cggtgattat | aaagatcatg | acatcgatta | caaggatgac | 60 |
| gatgacaaga | tggcccccaa | gaagaagagg | aaggtgggcc | gcggatctgt | ggatctacgc | 120 |
| acgctcggct | acagtcagca | gcagcaagag | aagatcaaac | cgaaggtgcg | ttcgacagtg | 180 |
| gcgcagcacc | acgaggcact | ggtgggccat | gggtttacac | acgcgcacat | cgttgcgctc | 240 |
| agccaacacc | cggcagcgtt | agggaccgtc | gctgtcacgt | atcagcacat | aatcacggcg | 300 |
| ttgccagagg | cgacacacga | agacatcgtt | ggcgtcggca | acagtggtc | cggcgcacgc | 360 |
| gccctggagg | ccttgctcac | ggatgcgggg | gagttgagag | gtccgccgtt | acagttggac | 420 |
| acaggccaac | ttgtgaagat | tgcaaaacgt | ggcggcgtga | ccgcaatgga | ggcagtgcat | 480 |
| gcatcgcgca | atgcactgac | gggtgccccc | ctgaacctga | ccccggacca | agtggtggct | 540 |
| atcgccagca | acattggcgg | caagcaagcg | ctcgaaacgg | tgcagcggct | gttgccggtg | 600 |
| ctgtgccagg | accatggcct | gaccccggac | caagtggtgg | ctatcgccag | caacaatggc | 660 |
| ggcaagcaag | cgctcgaaac | ggtgcagcgg | ctgttgccgg | tgctgtgcca | ggaccatggc | 720 |
| ctgaccccgg | accaagtggt | ggctatcgcc | agccacgatg | gcggcaagca | agcgctcgaa | 780 |
| acggtgcagc | ggctgttgcc | ggtgctgtgc | caggaccatg | gcctgacccc | ggaccaagtg | 840 |
| gtggctatcg | ccagccacga | tggcggcaag | caagcgctcg | aaacggtgca | gcggctgttg | 900 |
| ccggtgctgt | gccaggacca | tggcctgacc | ccggaccaag | tggtggctat | cgccagcaac | 960 |
| ggtggcggca | agcaagcgct | cgaaacggtg | cagcggctgt | tgccggtgct | gtgccaggac | 1020 |
| catggcctga | ccccggacca | agtggtggct | atcgccagca | acaatggcgg | caagcaagcg | 1080 |
| ctcgaaacgg | tgcagcggct | gttgccggtg | ctgtgccagg | accatggcct | gaccccggac | 1140 |
| caagtggtgg | ctatcgccag | caacattggc | ggcaagcaag | cgctcgaaac | ggtgcagcgg | 1200 |
| ctgttgccgg | tgctgtgcca | ggaccatggc | ctgaccccgg | accaagtggt | ggctatcgcc | 1260 |
| agcaacaatg | gcggcaagca | agcgctcgaa | acggtgcagc | ggctgttgcc | ggtgctgtgc | 1320 |
| caggaccatg | gcctgacccc | ggaccaagtg | gtggctatcg | ccagcaacgg | tggcggcaag | 1380 |
| caagcgctcg | aaacggtgca | gcggctgttg | ccggtgctgt | gccaggacca | tggcctgacc | 1440 |
| ccggaccaag | tggtggctat | cgccagccac | gatggcggca | agcaagcgct | cgaaacggtg | 1500 |
| cagcggctgt | tgccggtgct | gtgccaggac | catggcctga | ccccggacca | agtggtggct | 1560 |
| atcgccagca | acattggcgg | caagcaagcg | ctcgaaacgg | tgcagcggct | gttgccggtg | 1620 |
| ctgtgccagg | accatggcct | gactccggac | caagtggtgg | ctatcgccag | ccacgatggc | 1680 |
| ggcaagcaag | cgctcgaaac | ggtgcagcgg | ctgttgccgg | tgctgtgcca | ggaccatggc | 1740 |
| ctgaccccgg | accaagtggt | ggctatcgcc | agccacgatg | gcggcaagca | agcgctcgaa | 1800 |

-continued

```
acggtgcagc ggctgttgcc ggtgctgtgc caggaccatg gcctgacccc ggaccaagtg   1860
gtggctatcg ccagccacga tggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt tgccggtgct gtgccaggac   2040
catggcctga ccccggacca agtggtggct atcgccagcc acgatggcgg caagcaagcg   2100
ctcgaaacgg tgcagcggct gttgccggtc ctgtgccagg accatggcct gaccccggac   2160
caagtggtgg ctatcgccag ccacgatggc ggcaagcaag cgctcgaaac ggtgcagcgg   2220
ctgttgccgg tgctgtgcca ggaccatggc ctgaccccgg accaagtggt ggctatcgcc   2280
agcaacggtg gcggcaagca agcgctcgaa agcattgtgg cccagctgag ccggcctgat   2340
ccggcgttgg ccgcgttgac caacgacgac cacctcgtcg ccttggcctg cctcggcgga   2400
cgtcctgcca tggatgcagt gaaaaaggga ttgccgcacg cgccggaatt gatcagaaga   2460
gtcaatcgcc gtattggcga acgcacgtcc catcgcgttg ccggatccaa ggctagcccg   2520
aaaaagaaac gcaaagttgg gcgcgccgac gcgctggacg atttcgatct cgacatgctg   2580
ggttctgatg ccctcgatga ctttgacctg gatatgttgg aagcgacgc attggatgac   2640 tttgatctgg acatgctcgg ctccgatgct ctggacgatt tcgatctcga tatgttaatt   2700
aactacccgt acgacgttcc ggactacgct tcttga   2736
```

<210> SEQ ID NO 48
<211> LENGTH: 911
<212> TYPE: PRT
<213> ORGANISM: Unknown
<220> FEATURE:
<223> OTHER INFORMATION: Synthetic peptide

<400> SEQUENCE: 48

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
```

```
                195                 200                 205
Pro Asp Gln Val Val Ala Ile Ala Ser Asn Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Ile Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620
```

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser His Asp Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser Asn Gly Gly Gly Lys Gln Ala
    755                 760                 765

Leu Glu Ser Ile Val Ala Gln Leu Ser Arg Pro Asp Pro Ala Leu Ala
770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
            805                 810                 815

Leu Ile Arg Arg Val Asn Arg Arg Ile Gly Glu Arg Thr Ser His Arg
        820                 825                 830

Val Ala Gly Ser Lys Ala Ser Pro Lys Lys Arg Lys Val Gly Arg
    835                 840                 845

Ala Asp Ala Leu Asp Asp Phe Asp Leu Asp Met Leu Gly Ser Asp Ala
850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
            885                 890                 895

Asp Met Leu Ile Asn Tyr Pro Tyr Asp Val Pro Asp Tyr Ala Ser
        900                 905                 910

<210> SEQ ID NO 49
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 49
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca aacagtggtc cggcgcacgc   360
gccctggagg ccttgctcac ggatgcgggg gagttgagag gtccgccgtt acagttggac   420

```
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagca acattggcgg caagcaagcg ctcgaaacgg tgcagcggct gttgccggtg      600
ctgtgccagg accatggcct gaccccggac caagtggtgg ctatcgccag ccacgatggc      660
ggcaagcaag cgctcgaaac ggtgcagcgg ctgttgccgg tgctgtgcca ggaccatggc      720
ctgaccccgg accaagtggt ggctatcgcc agcaacaatg gcggcaagca agcgctcgaa      780
acggtgcagc ggctgttgcc ggtgctgtgc caggaccatg gcctgacccc ggaccaagtg      840
gtggctatcg ccagccacga tggcggcaag caagcgctcg aaacggtgca gcggctgttg      900
ccggtgctgt gccaggacca tggcctgacc ccggaccaag tggtggctat cgccagcaac      960
attggcggca agcaagcgct cgaaacggtg cagcggctgt tgccggtgct gtgccaggac     1020
catggcctga ccccggacca agtggtggct atcgccagca acaatggcgg caagcaagcg     1080
ctcgaaacgg tgcagcggct gttgccggtg ctgtgccagg accatggcct gaccccggac     1140
caagtggtgg ctatcgccag caacattggc ggcaagcaag cgctcgaaac ggtgcagcgg     1200
ctgttgccgg tgctgtgcca ggaccatggc ctgaccccgg accaagtggt ggctatcgcc     1260
agcaacggtg cggcaagca agcgctcgaa acggtgcagc ggctgttgcc ggtgctgtgc     1320
caggaccatg gcctgacccc ggaccaagtg gtggctatcg ccagcaacat tggcggcaag     1380
caagcgctcg aaacggtgca gcggctgttg ccggtgctgt gccaggacca tggcctgacc     1440
ccggaccaag tggtggctat cgccagcaac attggcggca agcaagcgct cgaaacggtg     1500
cagcggctgt tgccggtgct gtgccaggac catggcctga ccccggacca agtggtggct     1560
atcgccagca acaatggcgg caagcaagcg ctcgaaacgg tgcagcggct gttgccggtg     1620
ctgtgccagg accatggcct gactccggac caagtggtgg ctatcgccag caacattggc     1680
ggcaagcaag cgctcgaaac ggtgcagcgg ctgttgccgg tgctgtgcca ggaccatggc     1740
ctgaccccgg accaagtggt ggctatcgcc agcaacattg gcggcaagca agcgctcgaa     1800
acggtgcagc ggctgttgcc ggtgctgtgc caggaccatg gcctgacccc ggaccaagtg     1860
gtggctatcg ccagccacga tggcggcaag caagcgctcg aaacggtgca gcggctgttg     1920
ccggtgctgt gccaggacca tggcctgacc ccggaccaag tggtggctat cgccagccac     1980
gatggcggca agcaagcgct cgaaacggtg cagcggctgt tgccggtgct gtgccaggac     2040
catggcctga ccccggacca agtggtggct atcgccagca cattggcgg caagcaagcg     2100 ctcgaaacgg tgcagcggct gttgccggtg ctgtgccagg accatggcct gaccccggac     2160
caagtggtgg ctatcgccag caacaatggc ggcaagcaag cgctcgaaac ggtgcagcgg     2220
ctgttgccgg tgctgtgcca ggaccatggc ctgaccccgg accaagtggt ggctatcgcc     2280
agcaacggtg cggcaagca agcgctcgaa agcattgtgg cccagctgag ccggcctgat     2340
ccggcgttgg ccgcgttgac caacgacgac cacctcgtcg ccttggcctg cctcggcgga     2400
cgtcctgcca tggatgcagt gaaaaaggga ttgccgcacg cgccggaatt gatcagaaga     2460
gtcaatcgcc gtattggcga acgcacgtcc catcgcgttg ccggatccaa ggctagcccg     2520
aaaaagaaac gcaaagttgg gcgcgccgac gcgctggacg atttcgatct cgacatgctg     2580
ggttctgatg ccctcgatga ctttgacctg gatatgttgg aagcgacgc attggatgac     2640 tttgatctgg acatgctcgg ctccgatgct ctggacgatt tcgatctcga tatgttaatt     2700
aactacccgt acgacgttcc ggactacgct tcttga                              2736
```

<210> SEQ ID NO 50
<211> LENGTH: 911
<212> TYPE: PRT
<213> ORGANISM: Unknown
<220> FEATURE:
<223> OTHER INFORMATION: Synthetic peptide

<400> SEQUENCE: 50

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
```

```
            370                 375                 380
Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser Asn Ile Gly Gly Lys Gln Ala Leu Glu
        450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Asn Gly Gly Lys
                515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Ile Gly Gly Lys Gln Ala Leu Glu Thr Val Gln Arg Leu Leu Pro Val
                595                 600                 605

Leu Cys Gln Asp His Gly Leu Thr Pro Asp Gln Val Val Ala Ile Ala
            610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
                660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Thr Val
        690                 695                 700

Gln Arg Leu Leu Pro Val Leu Cys Gln Asp His Gly Leu Thr Pro Asp
705                 710                 715                 720

Gln Val Val Ala Ile Ala Ser Asn Asn Gly Gly Lys Gln Ala Leu Glu
                725                 730                 735

Thr Val Gln Arg Leu Leu Pro Val Leu Cys Gln Asp His Gly Leu Thr
                740                 745                 750

Pro Asp Gln Val Val Ala Ile Ala Ser Asn Gly Gly Lys Gln Ala
            755                 760                 765

Leu Glu Ser Ile Val Ala Gln Leu Ser Arg Pro Asp Pro Ala Leu Ala
            770                 775                 780

Ala Leu Thr Asn Asp His Leu Val Ala Leu Ala Cys Leu Gly Gly
785                 790                 795                 800
```

```
Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Arg Lys Val Gly Arg
        835                 840                 845

Ala Asp Ala Leu Asp Asp Phe Asp Leu Asp Met Leu Gly Ser Asp Ala
    850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
                900                 905                 910

<210> SEQ ID NO 51
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 51
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc ggcgcacgc      360 gccctggagg ccttgctcac ggatgcgggg agttgagag gtccgccgtt acagttggac      420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca caatggcgg caagcaagcg ctcgaaacgg tgcagcggct gttgccggtg     600
ctgtgccagg accatggcct gaccccggac caagtggtgg ctatcgccag caacggtggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagcaacgg tggcggcaag caagcgctcg aaacggtgca gcggctgttg     900
ccggtgctgt gccaggacca tggcctgacc ccggaccaag tggtggctat cgccagcaac     960
aatggcggca agcaagcgct cgaaacggtg cagcggctgt tgccggtgct gtgccaggac    1020
catggcctga ccccggacca agtggtggct atcgccagca caatggcgg caagcaagcg    1080 ctcgaaacgg tgcagcggct gttgccggtg ctgtgccagg accatggcct gaccccggac    1140
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agcaacggtg gcggcaagca agcgctcgaa acggtgcagc ggctgttgcc ggtgctgtgc    1320
caggaccatg gcctgacccc ggaccaagtg gtggctatcg ccagcaacgg tggcggcaag    1380
caagcgctcg aaacggtgca gcggctgttg ccggtgctgt gccaggacca tggcctgacc    1440
```

```
ccggaccaag tggtggctat cgccagcaac aatggcggca agcaagcgct cgaaacggtg    1500
cagcggctgt tgccggtgct gtgccaggac catggcctga ccccggacca agtggtggct    1560
atcgccagca acggtggcgg caagcaagcg ctcgaaacgg tgcagcggct gttgccggtg    1620
ctgtgccagg accatggcct gactccggac caagtggtgg ctatcgccag caacggtggc    1680
ggcaagcaag cgctcgaaac ggtgcagcgg ctgttgccgg tgctgtgcca ggaccatggc    1740
ctgaccccgg accaagtggt ggctatcgcc agccacgatg cggcaagca agcgctcgaa     1800 acggtgcagc ggctgttgcc ggtgctgtgc caggaccatg gcctgacccc ggaccaagtg    1860
gtggctatcg ccagccacga tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca agtggtggct atcgccagca acattggcgg caagcaagcg    2100
ctcgaaacgg tgcagcggct gttgccggtg ctgtgccagg accatggcct gaccccggac    2160
caagtggtgg ctatcgccag caacattggc ggcaagcaag cgctcgaaac ggtgcagcgg    2220
ctgttgccgg tgctgtgcca ggaccatggc ctgaccccgg accaagtggt ggctatcgcc    2280
agcaacggtg gcggcaagca agcgctcgaa agcattgtgg cccagctgag ccggcctgat    2340
ccggcgttgg ccgcgttgac caacgacgac cacctcgtcg ccttggcctg cctcggcgga    2400
cgtcctgcca tggatgcagt gaaaaaggga ttgccgcacg cgccggaatt gatcagaaga    2460
gtcaatcgcc gtattggcga acgcacgtcc catcgcgttg ccggatccaa ggctagcccg    2520
aaaaagaaac gcaaagttgg gcgcgccgac gcgctggacg atttcgatct cgacatgctg    2580
ggttctgatg ccctcgatga cttttgacctg gatatgttgg aagcgacgc attggatgac     2640 tttgatctgg acatgctcgg ctccgatgct ctggacgatt cgatctcga tatgttaatt     2700 aactacccgt acgacgttcc ggactacgct tcttga                              2736
```

<210> SEQ ID NO 52
<211> LENGTH: 911
<212> TYPE: PRT
<213> ORGANISM: Unknown
<220> FEATURE:
<223> OTHER INFORMATION: Synthetic peptide

<400> SEQUENCE: 52

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

```
Ala Gly Glu Leu Arg Gly Pro Pro Leu Gln Leu Asp Thr Gly Gln Leu
    130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Gly Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Gly Gly
```

```
545                 550                 555                 560
Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser Asn Ile Gly Gly Lys Gln Ala Leu Glu
                725                 730                 735

Thr Val Gln Arg Leu Leu Pro Val Leu Cys Gln Asp His Gly Leu Thr
            740                 745                 750

Pro Asp Gln Val Val Ala Ile Ala Ser Asn Gly Gly Lys Gln Ala
        755                 760                 765

Leu Glu Ser Ile Val Ala Gln Leu Ser Arg Pro Asp Pro Ala Leu Ala
    770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Arg Lys Val Gly Arg
        835                 840                 845

Ala Asp Ala Leu Asp Asp Phe Asp Leu Asp Met Leu Gly Ser Asp Ala
850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
            900                 905                 910

<210> SEQ ID NO 53
<211> LENGTH: 2940
<212> TYPE: DNA
<213> ORGANISM: Artificial sequence
<220> FEATURE:
<223> OTHER INFORMATION: Synthetic oligonucleotide

<400> SEQUENCE: 53
atggactaca aagaccatga cggtgattat aaagatcatg acatcgatta caaggatgac    60
```

```
gatgacaaga tggcccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc     360 gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agcaacggtg gcggcaagca agcgctcgaa    780
acggtgcagc ggctgttgcc ggtgctgtgc caggaccatg gcctgacccc ggaccaagtg    840
gtggctatcg ccagcaacat tggcggcaag caagcgctcg aaacggtgca gcggctgttg    900
ccggtgctgt gccaggacca tggcctgacc ccggaccaag tggtggctat cgccagcaac    960
aatggcggca agcaagcgct cgaaacggtg cagcggctgt tgccggtgct gtgccaggac   1020
catggcctga ccccggacca agtggtggct atcgccagca caatggcgg caagcaagcg    1080 ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agccacgatg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt tgccggtgct gtgccaggac catggcctga ccccggacca agtggtggct   1560
atcgccagca cggtggcgg caagcaagcg ctcgaaacgg tgcagcggct gttgccggtg    1620
ctgtgccagg accatggcct gaccccggac caagtggtgg ctatcgccag ccacgatggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgactcc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca cattggcgg caagcaagcg    2100 ctcgaaacgg tgcagcggct gttgccggtg ctgtgccagg accatggcct gaccccggac   2160
caagtggtgg ctatcgccag caacaatggc ggcaagcaag cgctcgaaac ggtgcagcgg   2220
ctgttgccgg tgctgtgcca ggaccatggc ctgaccccgg accaagtggt ggctatcgcc   2280
agccacgatg gcggcaagca agcgctcgaa acggtgcagc ggctgttgcc ggtgctgtgc   2340
caggaccatg gcctgacccc ggaccaagtg gtggctatcg ccagcaacat tggcggcaag   2400
```

```
caagcgctcg aaacggtgca gcggctgttg ccggtgctgt gccaggacca tggcctgacc    2460
ccggaccaag tggtggctat cgccagcaac ggtggcggca agcaagcgct cgaaagcatt    2520
gtggcccagc tgagccggcc tgatccggcg ttggccgcgt tgaccaacga cgaccacctc    2580
gtcgccttgg cctgcctcgg cggacgtcct gccatggatg cagtgaaaaa gggattgccg    2640
cacgcgccgg aattgatcag aagagtcaat cgccgtattg gcgaacgcac gtcccatcgc    2700
gttgccggat ccaaggctag cccgaaaaag aaacgcaaag ttgggcgcgc cgacgcgctg    2760
gacgatttcg atctcgacat gctgggttct gatgccctcg atgactttga cctggatatg    2820
ttgggaagcg acgcattgga tgactttgat ctggacatgc tcggctccga tgctctggac    2880
gatttcgatc tcgatatgtt aattaactac ccgtacgacg ttccggacta cgcttcttga    2940
```

<210> SEQ ID NO 54
<211> LENGTH: 979
<212> TYPE: PRT
<213> ORGANISM: Unknown
<220> FEATURE:
<223> OTHER INFORMATION: Synthetic peptide

<400> SEQUENCE: 54

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Lys
                245                 250                 255

Gln Ala Leu Glu Thr Val Gln Arg Leu Leu Pro Val Leu Cys Gln Asp
            260                 265                 270
```

-continued

```
His Gly Leu Thr Pro Asp Gln Val Ala Ile Ala Ser Asn Ile Gly
        275                 280                 285
Gly Lys Gln Ala Leu Glu Thr Val Gln Arg Leu Leu Pro Val Leu Cys
    290                 295                 300
Gln Asp His Gly Leu Thr Pro Asp Gln Val Val Ala Ile Ala Ser Asn
305                 310                 315                 320
Asn Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
            340                 345                 350
Ser Asn Asn Gly Gly Lys Gln Ala Leu Glu Thr Val Gln Arg Leu Leu
        355                 360                 365
Pro Val Leu Cys Gln Asp His Gly Leu Thr Pro Asp Gln Val Val Ala
    370                 375                 380
Ile Ala Ser Asn Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser His Asp Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser Asn Gly Gly Lys
        515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser His Asp Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Ile Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
    610                 615                 620
Ser Asn Ile Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser Asn Ile Gly Gly Lys Gln Ala Leu Glu Thr Val Gln Arg
            660                 665                 670
Leu Leu Pro Val Leu Cys Gln Asp His Gly Leu Thr Pro Asp Gln Val
        675                 680                 685
Val Ala Ile Ala Ser Asn Ile Gly Gly Lys Gln Ala Leu Glu Thr Val
```

```
              690                 695                 700
Gln Arg Leu Leu Pro Val Leu Cys Gln Asp His Gly Leu Thr Pro Asp
705                 710                 715                 720
Gln Val Val Ala Ile Ala Ser Asn Asn Gly Gly Lys Gln Ala Leu Glu
                725                 730                 735
Thr Val Gln Arg Leu Leu Pro Val Leu Cys Gln Asp His Gly Leu Thr
                740                 745                 750
Pro Asp Gln Val Val Ala Ile Ala Ser His Asp Gly Gly Lys Gln Ala
                755                 760                 765
Leu Glu Thr Val Gln Arg Leu Leu Pro Val Leu Cys Gln Asp His Gly
            770                 775                 780
Leu Thr Pro Asp Gln Val Val Ala Ile Ala Ser Asn Ile Gly Gly Lys
785                 790                 795                 800
Gln Ala Leu Glu Thr Val Gln Arg Leu Leu Pro Val Leu Cys Gln Asp
                805                 810                 815
His Gly Leu Thr Pro Asp Gln Val Val Ala Ile Ala Ser Asn Gly Gly
                820                 825                 830
Gly Lys Gln Ala Leu Glu Ser Ile Val Ala Gln Leu Ser Arg Pro Asp
                835                 840                 845
Pro Ala Leu Ala Ala Leu Thr Asn Asp His Leu Val Ala Leu Ala
850                 855                 860
Cys Leu Gly Gly Arg Pro Ala Met Asp Ala Val Lys Lys Gly Leu Pro
865                 870                 875                 880
His Ala Pro Glu Leu Ile Arg Arg Val Asn Arg Arg Ile Gly Glu Arg
                885                 890                 895
Thr Ser His Arg Val Ala Gly Ser Lys Ala Ser Pro Lys Lys Lys Arg
                900                 905                 910
Lys Val Gly Arg Ala Asp Ala Leu Asp Asp Phe Asp Leu Asp Met Leu
                915                 920                 925
Gly Ser Asp Ala Leu Asp Asp Phe Asp Leu Asp Met Leu Gly Ser Asp
                930                 935                 940
Ala Leu Asp Asp Phe Asp Leu Asp Met Leu Gly Ser Asp Ala Leu Asp
945                 950                 955                 960
Asp Phe Asp Leu Asp Met Leu Ile Asn Tyr Pro Tyr Asp Val Pro Asp
                965                 970                 975
Tyr Ala Ser

<210> SEQ ID NO 55
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 55
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt gcgtcggca aacagtggtc cggcgcacgc     360
gccctggagg ccttgctcac ggatgcgggg gagttgagag gtccgccgtt acagttggac     420
```

```
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agcaacattg gcggcaagca agcgctcgaa    780
acggtgcagc ggctgttgcc ggtgctgtgc caggaccatg gcctgacccc ggaccaagtg    840
gtggctatcg ccagcaacaa tggcggcaag caagcgctcg aaacggtgca gcggctgttg    900
ccggtgctgt gccaggacca tggcctgacc ccggaccaag tggtggctat cgccagccac    960
gatggcggca agcaagcgct cgaaacggtg cagcggctgt tgccggtgct gtgccaggac   1020
catggcctga ccccggacca agtggtggct atcgccagcc acgatggcgg caagcaagcg   1080
ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agccacgatg cggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagcaac attggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag ccacgatggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacaa tggcggcaag caagcgctcg aaacggtgca gcggctgttg   1920
ccggtgctgt gccaggacca tggcctgacc ccggaccaag tggtggctat cgccagccac   1980
gatggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcc ggcctgatcc ggcgttggcc gcgttgacca acgacgacca cctcgtcgcc   2280
ttggcctgcc tcggcggacg tcctgccatg gatgcagtga aaagggatt gccgcacgcg   2340 ccggaattga tcagaagagt caatcgccgt attggcgaac gcacgtccca tcgcgttgcc   2400
ggatccaagg ctagcccgaa aaagaaacgc aaagttgggc gcgccgacgc gctggacgat   2460
ttcgatctcg acatgctggg ttctgatgcc ctcgatgact ttgacctgga tatgttggga   2520
agcgacgcat ggatgacttt tgatctggac atgctcggct ccgatgctct ggacgatttc   2580
gatctcgata tgttaattaa ctacccgtac gacgttccgg actacgcttc ttga         2634
```

<210> SEQ ID NO 56
<211> LENGTH: 877
<212> TYPE: PRT
<213> ORGANISM: Unknown

<220> FEATURE:
<223> OTHER INFORMATION: Synthetic peptide

<400> SEQUENCE: 56

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser Asn Gly Gly Gly Lys Gln Ala Leu Glu Thr Val Gln Arg
385                 390                 395                 400
```

```
Leu Leu Pro Val Leu Cys Gln Asp His Gly Leu Thr Pro Asp Gln Val
            405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
    770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815
```

```
Ala Leu Asp Asp Phe Asp Leu Asp Met Leu Gly Ser Asp Ala Leu Asp
                820                 825                 830

Asp Phe Asp Leu Asp Met Leu Gly Ser Asp Ala Leu Asp Phe Asp
            835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 57
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 57
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca aacagtggtc cggcgcacgc     360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca acattggcgg caagcaagcg ctcgaaacgg tgcagcggct gttgccggtg     600
ctgtgccagg accatggcct gaccccggac caagtggtgg ctatcgccag caacaatggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagcaacgg tggcggcaag caagcgctcg aaacggtgca gcggctgttg     900
ccggtgctgt gccaggacca tggcctgacc ccggaccaag tggtggctat cgccagccac     960
gatggcggca agcaagcgct cgaaacggtg cagcggctgt tgccggtgct gtgccaggac    1020
catggcctga ccccggacca agtggtggct atcgccagca acgtggcggc aagcaagcg    1080 ctcgaaacgg tgcagcggct gttgccggtg ctgtgccagg accatggcct gaccccggac    1140
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagcaac ggtggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag ccacgatggc    1680
ggcaagcaag cgctcgaaac ggtgcagcgg ctgttgccgg tgctgtgcca ggaccatggc    1740
```

```
ctgaccccgg accaagtggt ggctatcgcc agccacgatg gcggcaagca agcgctcgaa    1800
acggtgcagc ggctgttgcc ggtgctgtgc caggaccatg gcctgacccc ggaccaagtg    1860
gtggctatcg ccagccacga tggcggcaag caagcgctcg aaacggtgca gcggctgttg    1920
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca acgtggcgg caagcaagcg    2100 ctcgaaagca ttgtggccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat tggcgaacgc    2280
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 58
<211> LENGTH: 843
<212> TYPE: PRT
<213> ORGANISM: Unknown
<220> FEATURE:
<223> OTHER INFORMATION: Synthetic peptide

<400> SEQUENCE: 58

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala

```
              210                 215                 220
Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser Asn Gly Gly
                275                 280                 285

Gly Lys Gln Ala Leu Glu Thr Val Gln Arg Leu Leu Pro Val Leu Cys
            290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Gly Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
            370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Asp His Gly Leu Thr Pro Asp
                435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser His Asp Gly Gly Lys
                515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
                580                 585                 590

Asp Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
            610                 615                 620

Ser His Asp Gly Gly Lys Gln Ala Leu Glu Thr Val Gln Arg Leu Leu
625                 630                 635                 640
```

```
Pro Val Leu Cys Gln Asp His Gly Leu Thr Pro Asp Gln Val Val Ala
            645                 650                 655

Ile Ala Ser Asn Gly Gly Lys Gln Ala Leu Glu Thr Val Gln Arg
        660                 665                 670

Leu Leu Pro Val Leu Cys Gln Asp His Gly Leu Thr Pro Asp Gln Val
        675                 680                 685

Val Ala Ile Ala Ser Asn Gly Gly Lys Gln Ala Leu Glu Ser Ile
    690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
        770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 59
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 59
atggactaca aagaccatga cggtgattat aaagatcatg acatcgatta caaggatgac      60
gatgacaaga tggccccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac gcgcacacat cgttgcgctc     240
agccaacacc cggcagcgtt agggaccgtc gctgtcacgt atcagcacat aatcacggcg     300
ttgccagagg cgacacacga agacatcgtt ggcgtcggca aacagtggtc cggcgcacgc     360
gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagccacga tggcggcaag caagcgctcg aaacggtgca gcggctgttg     900
```

-continued

```
ccggtgctgt gccaggacca tggcctgacc ccggaccaag tggtggctat cgccagcaac      960
ggtggcggca agcaagcgct cgaaacggtg cagcggctgt tgccggtgct gtgccaggac     1020
catggcctga ccccggacca agtggtggct atcgccagca acattggcgg caagcaagcg     1080
ctcgaaacgg tgcagcggct gttgccggtg ctgtgccagg accatggcct gaccccggac     1140
caagtggtgg ctatcgccag caacaatggc ggcaagcaag cgctcgaaac ggtgcagcgg     1200
ctgttgccgg tgctgtgcca ggaccatggc ctgaccccgg accaagtggt ggctatcgcc     1260
agcaacattg gcggcaagca agcgctcgaa acggtgcagc ggctgttgcc ggtgctgtgc     1320
caggaccatg gcctgacccc ggaccaagtg gtggctatcg ccagcaacgg tggcggcaag     1380
caagcgctcg aaacggtgca gcggctgttg ccggtgctgt gccaggacca tggcctgacc     1440
ccggaccaag tggtggctat cgccagcaac aatggcggca agcaagcgct cgaaacggtg     1500
cagcggctgt tgccggtgct gtgccaggac catggcctga ccccggacca agtggtggct     1560
atcgccagca acattggcgg caagcaagcg ctcgaaacgg tgcagcggct gttgccggtg     1620
ctgtgccagg accatggcct gaccccggac caagtggtgg ctatcgccag caacattggc     1680
ggcaagcaag cgctcgaaac ggtgcagcgg ctgttgccgg tgctgtgcca ggaccatggc     1740
ctgaccccgg accaagtggt ggctatcgcc agcaacaatg gcggcaagca agcgctcgaa     1800
acggtgcagc ggctgttgcc ggtgctgtgc caggaccatg gcctgacccc ggaccaagtg     1860
gtggctatcg ccagcaacgg tggcggcaag caagcgctcg aaacggtgca gcggctgttg     1920
ccggtgctgt gccaggacca tggcctgacc ccggaccaag tggtggctat cgccagccac     1980
gatggcggca agcaagcgct cgaaacggtg cagcggctgt tgccggtgct gtgccaggac     2040
catggcctga ccccggacca agtggtggct atcgccagca acggtggcgg caagcaagcg     2100
ctcgaaagca ttgtggccca gctgagccgg cctgatccgg cgttggccgc gttgaccaac     2160
gacgaccacc tcgtcgcctt ggcctgcctc ggcggacgtc ctgccatgga tgcagtgaaa     2220
aagggattgc cgcacgcgcc ggaattgatc agaagagtca atcgccgtat ggcgaacgc      2280
acgtcccatc gcgttgccgg atccaaggct agcccgaaaa agaaacgcaa agttgggcgc     2340
gccgacgcgc tggacgattt cgatctcgac atgctgggtt ctgatgccct cgatgacttt     2400
gacctggata tgttgggaag cgacgcattg gatgactttg atctggacat gctcggctcc     2460
gatgctctgg acgatttcga tctcgatatg ttaattaact acccgtacga cgttccggac     2520
tacgcttctt ga                                                        2532
```

<210> SEQ ID NO 60
<211> LENGTH: 843
<212> TYPE: PRT
<213> ORGANISM: Unknown
<220> FEATURE:
<223> OTHER INFORMATION: Synthetic peptide

<400> SEQUENCE: 60

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60
```

```
Glu Ala Leu Val Gly His Gly Phe Thr His Ala His Ile Val Ala Leu
 65                  70                  75                  80

Ser Gln His Pro Ala Ala Leu Gly Thr Val Ala Thr Tyr Gln His
                 85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
        130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
        290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Ile Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
```

```
                    485                 490                 495
Leu Glu Thr Val Gln Arg Leu Leu Pro Val Leu Cys Gln Asp His Gly
                500                 505                 510

Leu Thr Pro Asp Gln Val Val Ala Ile Ala Ser Asn Ile Gly Gly Lys
            515                 520                 525

Gln Ala Leu Glu Thr Val Gln Arg Leu Leu Pro Val Leu Cys Gln Asp
        530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Gly Gly Lys Gln Ala Leu Glu Ser Ile
690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 61
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 61
atggactaca aagaccatga cggtgattat aaagatcatg acatcgatta caaggatgac      60
```

-continued

```
gatgacaaga tggcccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc     360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagca acattggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
attggcggca agcaagcgct cgaaacggtg cagcggctgt tgccggtgct gtgccaggac   1020
catggcctga ccccggacca gtggtggct atcgccagcc acgatggcgg caagcaagcg   1080
ctcgaaacgg tgcagcggct gttgccggtg ctgtgccagg accatggcct gaccccggac   1140
caagtggtgg ctatcgccag ccacgatggc ggcaagcaag cgctcgaaac ggtgcagcgg   1200
ctgttgccgg tgctgtgcca ggaccatggc ctgaccccgg accaagtggt ggctatcgcc   1260
agccacgatg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt tgccggtgct gtgccaggac catggcctga ccccggacca gtggtggct   1560
atcgccagca acgtggcgg caagcaagcg ctcgaaacgg tgcagcggct gttgccggtg    1620
ctgtgccagg accatggcct gaccccggac caagtggtgg ctatcgccag caacaatggc   1680
ggcaagcaag cgctcgaaac ggtgcagcgg ctgttgccgg tgctgtgcca ggaccatggc   1740
ctgaccccgg accaagtggt ggctatcgcc agcaacggtg gcggcaagca agcgctcgaa   1800
acggtgcagc ggctgttgcc ggtgctgtgc caggaccatg gcctgacccc ggaccaagtg   1860
gtggctatcg ccagcaacgg tggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt tgccggtgct gtgccaggac   2040
catggcctga ccccggacca gtggtggct atcgccagcc acgatggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaac ggtgcagcgg   2220
ctgttgccgg tgctgtgcca ggaccatggc ctgaccccgg accaagtggt ggctatcgcc   2280
agcaacaatg gcggcaagca agcgctcgaa acggtgcagc ggctgttgcc ggtgctgtgc   2340
caggaccatg gcctgacccc ggaccaagtg gtggctatcg ccagcaacgg tggcggcaag   2400
```

```
caagcgctcg aaagcattgt ggcccagctg agccggcctg atccggcgtt ggccgcgttg    2460
accaacgacg accacctcgt cgccttggcc tgcctcggcg acgtcctgc catggatgca     2520 gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                 2838
```

<210> SEQ ID NO 62
<211> LENGTH: 945
<212> TYPE: PRT
<213> ORGANISM: Unknown
<220> FEATURE:
<223> OTHER INFORMATION: Synthetic peptide

<400> SEQUENCE: 62

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
        275                 280                 285
```

```
Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Gly Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Gly Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Gly Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
690                 695                 700
```

Gln Arg Leu Leu Pro Val Leu Cys Gln Asp His Gly Leu Thr Pro Asp
705                 710                 715                 720

Gln Val Val Ala Ile Ala Ser Asn Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser Asn Asn Gly Gly Lys Gln Ala
    755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Gly Gly Gly Lys
785                 790                 795                 800

Gln Ala Leu Glu Ser Ile Val Ala Gln Leu Ser Arg Pro Asp Pro Ala
            805                 810                 815

Leu Ala Ala Leu Thr Asn Asp His Leu Val Ala Leu Ala Cys Leu
        820                 825                 830

Gly Gly Arg Pro Ala Met Asp Ala Val Lys Lys Gly Leu Pro His Ala
    835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Arg Lys Val
865                 870                 875                 880

Gly Arg Ala Asp Ala Leu Asp Asp Phe Asp Leu Asp Met Leu Gly Ser
            885                 890                 895

Asp Ala Leu Asp Asp Phe Asp Leu Asp Met Leu Gly Ser Asp Ala Leu
        900                 905                 910

Asp Asp Phe Asp Leu Asp Met Leu Gly Ser Asp Ala Leu Asp Phe
    915                 920                 925

Asp Leu Asp Met Leu Ile Asn Tyr Pro Tyr Asp Val Pro Asp Tyr Ala
930                 935                 940

Ser
945

<210> SEQ ID NO 63
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 63
atggactaca aagaccatga cggtgattat aaagatcatg acatcgatta caaggatgac       60
gatgacaaga tggcccccaa gaagaagagg aaggtgggcc gcggatctgt ggatctacgc      120
acgctcggct acagtcagca gcagcaagag aagatcaaac cgaaggtgcg ttcgacagtg      180
gcgcagcacc acgaggcact ggtgggccat gggtttacac gcgcgcacat cgttgcgctc      240
agccaacacc cggcagcgtt agggaccgtc gctgtcacgt atcagcacat aatcacgggc      300
ttgccagagg cgacacacga agacatcgtt ggcgtcggca acagtggtc cggcgcacgc      360 gccctggagg ccttgctcac ggatgcgggg gagttgagag gtccgccgtt acagttggac      420
acaggccaac ttgtgaagat tgcaaaacgt ggcggcgtga ccgcaatgga ggcagtgcat      480
gcatcgcgca atgcactgac gggtgccccc ctgaacctga ccccggacca agtggtggct      540
atcgccagcc acgatggcgg caagcaagcg ctcgaaacgg tgcagcggct gttgccggtg      600
ctgtgccagg accatggcct gaccccggac caagtggtgg ctatcgccag caacggtggc      660

```
ggcaagcaag cgctcgaaac ggtgcagcgg ctgttgccgg tgctgtgcca ggaccatggc    720
ctgaccccgg accaagtggt ggctatcgcc agcaacggtg gcggcaagca agcgctcgaa    780
acggtgcagc ggctgttgcc ggtgctgtgc caggaccatg gcctgacccc ggaccaagtg    840
gtggctatcg ccagcaacaa tggcggcaag caagcgctcg aaacggtgca gcggctgttg    900
ccggtgctgt gccaggacca tggcctgacc ccggaccaag tggtggctat cgccagcaac    960
aatggcggca agcaagcgct cgaaacggtg cagcggctgt tgccggtgct gtgccaggac   1020
catggcctga ccccggacca agtggtggct atcgccagca cattggcgg caagcaagcg   1080 ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacggtg gcggcaagca agcgctcgaa acggtgcagc ggctgttgcc ggtgctgtgc   1320
caggaccatg gcctgacccc ggaccaagtg gtggctatcg ccagcaacaa tggcggcaag   1380
caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt tgccggtgct gtgccaggac catggcctga ccccggacca agtggtggct   1560
atcgccagca cattggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacaa tggcggcaag caagcgctcg aaacggtgca gcggctgttg   1920
ccggtgctgt gccaggacca tggcctgacc ccggaccaag tggtggctat cgccagcaac   1980
aatggcggca agcaagcgct cgaaacggtg cagcggctgt tgccggtgct gtgccaggac   2040
catggcctga ccccggacca agtggtggct atcgccagca cattggcgg caagcaagcg   2100 ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact acccgtacga cgttccggac   2520
tacgcttctt ga                                                       2532
```

<210> SEQ ID NO 64
<211> LENGTH: 843
<212> TYPE: PRT
<213> ORGANISM: Unknown
<220> FEATURE:
<223> OTHER INFORMATION: Synthetic peptide

<400> SEQUENCE: 64

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val

-continued

```
                20                  25                  30
Gly Arg Gly Ser Val Asp Leu Arg Thr Leu Gly Tyr Ser Gln Gln Gln
                35                  40                  45
Gln Glu Lys Ile Lys Pro Lys Val Arg Ser Thr Val Ala Gln His His
 50                  55                  60
Glu Ala Leu Val Gly His Gly Phe Thr His Ala His Ile Val Ala Leu
 65                  70                  75                  80
Ser Gln His Pro Ala Ala Leu Gly Thr Val Ala Val Thr Tyr Gln His
                85                  90                  95
Ile Ile Thr Ala Leu Pro Glu Ala Thr His Glu Asp Ile Val Gly Val
                100                 105                 110
Gly Lys Gln Trp Ser Gly Ala Arg Ala Leu Glu Ala Leu Leu Thr Asp
                115                 120                 125
Ala Gly Glu Leu Arg Gly Pro Pro Leu Gln Leu Asp Thr Gly Gln Leu
                130                 135                 140
Val Lys Ile Ala Lys Arg Gly Gly Val Thr Ala Met Glu Ala Val His
145                 150                 155                 160
Ala Ser Arg Asn Ala Leu Thr Gly Ala Pro Leu Asn Leu Thr Pro Asp
                165                 170                 175
Gln Val Val Ala Ile Ala Ser His Asp Gly Gly Lys Gln Ala Leu Glu
                180                 185                 190
Thr Val Gln Arg Leu Leu Pro Val Leu Cys Gln Asp His Gly Leu Thr
                195                 200                 205
Pro Asp Gln Val Val Ala Ile Ala Ser Asn Gly Gly Gly Lys Gln Ala
                210                 215                 220
Leu Glu Thr Val Gln Arg Leu Leu Pro Val Leu Cys Gln Asp His Gly
225                 230                 235                 240
Leu Thr Pro Asp Gln Val Val Ala Ile Ala Ser Asn Gly Gly Gly Lys
                245                 250                 255
Gln Ala Leu Glu Thr Val Gln Arg Leu Leu Pro Val Leu Cys Gln Asp
                260                 265                 270
His Gly Leu Thr Pro Asp Gln Val Val Ala Ile Ala Ser Asn Asn Gly
                275                 280                 285
Gly Lys Gln Ala Leu Glu Thr Val Gln Arg Leu Leu Pro Val Leu Cys
                290                 295                 300
Gln Asp His Gly Leu Thr Pro Asp Gln Val Val Ala Ile Ala Ser Asn
305                 310                 315                 320
Asn Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
                340                 345                 350
Ser Asn Ile Gly Gly Lys Gln Ala Leu Glu Thr Val Gln Arg Leu Leu
                355                 360                 365
Pro Val Leu Cys Gln Asp His Gly Leu Thr Pro Asp Gln Val Val Ala
                370                 375                 380
Ile Ala Ser Asn Asn Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser Asn Gly Gly Gly Lys Gln Ala Leu Glu Thr Val
                420                 425                 430
Gln Arg Leu Leu Pro Val Leu Cys Gln Asp His Gly Leu Thr Pro Asp
                435                 440                 445
```

Gln Val Val Ala Ile Ala Ser Asn Asn Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Ile Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Asn Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Ser Ile
    690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
    770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
        835                 840

<210> SEQ ID NO 65
<211> LENGTH: 2532

<212> TYPE: DNA
<213> ORGANISM: Artificial sequence
<220> FEATURE:
<223> OTHER INFORMATION: Synthetic oligonucleotide

<400> SEQUENCE: 65

```
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc    360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
ctgtgccagg accatggcct gaccccggac caagtggtgg ctatcgccag caacggtggc   660
ggcaagcaag cgctcgaaac ggtgcagcgg ctgttgccgg tgctgtgcca ggaccatggc   720
ctgaccccgg accaagtggt ggctatcgcc agcaacggtg gcggcaagca agcgctcgaa   780
acggtgcagc ggctgttgcc ggtgctgtgc caggaccatg gcctgacccc ggaccaagtg   840
gtggctatcg ccagcaacaa tggcggcaag caagcgctcg aaacggtgca gcggctgttg   900
ccggtgctgt gccaggacca tggcctgacc ccggaccaag tggtggctat cgccagcaac   960
aatggcggca agcaagcgct cgaaacggtg cagcggctgt tgccggtgct gtgccaggac  1020
catggcctga ccccggacca agtggtggct atcgccagca cattggcgg caagcaagcg  1080
ctcgaaacgg tgcagcggct gttgccggtg ctgtgccagg accatggcct gaccccggac  1140
caagtggtgg ctatcgccag caacaatggc ggcaagcaag cgctcgaaac ggtgcagcgg  1200
ctgttgccgg tgctgtgcca ggaccatggc ctgaccccgg accaagtggt ggctatcgcc  1260
agcaacggtg gcggcaagca agcgctcgaa acggtgcagc ggctgttgcc ggtgctgtgc  1320
caggaccatg gcctgacccc ggaccaagtg gtggctatcg ccagcaacaa tggcggcaag  1380
caagcgctcg aaacggtgca gcggctgttg ccggtgctgt gccaggacca tggcctgacc  1440
ccggaccaag tggtggctat cgccagccac gatggcggca agcaagcgct cgaaacggtg  1500
cagcggctgt tgccggtgct gtgccaggac catggcctga ccccggacca agtggtggct  1560
atcgccagca cattggcgg caagcaagcg ctcgaaacgg tgcagcggct gttgccggtg  1620
ctgtgccagg accatggcct gaccccggac caagtggtgg ctatcgccag caacattggc  1680
ggcaagcaag cgctcgaaac ggtgcagcgg ctgttgccgg tgctgtgcca ggaccatggc  1740
ctgaccccgg accaagtggt ggctatcgcc agcaacattg gcggcaagca agcgctcgaa  1800
acggtgcagc ggctgttgcc ggtgctgtgc caggaccatg gcctgacccc ggaccaagtg  1860
gtggctatcg ccagcaacaa tggcggcaag caagcgctcg aaacggtgca gcggctgttg  1920
ccggtgctgt gccaggacca tggcctgacc ccggaccaag tggtggctat cgccagcaac  1980
aatggcggca agcaagcgct cgaaacggtg cagcggctgt tgccggtgct gtgccaggac  2040
catggcctga ccccggacca agtggtggct atcgccagca cggtggcgg caagcaagcg  2100
ctcgaaagca ttgtggccca gctgagccgg cctgatccgg cgttggccgc gttgaccaac  2160
```

```
gacgaccacc tcgtcgcctt ggcctgcctc ggcggacgtc ctgccatgga tgcagtgaaa    2220
aagggattgc cgcacgcgcc ggaattgatc agaagagtca atcgccgtat tggcgaacgc    2280
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                         2532
```

```
<210> SEQ ID NO 66
<211> LENGTH: 843
<212> TYPE: PRT
<213> ORGANISM: Unknown
<220> FEATURE:
<223> OTHER INFORMATION: Synthetic peptide

<400> SEQUENCE: 66
```

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys

-continued

```
            290                 295                 300
Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Ile Gly Gly Lys Gln Ala Leu Glu Thr Val Gln Arg Leu Leu
                355                 360                 365

Pro Val Leu Cys Gln Asp His Gly Leu Thr Pro Asp Gln Val Val Ala
                370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Lys Gln Ala Leu Glu Thr Val
                420                 425                 430

Gln Arg Leu Leu Pro Val Leu Cys Gln Asp His Gly Leu Thr Pro Asp
                435                 440                 445

Gln Val Val Ala Ile Ala Ser Asn Asn Gly Gly Lys Gln Ala Leu Glu
                450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Ile Gly Gly Lys
                515                 520                 525

Gln Ala Leu Glu Thr Val Gln Arg Leu Leu Pro Val Leu Cys Gln Asp
                530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Ile Gly Gly Lys Gln Ala Leu Glu Thr Val Gln Arg Leu Leu Pro Val
                595                 600                 605

Leu Cys Gln Asp His Gly Leu Thr Pro Asp Gln Val Val Ala Ile Ala
                610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Asn Gly Gly Lys Gln Ala Leu Glu Thr Val Gln Arg
                660                 665                 670

Leu Leu Pro Val Leu Cys Gln Asp His Gly Leu Thr Pro Asp Gln Val
                675                 680                 685

Val Ala Ile Ala Ser Asn Gly Gly Gly Lys Gln Ala Leu Glu Ser Ile
                690                 695                 700

Val Ala Gln Leu Ser Arg Pro Asp Pro Ala Leu Ala Ala Leu Thr Asn
705                 710                 715                 720
```

```
Asp Asp His Leu Val Ala Leu Ala Cys Leu Gly Gly Arg Pro Ala Met
            725                 730                 735

Asp Ala Val Lys Lys Gly Leu Pro His Ala Pro Glu Leu Ile Arg Arg
        740                 745                 750

Val Asn Arg Arg Ile Gly Glu Arg Thr Ser His Arg Val Ala Gly Ser
    755                 760                 765

Lys Ala Ser Pro Lys Lys Arg Lys Val Gly Arg Ala Asp Ala Leu
770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
            805                 810                 815

Met Leu Gly Ser Asp Ala Leu Asp Phe Asp Leu Asp Met Leu Ile
            820                 825                 830

Asn Tyr Pro Tyr Asp Val Pro Asp Tyr Ala Ser
        835                 840
```

<210> SEQ ID NO 67
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 67

| | | | | | |
|---|---|---|---|---|---|
| atggactaca | aagaccatga | cggtgattat | aaagatcatg | acatcgatta | caaggatgac | 60 |
| gatgacaaga | tggcccccaa | gaagaagagg | aaggtgggcc | gcggatctgt | ggatctacgc | 120 |
| acgctcggct | acagtcagca | gcagcaagag | aagatcaaac | cgaaggtgcg | ttcgacagtg | 180 |
| gcgcagcacc | acgaggcact | ggtgggccat | gggtttacac | acgcgcacat | cgttgcgctc | 240 |
| agccaacacc | cggcagcgtt | agggaccgtc | gctgtcacgt | atcagcacat | aatcacggcg | 300 |
| ttgccagagg | cgacacacga | agacatcgtt | ggcgtcggca | aacagtggtc | cggcgcacgc | 360 |
| gccctggagg | ccttgctcac | ggatgcgggg | gagttgagag | gtccgccgtt | acagttggac | 420 |
| acaggccaac | ttgtgaagat | tgcaaaacgt | ggcggcgtga | ccgcaatgga | ggcagtgcat | 480 |
| gcatcgcgca | atgcactgac | gggtgccccc | ctgaacctga | ccccggacca | agtggtggct | 540 |
| atcgccagcc | acgatggcgg | caagcaagcg | ctcgaaacgg | tgcagcggct | gttgccggtg | 600 |
| ctgtgccagg | accatggcct | gaccccggac | caagtggtgg | ctatcgccag | caacggtggc | 660 |
| ggcaagcaag | cgctcgaaac | ggtgcagcgg | ctgttgccgg | tgctgtgcca | ggaccatggc | 720 |
| ctgaccccgg | accaagtggt | ggctatcgcc | agcaacaatg | gcggcaagca | agcgctcgaa | 780 |
| acggtgcagc | ggctgttgcc | ggtgctgtgc | caggaccatg | cctgacccc | ggaccaagtg | 840 |
| gtggctatcg | ccagcaacgg | tggcggcaag | caagcgctcg | aaacggtgca | gcggctgttg | 900 |
| ccggtgctgt | gccaggacca | tggcctgacc | ccggaccaag | tggtggctat | cgccagcaac | 960 |
| aatggcggca | agcaagcgct | cgaaacggtg | cagcggctgt | tgccggtgct | gtgccaggac | 1020 |
| catggcctga | ccccggacca | agtggtggct | atcgccagca | acaatggcgg | caagcaagcg | 1080 |
| ctcgaaacgg | tgcagcggct | gttgccggtg | ctgtgccagg | accatggcct | gaccccggac | 1140 |
| caagtggtgg | ctatcgccag | caacattggc | ggcaagcaag | cgctcgaaac | ggtgcagcgg | 1200 |
| ctgttgccgg | tgctgtgcca | ggaccatggc | ctgaccccgg | accaagtggt | ggctatcgcc | 1260 |
| agccacgatg | gcggcaagca | agcgctcgaa | acggtgcagc | ggctgttgcc | ggtgctgtgc | 1320 |

```
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agcaacattg gcggcaagca agcgctcgaa    1800
acggtgcagc ggctgttgcc ggtgctgtgc caggaccatg gcctgacccc ggaccaagtg    1860
gtggctatcg ccagcaacaa tggcggcaag caagcgctcg aaacggtgca gcggctgttg    1920
ccggtgctgt gccaggacca tggcctgacc ccggaccaag tggtggctat cgccagcaac    1980
attggcggca agcaagcgct cgaaacggtg cagcggctgt tgccggtgct gtgccaggac    2040
catggcctga ccccggacca agtggtggct atcgccagca acggtggcgg caagcaagcg    2100
ctcgaaagca ttgtggccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat tggcgaacgc    2280
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 68
<211> LENGTH: 843
<212> TYPE: PRT
<213> ORGANISM: Unknown
<220> FEATURE:
<223> OTHER INFORMATION: Synthetic peptide

<400> SEQUENCE: 68

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140
```

```
Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
            165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
```

```
                    565                 570                 575
Gln Asp His Gly Leu Thr Pro Asp Gln Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Ala Ile Ala
    610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Ala
                645                 650                 655

Ile Ala Ser Asn Ile Gly Gly Lys Gln Ala Leu Glu Thr Val Gln Arg
                660                 665                 670

Leu Leu Pro Val Leu Cys Gln Asp His Gly Leu Thr Pro Asp Gln Val
        675                 680                 685

Val Ala Ile Ala Ser Asn Gly Gly Gly Lys Gln Ala Leu Glu Ser Ile
        690                 695                 700

Val Ala Gln Leu Ser Arg Pro Asp Pro Ala Leu Ala Ala Leu Thr Asn
705                 710                 715                 720

Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
                740                 745                 750

Val Asn Arg Arg Ile Gly Glu Arg Thr Ser His Arg Val Ala Gly Ser
                755                 760                 765

Lys Ala Ser Pro Lys Lys Arg Lys Val Gly Arg Ala Asp Ala Leu
    770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
                820                 825                 830

Asn Tyr Pro Tyr Asp Val Pro Asp Tyr Ala Ser
            835                 840
```

<210> SEQ ID NO 69
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 69

```
atggactaca aagaccatga cggtgattat aaagatcatg acatcgatta caaggatgac    60
gatgacaaga tggccccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc    360 gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
```

```
gcatcgcgca atgcactgac gggtgccccc ctgaacctga ccccggacca agtggtggct      540
atcgccagca acattggcgg caagcaagcg ctcgaaacgg tgcagcggct gttgccggtg      600
ctgtgccagg accatggcct gaccccggac caagtggtgg ctatcgccag caacattggc      660
ggcaagcaag cgctcgaaac ggtgcagcgg ctgttgccgg tgctgtgcca ggaccatggc      720
ctgaccccgg accaagtggt ggctatcgcc agcaacattg gcggcaagca agcgctcgaa      780
acggtgcagc ggctgttgcc ggtgctgtgc caggaccatg gcctgacccc ggaccaagtg      840
gtggctatcg ccagcaacaa tggcggcaag caagcgctcg aaacggtgca gcggctgttg      900
ccggtgctgt gccaggacca tggcctgacc ccggaccaag tggtggctat cgccagcaac      960
attggcggca agcaagcgct cgaaacggtg cagcggctgt tgccggtgct gtgccaggac     1020
catggcctga ccccggacca agtggtggct atcgccagcc acgatggcgg caagcaagcg     1080
ctcgaaacgg tgcagcggct gttgccggtg ctgtgccagg accatggcct gaccccggac     1140
caagtggtgg ctatcgccag ccacgatggc ggcaagcaag cgctcgaaac ggtgcagcgg     1200
ctgttgccgg tgctgtgcca ggaccatggc ctgaccccgg accaagtggt ggctatcgcc     1260
agcaacattg gcggcaagca agcgctcgaa acggtgcagc ggctgttgcc ggtgctgtgc     1320
caggaccatg gcctgacccc ggaccaagtg gtggctatcg ccagccacga tggcggcaag     1380
caagcgctcg aaacggtgca gcggctgttg ccggtgctgt gccaggacca tggcctgacc     1440
ccggaccaag tggtggctat cgccagcaac attggcggca agcaagcgct cgaaacggtg     1500
cagcggctgt tgccggtgct gtgccaggac catggcctga ccccggacca agtggtggct     1560
atcgccagcc acgatggcgg caagcaagcg ctcgaaacgg tgcagcggct gttgccggtg     1620
ctgtgccagg accatggcct gaccccggac caagtggtgg ctatcgccag ccacgatggc     1680
ggcaagcaag cgctcgaaac ggtgcagcgg ctgttgccgg tgctgtgcca ggaccatggc     1740
ctgaccccgg accaagtggt ggctatcgcc agccacgatg gcggcaagca agcgctcgaa     1800
acggtgcagc ggctgttgcc ggtgctgtgc caggaccatg gcctgacccc ggaccaagtg     1860
gtggctatcg ccagcaacat tggcggcaag caagcgctcg aaacggtgca gcggctgttg     1920
ccggtgctgt gccaggacca tggcctgacc ccggaccaag tggtggctat cgccagcaac     1980
ggtggcggca agcaagcgct cgaaacggtg cagcggctgt tgccggtgct gtgccaggac     2040
catggcctga ccccggacca agtggtggct atcgccagca acaatggcgg caagcaagcg     2100
ctcgaaacgg tgcagcggct gttgccggtg ctgtgccagg accatggcct gaccccggac     2160
caagtggtgg ctatcgccag caacattggc ggcaagcaag cgctcgaaac ggtgcagcgg     2220
ctgttgccgg tgctgtgcca ggaccatggc ctgaccccgg accaagtggt ggctatcgcc     2280
agccacgatg gcggcaagca agcgctcgaa agcattgtgg cccagctgag ccggcctgat     2340
ccggcgttgg ccgcgttgac caacgacgac cacctcgtcg ccttggcctg cctcggcgga     2400
cgtcctgcca tggatgcagt gaaaaaggga ttgccgcacg cgccggaatt gatcagaaga     2460
gtcaatcgcc gtattggcga acgcacgtcc catcgcgttg ccggatccaa ggctagcccg     2520
aaaaagaaac gcaaagttgg gcgcgccgac gcgctggacg atttcgatct cgacatgctg     2580
ggttctgatg ccctcgatga cttttgacctg gatatgttgg gaagcgacgc attggatgac     2640
tttgatctgg acatgctcgg ctccgatgct ctggacgatt tcgatctcga tatgttaatt     2700
aactacccgt acgacgttcc ggactacgct tcttga                              2736
```

<210> SEQ ID NO 70
<211> LENGTH: 911

```
<212> TYPE: PRT
<213> ORGANISM: Unknown
<220> FEATURE:
<223> OTHER INFORMATION: Synthetic peptide

<400> SEQUENCE: 70

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Asp Leu Arg Thr Leu Gly Tyr Ser Gln Gln Gln
            35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Ile Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Ile Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380
```

```
Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
            405                 410                 415

Val Ala Ile Ala Ser Asn Ile Gly Gly Lys Gln Ala Leu Glu Thr Val
        420                 425                 430

Gln Arg Leu Leu Pro Val Leu Cys Gln Asp His Gly Leu Thr Pro Asp
    435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
            485                 490                 495

Leu Glu Thr Val Gln Arg Leu Leu Pro Val Leu Cys Gln Asp His Gly
        500                 505                 510

Leu Thr Pro Asp Gln Val Val Ala Ile Ala Ser His Asp Gly Gly Lys
    515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
            565                 570                 575

Gln Asp His Gly Leu Thr Pro Asp Gln Val Val Ala Ile Ala Ser His
        580                 585                 590

Asp Gly Gly Lys Gln Ala Leu Glu Thr Val Gln Arg Leu Leu Pro Val
    595                 600                 605

Leu Cys Gln Asp His Gly Leu Thr Pro Asp Gln Val Val Ala Ile Ala
610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser Asn Asn Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Ile Gly Gly Lys Gln Ala Leu Glu
            725                 730                 735

Thr Val Gln Arg Leu Leu Pro Val Leu Cys Gln Asp His Gly Leu Thr
        740                 745                 750

Pro Asp Gln Val Val Ala Ile Ala Ser His Asp Gly Gly Lys Gln Ala
    755                 760                 765

Leu Glu Ser Ile Val Ala Gln Leu Ser Arg Pro Asp Pro Ala Leu Ala
770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
```

```
                    805                 810                 815
Leu Ile Arg Arg Val Asn Arg Arg Ile Gly Glu Arg Thr Ser His Arg
                820                 825                 830

Val Ala Gly Ser Lys Ala Ser Pro Lys Lys Arg Lys Val Gly Arg
            835                 840                 845

Ala Asp Ala Leu Asp Asp Phe Asp Leu Asp Met Leu Gly Ser Asp Ala
        850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
                900                 905                 910

<210> SEQ ID NO 71
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 71
atggactaca aagaccatga cggtgattat aaagatcatg acatcgatta caaggatgac     60
gatgacaaga tggccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca acagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag caacggtggc    660
ggcaagcaag cgctcgaaac ggtgcagcgg ctgttgccgg tgctgtgcca ggaccatggc    720
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagcaacat tggcggcaag caagcgctcg aaacggtgca gcggctgttg    900
ccggtgctgt gccaggacca tggcctgacc ccggaccaag tggtggctat cgccagcaac    960
aatggcggca agcaagcgct cgaaacggtg cagcggctgt tgccggtgct gtgccaggac   1020
catggcctga ccccggacca agtggtggct atcgccagca acaatggcgg caagcaagcg   1080
ctcgaaacgg tgcagcggct gttgccggtg ctgtgccagg accatggcct gaccccggac   1140
caagtggtgg ctatcgccag caacattggc ggcaagcaag cgctcgaaac ggtgcagcgg   1200
ctgttgccgg tgctgtgcca ggaccatggc ctgaccccgg accaagtggt ggctatcgcc   1260
agcaacattg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
```

```
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acggtggcgg caagcaagcg   2100
ctcgaaagca ttgtggccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact acccgtacga cgttccggac   2520
tacgcttctt ga   2532

<210> SEQ ID NO 72
<211> LENGTH: 843
<212> TYPE: PRT
<213> ORGANISM: Unknown
<220> FEATURE:
<223> OTHER INFORMATION: Synthetic peptide

<400> SEQUENCE: 72

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175
```

```
Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
            195                 200                 205

Pro Asp Gln Val Val Ala Ile Ala Ser Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Ile Gly
            275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
            370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
            515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590
```

Ile Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
    610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
    675                 680                 685

Val Ala Ile Ala Ser Asn Gly Gly Gly Lys Gln Ala Leu Glu Ser Ile
690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
    755                 760                 765

Lys Ala Ser Pro Lys Lys Lys Arg Lys Val Gly Arg Ala Asp Ala Leu
770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
            820                 825                 830

Asn Tyr Pro Tyr Asp Val Pro Asp Tyr Ala Ser
    835                 840

<210> SEQ ID NO 73
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 73
atggactaca aagaccatga cggtgattat aaagatcatg acatcgatta caaggatgac    60
gatgacaaga tggccccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc   360 gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
ctgtgccagg accatggcct gaccccggac caagtggtgg ctatcgccag ccacgatggc   660

```
ggcaagcaag cgctcgaaac ggtgcagcgg ctgttgccgg tgctgtgcca ggaccatggc    720
ctgaccccgg accaagtggt ggctatcgcc agcaacattg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagccac    960
gatggcggca agcaagcgct cgaaacggtg cagcggctgt tgccggtgct gtgccaggac   1020
catggcctga ccccggacca agtggtggct atcgccagca acggtggcgg caagcaagcg   1080
ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agcaacaatg gcggcaagca agcgctcgaa acggtgcagc ggctgttgcc ggtgctgtgc   1320
caggaccatg gcctgacccc ggaccaagtg gtggctatcg ccagccacga tggcggcaag   1380
caagcgctcg aaacggtgca gcggctgttg ccggtgctgt gccaggacca tggcctgacc   1440
ccggaccaag tggtggctat cgccagccac gatggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacattggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag caacaatggc ggcaagcaag cgctcgaaac ggtgcagcgg   2220
ctgttgccgg tgctgtgcca ggaccatggc ctgaccccgg accaagtggt ggctatcgcc   2280
agcaacattg gcggcaagca agcgctcgaa acggtgcagc ggctgttgcc ggtgctgtgc   2340
caggaccatg gcctgacccc ggaccaagtg gtggctatcg ccagcaacgg tggcggcaag   2400
caagcgctcg aaagcattgt ggcccagctg agccggcctg atccggcgtt ggccgcgttg   2460
accaacgaca ccacctcgt cgccttggcc tgcctcggcg acgtcctgc catggatgca   2520 gtgaaaaagg gattgccgca cgcgccggaa ttgatcagaa gagtcaatcg ccgtattggc   2580
gaacgcacgt cccatcgcgt tgccggatcc aaggctagcc cgaaaaagaa acgcaaagtt   2640
gggcgcgccg acgcgctgga cgatttcgat ctcgacatgc tgggttctga tgccctcgat   2700
gactttgacc tggatatgtt gggaagcgac gcattggatg actttgatct ggacatgctc   2760
ggctccgatg ctctggacga tttcgatctc gatatgttaa ttaactaccc gtacgacgtt   2820
ccggactacg cttcttga                                                 2838
```

<210> SEQ ID NO 74
<211> LENGTH: 945
<212> TYPE: PRT

<213> ORGANISM: Unknown
<220> FEATURE:
<223> OTHER INFORMATION: Synthetic peptide

<400> SEQUENCE: 74

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Asp Leu Arg Thr Leu Gly Tyr Ser Gln Gln Gln
            35                  40                  45

Gln Glu Lys Ile Lys Pro Lys Val Arg Ser Thr Val Ala Gln His His
50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
                180                 185                 190

Thr Val Gln Arg Leu Leu Pro Val Leu Cys Gln Asp His Gly Leu Thr
            195                 200                 205

Pro Asp Gln Val Val Ala Ile Ala Ser His Asp Gly Gly Lys Gln Ala
            210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser His Asp Gly
            275                 280                 285

Gly Lys Gln Ala Leu Glu Thr Val Gln Arg Leu Leu Pro Val Leu Cys
            290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Gly Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser Asn Gly Gly Gly Lys Gln Ala Leu Glu Thr Val Gln Arg
```

```
                385                 390                 395                 400
         Leu Leu Pro Val Leu Cys Gln Asp His Gly Leu Thr Pro Asp Gln Val
                         405                 410                 415

Val Ala Ile Ala Ser Asn Asn Gly Gly Lys Gln Ala Leu Glu Thr Val
                     420                 425                 430

Gln Arg Leu Leu Pro Val Leu Cys Gln Asp His Gly Leu Thr Pro Asp
                     435                 440                 445

Gln Val Val Ala Ile Ala Ser His Asp Gly Gly Lys Gln Ala Leu Glu
                 450                 455                 460

Thr Val Gln Arg Leu Leu Pro Val Leu Cys Gln Asp His Gly Leu Thr
         465                 470                 475                 480

Pro Asp Gln Val Val Ala Ile Ala Ser His Asp Gly Gly Lys Gln Ala
                         485                 490                 495

Leu Glu Thr Val Gln Arg Leu Leu Pro Val Leu Cys Gln Asp His Gly
                     500                 505                 510

Leu Thr Pro Asp Gln Val Val Ala Ile Ala Ser Asn Asn Gly Gly Lys
                     515                 520                 525

Gln Ala Leu Glu Thr Val Gln Arg Leu Leu Pro Val Leu Cys Gln Asp
                 530                 535                 540

His Gly Leu Thr Pro Asp Gln Val Val Ala Ile Ala Ser Asn Ile Gly
         545                 550                 555                 560

Gly Lys Gln Ala Leu Glu Thr Val Gln Arg Leu Leu Pro Val Leu Cys
                         565                 570                 575

Gln Asp His Gly Leu Thr Pro Asp Gln Val Val Ala Ile Ala Ser Asn
                     580                 585                 590

Ile Gly Gly Lys Gln Ala Leu Glu Thr Val Gln Arg Leu Leu Pro Val
                     595                 600                 605

Leu Cys Gln Asp His Gly Leu Thr Pro Asp Gln Val Val Ala Ile Ala
                 610                 615                 620

Ser Asn Ile Gly Gly Lys Gln Ala Leu Glu Thr Val Gln Arg Leu Leu
         625                 630                 635                 640

Pro Val Leu Cys Gln Asp His Gly Leu Thr Pro Asp Gln Val Val Ala
                         645                 650                 655

Ile Ala Ser Asn Ile Gly Gly Lys Gln Ala Leu Glu Thr Val Gln Arg
                     660                 665                 670

Leu Leu Pro Val Leu Cys Gln Asp His Gly Leu Thr Pro Asp Gln Val
                     675                 680                 685

Val Ala Ile Ala Ser Asn Ile Gly Gly Lys Gln Ala Leu Glu Thr Val
                 690                 695                 700

Gln Arg Leu Leu Pro Val Leu Cys Gln Asp His Gly Leu Thr Pro Asp
         705                 710                 715                 720

Gln Val Val Ala Ile Ala Ser Asn Asn Gly Gly Lys Gln Ala Leu Glu
                         725                 730                 735

Thr Val Gln Arg Leu Leu Pro Val Leu Cys Gln Asp His Gly Leu Thr
                     740                 745                 750

Pro Asp Gln Val Val Ala Ile Ala Ser Asn Ile Gly Gly Lys Gln Ala
                     755                 760                 765

Leu Glu Thr Val Gln Arg Leu Leu Pro Val Leu Cys Gln Asp His Gly
                 770                 775                 780

Leu Thr Pro Asp Gln Val Val Ala Ile Ala Ser Asn Gly Gly Gly Lys
         785                 790                 795                 800

Gln Ala Leu Glu Ser Ile Val Ala Gln Leu Ser Arg Pro Asp Pro Ala
                         805                 810                 815
```

```
Leu Ala Ala Leu Thr Asn Asp Asp His Leu Val Ala Leu Ala Cys Leu
            820                 825                 830

Gly Gly Arg Pro Ala Met Asp Ala Val Lys Lys Gly Leu Pro His Ala
            835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Arg Lys Val
865                 870                 875                 880

Gly Arg Ala Asp Ala Leu Asp Asp Phe Asp Leu Asp Met Leu Gly Ser
                885                 890                 895

Asp Ala Leu Asp Asp Phe Asp Leu Asp Met Leu Gly Ser Asp Ala Leu
            900                 905                 910

Asp Asp Phe Asp Leu Asp Met Leu Gly Ser Asp Ala Leu Asp Asp Phe
            915                 920                 925

Asp Leu Asp Met Leu Ile Asn Tyr Pro Tyr Asp Val Pro Asp Tyr Ala
            930                 935                 940

Ser
945

<210> SEQ ID NO 75
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 75
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagca acgtggcggg caagcaagcg ctcgaaacgg tgcagcggct gttgccggtg    600
ctgtgccagg accatggcct gaccccggac caagtggtgg ctatcgccag caacaatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca agtggtggct atcgccagcc acgatggcgg caagcaagcg   1080
ctcgaaacgg tgcagcggct gttgccggtg ctgtgccagg accatggcct gaccccggac   1140
caagtggtgg ctatcgccag ccacgatggc ggcaagcaag cgctcgaaac ggtgcagcgg   1200
ctgttgccgg tgctgtgcca ggaccatggc ctgaccccgg accaagtggt ggctatcgcc   1260
```

```
agccacgatg gcggcaagca agcgctcgaa acggtgcagc ggctgttgcc ggtgctgtgc    1320
caggaccatg gcctgacccc ggaccaagtg gtggctatcg ccagcaacat ggcggcaag    1380 caagcgctcg aaacggtgca gcggctgttg ccggtgctgt gccaggacca tggcctgacc    1440
ccggaccaag tggtggctat cgccagcaac aatggcggca agcaagcgct cgaaacggtg    1500
cagcggctgt tgccggtgct gtgccaggac catggcctga ccccggacca agtggtggct    1560
atcgccagca acaatggcgg caagcaagcg ctcgaaacgg tgcagcggct gttgccggtg    1620
ctgtgccagg accatggcct gaccccggac caagtggtgg ctatcgccag caacaatggc    1680
ggcaagcaag cgctcgaaac ggtgcagcgg ctgttgccgg tgctgtgcca ggaccatggc    1740
ctgaccccgg accaagtggt ggctatcgcc agcaacaatg gcggcaagca agcgctcgaa    1800
acggtgcagc ggctgttgcc ggtgctgtgc caggaccatg gcctgacccc ggaccaagtg    1860
gtggctatcg ccagcaacat ggcggcaag caagcgctcg aaacggtgca gcggctgttg    1920
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca acggtggcgg caagcaagcg    2100
ctcgaaagca ttgtggccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat ggcgaacgc    2280 acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg atgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 76
<211> LENGTH: 843
<212> TYPE: PRT
<213> ORGANISM: Unknown
<220> FEATURE:
<223> OTHER INFORMATION: Synthetic peptide

<400> SEQUENCE: 76

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125
```

```
Ala Gly Glu Leu Arg Gly Pro Pro Leu Gln Leu Asp Thr Gly Gln Leu
    130                 135                 140

Val Lys Ile Ala Lys Arg Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Gly Gly Lys Gln Ala Leu Glu
                180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Asn Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser His Asp Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser His Asp Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Asp His Gly Leu Thr Pro Asp
        435                 440                 445

Gln Val Val Ala Ile Ala Ser Asn Ile Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Asn Gly
```

Gly Lys Gln Ala Leu Glu Thr Val Gln Arg Leu Leu Pro Val Leu Cys
545                 550                 555                 560

Gln Asp His Gly Leu Thr Pro Asp Gln Val Val Ala Ile Ala Ser Asn
            565                 570                 575

Asn Gly Gly Lys Gln Ala Leu Glu Thr Val Gln Arg Leu Leu Pro Val
                580                 585                 590

Leu Cys Gln Asp His Gly Leu Thr Pro Asp Gln Val Val Ala Ile Ala
        595                 600                 605

Ser Asn Ile Gly Gly Lys Gln Ala Leu Glu Thr Val Gln Arg Leu Leu
610                 615                 620

Pro Val Leu Cys Gln Asp His Gly Leu Thr Pro Asp Gln Val Val Ala
        625                 630                 635                 640

Ile Ala Ser Asn Gly Gly Lys Gln Ala Leu Glu Thr Val Gln Arg
            645                 650                 655

Leu Leu Pro Val Leu Cys Gln Asp His Gly Leu Thr Pro Asp Gln Val
                660                 665                 670

Val Ala Ile Ala Ser Asn Gly Gly Lys Gln Ala Leu Glu Ser Ile
        675                 680                 685

Val Ala Gln Leu Ser Arg Pro Asp Pro Ala Leu Ala Ala Leu Thr Asn
690                 695                 700

Asp Asp His Leu Val Ala Leu Ala Cys Leu Gly Gly Arg Pro Ala Met
705                 710                 715                 720

Asp Ala Val Lys Lys Gly Leu Pro His Ala Pro Glu Leu Ile Arg Arg
            725                 730                 735

Val Asn Arg Arg Ile Gly Glu Arg Thr Ser His Arg Val Ala Gly Ser
                740                 745                 750

Lys Ala Ser Pro Lys Lys Arg Lys Val Gly Arg Ala Asp Ala Leu
        755                 760                 765

Asp Asp Phe Asp Leu Asp Met Leu Gly Ser Asp Ala Leu Asp Asp Phe
770                 775                 780

Asp Leu Asp Met Leu Gly Ser Asp Ala Leu Asp Asp Phe Asp Leu Asp
        785                 790                 795                 800

Met Leu Gly Ser Asp Ala Leu Asp Asp Phe Asp Leu Asp Met Leu Ile
            805                 810                 815

Asn Tyr Pro Tyr Asp Val Pro Asp Tyr Ala Ser
                820                 825                 830

835                 840

<210> SEQ ID NO 77
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 77
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420

-continued

```
acaggccaac ttgtgaagat tgcaaaacgt ggcggcgtga ccgcaatgga ggcagtgcat    480
gcatcgcgca atgcactgac gggtgccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag caacggtggc    660
ggcaagcaag cgctcgaaac ggtgcagcgg ctgttgccgg tgctgtgcca ggaccatggc    720
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagcaacgg tggcggcaag caagcgctcg aaacggtgca gcggctgttg    900
ccggtgctgt gccaggacca tggcctgacc ccggaccaag tggtggctat cgccagccac    960
gatggcggca agcaagcgct cgaaacggtg cagcggctgt tgccggtgct gtgccaggac   1020
catggcctga ccccggacca agtggtggct atcgccagca cattggcgg caagcaagcg   1080 ctcgaaacgg tgcagcggct gttgccggtg ctgtgccagg accatggcct gaccccggac   1140
caagtggtgg ctatcgccag ccacgatggc ggcaagcaag cgctcgaaac ggtgcagcgg   1200
ctgttgccgg tgctgtgcca ggaccatggc ctgaccccgg accaagtggt ggctatcgcc   1260
agcaacattg gcggcaagca agcgctcgaa acggtgcagc ggctgttgcc ggtgctgtgc   1320
caggaccatg gcctgacccc ggaccaagtg gtggctatcg ccagcaacat tggcggcaag   1380
caagcgctcg aaacggtgca gcggctgttg ccggtgctgt gccaggacca tggcctgacc   1440
ccggaccaag tggtggctat cgccagcaac attggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacaatggc   1680
ggcaagcaag cgctcgaaac ggtgcagcgg ctgttgccgg tgctgtgcca ggaccatggc   1740
ctgaccccgg accaagtggt ggctatcgcc agcaacattg gcggcaagca agcgctcgaa   1800
acggtgcagc ggctgttgcc ggtgctgtgc caggaccatg gcctgacccc ggaccaagtg   1860
gtggctatcg ccagcaacat tggcggcaag caagcgctcg aaacggtgca gcggctgttg   1920
ccggtgctgt gccaggacca tggcctgacc ccggaccaag tggtggctat cgccagcaac   1980
attggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaagca ttgtgcccca gctgagccgg cctgatccgg cgttggccgc gttgaccaac   2160
gacgaccacc tcgtcgcctt ggcctgcctc ggcggacgtc ctgccatgga tgcagtgaaa   2220
aagggattgc cgcacgcgcc ggaattgatc agaagagtca atcgccgtat tggcgaacgc   2280
acgtcccatc gcgttgccgg atccaaggct agcccgaaaa agaaacgcaa agttgggcgc   2340
gccgacgcgc tggacgattt cgatctcgac atgctgggtt ctgatgccct cgatgacttt   2400
gacctggata tgttgggaag cgacgcattg gatgactttg atctggacat gctcggctcc   2460
gatgctctgg acgatttcga tctcgatatg ttaattaact acccgtacga cgttccggac   2520
tacgcttctt ga                                                       2532
```

<210> SEQ ID NO 78
<211> LENGTH: 843
<212> TYPE: PRT
<213> ORGANISM: Unknown
<220> FEATURE:

<223> OTHER INFORMATION: Synthetic peptide

<400> SEQUENCE: 78

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser Asn Gly Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Ile Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
370                 375                 380

Ile Ala Ser His Asp Gly Gly Lys Gln Ala Leu Glu Thr Val Gln Arg
385                 390                 395                 400
```

```
Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Ile Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Ile Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Ile Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Ser Ile
    690                 695                 700

Val Ala Gln Leu Ser Arg Pro Asp Pro Ala Leu Ala Ala Leu Thr Asn
705                 710                 715                 720

Asp Asp His Leu Val Ala Leu Ala Cys Leu Gly Gly Arg Pro Ala Met
                725                 730                 735

Asp Ala Val Lys Lys Gly Leu Pro His Ala Pro Glu Leu Ile Arg Arg
            740                 745                 750

Val Asn Arg Arg Ile Gly Glu Arg Thr Ser His Arg Val Ala Gly Ser
        755                 760                 765

Lys Ala Ser Pro Lys Lys Arg Lys Val Gly Arg Ala Asp Ala Leu
    770                 775                 780

Asp Asp Phe Asp Leu Asp Met Leu Gly Ser Asp Ala Leu Asp Asp Phe
785                 790                 795                 800

Asp Leu Asp Met Leu Gly Ser Asp Ala Leu Asp Asp Phe Asp Leu Asp
                805                 810                 815

Met Leu Gly Ser Asp Ala Leu Asp Asp Phe Asp Leu Asp Met Leu Ile
```

820                 825                 830
Asn Tyr Pro Tyr Asp Val Pro Asp Tyr Ala Ser
        835                 840

<210> SEQ ID NO 79
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 79

| | | | | | |
|---|---|---|---|---|---|
| atggactaca | aagaccatga | cggtgattat | aaagatcatg | acatcgatta | caaggatgac | 60 |
| gatgacaaga | tggcccccaa | gaagaagagg | aaggtgggcc | gcggatctgt | ggatctacgc | 120 |
| acgctcggct | acagtcagca | gcagcaagag | aagatcaaac | cgaaggtgcg | ttcgacagtg | 180 |
| gcgcagcacc | acgaggcact | ggtgggccat | gggtttacac | acgcgcacat | cgttgcgctc | 240 |
| agccaacacc | cggcagcgtt | agggaccgtc | gctgtcacgt | atcagcacat | aatcacggcg | 300 |
| ttgccagagg | cgacacacga | agacatcgtt | ggcgtcggca | acagtggtc | cggcgcacgc | 360 |
| gccctggagg | ccttgctcac | ggatgcgggg | gagttgagag | gtccgccgtt | acagttggac | 420 |
| acaggccaac | ttgtgaagat | tgcaaaacgt | ggcggcgtga | ccgcaatgga | ggcagtgcat | 480 |
| gcatcgcgca | atgcactgac | gggtgccccc | ctgaacctga | ccccggacca | agtggtggct | 540 |
| atcgccagca | acaatggcgg | caagcaagcg | ctcgaaacgg | tgcagcggct | gttgccggtg | 600 |
| ctgtgccagg | accatggcct | gaccccggac | caagtggtgg | ctatcgccag | caacggtggc | 660 |
| ggcaagcaag | cgctcgaaac | ggtgcagcgg | ctgttgccgg | tgctgtgcca | ggaccatggc | 720 |
| ctgaccccgg | accaagtggt | ggctatcgcc | agcaacggtg | gcggcaagca | agcgctcgaa | 780 |
| acggtgcagc | ggctgttgcc | ggtgctgtgc | caggaccatg | gcctgacccc | ggaccaagtg | 840 |
| gtggctatcg | ccagcaacaa | tggcggcaag | caagcgctcg | aaacggtgca | gcggctgttg | 900 |
| ccggtgctgt | gccaggacca | tggcctgacc | ccggaccaag | tggtggctat | cgccagcaac | 960 |
| aatggcggca | agcaagcgct | cgaaacggtg | cagcggctgt | tgccggtgct | gtgccaggac | 1020 |
| catggcctga | ccccggacca | agtggtggct | atcgccagca | acaatggcgg | caagcaagcg | 1080 |
| ctcgaaacgg | tgcagcggct | gttgccggtg | ctgtgccagg | accatggcct | gaccccggac | 1140 |
| caagtggtgg | ctatcgccag | ccacgatggc | ggcaagcaag | cgctcgaaac | ggtgcagcgg | 1200 |
| ctgttgccgg | tgctgtgcca | ggaccatggc | ctgaccccgg | accaagtggt | ggctatcgcc | 1260 |
| agcaacattg | gcggcaagca | agcgctcgaa | acggtgcagc | ggctgttgcc | ggtgctgtgc | 1320 |
| caggaccatg | gcctgacccc | ggaccaagtg | gtggctatcg | ccagcaacgg | tggcggcaag | 1380 |
| caagcgctcg | aaacggtgca | gcggctgttg | ccggtgctgt | gccaggacca | tggcctgacc | 1440 |
| ccggaccaag | tggtggctat | cgccagccac | gatggcggca | agcaagcgct | cgaaacggtg | 1500 |
| cagcggctgt | tgccggtgct | gtgccaggac | catggcctga | ccccggacca | agtggtggct | 1560 |
| atcgccagca | acattggcgg | caagcaagcg | ctcgaaacgg | tgcagcggct | gttgccggtg | 1620 |
| ctgtgccagg | accatggcct | gaccccggac | caagtggtgg | ctatcgccag | caacggtggc | 1680 |
| ggcaagcaag | cgctcgaaac | ggtgcagcgg | ctgttgccgg | tgctgtgcca | ggaccatggc | 1740 |
| ctgaccccgg | accaagtggt | ggctatcgcc | agccacgatg | gcggcaagca | agcgctcgaa | 1800 |
| acggtgcagc | ggctgttgcc | ggtgctgtgc | caggaccatg | gcctgacccc | ggaccaagtg | 1860 |
| gtggctatcg | ccagccacga | tggcggcaag | caagcgctcg | aaacggtgca | gcggctgttg | 1920 |

```
ccggtgctgt gccaggacca tggcctgacc ccggaccaag tggtggctat cgccagccac   1980
gatggcggca agcaagcgct cgaaacggtg cagcggctgt tgccggtgct gtgccaggac   2040
catggcctga ccccggacca agtggtggct atcgccagca acattggcgg caagcaagcg   2100
ctcgaaacgg tgcagcggct gttgccggtg ctgtgccagg accatggcct gaccccggac   2160
caagtggtgg ctatcgccag ccacgatggc ggcaagcaag cgctcgaaac ggtgcagcgg   2220
ctgttgccgg tgctgtgcca ggaccatggc ctgaccccgg accaagtggt ggctatcgcc   2280
agccacgatg gcggcaagca agcgctcgaa acggtgcagc ggctgttgcc ggtgctgtgc   2340
caggaccatg gcctgacccc ggaccaagtg gtggctatcg ccagcaacgg tggcggcaag   2400
caagcgctcg aaagcattgt ggcccagctg agccggcctg atccggcgtt ggccgcgttg   2460
accaacgacg accacctcgt cgccttggcc tgcctcggcg acgtcctgc catggatgca    2520 gtgaaaaagg gattgccgca cgcgccggaa ttgatcagaa gagtcaatcg ccgtattggc   2580
gaacgcacgt cccatcgcgt tgccggatcc aaggctagcc cgaaaaagaa acgcaaagtt   2640
gggcgcgccg acgcgctgga cgatttcgat ctcgacatgc tgggttctga tgccctcgat   2700
gactttgacc tggatatgtt gggaagcgac gcattggatg actttgatct ggacatgctc   2760
ggctccgatg ctctggacga tttcgatctc gatatgttaa ttaactaccc gtacgacgtt   2820
ccggactacg cttcttga                                                 2838
```

<210> SEQ ID NO 80
<211> LENGTH: 945
<212> TYPE: PRT
<213> ORGANISM: Unknown
<220> FEATURE:
<223> OTHER INFORMATION: Synthetic peptide

<400> SEQUENCE: 80

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
            180                 185                 190

Thr Val Gln Arg Leu Leu Pro Val Leu Cys Gln Asp His Gly Leu Thr
```

```
            195                 200                 205
Pro Asp Gln Val Val Ala Ile Ala Ser Asn Gly Gly Gly Lys Gln Ala
210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Gly Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser Asn Gly Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Ile Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620
```

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
            645                 650                 655

Ile Ala Ser His Asp Gly Gly Lys Gln Ala Leu Glu Thr Val Gln Arg
                660                 665                 670

Leu Leu Pro Val Leu Cys Gln Asp His Gly Leu Thr Pro Asp Gln Val
        675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
            725                 730                 735

Thr Val Gln Arg Leu Leu Pro Val Leu Cys Gln Asp His Gly Leu Thr
                740                 745                 750

Pro Asp Gln Val Val Ala Ile Ala Ser His Asp Gly Gly Lys Gln Ala
        755                 760                 765

Leu Glu Thr Val Gln Arg Leu Leu Pro Val Leu Cys Gln Asp His Gly
770                 775                 780

Leu Thr Pro Asp Gln Val Val Ala Ile Ala Ser Asn Gly Gly Gly Lys
785                 790                 795                 800

Gln Ala Leu Glu Ser Ile Val Ala Gln Leu Ser Arg Pro Asp Pro Ala
            805                 810                 815

Leu Ala Ala Leu Thr Asn Asp Asp His Leu Val Ala Leu Ala Cys Leu
                820                 825                 830

Gly Gly Arg Pro Ala Met Asp Ala Val Lys Lys Gly Leu Pro His Ala
        835                 840                 845

Pro Glu Leu Ile Arg Arg Val Asn Arg Arg Ile Gly Glu Arg Thr Ser
850                 855                 860

His Arg Val Ala Gly Ser Lys Ala Ser Pro Lys Lys Lys Arg Lys Val
865                 870                 875                 880

Gly Arg Ala Asp Ala Leu Asp Asp Phe Asp Leu Asp Met Leu Gly Ser
            885                 890                 895

Asp Ala Leu Asp Asp Phe Asp Leu Asp Met Leu Gly Ser Asp Ala Leu
                900                 905                 910

Asp Asp Phe Asp Leu Asp Met Leu Gly Ser Asp Ala Leu Asp Asp Phe
        915                 920                 925

Asp Leu Asp Met Leu Ile Asn Tyr Pro Tyr Asp Val Pro Asp Tyr Ala
930                 935                 940

Ser
945

<210> SEQ ID NO 81
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 81
atggactaca aagaccatga cggtgattat aaagatcatg acatcgatta caaggatgac    60
gatgacaaga tggccccccaa gaagaagagg aaggtgggcc gcggatctgt ggatctacgc   120
acgctcggct acagtcagca gcagcaagag aagatcaaac cgaaggtgcg ttcgacagtg   180

```
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagcc acgatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagcaacgg tggcggcaag caagcgctcg aaacggtgca gcggctgttg     900
ccggtgctgt gccaggacca tggcctgacc ccggaccaag tggtggctat cgccagccac     960
gatggcggca agcaagcgct cgaaacggtg cagcggctgt tgccggtgct gtgccaggac    1020
catggcctga ccccggacca agtggtggct atcgccagcc acgatggcgg caagcaagcg    1080
ctcgaaacgg tgcagcggct gttgccggtg ctgtgccagg accatggcct gaccccggac    1140
caagtggtgg ctatcgccag caacattggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tggcggcaag    1380
caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agcaacaatg gcggcaagca agcgctcgaa    1800
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca agtggtggct atcgccagcc acgatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aaagaaacgc aaagttgggc gcgccgacgc gctgacgat    2460 ttcgatctcg acatgctggg ttctgatgcc ctcgatgact tgacctgga tatgttggga    2520
```

```
agcgacgcat tggatgactt tgatctggac atgctcggct ccgatgctct ggacgatttc    2580
gatctcgata tgttaattaa ctacccgtac gacgttccgg actacgcttc ttga          2634
```

<210> SEQ ID NO 82
<211> LENGTH: 877
<212> TYPE: PRT
<213> ORGANISM: Unknown
<220> FEATURE:
<223> OTHER INFORMATION: Synthetic peptide

<400> SEQUENCE: 82

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
            35                  40                  45

Gln Glu Lys Ile Lys Pro Lys Val Arg Ser Thr Val Ala Gln His His
        50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350
```

```
Ser His Asp Gly Gly Lys Gln Ala Leu Glu Thr Val Gln Arg Leu Leu
    355                 360                 365
Pro Val Leu Cys Gln Asp His Gly Leu Thr Pro Asp Gln Val Val Ala
370                 375                 380
Ile Ala Ser Asn Ile Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Asp His Gly Leu Thr Pro Asp
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Asp His Gly Leu Thr
465                 470                 475                 480
Pro Asp Gln Val Val Ala Ile Ala Ser Asn Ile Gly Gly Lys Gln Ala
                485                 490                 495
Leu Glu Thr Val Gln Arg Leu Leu Pro Val Leu Cys Gln Asp His Gly
            500                 505                 510
Leu Thr Pro Asp Gln Val Val Ala Ile Ala Ser His Asp Gly Gly Lys
        515                 520                 525
Gln Ala Leu Glu Thr Val Gln Arg Leu Leu Pro Val Leu Cys Gln Asp
    530                 535                 540
His Gly Leu Thr Pro Asp Gln Val Val Ala Ile Ala Ser Asn Ile Gly
545                 550                 555                 560
Gly Lys Gln Ala Leu Glu Thr Val Gln Arg Leu Leu Pro Val Leu Cys
                565                 570                 575
Gln Asp His Gly Leu Thr Pro Asp Gln Val Val Ala Ile Ala Ser Asn
            580                 585                 590
Asn Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
    610                 615                 620
Ser Asn Gly Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser His Asp Gly Gly Lys Gln Ala Leu Glu Thr Val Gln Arg
            660                 665                 670
Leu Leu Pro Val Leu Cys Gln Asp His Gly Leu Thr Pro Asp Gln Val
        675                 680                 685
Val Ala Ile Ala Ser His Asp Gly Gly Lys Gln Ala Leu Glu Thr Val
    690                 695                 700
Gln Arg Leu Leu Pro Val Leu Cys Gln Asp His Gly Leu Thr Pro Asp
705                 710                 715                 720
Gln Val Val Ala Ile Ala Ser Asn Gly Gly Lys Gln Ala Leu Glu
                725                 730                 735
Ser Ile Val Ala Gln Leu Ser Arg Pro Asp Pro Ala Leu Ala Ala Leu
            740                 745                 750
Thr Asn Asp His Leu Val Ala Leu Ala Cys Leu Gly Gly Arg Pro
        755                 760                 765
```

| Ala | Met | Asp | Ala | Val | Lys | Lys | Gly | Leu | Pro | His | Ala | Pro | Glu | Leu | Ile |
|---|---|---|---|---|---|---|---|---|---|---|---|---|---|---|---|
| | 770 | | | | 775 | | | | | 780 | | | | | |

| Arg | Arg | Val | Asn | Arg | Arg | Ile | Gly | Glu | Arg | Thr | Ser | His | Arg | Val | Ala |
|---|---|---|---|---|---|---|---|---|---|---|---|---|---|---|---|
| 785 | | | | | 790 | | | | | 795 | | | | | 800 |

| Gly | Ser | Lys | Ala | Ser | Pro | Lys | Lys | Lys | Arg | Lys | Val | Gly | Arg | Ala | Asp |
|---|---|---|---|---|---|---|---|---|---|---|---|---|---|---|---|
| | | | | 805 | | | | | 810 | | | | | 815 | |

| Ala | Leu | Asp | Asp | Phe | Asp | Leu | Asp | Met | Leu | Gly | Ser | Asp | Ala | Leu | Asp |
|---|---|---|---|---|---|---|---|---|---|---|---|---|---|---|---|
| | | | 820 | | | | | 825 | | | | | 830 | | |

| Asp | Phe | Asp | Leu | Asp | Met | Leu | Gly | Ser | Asp | Ala | Leu | Asp | Phe | Asp |
|---|---|---|---|---|---|---|---|---|---|---|---|---|---|---|
| | | 835 | | | | | 840 | | | | | 845 | | |

| Leu | Asp | Met | Leu | Gly | Ser | Asp | Ala | Leu | Asp | Asp | Phe | Asp | Leu | Asp | Met |
|---|---|---|---|---|---|---|---|---|---|---|---|---|---|---|---|
| 850 | | | | | 855 | | | | | 860 | | | | | |

| Leu | Ile | Asn | Tyr | Pro | Tyr | Asp | Val | Pro | Asp | Tyr | Ala | Ser |
|---|---|---|---|---|---|---|---|---|---|---|---|---|
| 865 | | | | | 870 | | | | | 875 | | |

<210> SEQ ID NO 83
<211> LENGTH: 2532
<212> TYPE: DNA
<213> ORGANISM: Artificial sequence
<220> FEATURE:
<223> OTHER INFORMATION: Synthetic oligonucleotide

<400> SEQUENCE: 83

```
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc   360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
ctgtgccagg accatggcct gaccccggac caagtggtgg ctatcgccag ccacgatggc   660
ggcaagcaag cgctcgaaac ggtgcagcgg ctgttgccgg tgctgtgcca ggaccatggc   720
ctgaccccgg accaagtggt ggctatcgcc agcaacaatg gcggcaagca agcgctcgaa   780
acggtgcagc ggctgttgcc ggtgctgtgc caggaccatg gcctgacccc ggaccaagtg   840
gtggctatcg ccagcaacaa tggcggcaag caagcgctcg aaacggtgca gcggctgttg   900
ccggtgctgt gccaggacca tggcctgacc ccggaccaag tggtggctat cgccagccac   960
gatggcggca agcaagcgct cgaaacggtg cagcggctgt tgccggtgct gtgccaggac  1020
catgcctga ccccggacca agtggtggct atcgccagca acgtggcgg caagcaagcg  1080
ctcgaaacgg tgcagcggct gttgccggtg ctgtgccagg accatggcct gaccccggac  1140
caagtggtgg ctatcgccag caacaatggc ggcaagcaag cgctcgaaac ggtgcagcgg  1200
ctgttgccgg tgctgtgcca ggaccatggc ctgaccccgg accaagtggt ggctatcgcc  1260
agcaacaatg gcggcaagca agcgctcgaa acggtgcagc ggctgttgcc ggtgctgtgc  1320
caggaccatg gcctgacccc ggaccaagtg gtggctatcg ccagcaacat ggcggcaag  1380
caagcgctcg aaacggtgca gcggctgttg ccggtgctgt gccaggacca tggcctgacc  1440
```

```
ccggaccaag tggtggctat cgccagccac gatggcggca agcaagcgct cgaaacggtg    1500
cagcggctgt tgccggtgct gtgccaggac catggcctga ccccggacca agtggtggct    1560
atcgccagcc acgatggcgg caagcaagcg ctcgaaacgg tgcagcggct gttgccggtg    1620
ctgtgccagg accatggcct gaccccggac caagtggtgg ctatcgccag ccacgatggc    1680
ggcaagcaag cgctcgaaac ggtgcagcgg ctgttgccgg tgctgtgcca ggaccatggc    1740
ctgaccccgg accaagtggt ggctatcgcc agcaacaatg gcggcaagca agcgctcgaa    1800
acggtgcagc ggctgttgcc ggtgctgtgc caggaccatg gcctgacccc ggaccaagtg    1860
gtggctatcg ccagcaacaa tggcggcaag caagcgctcg aaacggtgca gcggctgttg    1920
ccggtgctgt gccaggacca tggcctgacc ccggaccaag tggtggctat cgccagccac    1980
gatggcggca agcaagcgct cgaaacggtg cagcggctgt tgccggtgct gtgccaggac    2040
catggcctga ccccggacca agtggtggct atcgccagca acgtggcgg caagcaagcg    2100 ctcgaaagca ttgtgcccca gctgagccgg cctgatccgg cgttggccgc gttgaccaac    2160
gacgaccacc tcgtcgcctt ggcctgcctc ggcggacgtc ctgccatgga tgcagtgaaa    2220
aagggattgc cgcacgcgcc ggaattgatc agaagagtca atcgccgtat tggcgaacgc    2280
acgtcccatc gcgttgccgg atccaaggct agcccgaaaa agaaacgcaa agttgggcgc    2340
gccgacgcgc tggacgattt cgatctcgac atgctgggtt ctgatgccct cgatgacttt    2400
gacctggata tgttgggaag cgacgcattg gatgactttg atctggacat gctcggctcc    2460
gatgctctgg acgatttcga tctcgatatg ttaattaact acccgtacga cgttccggac    2520
tacgcttctt ga                                                        2532
```

<210> SEQ ID NO 84
<211> LENGTH: 843
<212> TYPE: PRT
<213> ORGANISM: Unknown
<220> FEATURE:
<223> OTHER INFORMATION: Synthetic peptide

<400> SEQUENCE: 84

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
```

```
                    165                 170                 175
        Gln Val Val Ala Ile Ala Ser His Asp Gly Gly Lys Gln Ala Leu Glu
                    180                 185                 190

Thr Val Gln Arg Leu Leu Pro Val Leu Cys Gln Asp His Gly Leu Thr
                    195                 200                 205

Pro Asp Gln Val Val Ala Ile Ala Ser His Asp Gly Gly Lys Gln Ala
                    210                 215                 220

Leu Glu Thr Val Gln Arg Leu Leu Pro Val Leu Cys Gln Asp His Gly
        225                 230                 235                 240

Leu Thr Pro Asp Gln Val Val Ala Ile Ala Ser Asn Asn Gly Gly Lys
                            245                 250                 255

Gln Ala Leu Glu Thr Val Gln Arg Leu Leu Pro Val Leu Cys Gln Asp
                            260                 265                 270

His Gly Leu Thr Pro Asp Gln Val Val Ala Ile Ala Ser Asn Asn Gly
                            275                 280                 285

Gly Lys Gln Ala Leu Glu Thr Val Gln Arg Leu Leu Pro Val Leu Cys
                            290                 295                 300

Gln Asp His Gly Leu Thr Pro Asp Gln Val Val Ala Ile Ala Ser His
        305                 310                 315                 320

Asp Gly Gly Lys Gln Ala Leu Glu Thr Val Gln Arg Leu Leu Pro Val
                            325                 330                 335

Leu Cys Gln Asp His Gly Leu Thr Pro Asp Gln Val Val Ala Ile Ala
                            340                 345                 350

Ser Asn Gly Gly Lys Gln Ala Leu Glu Thr Val Gln Arg Leu Leu
                    355                 360                 365

Pro Val Leu Cys Gln Asp His Gly Leu Thr Pro Asp Gln Val Val Ala
                    370                 375                 380

Ile Ala Ser Asn Asn Gly Gly Lys Gln Ala Leu Glu Thr Val Gln Arg
        385                 390                 395                 400

Leu Leu Pro Val Leu Cys Gln Asp His Gly Leu Thr Pro Asp Gln Val
                            405                 410                 415

Val Ala Ile Ala Ser Asn Asn Gly Gly Lys Gln Ala Leu Glu Thr Val
                            420                 425                 430

Gln Arg Leu Leu Pro Val Leu Cys Gln Asp His Gly Leu Thr Pro Asp
                    435                 440                 445

Gln Val Val Ala Ile Ala Ser Asn Ile Gly Gly Lys Gln Ala Leu Glu
                    450                 455                 460

Thr Val Gln Arg Leu Leu Pro Val Leu Cys Gln Asp His Gly Leu Thr
        465                 470                 475                 480

Pro Asp Gln Val Val Ala Ile Ala Ser His Asp Gly Gly Lys Gln Ala
                            485                 490                 495

Leu Glu Thr Val Gln Arg Leu Leu Pro Val Leu Cys Gln Asp His Gly
                            500                 505                 510

Leu Thr Pro Asp Gln Val Val Ala Ile Ala Ser His Asp Gly Gly Lys
                            515                 520                 525

Gln Ala Leu Glu Thr Val Gln Arg Leu Leu Pro Val Leu Cys Gln Asp
                    530                 535                 540

His Gly Leu Thr Pro Asp Gln Val Val Ala Ile Ala Ser His Asp Gly
        545                 550                 555                 560

Gly Lys Gln Ala Leu Glu Thr Val Gln Arg Leu Leu Pro Val Leu Cys
                            565                 570                 575

Gln Asp His Gly Leu Thr Pro Asp Gln Val Val Ala Ile Ala Ser Asn
                    580                 585                 590
```

```
Asn Gly Gly Lys Gln Ala Leu Glu Thr Val Gln Arg Leu Leu Pro Val
        595                 600                 605
Leu Cys Gln Asp His Gly Leu Thr Pro Asp Gln Val Val Ala Ile Ala
        610                 615                 620
Ser Asn Gly Gly Lys Gln Ala Leu Glu Thr Val Gln Arg Leu Leu
625                 630                 635                 640
Pro Val Leu Cys Gln Asp His Gly Leu Thr Pro Asp Gln Val Val Ala
                645                 650                 655
Ile Ala Ser His Asp Gly Gly Lys Gln Ala Leu Glu Thr Val Gln Arg
                660                 665                 670
Leu Leu Pro Val Leu Cys Gln Asp His Gly Leu Thr Pro Asp Gln Val
        675                 680                 685
Val Ala Ile Ala Ser Asn Gly Gly Lys Gln Ala Leu Glu Ser Ile
        690                 695                 700
Val Ala Gln Leu Ser Arg Pro Asp Pro Ala Leu Ala Ala Leu Thr Asn
705                 710                 715                 720
Asp His Leu Val Ala Leu Ala Cys Leu Gly Gly Arg Pro Ala Met
                725                 730                 735
Asp Ala Val Lys Lys Gly Leu Pro His Ala Pro Glu Leu Ile Arg Arg
        740                 745                 750
Val Asn Arg Arg Ile Gly Glu Arg Thr Ser His Arg Val Ala Gly Ser
        755                 760                 765
Lys Ala Ser Pro Lys Lys Lys Arg Lys Val Gly Arg Ala Asp Ala Leu
        770                 775                 780
Asp Asp Phe Asp Leu Asp Met Leu Gly Ser Asp Ala Leu Asp Asp Phe
785                 790                 795                 800
Asp Leu Asp Met Leu Gly Ser Asp Ala Leu Asp Asp Phe Asp Leu Asp
                805                 810                 815
Met Leu Gly Ser Asp Ala Leu Asp Asp Phe Asp Leu Asp Met Leu Ile
                820                 825                 830
Asn Tyr Pro Tyr Asp Val Pro Asp Tyr Ala Ser
        835                 840

<210> SEQ ID NO 85
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 85
atggactaca aagaccatga cggtgattat aaagatcatg acatcgatta caaggatgac    60
gatgacaaga tggcccccaa gaagaagagg aaggtgggcc gcggatctgt ggatctacgc   120
acgctcggct acagtcagca gcagcaagag aagatcaaac cgaaggtgcg ttcgacagtg   180
gcgcagcacc acgaggcact ggtgggccat gggtttacac acgcgcacat cgttgcgctc   240
agccaacacc cggcagcgtt agggaccgtc gctgtcacgt atcagcacat aatcacggcg   300
ttgccagagg cgacacacga agacatcgtt ggcgtcggca acagtggtc cggcgcacgc   360
gccctggagg ccttgctcac ggatgcgggg gagttgagag tccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
```

| | |
|---|---|
| ctgtgccagg accatggcct gaccccggac caagtggtgg ctatcgccag caacaatggc | 660 |
| ggcaagcaag cgctcgaaac ggtgcagcgg ctgttgccgg tgctgtgcca ggaccatggc | 720 |
| ctgaccccgg accaagtggt ggctatcgcc agccacgatg gcggcaagca agcgctcgaa | 780 |
| acggtgcagc ggctgttgcc ggtgctgtgc caggaccatg gcctgacccc ggaccaagtg | 840 |
| gtggctatcg ccagcaacat ggcggcaag caagcgctcg aaacggtgca gcggctgttg | 900 |
| ccggtgctgt gccaggacca tggcctgacc ccggaccaag tggtggctat cgccagcaac | 960 |
| aatggcggca agcaagcgct cgaaacggtg cagcggctgt tgccggtgct gtgccaggac | 1020 |
| catggcctga ccccggacca agtggtggct atcgccagcc acgatggcgg caagcaagcg | 1080 |
| ctcgaaacgg tgcagcggct gttgccggtg ctgtgccagg accatggcct gaccccggac | 1140 |
| caagtggtgg ctatcgccag caacattggc ggcaagcaag cgctcgaaac ggtgcagcgg | 1200 |
| ctgttgccgg tgctgtgcca ggaccatggc ctgaccccgg accaagtggt ggctatcgcc | 1260 |
| agccacgatg gcggcaagca agcgctcgaa acggtgcagc ggctgttgcc ggtgctgtgc | 1320 |
| caggaccatg gcctgacccc ggaccaagtg gtggctatcg ccagccacga tggcggcaag | 1380 |
| caagcgctcg aaacggtgca gcggctgttg ccggtgctgt gccaggacca tggcctgacc | 1440 |
| ccggaccaag tggtggctat cgccagccac gatggcggca agcaagcgct cgaaacggtg | 1500 |
| cagcggctgt tgccggtgct gtgccaggac catggcctga ccccggacca agtggtggct | 1560 |
| atcgccagcc acgatggcgg caagcaagcg ctcgaaacgg tgcagcggct gttgccggtg | 1620 |
| ctgtgccagg accatggcct gaccccggac caagtggtgg ctatcgccag caacaatggc | 1680 |
| ggcaagcaag cgctcgaaac ggtgcagcgg ctgttgccgg tgctgtgcca ggaccatggc | 1740 |
| ctgaccccgg accaagtggt ggctatcgcc agccacgatg gcggcaagca agcgctcgaa | 1800 |
| acggtgcagc ggctgttgcc ggtgctgtgc caggaccatg gcctgacccc ggaccaagtg | 1860 |
| gtggctatcg ccagcaacaa tggcggcaag caagcgctcg aaacggtgca gcggctgttg | 1920 |
| ccggtgctgt gccaggacca tggcctgacc ccggaccaag tggtggctat cgccagccac | 1980 |
| gatggcggca agcaagcgct cgaaacggtg cagcggctgt gccggtgct gtgccaggac | 2040 |
| catggcctga ccccggacca agtggtggct atcgccagcc acgatggcgg caagcaagcg | 2100 |
| ctcgaaacgg tgcagcggct gttgccggtg ctgtgccagg accatggcct gaccccggac | 2160 |
| caagtggtgg ctatcgccag ccacgatggc ggcaagcaag cgctcgaaag cattgtggcc | 2220 |
| cagctgagcc ggcctgatcc ggcgttggcc gcgttgacca acgacgacca cctcgtcgcc | 2280 |
| ttggcctgcc tcggcggacg tcctgccatg gatgcagtga aaaagggatt gccgcacgcg | 2340 |
| ccggaattga tcagaagagt caatcgccgt attggcgaac gcacgtccca tcgcgttgcc | 2400 |
| ggatccaagg ctagcccgaa aaagaaacgc aaagttgggc gcgccgacgc gctgacgat | 2460 |
| ttcgatctcg acatgctggg ttctgatgcc ctcgatgact tgacctgga tatgttggga | 2520 |
| agcgacgcat ggatgacttt gatctggac atgctcggct ccgatgctct ggacgatttc | 2580 |
| gatctcgata tgttaattaa ctaccgtac gacgttccgg actacgcttc ttga | 2634 |

<210> SEQ ID NO 86
<211> LENGTH: 877
<212> TYPE: PRT
<213> ORGANISM: Unknown
<220> FEATURE:
<223> OTHER INFORMATION: Synthetic peptide

<400> SEQUENCE: 86

Met Asp Tyr Lys Asp His Asp Gly Asp Tyr Lys Asp His Asp Ile Asp

-continued

```
1               5                   10                  15
Tyr Lys Asp Asp Asp Lys Met Ala Pro Lys Lys Arg Lys Val
                20                  25                  30
Gly Arg Gly Ser Val Asp Leu Arg Thr Leu Gly Tyr Ser Gln Gln Gln
                35                  40                  45
Gln Glu Lys Ile Lys Pro Lys Val Arg Ser Thr Val Ala Gln His His
50                  55                  60
Glu Ala Leu Val Gly His Gly Phe Thr His Ala His Ile Val Ala Leu
65                  70                  75                  80
Ser Gln His Pro Ala Ala Leu Gly Thr Val Ala Val Thr Tyr Gln His
                85                  90                  95
Ile Ile Thr Ala Leu Pro Glu Ala Thr His Glu Asp Ile Val Gly Val
                100                 105                 110
Gly Lys Gln Trp Ser Gly Ala Arg Ala Leu Glu Ala Leu Leu Thr Asp
                115                 120                 125
Ala Gly Glu Leu Arg Gly Pro Pro Leu Gln Leu Asp Thr Gly Gln Leu
                130                 135                 140
Val Lys Ile Ala Lys Arg Gly Gly Val Thr Ala Met Glu Ala Val His
145                 150                 155                 160
Ala Ser Arg Asn Ala Leu Thr Gly Ala Pro Leu Asn Leu Thr Pro Asp
                165                 170                 175
Gln Val Val Ala Ile Ala Ser His Asp Gly Gly Lys Gln Ala Leu Glu
                180                 185                 190
Thr Val Gln Arg Leu Leu Pro Val Leu Cys Gln Asp His Gly Leu Thr
                195                 200                 205
Pro Asp Gln Val Val Ala Ile Ala Ser Asn Asn Gly Gly Lys Gln Ala
210                 215                 220
Leu Glu Thr Val Gln Arg Leu Leu Pro Val Leu Cys Gln Asp His Gly
225                 230                 235                 240
Leu Thr Pro Asp Gln Val Val Ala Ile Ala Ser His Asp Gly Gly Lys
                245                 250                 255
Gln Ala Leu Glu Thr Val Gln Arg Leu Leu Pro Val Leu Cys Gln Asp
                260                 265                 270
His Gly Leu Thr Pro Asp Gln Val Val Ala Ile Ala Ser Asn Ile Gly
                275                 280                 285
Gly Lys Gln Ala Leu Glu Thr Val Gln Arg Leu Leu Pro Val Leu Cys
                290                 295                 300
Gln Asp His Gly Leu Thr Pro Asp Gln Val Val Ala Ile Ala Ser Asn
305                 310                 315                 320
Asn Gly Gly Lys Gln Ala Leu Glu Thr Val Gln Arg Leu Leu Pro Val
                325                 330                 335
Leu Cys Gln Asp His Gly Leu Thr Pro Asp Gln Val Val Ala Ile Ala
                340                 345                 350
Ser His Asp Gly Gly Lys Gln Ala Leu Glu Thr Val Gln Arg Leu Leu
                355                 360                 365
Pro Val Leu Cys Gln Asp His Gly Leu Thr Pro Asp Gln Val Val Ala
                370                 375                 380
Ile Ala Ser Asn Ile Gly Gly Lys Gln Ala Leu Glu Thr Val Gln Arg
385                 390                 395                 400
Leu Leu Pro Val Leu Cys Gln Asp His Gly Leu Thr Pro Asp Gln Val
                405                 410                 415
Val Ala Ile Ala Ser His Asp Gly Gly Lys Gln Ala Leu Glu Thr Val
                420                 425                 430
```

```
Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser His Asp Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Asn Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Phe Asp
        835                 840                 845
```

Leu Asp Met Leu Gly Ser Asp Ala Leu Asp Asp Phe Asp Leu Asp Met
850                 855                 860

Leu Ile Asn Tyr Pro Tyr Asp Val Pro Asp Tyr Ala Ser
865                 870                 875

<210> SEQ ID NO 87
<211> LENGTH: 2736
<212> TYPE: DNA
<213> ORGANISM: Artificial sequence
<220> FEATURE:
<223> OTHER INFORMATION: Synthetic oligonucleotide

<400> SEQUENCE: 87

| | |
|---|---|
| atggactaca aagaccatga cggtgattat aaagatcatg acatcgatta caaggatgac | 60 |
| gatgacaaga tggcccccaa gaagaagagg aaggtgggcc gcggatctgt ggatctacgc | 120 |
| acgctcggct acagtcagca gcagcaagag aagatcaaac cgaaggtgcg ttcgacagtg | 180 |
| gcgcagcacc acgaggcact ggtgggccat gggtttacac acgcgcacat cgttgcgctc | 240 |
| agccaacacc cggcagcgtt agggaccgtc gctgtcacgt atcagcacat aatcacggcg | 300 |
| ttgccagagg cgacacacga agacatcgtt ggcgtcggca acagtggtc cggcgcacgc | 360 |
| gccctggagg ccttgctcac ggatgcgggg gagttgagag gtccgccgtt acagttggac | 420 |
| acaggccaac ttgtgaagat tgcaaaacgt ggcggcgtga ccgcaatgga ggcagtgcat | 480 |
| gcatcgcgca tgcactgac gggtgccccc ctgaacctga ccccggacca agtggtggct | 540 |
| atcgccagcc acgatggcgg caagcaagcg ctcgaaacgg tgcagcggct gttgccggtg | 600 |
| ctgtgccagg accatggcct gaccccggac caagtggtgg ctatcgccag ccacgatggc | 660 |
| ggcaagcaag cgctcgaaac ggtgcagcgg ctgttgccgg tgctgtgcca ggaccatggc | 720 |
| ctgaccccgg accaagtggt ggctatcgcc agccacgatg gcggcaagca agcgctcgaa | 780 |
| acggtgcagc ggctgttgcc ggtgctgtgc caggaccatg gcctgacccc ggaccaagtg | 840 |
| gtggctatcg ccagcaacat tggcggcaag aagcgctcg aaacggtgca gcggctgttg | 900 |
| ccggtgctgt gccaggacca tggcctgacc ccggaccaag tggtggctat cgccagccac | 960 |
| gatggcggca agcaagcgct cgaaacggtg cagcggctgt tgccggtgct gtgccaggac | 1020 |
| catggcctga ccccggacca agtggtggct atcgccagca caatggcgg caagcaagcg | 1080 |
| ctcgaaacgg tgcagcggct gttgccggtg ctgtgccagg accatggcct gaccccggac | 1140 |
| caagtggtgg ctatcgccag caacaatggc ggcaagcaag cgctcgaaac ggtgcagcgg | 1200 |
| ctgttgccgg tgctgtgcca ggaccatggc ctgaccccgg accaagtggt ggctatcgcc | 1260 |
| agcaacaatg gcggcaagca agcgctcgaa acggtgcagc ggctgttgcc ggtgctgtgc | 1320 |
| caggaccatg gcctgacccc ggaccaagtg gtggctatcg ccagcaacaa tggcggcaag | 1380 |
| caagcgctcg aaacggtgca gcggctgttg ccggtgctgt gccaggacca tggcctgacc | 1440 |
| ccggaccaag tggtggctat cgccagccac gatggcggca agcaagcgct cgaaacggtg | 1500 |
| cagcggctgt tgccggtgct gtgccaggac catggcctga ccccggacca agtggtggct | 1560 |
| atcgccagcc acgatggcgg caagcaagcg ctcgaaacgg tgcagcggct gttgccggtg | 1620 |
| ctgtgccagg accatggcct gaccccggac caagtggtgg ctatcgccag ccacgatggc | 1680 |
| ggcaagcaag cgctcgaaac ggtgcagcgg ctgttgccgg tgctgtgcca ggaccatggc | 1740 |
| ctgaccccgg accaagtggt ggctatcgcc agcaacggtg gcggcaagca agcgctcgaa | 1800 |
| acggtgcagc ggctgttgcc ggtgctgtgc caggaccatg gcctgacccc ggaccaagtg | 1860 |
| gtggctatcg ccagcaacgg tggcggcaag caagcgctcg aaacggtgca gcggctgttg | 1920 |

-continued

```
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca acattggcgg caagcaagcg    2100
ctcgaaacgg tgcagcggct gttgccggtg ctgtgccagg accatggcct gaccccggac    2160
caagtggtgg ctatcgccag ccacgatggc ggcaagcaag cgctcgaaac ggtgcagcgg    2220
ctgttgccgg tgctgtgcca ggaccatggc ctgaccccgg accaagtggt ggctatcgcc    2280
agcaacggtg gcggcaagca agcgctcgaa agcattgtgg cccagctgag ccggcctgat    2340
ccggcgttgg ccgcgttgac caacgacgac cacctcgtcg ccttggcctg cctcggcgga    2400
cgtcctgcca tggatgcagt gaaaaaggga ttgccgcacg cgccggaatt gatcagaaga    2460
gtcaatcgcc gtattggcga acgcacgtcc atcgcgttg ccggatccaa ggctagcccg    2520
aaaaagaaac gcaaagttgg gcgcgccgac gcgctggacg atttcgatct cgacatgctg    2580
ggttctgatg ccctcgatga ctttgacctg gatatgttgg aagcgacgc attggatgac    2640 tttgatctgg acatgctcgg ctccgatgct ctggacgatt cgatctcga tatgttaatt    2700 aactacccgt acgacgttcc ggactacgct tcttga                              2736
```

<210> SEQ ID NO 88
<211> LENGTH: 911
<212> TYPE: PRT
<213> ORGANISM: Unknown
<220> FEATURE:
<223> OTHER INFORMATION: Synthetic peptide

<400> SEQUENCE: 88

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
                20                  25                  30

Gly Arg Gly Ser Val Asp Leu Arg Thr Leu Gly Tyr Ser Gln Gln Gln
                35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
                180                 185                 190

Thr Val Gln Arg Leu Leu Pro Val Leu Cys Gln Asp His Gly Leu Thr
            195                 200                 205

Pro Asp Gln Val Val Ala Ile Ala Ser His Asp Gly Gly Lys Gln Ala
```

-continued

```
            210                 215                 220
Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Ile Gly
        275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Asn Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser Asn Asn Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser His Asp Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser His Asp Gly Gly Lys
            515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Gly Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
610                 615                 620

Ser Asn Gly Gly Gly Lys Gln Ala Leu Glu Thr Val Gln Arg Leu Leu
625                 630                 635                 640
```

Pro Val Leu Cys Gln Asp His Gly Leu Thr Pro Asp Gln Val Val Ala
                645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
            675                 680                 685

Val Ala Ile Ala Ser Asn Ile Gly Gly Lys Gln Ala Leu Glu Thr Val
        690                 695                 700

Gln Arg Leu Leu Pro Val Leu Cys Gln Asp His Gly Leu Thr Pro Asp
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Asp His Gly Leu Thr
            740                 745                 750

Pro Asp Gln Val Val Ala Ile Ala Ser Asn Gly Gly Gly Lys Gln Ala
        755                 760                 765

Leu Glu Ser Ile Val Ala Gln Leu Ser Arg Pro Asp Pro Ala Leu Ala
    770                 775                 780

Ala Leu Thr Asn Asp His Leu Val Ala Leu Ala Cys Leu Gly Gly
785                 790                 795                 800

Arg Pro Ala Met Asp Ala Val Lys Lys Gly Leu Pro His Ala Pro Glu
                805                 810                 815

Leu Ile Arg Arg Val Asn Arg Arg Ile Gly Glu Arg Thr Ser His Arg
            820                 825                 830

Val Ala Gly Ser Lys Ala Ser Pro Lys Lys Lys Arg Lys Val Gly Arg
        835                 840                 845

Ala Asp Ala Leu Asp Asp Phe Asp Leu Asp Met Leu Gly Ser Asp Ala
    850                 855                 860

Leu Asp Asp Phe Asp Leu Asp Met Leu Gly Ser Asp Ala Leu Asp Asp
865                 870                 875                 880

Phe Asp Leu Asp Met Leu Gly Ser Asp Ala Leu Asp Asp Phe Asp Leu
                885                 890                 895

Asp Met Leu Ile Asn Tyr Pro Tyr Asp Val Pro Asp Tyr Ala Ser
            900                 905                 910

<210> SEQ ID NO 89
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 89
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540

```
atcgccagcc acgatggcgg caagcaagcg ctcgaaacgg tgcagcggct gttgccggtg    600
ctgtgccagg accatggcct gaccccggac caagtggtgg ctatcgccag ccacgatggc    660
ggcaagcaag cgctcgaaac ggtgcagcgg ctgttgccgg tgctgtgcca ggaccatggc    720
ctgaccccgg accaagtggt ggctatcgcc agccacgatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
ggtggcggca agcaagcgct cgaaacggtg cagcggctgt tgccggtgct gtgccaggac   1020
catggcctga ccccggacca agtggtggct atcgccagca acaatggcgg caagcaagcg   1080
ctcgaaacgg tgcagcggct gttgccggtg ctgtgccagg accatggcct gaccccggac   1140
caagtggtgg ctatcgccag caacaatggc ggcaagcaag cgctcgaaac ggtgcagcgg   1200
ctgttgccgg tgctgtgcca ggaccatggc ctgaccccgg accaagtggt ggctatcgcc   1260
agcaacggtg cggcaagca agcgctcgaa acggtgcagc ggctgttgcc ggtgctgtgc   1320
caggaccatg gcctgacccc ggaccaagtg gtggctatcg ccagcaacgg tggcggcaag   1380
caagcgctcg aaacggtgca gcggctgttg ccggtgctgt gccaggacca tggcctgacc   1440
ccggaccaag tggtggctat cgccagcaac ggtggcggca agcaagcgct cgaaacggtg   1500
cagcggctgt tgccggtgct gtgccaggac catggcctga ccccggacca agtggtggct   1560
atcgccagcc acgatggcgg caagcaagcg ctcgaaacgg tgcagcggct gttgccggtg   1620
ctgtgccagg accatggcct gaccccggac caagtggtgg ctatcgccag caacggtggc   1680
ggcaagcaag cgctcgaaac ggtgcagcgg ctgttgccgg tgctgtgcca ggaccatggc   1740
ctgaccccgg accaagtggt ggctatcgcc agccacgatg gcggcaagca agcgctcgaa   1800
acggtgcagc ggctgttgcc ggtgctgtgc caggaccatg gcctgacccc ggaccaagtg   1860
gtggctatcg ccagccacga tggcggcaag caagcgctcg aaacggtgca gcggctgttg   1920
ccggtgctgt gccaggacca tggcctgacc ccggaccaag tggtggctat cgccagcaac   1980
aatggcggca agcaagcgct cgaaacggtg cagcggctgt tgccggtgct gtgccaggac   2040
catggcctga ccccggacca agtggtggct atcgccagca acaatggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcg gcctgatcc ggcgttggcc gcgttgacca cgacgacca cctcgtcgcc   2280
ttggcctgcc tcggcggacg tcctgccatg gatgcagtga aaagggatt gccgcacgcg   2340
ccggaattga tcagaagagt caatcgccgt attggcgaac gcacgtccca tcgcgttgcc   2400
ggatccaagg ctagcccgaa aaagaaacgc aaagttgggc gcgccgacgc gctggacgat   2460
ttcgatctcg acatgctggg ttctgatgcc ctcgatgact tgacctgga tatgttggga   2520
agcgacgcat tggatgactt tgatctggac atgctcggct ccgatgctct ggacgatttc   2580
gatctcgata tgttaattaa ctacccgtac gacgttccgg actacgcttc ttga         2634
```

<210> SEQ ID NO 90
<211> LENGTH: 877
<212> TYPE: PRT
<213> ORGANISM: Unknown
<220> FEATURE:
<223> OTHER INFORMATION: Synthetic peptide

```
<400> SEQUENCE: 90

Met Asp Tyr Lys Asp His Asp Gly Asp Tyr Lys Asp His Asp Ile Asp
 1               5                  10                  15

Tyr Lys Asp Asp Asp Asp Lys Met Ala Pro Lys Lys Lys Arg Lys Val
                 20                  25                  30

Gly Arg Gly Ser Val Asp Leu Arg Thr Leu Gly Tyr Ser Gln Gln Gln
             35                  40                  45

Gln Glu Lys Ile Lys Pro Lys Val Arg Ser Thr Val Ala Gln His His
 50                  55                  60

Glu Ala Leu Val Gly His Gly Phe Thr His Ala His Ile Val Ala Leu
 65                  70                  75                  80

Ser Gln His Pro Ala Ala Leu Gly Thr Val Ala Val Thr Tyr Gln His
                 85                  90                  95

Ile Ile Thr Ala Leu Pro Glu Ala Thr His Glu Asp Ile Val Gly Val
             100                 105                 110

Gly Lys Gln Trp Ser Gly Ala Arg Ala Leu Glu Ala Leu Leu Thr Asp
             115                 120                 125

Ala Gly Glu Leu Arg Gly Pro Pro Leu Gln Leu Asp Thr Gly Gln Leu
 130                 135                 140

Val Lys Ile Ala Lys Arg Gly Gly Val Thr Ala Met Glu Ala Val His
 145                 150                 155                 160

Ala Ser Arg Asn Ala Leu Thr Gly Ala Pro Leu Asn Leu Thr Pro Asp
                 165                 170                 175

Gln Val Val Ala Ile Ala Ser His Asp Gly Gly Lys Gln Ala Leu Glu
             180                 185                 190

Thr Val Gln Arg Leu Leu Pro Val Leu Cys Gln Asp His Gly Leu Thr
             195                 200                 205

Pro Asp Gln Val Val Ala Ile Ala Ser His Asp Gly Gly Lys Gln Ala
 210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                 245                 250                 255

Gln Ala Leu Glu Thr Val Gln Arg Leu Leu Pro Val Leu Cys Gln Asp
             260                 265                 270

His Gly Leu Thr Pro Asp Gln Val Val Ala Ile Ala Ser His Asp Gly
             275                 280                 285

Gly Lys Gln Ala Leu Glu Thr Val Gln Arg Leu Leu Pro Val Leu Cys
 290                 295                 300

Gln Asp His Gly Leu Thr Pro Asp Gln Val Val Ala Ile Ala Ser Asn
305                 310                 315                 320

Gly Gly Gly Lys Gln Ala Leu Glu Thr Val Gln Arg Leu Leu Pro Val
                 325                 330                 335

Leu Cys Gln Asp His Gly Leu Thr Pro Asp Gln Val Val Ala Ile Ala
             340                 345                 350

Ser Asn Asn Gly Gly Lys Gln Ala Leu Glu Thr Val Gln Arg Leu Leu
             355                 360                 365

Pro Val Leu Cys Gln Asp His Gly Leu Thr Pro Asp Gln Val Val Ala
 370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                 405                 410                 415
```

```
Val Ala Ile Ala Ser Asn Gly Gly Lys Gln Ala Leu Glu Thr Val
            420                 425                 430

Gln Arg Leu Leu Pro Val Leu Cys Gln Asp His Gly Leu Thr Pro Asp
            435                 440                 445

Gln Val Val Ala Ile Ala Ser Asn Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser His Asp Gly Gly Lys
                515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
                580                 585                 590

Asp Gly Gly Lys Gln Ala Leu Glu Thr Val Gln Arg Leu Leu Pro Val
                595                 600                 605

Leu Cys Gln Asp His Gly Leu Thr Pro Asp Gln Val Val Ala Ile Ala
                610                 615                 620

Ser His Asp Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Asn Gly Gly Lys Gln Ala Leu Glu Thr Val Gln Arg
                660                 665                 670

Leu Leu Pro Val Leu Cys Gln Asp His Gly Leu Thr Pro Asp Gln Val
                675                 680                 685

Val Ala Ile Ala Ser Asn Asn Gly Gly Lys Gln Ala Leu Glu Thr Val
                690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
                725                 730                 735

Ser Ile Val Ala Gln Leu Ser Arg Pro Asp Pro Ala Leu Ala Ala Leu
                740                 745                 750

Thr Asn Asp His Leu Val Ala Leu Ala Cys Leu Gly Gly Arg Pro
                755                 760                 765

Ala Met Asp Ala Val Lys Lys Gly Leu Pro His Ala Pro Glu Leu Ile
                770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Ala Leu Asp
                820                 825                 830
```

```
Asp Phe Asp Leu Asp Met Leu Gly Ser Asp Ala Leu Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 91
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 91
atggactaca aagaccatga cggtgattat aaagatcatg acatcgatta caaggatgac      60
gatgacaaga tggcccccaa gaagaagagg aaggtgggcc gcggatctgt ggatctacgc     120
acgctcggct acagtcagca gcagcaagag aagatcaaac cgaaggtgcg ttcgacagtg     180
gcgcagcacc acgaggcact ggtgggccat gggtttacac acgcgcacat cgttgcgctc     240
agccaacacc cggcagcgtt agggaccgtc gctgtcacgt atcagcacat aatcacggcg     300
ttgccagagg cgacacacga agacatcgtt ggcgtcggca acagtggtc cggcgcacgc      360 gccctggagg ccttgctcac ggatgcgggg gagttgagag gtccgccgtt acagttggac     420
acaggccaac ttgtgaagat tgcaaaacgt ggcggcgtga ccgcaatgga ggcagtgcat     480
gcatcgcgca atgcactgac gggtgccccc ctgaacctga ccccggacca agtggtggct     540
atcgccagca acaatggcgg caagcaagcg ctcgaaacgg tgcagcggct gttgccggtg     600
ctgtgccagg accatggcct gaccccggac caagtggtgg ctatcgccag ccacgatggc     660
ggcaagcaag cgctcgaaac ggtgcagcgg ctgttgccgg tgctgtgcca ggaccatggc     720
ctgaccccgg accaagtggt ggctatcgcc agccacgatg gcggcaagca agcgctcgaa     780
acggtgcagc ggctgttgcc ggtgctgtgc caggaccatg gcctgacccc ggaccaagtg     840
gtggctatcg ccagcaacat tggcggcaag caagcgctcg aaacggtgca gcggctgttg     900
ccggtgctgt gccaggacca tggcctgacc ccggaccaag tggtggctat cgccagccac     960
gatggcggca agcaagcgct cgaaacggtg cagcggctgt tgccggtgct gtgccaggac    1020
catggcctga ccccggacca agtggtggct atcgccagca acgtggcgg caagcaagcg     1080 ctcgaaacgg tgcagcggct gttgccggtg ctgtgccagg accatggcct gaccccggac    1140
caagtggtgg ctatcgccag ccacgatggc ggcaagcaag cgctcgaaac ggtgcagcgg    1200
ctgttgccgg tgctgtgcca ggaccatggc ctgaccccgg accaagtggt ggctatcgcc    1260
agccacgatg gcggcaagca agcgctcgaa acggtgcagc ggctgttgcc ggtgctgtgc    1320
caggaccatg gcctgacccc ggaccaagtg gtggctatcg ccagccacga tgcggcaag    1380 caagcgctcg aaacggtgca gcggctgttg ccggtgctgt gccaggacca tggcctgacc    1440
ccggaccaag tggtggctat cgccagcaac attggcggca agcaagcgct cgaaacggtg    1500
cagcggctgt tgccggtgct gtgccaggac catggcctga ccccggacca agtggtggct    1560
atcgccagca acaatggcgg caagcaagcg ctcgaaacgg tgcagcggct gttgccggtg    1620
ctgtgccagg accatggcct gaccccggac caagtggtgg ctatcgccag caacattggc    1680
ggcaagcaag cgctcgaaac ggtgcagcgg ctgttgccgg tgctgtgcca ggaccatggc    1740
ctgaccccgg accaagtggt ggctatcgcc agccacgatg gcggcaagca agcgctcgaa    1800
```

```
acggtgcagc ggctgttgcc ggtgctgtgc caggaccatg gcctgacccc ggaccaagtg    1860
gtggctatcg ccagcaacgg tggcggcaag caagcgctcg aaacggtgca gcggctgttg    1920
ccggtgctgt gccaggacca tggcctgacc ccggaccaag tggtggctat cgccagcaac    1980
ggtggcggca agcaagcgct cgaaacggtg cagcggctgt tgccggtgct gtgccaggac    2040
catggcctga ccccggacca agtggtggct atcgccagca acaatggcgg caagcaagcg    2100
ctcgaaacgg tgcagcggct gttgccggtg ctgtgccagg accatggcct gaccccggac    2160
caagtggtgg ctatcgccag caacggtggc ggcaagcaag cgctcgaaag cattgtggcc    2220
cagctgagcc ggcctgatcc ggcgttggcc gcgttgacca acgacgacca cctcgtcgcc    2280
ttggcctgcc tcggcggacg tcctgccatg gatgcagtga aaaagggatt gccgcacgcg    2340
ccggaattga tcagaagagt caatcgccgt attggcgaac gcacgtccca tcgcgttgcc    2400
ggatccaagg ctagcccgaa aaagaaacgc aaagttgggc gcgccgacgc gctggacgat    2460
ttcgatctcg acatgctggg ttctgatgcc ctcgatgact tgacctgga tatgttggga    2520 agcgacgcat tggatgactt tgatctggac atgctcggct ccgatgctct ggacgatttc    2580
gatctcgata tgttaattaa ctacccgtac gacgttccgg actacgcttc ttga          2634
```

<210> SEQ ID NO 92
<211> LENGTH: 877
<212> TYPE: PRT
<213> ORGANISM: Unknown
<220> FEATURE:
<223> OTHER INFORMATION: Synthetic peptide

<400> SEQUENCE: 92

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser Asn Asn Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
    210                 215                 220
```

-continued

```
Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
            245                 250                 255

Gln Ala Leu Glu Thr Val Gln Arg Leu Leu Pro Val Leu Cys Gln Asp
        260                 265                 270

His Gly Leu Thr Pro Asp Gln Val Val Ala Ile Ala Ser Asn Ile Gly
    275                 280                 285

Gly Lys Gln Ala Leu Glu Thr Val Gln Arg Leu Leu Pro Val Leu Cys
290                 295                 300

Gln Asp His Gly Leu Thr Pro Asp Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Gly Gly Gly Lys Gln Ala Leu Glu Thr Val Gln Arg Leu Leu
        355                 360                 365

Pro Val Leu Cys Gln Asp His Gly Leu Thr Pro Asp Gln Val Val Ala
    370                 375                 380

Ile Ala Ser His Asp Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Gly Gly Lys
        515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Ile Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Gly Gly Gly Lys Gln Ala Leu Glu Thr Val Gln Arg Leu Leu
625                 630                 635                 640
```

```
Pro Val Leu Cys Gln Asp His Gly Leu Thr Pro Asp Gln Val Val Ala
            645                 650                 655

Ile Ala Ser Asn Gly Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser Asn Asn Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
    770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 93
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 93
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240
agccaacacc cggcagcgtt agggaccgtc gctgtcacgt atcagcacat aatcacggcg    300
ttgccagagg cgacacacga agacatcgtt ggcgtcggca aacagtggtc cggcgcacgc    360
gccctggagg ccttgctcac ggatgcgggg gagttgagag gtccgccgtt acagttggac    420
acaggccaac ttgtgaagat tgcaaaacgt ggcggcgtga ccgcaatgga ggcagtgcat    480
gcatcgcgca atgcactgac gggtgcccccc ctgaacctga ccccggacca agtggtggct    540
atcgccagcc acgatggcgg caagcaagcg ctcgaaacgg tgcagcggct gttgccggtg    600
ctgtgccagg accatggcct gaccccggac caagtggtgg ctatcgccag caacggtggc    660
ggcaagcaag cgctcgaaac ggtgcagcgg ctgttgccgg tgctgtgcca ggaccatggc    720
```

```
ctgaccccgg accaagtggt ggctatcgcc agcaacaatg gcggcaagca agcgctcgaa    780
acggtgcagc ggctgttgcc ggtgctgtgc caggaccatg gcctgacccc ggaccaagtg    840
gtggctatcg ccagccacga tggcggcaag caagcgctcg aaacggtgca gcggctgttg    900
ccggtgctgt gccaggacca tggcctgacc ccggaccaag tggtggctat cgccagcaac    960
attggcggca agcaagcgct cgaaacggtg cagcggctgt tgccggtgct gtgccaggac   1020
catggcctga ccccggacca agtggtggct atcgccagca acggtggcgg caagcaagcg   1080
ctcgaaacgg tgcagcggct gttgccggtg ctgtgccagg accatggcct gaccccggac   1140
caagtggtgg ctatcgccag caacggtggc ggcaagcaag cgctcgaaac ggtgcagcgg   1200
ctgttgccgg tgctgtgcca ggaccatggc ctgaccccgg accaagtggt ggctatcgcc   1260
agcaacggtg gcggcaagca agcgctcgaa acggtgcagc ggctgttgcc ggtgctgtgc   1320
caggaccatg gcctgacccc ggaccaagtg gtggctatcg ccagcaacat ggcggcaag   1380
caagcgctcg aaacggtgca gcggctgttg ccggtgctgt gccaggacca tggcctgacc   1440
ccggaccaag tggtggctat cgccagcaac aatggcggca agcaagcgct cgaaacggtg   1500
cagcggctgt tgccggtgct gtgccaggac catggcctga ccccggacca agtggtggct   1560
atcgccagca acaatggcgg caagcaagcg ctcgaaacgg tgcagcggct gttgccggtg   1620
ctgtgccagg accatggcct gaccccggac caagtggtgg ctatcgccag caacaatggc   1680
ggcaagcaag cgctcgaaac ggtgcagcgg ctgttgccgg tgctgtgcca ggaccatggc   1740
ctgaccccgg accaagtggt ggctatcgcc agcaacattg cggcaagca agcgctcgaa   1800
acggtgcagc ggctgttgcc ggtgctgtgc caggaccatg gcctgacccc ggaccaagtg   1860
gtggctatcg ccagcaacgg tggcggcaag caagcgctcg aaacggtgca gcggctgttg   1920
ccggtgctgt gccaggacca tggcctgacc ccggaccaag tggtggctat cgccagcaac   1980
ggtggcggca agcaagcgct cgaaacggtg cagcggctgt gccggtgct gtgccaggac   2040
catggcctga ccccggacca gtggtggct atcgccagcc acgatggcgg caagcaagcg   2100
ctcgaaacgg tgcagcggct gttgccggtg ctgtgccagg accatggcct gaccccggac   2160
caagtggtgg ctatcgccag caacggtggc ggcaagcaag cgctcgaaag cattgtggcc   2220
cagctgagcc ggcctgatcc ggcgttggcc gcgttgacca cgacgacca cctcgtcgcc   2280
ttggcctgcc tcggcggacg tcctgccatg gatgcagtga aaaagggatt gccgcacgcg   2340
ccggaattga tcagaagagt caatcgccgt attggcgaac gcacgtccca tcgcgttgcc   2400
ggatccaagg ctagcccgaa aaagaaacgc aaagttgggc gcgccgacgc gctggacgat   2460
ttcgatctcg acatgctggg ttctgatgcc ctcgatgact tgacctgga tatgttggga   2520
agcgacgcat tggatgactt tgatctggac atgctcggct ccgatgctct ggacgatttc   2580
gatctcgata tgttaattaa ctacccgtac gacgttccgg actacgcttc ttga         2634
```

<210> SEQ ID NO 94
<211> LENGTH: 877
<212> TYPE: PRT
<213> ORGANISM: Unknown
<220> FEATURE:
<223> OTHER INFORMATION: Synthetic peptide

<400> SEQUENCE: 94

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

```
Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
                100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
            130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
                180                 185                 190

Thr Val Gln Arg Leu Leu Pro Val Leu Cys Gln Asp His Gly Leu Thr
            195                 200                 205

Pro Asp Gln Val Val Ala Ile Ala Ser Asn Gly Gly Gly Lys Gln Ala
            210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser His Asp Gly
            275                 280                 285

Gly Lys Gln Ala Leu Glu Thr Val Gln Arg Leu Leu Pro Val Leu Cys
            290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Gly Gly Lys Gln Ala Leu Glu Thr Val Gln Arg Leu Leu
                355                 360                 365

Pro Val Leu Cys Gln Asp His Gly Leu Thr Pro Asp Gln Val Val Ala
    370                 375                 380

Ile Ala Ser Asn Gly Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Gly Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445
```

```
Gln Val Ala Ile Ala Ser Asn Ile Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Asn Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
        515                 520                 525

Gln Ala Leu Glu Thr Val Gln Arg Leu Leu Pro Val Leu Cys Gln Asp
530                 535                 540

His Gly Leu Thr Pro Asp Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser Asn Gly Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
770                 775                 780

Arg Arg Val Asn Arg Arg Ile Gly Glu Arg Thr Ser His Arg Val Ala
785                 790                 795                 800

Gly Ser Lys Ala Ser Pro Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Phe Asp
        835                 840                 845

Leu Asp Met Leu Gly Ser Asp Ala Leu Asp Asp Phe Asp Leu Asp Met
850                 855                 860

Leu Ile Asn Tyr Pro Tyr Asp Val Pro Asp Tyr Ala Ser
```

<210> SEQ ID NO 95
<211> LENGTH: 2838
<212> TYPE: DNA
<213> ORGANISM: Artificial sequence
<220> FEATURE:
<223> OTHER INFORMATION: Synthetic oligonucleotide

<400> SEQUENCE: 95

| | |
|---|---|
| atggactaca aagaccatga cggtgattat aaagatcatg acatcgatta caaggatgac | 60 |
| gatgacaaga tggcccccaa gaagaagagg aaggtgggcc gcggatctgt ggatctacgc | 120 |
| acgctcggct acagtcagca gcagcaagag aagatcaaac cgaaggtgcg ttcgacagtg | 180 |
| gcgcagcacc acgaggcact ggtgggccat gggtttacac acgcgcacat cgttgcgctc | 240 |
| agccaacacc cggcagcgtt agggaccgtc gctgtcacgt atcagcacat aatcacggcg | 300 |
| ttgccagagg cgacacacga agacatcgtt ggcgtcggca acagtggtc cggcgcacgc | 360 |
| gccctggagg ccttgctcac ggatgcgggg gagttgagg gtccgccgtt acagttggac | 420 |
| acaggccaac ttgtgaagat tgcaaaacgt ggcggcgtga ccgcaatgga ggcagtgcat | 480 |
| gcatcgcgca atgcactgac gggtgccccc ctgaacctga ccccggacca agtggtggct | 540 |
| atcgccagcc acgatggcgg caagcaagcg ctcgaaacgg tgcagcggct gttgccggtg | 600 |
| ctgtgccagg accatggcct gaccccggac caagtggtgg ctatcgccag ccacgatggc | 660 |
| ggcaagcaag cgctcgaaac ggtgcagcgg ctgttgccgg tgctgtgcca ggaccatggc | 720 |
| ctgaccccgg accaagtggt ggctatcgcc agccacgatg gcggcaagca agcgctcgaa | 780 |
| acggtgcagc ggctgttgcc ggtgctgtgc caggaccatg gcctgacccc ggaccaagtg | 840 |
| gtggctatcg ccagccacga tggcggcaag caagcgctcg aaacggtgca gcggctgttg | 900 |
| ccggtgctgt gccaggacca tggcctgacc ccggaccaag tggtggctat cgccagcaac | 960 |
| attggcggca agcaagcgct cgaaacggtg cagcggctgt tgccggtgct gtgccaggac | 1020 |
| catggcctga ccccggacca agtggtggct atcgccagca acaatggcgg caagcaagcg | 1080 |
| ctcgaaacgg tgcagcggct gttgccggtg ctgtgccagg accatggcct gaccccggac | 1140 |
| caagtggtgg ctatcgccag caacaatggc ggcaagcaag cgctcgaaac ggtgcagcgg | 1200 |
| ctgttgccgg tgctgtgcca ggaccatggc ctgaccccgg accaagtggt ggctatcgcc | 1260 |
| agcaacattg gcggcaagca agcgctcgaa acggtgcagc ggctgttgcc ggtgctgtgc | 1320 |
| caggaccatg gcctgacccc ggaccaagtg gtggctatcg ccagcaacat tggcggcaag | 1380 |
| caagcgctcg aaacggtgca gcggctgttg ccggtgctgt gccaggacca tggcctgacc | 1440 |
| ccggaccaag tggtggctat cgccagcaac attggcggca agcaagcgct cgaaacggtg | 1500 |
| cagcggctgt tgccggtgct gtgccaggac catggcctga ccccggacca agtggtggct | 1560 |
| atcgccagca acaatggcgg caagcaagcg ctcgaaacgg tgcagcggct gttgccggtg | 1620 |
| ctgtgccagg accatggcct gaccccggac caagtggtgg ctatcgccag caacggtggc | 1680 |
| ggcaagcaag cgctcgaaac ggtgcagcgg ctgttgccgg tgctgtgcca ggaccatggc | 1740 |
| ctgaccccgg accaagtggt ggctatcgcc agcaacggtg gcggcaagca agcgctcgaa | 1800 |
| acggtgcagc ggctgttgcc ggtgctgtgc caggaccatg gcctgacccc ggaccaagtg | 1860 |
| gtggctatcg ccagcaacgg tggcggcaag caagcgctcg aaacggtgca gcggctgttg | 1920 |
| ccggtgctgt gccaggacca tggcctgacc ccggaccaag tggtggctat cgccagcaac | 1980 |
| attggcggca agcaagcgct cgaaacggtg cagcggctgt tgccggtgct gtgccaggac | 2040 |

```
catggcctga ccccggacca agtggtggct atcgccagca acattggcgg caagcaagcg    2100
ctcgaaacgg tgcagcggct gttgccggtg ctgtgccagg accatggcct gaccccggac    2160
caagtggtgg ctatcgccag caacaatggc ggcaagcaag cgctcgaaac ggtgcagcgg    2220
ctgttgccga tgctgtgcca ggaccatggc ctgaccccgg accaagtggt ggctatcgcc    2280
agcaacattg gcggcaagca agcgctcgaa acggtgcagc ggctgttgcc ggtgctgtgc    2340
caggaccatg gcctgacccc ggaccaagtg gtggctatcg ccagcaacgg tggcggcaag    2400
caagcgctcg aaagcattgt ggcccagctg agccggcctg atccggcgtt ggccgcgttg    2460
accaacgacg accacctcgt cgccttggcc tgcctcggcg acgtcctgc catggatgca     2520 gtgaaaaagg gattgccgca cgcgccggaa ttgatcagaa gagtcaatcg ccgtattggc    2580
gaacgcacgt cccatcgcgt tgccggatcc aaggctagcc cgaaaaagaa acgcaaagtt    2640
gggcgcgccg acgcgctgga cgatttcgat ctcgacatgc tgggttctga tgccctcgat    2700
gactttgacc tggatatgtt gggaagcgac gcattggatg actttgatct ggacatgctc    2760
ggctccgatg ctctggacga tttcgatctc gatatgttaa ttaactaccc gtacgacgtt    2820
ccggactacg cttcttga                                                  2838
```

<210> SEQ ID NO 96
<211> LENGTH: 945
<212> TYPE: PRT
<213> ORGANISM: Unknown
<220> FEATURE:
<223> OTHER INFORMATION: Synthetic peptide

<400> SEQUENCE: 96

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Asp Leu Arg Thr Leu Gly Tyr Ser Gln Gln Gln
        35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
        115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
        195                 200                 205

Pro Asp Gln Val Val Ala Ile Ala Ser His Asp Gly Gly Lys Gln Ala
```

```
                210                 215                 220
Leu Glu Thr Val Gln Arg Leu Leu Pro Val Leu Cys Gln Asp His Gly
225                 230                 235                 240

Leu Thr Pro Asp Gln Val Val Ala Ile Ala Ser His Asp Gly Gly Lys
                245                 250                 255

Gln Ala Leu Glu Thr Val Gln Arg Leu Leu Pro Val Leu Cys Gln Asp
                260                 265                 270

His Gly Leu Thr Pro Asp Gln Val Val Ala Ile Ala Ser His Asp Gly
                275                 280                 285

Gly Lys Gln Ala Leu Glu Thr Val Gln Arg Leu Leu Pro Val Leu Cys
            290                 295                 300

Gln Asp His Gly Leu Thr Pro Asp Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
                340                 345                 350

Ser Asn Asn Gly Gly Lys Gln Ala Leu Glu Thr Val Gln Arg Leu Leu
            355                 360                 365

Pro Val Leu Cys Gln Asp His Gly Leu Thr Pro Asp Gln Val Val Ala
            370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
                420                 425                 430

Gln Arg Leu Leu Pro Val Leu Cys Gln Asp His Gly Leu Thr Pro Asp
            435                 440                 445

Gln Val Val Ala Ile Ala Ser Asn Ile Gly Gly Lys Gln Ala Leu Glu
            450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Ile Gly Gly Lys Gln Ala
                485                 490                 495

Leu Glu Thr Val Gln Arg Leu Leu Pro Val Leu Cys Gln Asp His Gly
                500                 505                 510

Leu Thr Pro Asp Gln Val Val Ala Ile Ala Ser Asn Asn Gly Gly Lys
            515                 520                 525

Gln Ala Leu Glu Thr Val Gln Arg Leu Leu Pro Val Leu Cys Gln Asp
            530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
                580                 585                 590

Gly Gly Gly Lys Gln Ala Leu Glu Thr Val Gln Arg Leu Leu Pro Val
            595                 600                 605

Leu Cys Gln Asp His Gly Leu Thr Pro Asp Gln Val Val Ala Ile Ala
            610                 615                 620

Ser Asn Gly Gly Gly Lys Gln Ala Leu Glu Thr Val Gln Arg Leu Leu
625                 630                 635                 640
```

Pro Val Leu Cys Gln Asp His Gly Leu Thr Pro Asp Gln Val Val Ala
            645                 650                 655

Ile Ala Ser Asn Ile Gly Gly Lys Gln Ala Leu Glu Thr Val Gln Arg
        660                 665                 670

Leu Leu Pro Val Leu Cys Gln Asp His Gly Leu Thr Pro Asp Gln Val
    675                 680                 685

Val Ala Ile Ala Ser Asn Ile Gly Gly Lys Gln Ala Leu Glu Thr Val
690                 695                 700

Gln Arg Leu Leu Pro Val Leu Cys Gln Asp His Gly Leu Thr Pro Asp
705                 710                 715                 720

Gln Val Val Ala Ile Ala Ser Asn Asn Gly Gly Lys Gln Ala Leu Glu
                725                 730                 735

Thr Val Gln Arg Leu Leu Pro Val Leu Cys Gln Asp His Gly Leu Thr
            740                 745                 750

Pro Asp Gln Val Val Ala Ile Ala Ser Asn Ile Gly Gly Lys Gln Ala
        755                 760                 765

Leu Glu Thr Val Gln Arg Leu Leu Pro Val Leu Cys Gln Asp His Gly
    770                 775                 780

Leu Thr Pro Asp Gln Val Val Ala Ile Ala Ser Asn Gly Gly Gly Lys
785                 790                 795                 800

Gln Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu
            820                 825                 830

Gly Gly Arg Pro Ala Met Asp Ala Val Lys Lys Gly Leu Pro His Ala
        835                 840                 845

Pro Glu Leu Ile Arg Arg Val Asn Arg Arg Ile Gly Glu Arg Thr Ser
    850                 855                 860

His Arg Val Ala Gly Ser Lys Ala Ser Pro Lys Lys Arg Lys Val
865                 870                 875                 880

Gly Arg Ala Asp Ala Leu Asp Phe Asp Leu Asp Met Leu Gly Ser
                885                 890                 895

Asp Ala Leu Asp Asp Phe Asp Leu Asp Met Leu Gly Ser Asp Ala Leu
            900                 905                 910

Asp Asp Phe Asp Leu Asp Met Leu Gly Ser Asp Ala Leu Asp Asp Phe
        915                 920                 925

Asp Leu Asp Met Leu Ile Asn Tyr Pro Tyr Asp Val Pro Asp Tyr Ala
    930                 935                 940

Ser
945

<210> SEQ ID NO 97
<211> LENGTH: 2634
<212> TYPE: DNA
<213> ORGANISM: Artificial sequence
<220> FEATURE:
<223> OTHER INFORMATION: Synthetic oligonucleotide

<400> SEQUENCE: 97
atggactaca aagaccatga cggtgattat aaagatcatg acatcgatta caaggatgac      60
gatgacaaga tggccccccaa gaagaagagg aaggtgggcc gcggatctgt ggatctacgc    120
acgctcggct acagtcagca gcagcaagag aagatcaaac cgaaggtgcg ttcgacagtg    180
gcgcagcacc acgaggcact ggtgggccat gggtttacac acgcgcacat cgttgcgctc    240

-continued

```
agccaacacc cggcagcgtt agggaccgtc gctgtcacgt atcagcacat aatcacggcg   300
ttgccagagg cgacacacga agacatcgtt ggcgtcggca aacagtggtc cggcgcacgc   360
gccctggagg ccttgctcac ggatgcgggg gagttgagag gtccgccgtt acagttggac   420
acaggccaac ttgtgaagat tgcaaaacgt ggcggcgtga ccgcaatgga ggcagtgcat   480
gcatcgcgca atgcactgac gggtgccccc ctgaacctga ccccggacca agtggtggct   540
atcgccagcc acgatggcgg caagcaagcg ctcgaaacgg tgcagcggct gttgccggtg   600
ctgtgccagg accatggcct gaccccggac caagtggtgg ctatcgccag caacaatggc   660
ggcaagcaag cgctcgaaac ggtgcagcgg ctgttgccgg tgctgtgcca ggaccatggc   720
ctgaccccgg accaagtggt ggctatcgcc agcaacattg gcggcaagca agcgctcgaa   780
acggtgcagc ggctgttgcc ggtgctgtgc caggaccatg gcctgacccc ggaccaagtg   840
gtggctatcg ccagcaacgg tggcggcaag caagcgctcg aaacggtgca gcggctgttg   900
ccggtgctgt gccaggacca tggcctgacc ccggaccaag tggtggctat cgccagcaac   960
aatggcggca agcaagcgct cgaaacggtg cagcggctgt tgccggtgct gtgccaggac  1020
catggcctga ccccggacca agtggtggct atcgccagca acgtggcgg caagcaagcg  1080
ctcgaaacgg tgcagcggct gttgccggtg ctgtgccagg accatggcct gaccccggac  1140
caagtggtgg ctatcgccag caacaatggc ggcaagcaag cgctcgaaac ggtgcagcgg  1200
ctgttgccgg tgctgtgcca ggaccatggc ctgaccccgg accaagtggt ggctatcgcc  1260
agcaacattg gcggcaagca agcgctcgaa acggtgcagc ggctgttgcc ggtgctgtgc  1320
caggaccatg gcctgacccc ggaccaagtg gtggctatcg ccagccacga tggcggcaag  1380
caagcgctcg aaacggtgca gcggctgttg ccggtgctgt gccaggacca tggcctgacc  1440
ccggaccaag tggtggctat cgccagcaac ggtggcggca agcaagcgct cgaaacggtg  1500
cagcggctgt tgccggtgct gtgccaggac catggcctga ccccggacca agtggtggct  1560
atcgccagca acaatggcgg caagcaagcg ctcgaaacgg tgcagcggct gttgccggtg  1620
ctgtgccagg accatggcct gaccccggac caagtggtgg ctatcgccag caacggtggc  1680
ggcaagcaag cgctcgaaac ggtgcagcgg ctgttgccgg tgctgtgcca ggaccatggc  1740
ctgaccccgg accaagtggt ggctatcgcc agccacgatg gcggcaagca agcgctcgaa  1800
acggtgcagc ggctgttgcc ggtgctgtgc caggaccatg gcctgacccc ggaccaagtg  1860
gtggctatcg ccagcaacgg tggcggcaag caagcgctcg aaacggtgca gcggctgttg  1920
ccggtgctgt gccaggacca tggcctgacc ccggaccaag tggtggctat cgccagccac  1980
gatggcggca agcaagcgct cgaaacggtg cagcggctgt tgccggtgct gtgccaggac  2040
catggcctga ccccggacca agtggtggct atcgccagcc acgatggcgg caagcaagcg  2100
ctcgaaacgg tgcagcggct gttgccggtg ctgtgccagg accatggcct gaccccggac  2160
caagtggtgg ctatcgccag caacggtggc ggcaagcaag cgctcgaaag cattgtggcc  2220
cagctgagcc ggcctgatcc ggcgttggcc gcgttgacca acgacgacca cctcgtcgcc  2280
ttggcctgcc tcggcggacg tcctgccatg gatgcagtga aaagggatt gccgcacgcg  2340
ccggaattga tcagaagagt caatcgccgt attggcgaac gcacgtccca tcgcgttgcc  2400
ggatccaagg ctagcccgaa aaagaaacgc aaagttgggc gcgccgacgc gctggacgat  2460
ttcgatctcg acatgctggg ttctgatgcc ctcgatgact tgacctgga tatgttggga  2520
agcgacgcat ggatgacttt tgatctggac atgctcggct ccgatgctct ggacgatttc  2580
gatctcgata tgttaattaa ctacccgtac gacgttccgg actacgcttc ttga        2634
```

<210> SEQ ID NO 98
<211> LENGTH: 877
<212> TYPE: PRT
<213> ORGANISM: Unknown
<220> FEATURE:
<223> OTHER INFORMATION: Synthetic peptide

<400> SEQUENCE: 98

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Asp Leu Arg Thr Leu Gly Tyr Ser Gln Gln Gln
            35                  40                  45

Gln Glu Lys Ile Lys Pro Lys Val Arg Ser Thr Val Ala Gln His His
    50                  55                  60

Glu Ala Leu Val Gly His Gly Phe Thr His Ala His Ile Val Ala Leu
65                  70                  75                  80

Ser Gln His Pro Ala Ala Leu Gly Thr Val Ala Val Thr Tyr Gln His
                85                  90                  95

Ile Ile Thr Ala Leu Pro Glu Ala Thr His Glu Asp Ile Val Gly Val
            100                 105                 110

Gly Lys Gln Trp Ser Gly Ala Arg Ala Leu Glu Ala Leu Leu Thr Asp
            115                 120                 125

Ala Gly Glu Leu Arg Gly Pro Pro Leu Gln Leu Asp Thr Gly Gln Leu
    130                 135                 140

Val Lys Ile Ala Lys Arg Gly Gly Val Thr Ala Met Glu Ala Val His
145                 150                 155                 160

Ala Ser Arg Asn Ala Leu Thr Gly Ala Pro Leu Asn Leu Thr Pro Asp
                165                 170                 175

Gln Val Val Ala Ile Ala Ser His Asp Gly Gly Lys Gln Ala Leu Glu
            180                 185                 190

Thr Val Gln Arg Leu Leu Pro Val Leu Cys Gln Asp His Gly Leu Thr
    195                 200                 205

Pro Asp Gln Val Val Ala Ile Ala Ser Asn Asn Gly Gly Lys Gln Ala
    210                 215                 220

Leu Glu Thr Val Gln Arg Leu Leu Pro Val Leu Cys Gln Asp His Gly
225                 230                 235                 240

Leu Thr Pro Asp Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Gly Gly
        275                 280                 285

Gly Lys Gln Ala Leu Glu Thr Val Gln Arg Leu Leu Pro Val Leu Cys
    290                 295                 300

Gln Asp His Gly Leu Thr Pro Asp Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser Asn Gly Gly Gly Lys Gln Ala Leu Glu Thr Val Gln Arg Leu Leu
        355                 360                 365
```

-continued

```
Pro Val Leu Cys Gln Asp His Gly Leu Thr Pro Asp Gln Val Val Ala
    370                 375                 380

Ile Ala Ser Asn Asn Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Asp His Gly Leu Thr Pro Asp
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Leu Thr
465                 470                 475                 480

Pro Asp Gln Val Val Ala Ile Ala Ser Asn Gly Gly Lys Gln Ala
                485                 490                 495

Leu Glu Thr Val Gln Arg Leu Leu Pro Val Leu Cys Gln Asp His Gly
            500                 505                 510

Leu Thr Pro Asp Gln Val Val Ala Ile Ala Ser Asn Asn Gly Gly Lys
    515                 520                 525

Gln Ala Leu Glu Thr Val Gln Arg Leu Leu Pro Val Leu Cys Gln Asp
    530                 535                 540

His Gly Leu Thr Pro Asp Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Asp His Gly Leu Thr Pro Asp Gln Val Val Ala Ile Ala
    610                 615                 620

Ser Asn Gly Gly Gly Lys Gln Ala Leu Glu Thr Val Gln Arg Leu Leu
625                 630                 635                 640

Pro Val Leu Cys Gln Asp His Gly Leu Thr Pro Asp Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Asp His Gly Leu Thr Pro Asp Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Asp His Gly Leu Thr Pro Asp
705                 710                 715                 720

Gln Val Val Ala Ile Ala Ser Asn Gly Gly Lys Gln Ala Leu Glu
                725                 730                 735

Ser Ile Val Ala Gln Leu Ser Arg Pro Asp Pro Ala Leu Ala Ala Leu
            740                 745                 750

Thr Asn Asp His Leu Val Ala Leu Ala Cys Leu Gly Gly Arg Pro
        755                 760                 765

Ala Met Asp Ala Val Lys Lys Gly Leu Pro His Ala Pro Glu Leu Ile
    770                 775                 780
```

```
Arg Arg Val Asn Arg Arg Ile Gly Glu Arg Thr Ser His Arg Val Ala
785                 790                 795                 800

Gly Ser Lys Ala Ser Pro Lys Lys Lys Arg Lys Val Gly Arg Ala Asp
                805                 810                 815

Ala Leu Asp Asp Phe Asp Leu Asp Met Leu Gly Ser Asp Ala Leu Asp
            820                 825                 830

Asp Phe Asp Leu Asp Met Leu Gly Ser Asp Ala Leu Asp Asp Phe Asp
        835                 840                 845

Leu Asp Met Leu Gly Ser Asp Ala Leu Asp Asp Phe Asp Leu Asp Met
    850                 855                 860

Leu Ile Asn Tyr Pro Tyr Asp Val Pro Asp Tyr Ala Ser
865                 870                 875

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Asp Tyr Lys Asp Asp Asp Asp Lys
1               5
```

COMPOSITIONS AND METHODS FOR THE INDUCTION AND TUNING OF GENE EXPRESSION

CROSS REFERENCE TO RELATED APPLICATION

This application is a continuation of U.S. application Ser. No. 14/220,116, filed Mar. 19, 2014, now U.S. Pat. No. 9,828,582, which claims priority to U.S. Provisional Application No. 61/803,254, filed Mar. 19, 2013, the entire contents of each of which are hereby incorporated by reference.

STATEMENT OF GOVERNMENT INTEREST

This invention was made with government support under federal grant number DP2OD008586 awarded by the National Institutes of Health and CBET-1151035 awarded by the National Science Foundation. The U.S. Government has certain rights to this invention.

SEQUENCE LISTING

The sequence listing is filed with the application in electronic format only and is incorporated by reference herein. The sequence listing text file "028193-9177-US01_As_Filed_Sequence_List.txt" filed on Dec. 21, 2021, was created on Dec. 21, 2021, and is 322,428 bytes in size.

TECHNICAL FIELD

The present disclosure relates to the field of inducing mammalian gene expression using combinations of engineered transcription activator-like effectors transcription factors (TALE-TFs).

BACKGROUND

Synthetic biology aims to study the control of gene expression by constructing gene regulation systems from the "bottom-up" in order to better understand natural biological systems and develop useful tools for biotechnology. Despite many significant accomplishments, this field has largely been limited to studying artificial promoter transgene systems with one or two transactivators, typically in microorganisms. In contrast, the natural regulation of mammalian gene expression is extraordinarily complex. This level of complexity has not yet been achieved in synthetic gene regulation systems and has not been possible for the regulation of endogenous genes.

Several TALE-TFs have recently been reported to regulate native mammalian gene expression. However, the recent emergence of technologies for engineering transcription activator-like effectors (TALEs) targeted to almost any DNA sequence provides a unique opportunity for recapitulating this natural complexity. However, the levels of gene activation in these studies were modest and several genes could not be induced (Table 1). Therefore there is clear need for improvements to gene activation strategies that capitalize on the synthetic TALE-TF technology.

TABLE 1

Published TALE-TFs Targeting Human Genes.

| Reference | Gene | Activation Domain | Assay | Fold-Increase |
|---|---|---|---|---|
| Zhang et al., *Nature Biotechnology* (2011) | SOX2 | VP64 | qRT-PCR | 5.5 |
| | KLF4 | VP64 | qRT-PCR | 2.2 |
| | MYC | VP64 | qRT-PCR | n.d. |
| | OCT4 | VP64 | qRT-PCR | n.d. |
| Miller et al., *Nature Biotechnology* (2011) | NTF3 | VP16 | qRT-PCR | 30 |
| Geissler et al., *PLoS One* (2011) | PUMA | VP16 | qRT-PCR | 1.5 |
| | IFNA1 | VP16 | qRT-PCR | 3 |
| | IFNB1 | VP16 | qRT-PCR | 3.5 |
| Bultmann et al., *Nucleic Acids Research* (2012) | OCT4 | VP16 | qRT-PCR | n.d.[1] |
| Cong et al., *Nature Communications* (2012) | CACNA1C | VP64 | qRT-PCR | 3-5 |
| Tremblay et al., *Human Gene Therapy* (2012) | FXN | VP64 | qRT-PCR | 1.1-3.1 |
| Garg et al., *Nucleic Acids Research* (2012) | OSGIN2 | VP64 | qRT-PCR | 4.8 |
| | ZC3H10 | VP64 | qRT-PCR | 1.3 | n.d. = not detected

[1] undetectable in control, induced only with chromatin-modifying drugs

SUMMARY

The present invention is directed to a method of modulating mammalian gene expression in a cell. The method comprises contacting the cell with two or more transcription activator-like effector transcription factors (TALE-TFs) that bind to a target gene. The method further comprises contacting the cell with a chromatin modifying drug. The TALE-TFs may bind to different target regions within the target gene. The target regions may be separated by at least one nucleotide. The target regions may be separated by about 15 to about 700 base pairs. At least one target region may be within a non-open chromatin region. At least one target region may be within an open chromatin region. At least one target region may be within the promoter region of the target gene. At least one target region may be within the enhancer region of the target gene. At least one target region may be within the transcribed region of the target gene. At least one target region may be within a region upstream of the transcription start site of the target gene. At least one target region may be located between about 1 to about 1000 base pairs upstream of the transcription start site of the target gene. At least one target region may be located between about 1 to about 600 base pairs upstream of the transcription start site of the target gene. The target regions may be within a region upstream of the transcription start site of the target gene. The gene expression may be induced. The TALE-TFs may each comprise a transcription activation domain. The TALE-TFs may comprise the same transcription activation domain. The TALE-TFs may comprise different transcription activation domains. The transcription activation domain may comprise at least one VP16 transcription activation domain repeat. The transcription activation domain comprises at least one of VP16 transcription activation domain repeat, VP64 transcription activation domain, p65 transcription activation domain, or combinations thereof. The TALE-TFs may each comprise about 15 to about 19 RVD modules. Between about two to about ten TALE-TFs may be used. Three TALE-TFs may be used. Four TALE-TFs may be used. Five TALE-TFs may be used. Six TALE-TFs may be used. The TALE-TFs may binds to a nucleotide sequence comprising one of SEQ ID NOs: 1-29, or the complement thereof. The TALE-TFs may comprise an amino acid sequence selected from the group consisting of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a method of modulating mammalian gene expression in a cell without the use of chromatin modifying drug. The method comprises contacting the cell with two or more transcription activator-like effector transcription factors (TALE-TFs) that bind to a target gene. The TALE-TFs may bind to different target regions within the target gene. The target regions may be separated by at least one nucleotide. The target regions may be separated by about 15 to about 700 base pairs. At least one target region may be within a non-open chromatin region. At least one target region may be within an open chromatin region. At least one target region may be within the promoter region of the target gene. At least one target region may be within the enhancer region of the target gene. At least one target region may be within the transcribed region of the target gene. At least one target region may be within a region upstream of the transcription start site of the target gene. At least one target region may be located between about 1 to about 1000 base pairs upstream of the transcription start site of the target gene. At least one target region may be located between about 1 to about 600 base pairs upstream of the transcription start site of the target gene. The target regions may be within a region upstream of the transcription start site of the target gene. The gene expression may be induced. The TALE-TFs may each comprise a transcription activation domain. The TALE-TFs may comprise the same transcription activation domain. The TALE-TFs may comprise different transcription activation domains. The transcription activation domain may comprise at least one VP16 transcription activation domain repeat. The transcription activation domain comprises at least one of VP16 transcription activation domain repeat, VP64 transcription activation domain, p65 transcription activation domain, or combinations thereof. The TALE-TFs may each comprise about 15 to about 19 RVD modules. Between about two to about ten TALE-TFs may be used. Three TALE-TFs may be used. Four TALE-TFs may be used. Five TALE-TFs may be used. Six TALE-TFs may be used. The TALE-TFs may binds to a nucleotide sequence comprising one of SEQ ID NOs: 1-29, or the complement thereof. The TALE-TFs may comprise an amino acid sequence selected from the group consisting of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a composition for inducing mammalian gene expression in a cell. The composition comprises two or more transcription activator-like effector transcription factors (TALE-TFs) that bind to a target gene. The TALE-TFs may bind to a nucleotide sequence comprising one of SEQ ID NOs: 1-28, or the complement thereof. The TALE-TFs may comprise an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a composition for inducing mammalian gene expression in a cell. The composition comprises an isolated polynucleotide sequence encoding at least one transcription activator-like effector transcription factor (TALE-TF) that binds to a target gene. The more than one TALE-TF may be encoded by the isolated polynucleotide sequence. The two or more TALE-TFs may be encoded by two or more polynucleotide sequences. The TALE-TFs may bind to a nucleotide sequence comprising one of SEQ ID NOs: 1-28, or the complement thereof. The TALE-TFs may comprise an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TFs may be encoded by a polynucleotide sequence selected from the group consisting of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof. The target gene may be IL1RN, KLK3, CEACAM5, and ERBB2.

The present invention is directed to a cell comprising said composition.

The present invention is directed to a kit comprising said composition or said cell.

The present invention is directed to a kit for inducing mammalian gene expression in a cell. The kit comprises said composition or said cell.

BRIEF DESCRIPTION OF THE DRAWINGS

FIGS. 1A-1N show synergistic activation of gene expression by combinations of TALE-TFs. (FIG. 1A) Structure and sequence of TALE-TFs in this study. (FIG. 1B) Genomic positions of TALE-TF target sites in the CEACAM5, KLK3, IL1RN, and ERBB2 genes (hg19 coordinates) are indicated by black boxes. Transcribed and coding regions are indicated by dashed arrow and solid arrow, respectively. (FIGS. 1C-1F) Relative luciferase activity (RLA) in promoter reporter assays. (FIGS. 1G-1J) Relative mRNA expression levels measured by quantitative RT-PCR and (FIGS. 1K-1N) protein expression levels assayed by ELISA or Western blot for each target gene in human cells transfected with the indicated TALE-TFs. Each gene is organized by column. n=3 unless indicated otherwise in the Examples. Mean±SEM and P<0.0001 by ANOVA for all bar graphs.

FIGS. 2A-2H show combinatorial regulation of gene expression by TALE-TFs. (FIGS. 2A-2C) All possible 63 combinations of six TALE-TFs targeting the IL1RN, KLK3, and CEACAM5 genes were tested for activation of a luciferase reporter plasmid and ordered according to number of TALE-TFs and magnitude of relative luciferase activity (RLA). Samples receiving the same number of TALE-TFs are indicated by line or no line. Data are shown as the mean±SEM (n=3) independent experiments. P<0.0001 by ANOVA for all three data sets (Table 2). (FIG. 2D) The average RLA for the indicated number of TALE-TFs for each gene. (FIG. 2E) The fold increase of RLA for each number of TALE-TFs relative to the average RLA for one less TALE-TF is presented for each gene. (FIGS. 2F-2H) The measured values for all 63 combinations of TALE-TFs are plotted versus the values fit by the polynomial model, along with y=x (solid line).

Figures 3A, 3B, 3C, 3D:
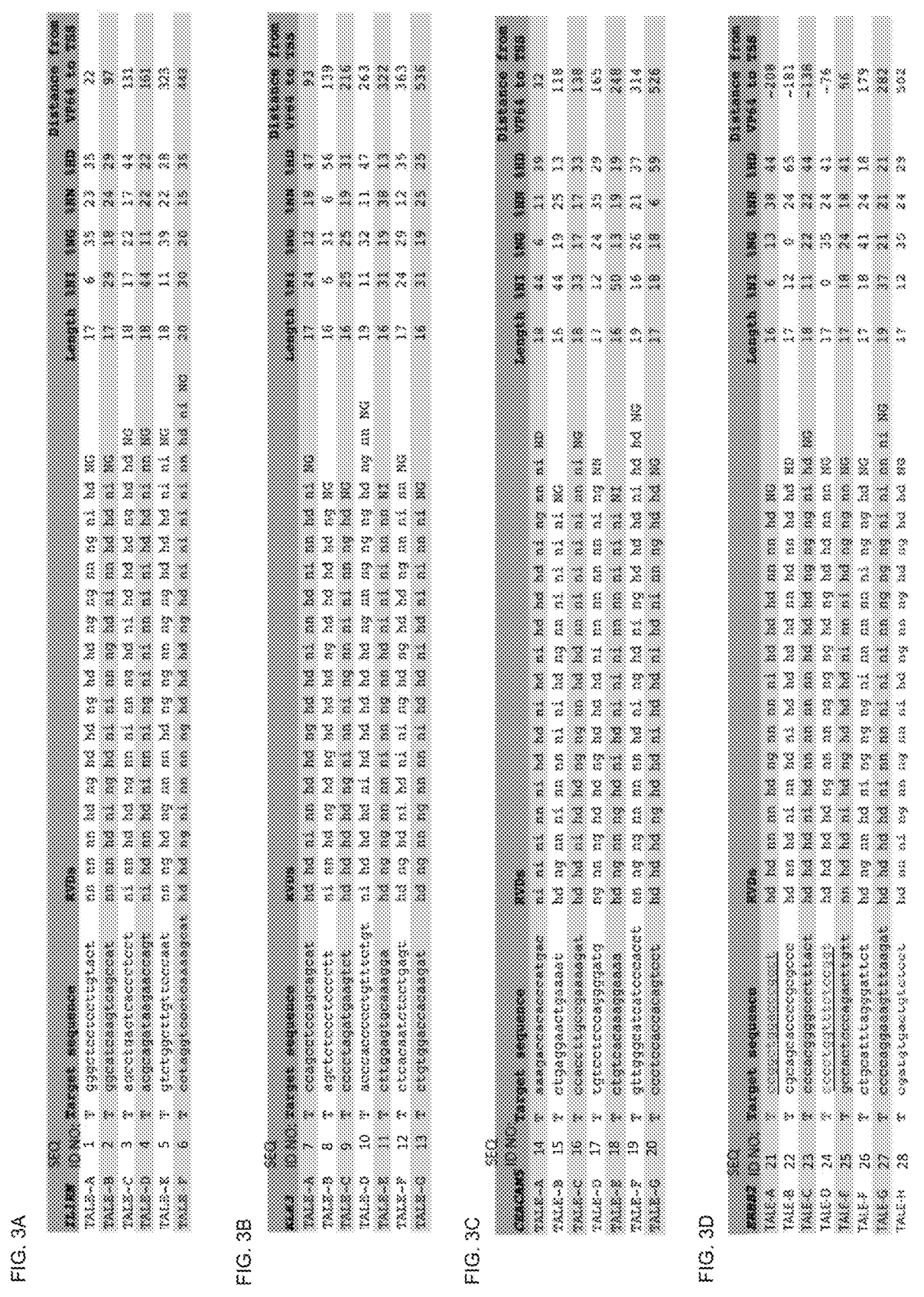

FIGS. 3A-3D show the TALE-TFs, the target sequence, RVDs, length, percent RVD composition and distance to the TSS of the target genes. The underlined target sequences are located in the minus strand.

FIG. 5A shows the relative luciferase activities and FIG. 5B shows a Western blot of the cell lysates analyzed with anti-HA and anti-GAPDH antibodies.

FIGS. 9A-9I show the mathematical expression of combinatorial regulation of gene activation by TALE-TFs.

DETAILED DESCRIPTION

Figure 2F:
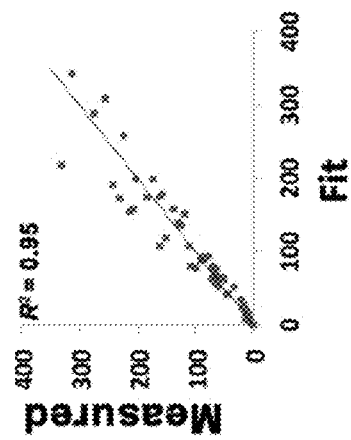
Figure 2G:
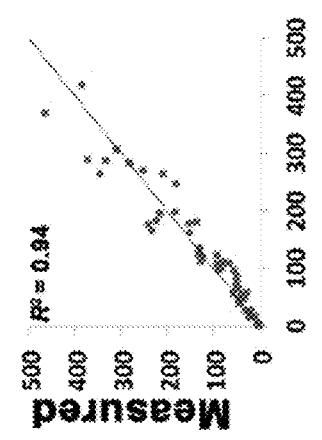
Figure 2H:
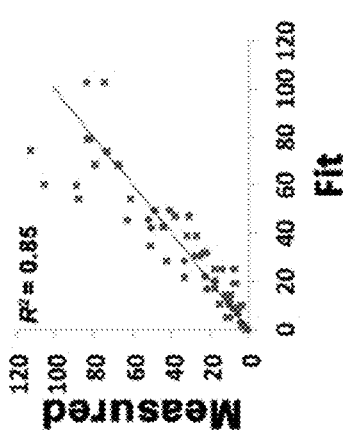

The present disclosure provides compositions and methods of modulating gene expression that include combinations of engineered TALE-TFs. The combinations of engineered TALE-TFs target endogenous gene promoters, including regions of closed chromatin upstream of silenced genes, and induce substantial gene activation. The combinations also allow tuning of gene expression levels that broadly enables synthetic biology, gene therapy and biotechnology.

The combinatorial regulation of endogenous mammalian genes in their natural chromosomal context is achieved by engineering several TALE-TFs to bind nearby sites upstream of the transcriptional start site (TSS) for a target gene. These combinations of independent TALE-TFs can be manipulated to control gene activation. Synergistic regulation of gene expression by multiple transcriptional activators occurs via simultaneous binding and stabilization of components of the pre-initiation complex. Endogenous genes were activated with combinations of engineered transcription factors. Gene expression levels were tuned by systematically varying these combinations.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Binding region," "target region," or "target sequence" as used interchangeably herein refers to the region within the target gene that is recognized and bound by a TALE-TF. The TALE DNA-binding domain of the TALE-TF recognizes and binds to the binding region. The binding region may include a nucleotide sequence of SEQ ID NO: 1-28, or a complement thereof.

"Chromatin" as used herein refers to an organized complex of chromosomal DNA associated with histones.

"Closed chromatin" or "heterochromatin" as used interchangeably herein refers to a tightly packed form of DNA. Closed chromatin may be inaccessible to DNaseI. "Open chromatin" or "euchromatin" as used interchangeably herein refers to a lightly packed form of chromatin that is rich in gene concentration and is often under active transcription. Open chromatin may be accessible to DNaseI.

"Chromatin modifying drug" as used herein refers to drugs that cause chromatin remodeling, i.e., dynamic modification of chromatin architecture, and allow access of condensed genomic DNA to the regulatory transcription machinery proteins, and thereby helps to control gene expression. Chromatin modifying drug function by 1) covalent histone modifications by specific enzymes, i.e., histone acetyltransferases (HATs), deacetylases, methyltransferases, and kinases, and 2) ATP-dependent chromatin remodeling complexes which either move, eject or restructure nucleosomes.

"Coding sequence", "coding region" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"DNase I hypersensitive sites" are regions of chromatin that are sensitive to cleavage by the DNase I enzyme. In these specific regions of the genome, chromatin has lost its condensed structure, thus exposing the DNA and making it accessible. These accessible chromatin zones are functionally related to transcriptional activity, since this remodeled state is necessary for the binding of proteins such as transcription factors.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may affect the regulatory sequence. The genetic disease may be, but not limited to DMD, cystic fibrosis, Huntington's chorea, familial hypercholesterolemia (LDL receptor defect), hepatoblastoma, Wilson's disease, congenital hepatic *porphyria*, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, Friedreich's ataxia, choroidal neovascularization, cancer, amyotrophic lateral sclerosis, diabetic wounds, and Tay-Sachs disease.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within the DNA recognition motif (also known as "RVD module"), which includes 33-35 amino acids, of the TALE DNA-binding domain. The RVD determines the nucleotide specificity of the RVD module. RVD modules may be combined to produce an RVD array. The "RVD array length" as used herein refers to the number of RVD modules that corresponds to the length of the nucleotide sequence within the target region that is recognized by the TALE-TF, i.e., the binding region.

"Silenced gene" as used herein refers to a gene that is turned off or prevented from being expressed, i.e., transcribed. Gene silencing may occur when large sections of chromosomal DNA are shut down, such as by incorporating the DNA to be silenced into heterochromatin, that is already silent. A gene may be transcriptional silenced by DNA methylation, wherein a methyl group is attached to certain points on a nucleic acid strand and can prevent transcription.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene includes the regulatory regions, such as the promoter and enhancer regions, the transcribed regions, which include the coding regions, and other function sequence regions.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors.

"Transcription activator-like effector transcription factors" or "TALE-TFs" as used interchangeably herein refers to engineered fusion proteins of the transcription activation domain of a transcription factors, such as VP64, and a designed TALE DNA-binding domain that may be targeted to a custom DNA sequence.

"Transcriptional Start Site" or "TSS" as used interchangeably herein refers to the first nucleotide of a transcribed DNA sequence where RNA polymerase begins synthesizing the RNA transcript.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a TALE-TF protein comprising the polypeptide sequence of one of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The vector may include a polynucleotide sequence of one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. TALE-TFs

Provided herein are TALE-TFs for use in modulating gene expression of a target gene. Each TALE-TF has two distinct protein domains that carry out individual molecular functions: (i) a repeat variable diresidue region that binds to DNA at user-specified sequences (i.e., the DNA binding domain), and (ii) a transcription activation domain, such as VP64 effector domain, that recruits the basal transcriptional machinery (FIG. 1A). This design permits rapid construction of synthetic transcription factors that function as autonomous units. The TALE-TFs may be designed to target any gene, including genes involved in a genetic disease. The target gene may be in a region of open or closed chromatin.

(a) TALE DNA Binding Domain

The TALE DNA-binding domain may have an RVD array length from 1 to 30 modules, from 1 to 25 modules, from 1 to 20 modules, from 1 to 15 modules, from 5 to 30 modules, from 5 to 25 modules, from 5 to 20 modules, from 5 to 15 modules, from 7 to 25 modules, from 7 to 23 modules, from 7 to 20 modules, from 10 to 30 modules, from 10 to 25 modules, from 10 to 20 modules, from 10 to 15 modules, from 15 to 30 modules, from 15 to 25 modules, from 15 to 20 modules, from 15 to 19 modules, from 16 to 26 modules, from 16 to 41 modules, from 20 to 30 modules, or from 20 to 25 modules in length. The RVD array length may be 5 modules, 8 modules, 10 modules, 11 modules, 12 modules, 13 modules, 14 modules, 15 modules, 16 modules, 17 modules, 18 modules, 19 modules, 20 modules, 22 modules, 25 modules or 30 modules.

The TALE-TF may target at least one of a promoter region, an enhancer region or a transcribed region of a target gene. The TALE-TF may target a binding region comprising the nucleic acid sequence of one of SEQ ID NOs:1-28, or variants thereof. The TALE-TF may include a polypeptide sequence of at least one of SEQ ID NOs: 44, 46, 48, 50, 52, 54, 56, 58, 60, 62, 64, 66, 68, 70, 72, 74, 76, 78, 80, 82, 84, 86, 88, 90, 92, 94, 96, or 98, or variants thereof. The TALE-TF may include a polynucleotide sequence of at least one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

The TALE-TF may target a region that is at least about 1 base pair to about 1000 base pairs, at least about 10 base pairs to about 1000 base pairs, at least about 50 base pairs to about 1000 base pairs, 100 base pair to about 1000 base pairs, at least about 150 base pairs to about 1000 base pairs, at least about 200 base pairs to about 1000 base pairs, 250 base pair to about 1000 base pairs, at least about 300 base pairs to about 1000 base pairs, at least about 350 base pairs to about 1000 base pairs, 400 base pair to about 1000 base pairs, at least about 450 base pairs to about 1000 base pairs, at least about 500 base pairs to about 1000 base pairs, 550 base pair to about 1000 base pairs, at least about 600 base pairs to about 1000 base pairs, at least about 650 base pairs to about 1000 base pairs, at least about 1 base pair to about 900 base pairs, at least about 10 base pairs to about 900 base pairs, at least about 50 base pairs to about 900 base pairs, 100 base pair to about 900 base pairs, at least about 150 base pairs to about 900 base pairs, at least about 200 base pairs to about 900 base pairs, 250 base pair to about 900 base pairs, at least about 300 base pairs to about 900 base pairs, at least about 350 base pairs to about 900 base pairs, 400 base pair to about 900 base pairs, at least about 450 base pairs to about 900 base pairs, at least about 500 base pairs to about 900 base pairs, 550 base pair to about 900 base pairs, at least about 600 base pairs to about 900 base pairs, at least about 650 base pairs to about 900 base pairs, at least about 1 base pair to about 800 base pairs, at least about 10 base pairs to about 800 base pairs, at least about 50 base pairs to about 800 base pairs, 100 base pair to about 800 base pairs, at least about 150 base pairs to about 800 base pairs, at least about 200 base pairs to about 800 base pairs, 250 base pair to about 800 base pairs, at least about 300 base pairs to about 800 base pairs, at least about 350 base pairs to about 800 base pairs, 400 base pair to about 800 base pairs, at least about 450 base pairs to about 800 base pairs, at least about 500 base pairs to about 800 base pairs, 550 base pair to about 800 base pairs, at least about 600 base pairs to about 800 base pairs, at least about 1 base pair to about 700 base pairs, at least about 10 base pairs to about 700 base pairs, at least about 50 base pairs to about 700 base pairs, 100 base pair to about 700 base pairs, at least about 150 base pairs to about 700 base pairs, at least about 200 base pairs to about 700 base pairs, 250 base pair to about 700 base pairs, at least about 300 base pairs to about 700 base pairs, at least about 350 base pairs to about 700 base pairs, 400 base pair to about 700 base pairs, at least about 450 base pairs to about 700 base pairs, at least about 500 base pairs to about 700 base pairs, at least about 1 base pair to about 600 base pairs, at least about 10 base pairs to about 600 base pairs, at least about 50 base pairs to about 600 base pairs, 100 base pair to about 600 base pairs, at least about 150 base pairs to about 600 base pairs, at least about 200 base pairs to about 600 base pairs, 250 base pair to about 600 base pairs, at least about 300 base pairs to about 600 base pairs, at least about 350 base pairs to about 600 base pairs, or at least about 400 base pair to about 600 base pairs upstream from the TSS. The TALE-TF may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, at least about 250 base pairs, at least about 260 base pairs, at least about 270 base pairs, at least about 280 base pairs, at least about 290 base pairs, at least about 300 base pairs, at least about 310 base pairs, at least about 320, at least about 330, at least about 340 base pairs, at least about 350 base pairs, at least about 360 base pairs, at least about 370 base pairs, at least about 380 base pairs, at least about 390 base pairs, at least about 400 base pairs upstream, at least about 410 base pairs, at least about 420, at least about 430, at least about 440 base pairs, at least about 450 base pairs, at least about 460 base pairs, at least about 470 base pairs, at least about 480 base pairs, at least about 490 base pairs, at least about 500 base pairs, at least about 510 base pairs, at least about 520, at least about 530, at least about 540 base pairs, at least about 550 base pairs, at least about 560 base pairs, at least about 570 base pairs, at least about 180 base pairs, at least about 590 base pairs, at least about 600 base pairs, at least about 610 base pairs, at least about 620, at least about 130, at least about 640 base pairs, at least about 650 base pairs, at least about 660 base pairs, at least about 670 base pairs, at least about 680 base pairs, at least about 690 base pairs, at least about 700 base pairs, at least about 710 base pairs, at least about 720, at least about 730, at least about 740 base pairs, at least about 750 base pairs, at least about 760 base pairs, at least about 770 base pairs, at least about 780 base pairs, at least about 790 base pairs, at least about 800 base pairs, at least about 810 base pairs, at least about 820, at least about 830, at least about 840 base pairs, at least about 850 base pairs, at least about 860 base pairs, at least about 870 base pairs, at least about 880 base pairs, at least about 890 base pairs, at least about 900 base pairs, at least about 910 base pairs, at least about 920, at least about 930, at least about 940 base pairs, at least about 950 base pairs, at least about 960 base pairs, at least about 970 base pairs, at least about 980 base pairs, at least about 990 base pairs, or at least about 1000 base pairs upstream from the TSS.

The TALE-TF may target a region that is at least about 1 base pair to at least about 250 base pairs, at least about 50 base pairs to at least about 200 base pairs, or at least about 100 base pair to at least about 200 base pairs downstream from the TSS. The TALE-TF may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, or at least about 250 base pairs downstream from the TSS.

(b) Transcriptional Activation Activity

The TALE-TFs includes a polypeptide domain having transcription activation activity, i.e., a transactivation domain or transcriptional activation domain. The transcriptional activation domains activate transcription from a promoter by contacting the transcriptional machinery (general transcription factors and RNA polymerase) either directly or through other proteins known as co-activations. Transcription activation domains include acidic domains, which are rich in acidic amino acids (e.g., DDD, EEE), glutamine-rich domains, and proline-rich domains. The transactivation domain may include a VP16 protein, multiple VP16 proteins, such as a VP64 domain, or p65 domain of NF kappa B transcription activator activity. The TALE-TF may include at least one of VP16 transcription activation domain repeat, VP64 transcription activation domain, p65 transcription activation domain, or combinations thereof.

(c) Gene Targets

The TALE-TFs may be designed to target and modulate the expression of any target gene. The target gene may be any mammalian gene. For example, the TALE-TFs may target a mammalian gene, such as IL1RN, KLK3, CEACAM5, ERBB2, ASCL1, NANOG, VEGFA, TERT, IL1B, ILIR2, HBG1, HBG2, MYOD1, HBG1/2, UTRN, FXN, SERPINF1, BAX, SERPINB5, VEFGA, POU5F1, and DMD.

3. Compositions

The present disclosure also provides compositions of at least two TALE-TFs, as described above, or polynucleotide sequences encoding said TALE-TFs, that are administered to a mammalian cell to induce and modulate gene expression of a target gene. These combinations of TALE-TFs may target a closed or open chromatin gene region. These combinations of TALE-TFs may be used with or without chromatin modifying drug. These combinations of TALE-TFs may target DNaseI sensitive regions or DNaseI insensitive regions.

In some embodiments, the composition induces the gene expression of a target gene by at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least 15 fold, at least 20 fold, at least 30 fold, at least 40 fold, at least 50 fold, at least 60 fold, at least 70 fold, at least 80 fold, at least 90 fold, at least 100 fold, at least about 110 fold, at least 120 fold, at least 130 fold, at least 140 fold, at least 150 fold, at least 160 fold, at least 170 fold, at least 180 fold, at least 190 fold, at least 200 fold, at least about 300 fold, at least 400 fold, at least 500 fold, at least 600 fold, at least 700 fold, at least 800 fold, at least 900 fold, or at least 1000 fold compared to a control level of gene expression. A control level of gene expression of the target gene may be the level of gene expression of the target gene in a cell that is not treated with any TALE-TF or is treated with only one TALE-TF.

The compositions may include from at least about two TALE-TFs to at least about fifty TALE-TFs, from at least about three TALE-TFs to at least about fifty TALE-TFs, from at least about four TALE-TFs to at least about fifty TALE-TFs, from at least about five TALE-TFs to at least about fifty TALE-TFs, from at least about ten TALE-TFs to at least about fifty TALE-TFs, from at least about fifteen TALE-TFs to at least about fifty TALE-TFs, from at least about twenty TALE-TFs to at least about fifty TALE-TFs, from at least about twenty-five TALE-TFs to at least about fifty TALE-TFs, from at least about two TALE-TFs to at least about twenty-five TALE-TFs, from at least about three TALE-TFs to at least about twenty-five TALE-TFs, from at least about four TALE-TFs to at least about twenty-five TALE-TFs, from at least about five TALE-TFs to at least about twenty-five TALE-TFs, from at least about ten TALE-TFs to at least about twenty-five TALE-TFs, from at least about fifteen TALE-TFs to at least about twenty-five TALE-TFs, from at least about twenty TALE-TFs to at least about twenty-five TALE-TFs, from at least about twenty-five TALE-TFs to at least about twenty-five TALE-TFs. The compositions may include at least two, at least three, at least four, at least five, at least six, at least seven, at least eight, at least nine, at least ten or at least fifteen TALE-TFs. The number of TALE-TFs administered to the cell may be at least two TALE-TFs, at least three TALE-TFs at least four TALE-TFs, at least five TALE-TFs, at least six TALE-TFs, at least seven TALE-TFs, at least eight TALE-TFs, at least nine TALE-TFs, at least ten TALE-TFs, at least fifteen TALE-TFs, at least twenty TALE-TFs, at least thirty TALE-TFs, or at least fifty TALE-TFs.

The TALE-TFs of the composition may have the same and/or different transcriptional activation domain. In some embodiments, the TALE-TFs may have the same transcriptional activation domains. In some embodiments, at least two, at least three, at least four, at least five, at least six, at least seven, at least eight, at least nine, at least ten, at least fifteen, at least twenty, at least thirty, at least forty or at least fifty of the TALE-TFs have the same transcriptional activation domains. In some embodiments, the TALE-TFs may have different transcriptional activation domains. In some embodiments, at least two, at least three, at least four, at least five, at least six, at least seven, at least eight, at least nine, or at least ten of the TALE-TFs have different transcriptional activation domains.

In some embodiments, the TALE-TFs in the composition may bind different target regions that are either upstream or downstream from the TSS. In some embodiments, all of the TALE-TF in the composition may bind to different target regions that are upstream from the TSS. In some embodiments, all of the TALE-TF in the composition may bind to different target regions that are downstream from the TSS. In some embodiments, the TALE-TFs in the composition may bind different target regions, wherein at least one of the target regions is upstream from the TSS and at least one of the target regions is downstream from the TSS.

The target regions of the TALE-TFs may be separated by at least about 1 nucleotide to about 1000 base pairs. For example, the target regions may be separated by at least about 1 base pair, at least about 2 base pairs, at least about 3 base pairs, at least about 4 base pairs, at least about 5 base pairs, at least about 6 base pairs, at least about 7 base pairs, at least about 8 base pairs, at least about 9 base pairs, at least about 10 base pairs, at least about 20 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120 base pairs, at least about 130 base pairs, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220 base pairs, at least about 230 base pairs, at least about 240 base pairs, at least about 250 base pairs, at least about 260 base pairs, at least about 270 base pairs, at least about 280 base pairs, at least about 290 base pairs, at least about 300 base pairs, at least about 310 base pairs, at least about 320 base pairs, at least about 330 base pairs, at least about 340 base pairs, at least about 350 base pairs, at least about 360 base pairs, at least about 370 base pairs, at least about 380 base pairs, at least about 390 base pairs, at least about 400 base pairs, at least about 410 base pairs, at least about 420 base pairs, at least about 430 base pairs, at least about 440 base pairs, at least about 450 base pairs, at least about 460 base pairs, at least about 470 base pairs, at least about 480 base pairs, at least about 490 base pairs, at least about 500 base pairs, at least about 510 base pairs, at least about 520 base pairs, at least about 530 base pairs, at least about 540 base pairs, at least about 550 base pairs, at least about 560 base pairs, at least about 570 base pairs, at least about 580 base pairs, at least about 590 base pairs, at least about 600 base pairs, at least about 700 base pairs, at least about 800 base pairs, at least about 900 base pairs, or at least about 1000 base pairs.

4. Constructs and Plasmids

The genetic constructs may comprise a nucleic acid sequence that encodes the TALE-TFs disclosed herein. The genetic construct, such as a plasmid, may comprise a nucleic acid that encodes the TALE-TFs. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adeno-associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The nucleic acid sequences may make up a genetic construct that may be a vector. The vector may be capable of expressing the TALE-TFs in the cell of a mammal. The vector may be recombinant. The vector may comprise heterologous nucleic acid encoding the TALE-TFs. The vector may be a plasmid. The vector may be useful for transfecting cells with nucleic acid encoding the TALE-TFs, which the transformed host cell is cultured and maintained under conditions wherein expression of the TALE-TFs takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the TALE-TFs and may further comprise an initiation codon, which may be upstream of the TALE-TFs coding sequence, and a stop codon, which may be downstream of the TALE-TFs. The initiation and termination codon may be in frame with the TALE-TFs coding sequence. The vector may also comprise a promoter that is operably linked to the TALE-TFs coding sequence TALE-TFs. The promoter operably linked to the TALE-TFs coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the TALE-TFs coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the TALE-TFs coding sequence. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extra-chromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the TALE-TFs, such as the nucleic acid sequence of at least one of SEQ ID NOs: 43, 45, 47, 49, 51, 53, 55, 57, 59, 61, 63, 65, 67, 69, 71, 73, 75, 77, 79, 81, 83, 85, 87, 89, 91, 93, 95, or 97, or variants thereof.

5. Methods of Use

Potential applications of the combination of TALE-TFs are diverse across many areas of science and biotechnology. The combination of TALE-TFs may be used to induce and modulate mammalian gene expression. The combination of TALE-TFs may be used to transdifferentiate a cell and/or activate genes related to cell and gene therapy, genetic reprogramming, and regenerative medicine. The combination of TALE-TFs may be used to reprogram cell lineage specification. Activation of endogenous genes encoding the key regulators of cell fate, rather than forced overexpression of these factors, may potentially lead to more rapid, efficient, stable, or specific methods for genetic reprogramming and transdifferentiation. Combination of TALE-TFs could provide a greater diversity of transcriptional activators to complement other tools for modulating mammalian gene expression. The combination of TALE-TFs may be used to compensate for genetic defects, suppress angiogenesis, inactivate oncogenes, activate silenced tumor suppressors, regenerate tissue or reprogram genes.

6. Methods of Activating Gene Expression

The present disclosure provides a mechanism for activating the expression of endogenous mammalian genes based on targeting a transcriptional activator to promoters via combinations of TALE-TF, as described above. The combination of TALE-TFs may activate silenced genes without the use of chromatin modifying drugs. The combination of TALE-TFs target regions upstream of the TSS of the target gene substantially induced gene expression of the target gene. The combination of polynucleotides encoding the TALE-TFs can also be transfected directly to cells. Combination of TALE-TFs targeted to a single promoter as well as simultaneous targeting of multiple promoters by different combination of TALE-TFs targeting different target genes is also envisioned.

The method may include administering to a cell or subject a combination of TALE-TFs, compositions of TALE-TFs, or one or more polynucleotides or vectors encoding said combination of TALE-TFs, as described above. The method may include administering a combination of TALE-TFs, compositions of TALE-TFs, or one or more polynucleotides or vectors encoding said combination of TALE-TFs, as described above, to a mammalian cell or subject.

7. Pharmaceutical Compositions

The TALE-TFs may be in a pharmaceutical composition. The pharmaceutical composition may comprise about 1 ng to about 10 mg of DNA encoding each of the TALE-TFs. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition containing the TALE-TFs may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the pharmaceutical composition containing the TALE-TFs at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the TALE-TFs may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

8. Methods of Delivery

Provided herein is a method for delivering the pharmaceutical formulations, preferably two or more TALE-TF, for providing genetic constructs and/or proteins of the TALE-TFs. The delivery of the TALE-TFs may be the transfection or electroporation of the TALE-TFs as one or more nucleic acid molecules that is expressed in the cell and delivered to the surface of the cell. The TALE-TF protein may be delivered to the cell. The nucleic acid molecules may be electroporated using BioRad Gene Pulser Xcell or Amaxa Nucleofector IIb devices or other electroporation device. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000.

The vector encoding a TALE-TFs protein may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a TALE-TFs protein may be introduced into a cell to induce gene expression of the target gene. For example, one or more nucleotide sequences encoding one or more TALE-TFs directed towards a target gene may be introduced into a mammalian cell. Upon delivery of the TALE-TFs to the cell, and thereupon the vector into the cells of the mammal, the transfected cells will express the TALE-TFs. The TALE-TFs may be administered to a mammal to induce or modulate gene expression of the target gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

9. Routes of Administration

The TALE-TFs and compositions thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The TALE-TFs and compositions thereof may be administered by traditional syringes, needleless injection devices, "microprojectile bombardment gone guns", or other physical methods such as electroporation ("EP"), "hydrodynamic method", or ultrasound.

10. Cell Types

Any of these delivery methods and/or routes of administration could be utilized with a myriad of cell types, for example, those cell types currently under investigation for cell-based therapies. The cell may be any mammalian cell, such as a HEK293T cell.

11. Kits

Provided herein is a kit, which may be used to induce mammalian gene expression in a cell. The kit comprises the above-described compositions or a cell that comprises said compositions, as well as instructions for using the compositions. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

At least one component may include at least two TALE-TFs, as described above, which specifically targets a gene. The TALE-TFs, as described above, may be included in the kit to specifically bind and target a particular target region upstream, within or downstream of the TSS of the target gene. For example, the TALE-TFs may be specific for a promoter region of a target gene.

The present invention has multiple aspects, illustrated by the following non-limiting examples.

12. Examples

The foregoing may be better understood by reference to the following examples, which are presented for purposes of illustration and are not intended to limit the scope of the invention.

Example 1

Methods

Cell culture and transfection. HEK293T cells were obtained from the American Tissue Collection Center (ATCC) through the Duke University Cancer Center Facilities and were maintained in Dulbecco's Modified Eagle's Medium supplemented with 10% fetal bovine serum and 1% penicillin and streptomycin at 37° C. with 5% CO2. HEK293T cells were transfected with Lipofectamine 2000 (Invitrogen) according to the manufacturer's instructions. Transfection efficiencies were routinely >95% as determined by flow cytometry after delivery of a control enhanced GFP expression plasmid. The amount of DNA used for lipofection was 800 ng per well in 24-well plates or 200 ng per well in 96-well plates. For luciferase reporter assays in 24-well plates, 100 ng of reporter plasmid was included with 700 ng of TALE-TF expression plasmid. When comparing single TALE-TFs to the combination of all TALE-TFs (FIGS. 1A-1N), the total amount of TALE-TF expression plasmid was held constant (800 ng of single TALE-TFs and 800 ng of total TALE-TF expression plasmid divided equally amongst each factor). When assessing the individual contribution of each TALE-TF (FIGS. 2A-2H), the amount of each TALE-TF was held constant at 116 ng, with empty expression plasmid added to a total of 700 ng. Amounts of DNA for transfections in 96-well plates were scaled accordingly.

Plasmids and TALE-TF. Tale-TFs were assembled using the Golden Gate TALEN and TAL effector kit obtained from Addgene (Cermak et al. Nucleic Acids Res 39:e82 (2011)). A destination vector for the final assembly step was created to include a FLAG® epitope tag (Sigma-Aldrich, St. Louis, Mo.; DYKDDDDK, SEQ ID NO: 99) and an SV40 NLS at the N terminus, a 152 residue deletion from the N terminus of the wild type TALE proteins that preserves the DNA binding ability of TALEs (Miller et al. Nat. Biotechnol. 29:143-148 (2011)), 63 wild type TAL amino acids after the repeat domain (Zhang et al., Nat. Biotechnol. 29: 149-153 (2011)), a C-terminal SV40 NLS, a VP64 domain that contains four repeats of the minimal activation domain of VP16, and an HA tag at the C terminus (FIG. 1A). TALE-TFs were designed to target within the 600 bp upstream of the transcriptional start site (FIG. 1B) on the basis of the criteria described by Cermak et al. TALE-TFs were designed downstream of the transcription start site for ERBB2, but upstream of the translation start site, on the basis of previous studies showing high activity of synthetic zinc finger transcription factors targeting this region (Beerli et al., PNAS 97:1495-1500 (2000)). The compositions of the TALE-TFs are provided in FIGS. 3A-3D.

The reporter plasmids were built by cloning PCR-amplified genomic DNA sequences upstream of the genes of interest IL1RN (chromosome 2, 113874366-113875462), KLK3 (chromosome 19, 51357466-51358177); CEACAM5 (chromosome 19, 42211804-42212651) and ERBB2 (chromosome 17, 37855857-37856492), in the vector pGL3-Basic (Promega). Coordinates are provided based on the hg19 reference genome.

Luciferase assays. Forty-eight hours after transfection, cells were collected into 96-well plates, washed with PBS once and lysed with 100 mM monobasic sodium phosphate and 0.2% Triton X-100. The lysate was incubated with Bright-Glo™ Substrate (Promega) in a 1:1 ratio and luciferase activity was measured using a Synergy 2 Multi-Mode Microplate Reader (BioTek). The results are expressed as relative luciferase activity (RLA), which is the average luciferase activity normalized to the luciferase activity in samples transfected with the reporter vector and the empty TALE-TF expression vector. Data are presented from three independent experiments performed with two biological replicates per experiment.

Western blot analysis Cells were lysed in 50 mM Tris-Cl (pH 7.4), 150 mM NaCl, 0.5% Triton X-100 and 0.1% SDS. Protein concentrations in cell lysates were measured by the BCA Protein Assay (Pierce). Lysates were mixed with loading buffer, boiled for 5 min, and equal amounts of protein were run in NuPAGE® Novex 4-12% Bis-Tris Gel polyacrylamide gels and transferred to nitrocellulose membranes. Non-specific antibody binding was blocked with 50 mM Tris/150 mM NaCl/0.1% Tween-20 (TBS-T) with 5% nonfat milk for 30 min. The membranes were incubated with primary antibodies (horseradish peroxidase (HRP)-conjugated anti-HA (Roche, clone 3F10) in 5% milk in TBS-T diluted 1:5000 for 30 min; anti-CEACAM5 (Cell Signaling Technology, clone CB30) in 5% milk in TBS-T diluted 1:1000 overnight; anti-GAPDH (Cell Signaling Technology, clone 14C10) in 5% milk in TBS-T diluted 1:5000 for 30 min; anti-ERBB2 (Cell Signaling Technology, clone 29D8) in 5% BSA in TBS-T diluted 1:2000 for 2 h). The membranes were then washed with TBS-T for 30 min. Membranes labeled with primary antibodies were incubated with rabbit HRP-conjugated antibody (Sigma-Aldrich, catalog number A6154) diluted 1:5000 for 30 min, and washed with TBS-T for 30 minutes. Membranes were visualized using the Immun-Star WesternC™ Chemiluminescence Kit (Bio-Rad) and images were captured using a ChemiDoc™ XRS+ System and processed using ImageLab software (Bio-Rad).

Enzyme-linked immunosorbent assay. Serum-free culture media (OPTI-MEM) was collected and frozen at −80° C. Human IL-1ra and KLK3 secretion into culture media was quantified via ELISA, according to the manufacturer's protocols (R&D Systems, Cat. No. DY280 and DKK300, respectively). For the IL-1Ra ELISA, the standard curve was prepared by diluting recombinant human IL-1ra in OPTI-MEM and the IL-1ra in culture media was measured undiluted. For the KLK3 ELISA, the standard curve was prepared by diluting recombinant KLK3 in the manufacturer's calibrator diluent and the samples were concentrated approximately eightfold by centrifugation through 3 k-Da MWCO filters for 20 minutes (Amicon Ultra, catalog number UFC500396). Reported values were corrected by the concentration factor for each sample.

For both assays, optical density was measured at 450 nm with a wavelength correction at 540 nm. Each standard and sample was assayed in duplicate. The duplicate readings were averaged and normalized by subtracting the average zero standard optical density. A standard curve was generated by log transforming the data and performing a linear regression of the IL-1ra or KLK3 concentration versus the optical density. The lower limit of detection was 50 pg/ml for human IL-1ra and 32 pg/ml for human KLK3. Data reported are the mean and s.e.m. of these individual values combined from multiple experiments (n=6 biological replicates for IL-1ra, n=4 biological replicates for KLK3).

Quantitative RT-PCR. Total RNA was isolated using the RNEASY® Plus RNA isolation kit (Qiagen). cDNA synthesis was performed using the SuperScript® VILO™ cDNA Synthesis Kit (Invitrogen). Realtime PCR using SsoFast™ EvaGreen® Supermix (Bio-Rad) was performed with the CFX96 Real-Time PCR Detection System (Bio-Rad) with 45 cycles, melting for 2 s at 95° C., and annealing and extension for 2 s at 55° C. Real-time PCR oligonucleotide primers (ERBB2, 5-AGCCGCGAGCACCCAAGT-3 (SEQ ID NO: 29), 5'-TTGGTGGGCAGGTAGGTGAGTT-3' (SEQ ID NO: 30); CEACAM5, 5'-TCCCCACA-GATGGTGCAT-3 (SEQ ID NO: 31), 5-GAACGGCGTG-GATTCAATAG-3' (SEQ ID NO: 32); KLK3, 5'-CTCGTGGCAGGGCAGTCT-3 (SEQ ID NO: 33), 5'-AGCTGTGGCTGACCTGAAAT-3' (SEQ ID NO: 34); IL1RN, 5'-GACCCTCTGGGAGAAAATCC-3 (SEQ ID NO: 35), 5'-GTCCTTGCAAGTATCCAGCA-3'(SEQ ID NO: 36); PSD4, 5'-GCAGCACCTCCTGGTCAC-3 (SEQ ID NO: 37), 5'-ATCCGACACATCCTGATTCC-3' (SEQ ID NO: 38); IL1F10, 5'-CCTCCCCATGGCAAGATACT-3 (SEQ ID NO: 39), 5-AGCAGTTGTCTGCAACAGGA-3' (SEQ ID NO: 40); and GAPDH, 5'-CAATGACCCCTT-CATTGACC-3'(SEQ ID NO: 41); 5'-TTGATTTTGGAGG-GATCTCG-3' (SEQ ID NO: 42)) were designed using Primer3Plus software and purchased from IDT. Primer specificity was confirmed by agarose gel electrophoresis and melting curve analysis. Reaction efficiencies over the appropriate dynamic range were calculated to ensure linearity of the standard curve. Data are presented from three independent experiments performed with two biological replicates per experiment.

Statistics. Statistical analysis were performed by single factor ANOVA with α=0.05 in Microsoft Office Excel 2007. Effect coefficients (Table 3) were determined using the regression tool in the data analysis add-in to Microsoft Office Excel 2007, with the relative luciferase activities (FIGS. 2A-2C, Table 2) serving as they input and an array of zeros and ones representing each TALE-TF combination as the x input.

Example 2

Combinations of TALE-TFs

Figure 4:
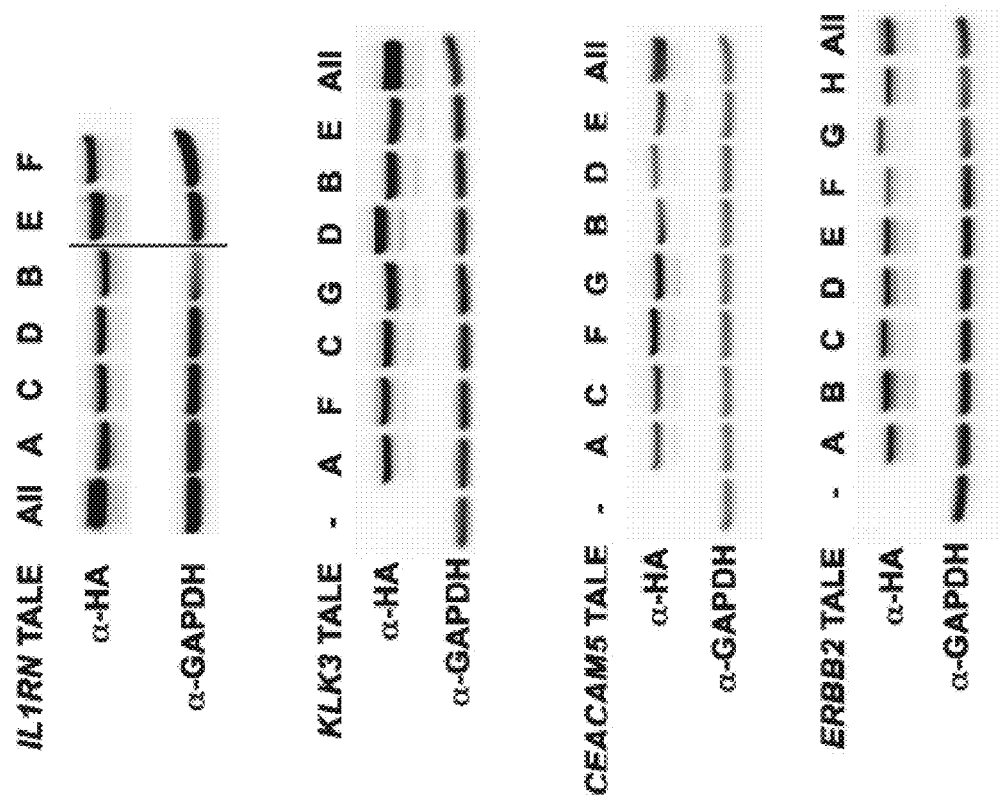
FIG. 4 shows the expression of TALE-TFs targeting IL1RN, KLK3, CEACAM5 and ERBB2 transfected into HEK293T cells.

Six, seven or eight TALE-TFs were targeted to the promoter regions of the IL1RN, KLK3 (also known as prostate-specific antigen (PSA)), CEACAM5 (also known as CEA), and ERBB2 which are implicated in immunomodulation, inflammation, and cancer (FIGS. 3A-3D). The target sites for these TALE-TFs were distributed within 600 bp of the TSS (FIG. 1). TALE-TF expression plasmids were transfected into HEK293T cells either individually or as a combination of all the TALE-TFs targeted to a particular promoter. After 2 days, cell lysates were analyzed by Western blot with anti-HA for TALE-TF expression and anti-GADPH as a loading control. The anti-HA antibody recognizes an HA tag fused to the VP64 domain at the C-terminus of the TALE-TF. The expression of the TALE-TFs was confirmed by western blot (FIG. 4). TALE-TF activity was measured in reporter assays in which luciferase was under the control of the respective gene promoter (FIGS. 1C-1F). Most individual TALE-TFs activated the co-transfected plasmid reporters, but only modestly, as in previous studies (Table 1). However, the delivery of combinations of TALE-TFs led to substantial synergistic effects on gene activation. The synergistic activation of the plasmid-based reporters was recapitulated in the upregulation of the native genes in their natural chromosomal context as determined by quantitative reverse transcription PCR (qRT-PCR), including increases in mRNA abundance greater than 10,000-fold (FIGS. 1G-1J). Detection of induced protein expression of IL-1ra, (encoded by IL1RN), KLK3, CEACAM5, and ERBB-2 by ELISA and western blot validated the functional outcome of the activation of these genes (FIGS. 1K-1N). In particular, expression of IL-1ra, KLK3 and CEACAM5 protein was reproducibly detected in samples with combinations of TALE-TFs. Low expression of ERBB-2 was found in control samples and cells transfected with single TALE-TFs, but its expression was substantially enhanced in cells transfected with all TALE-TFs (FIG. 1N).

Figure 5A:
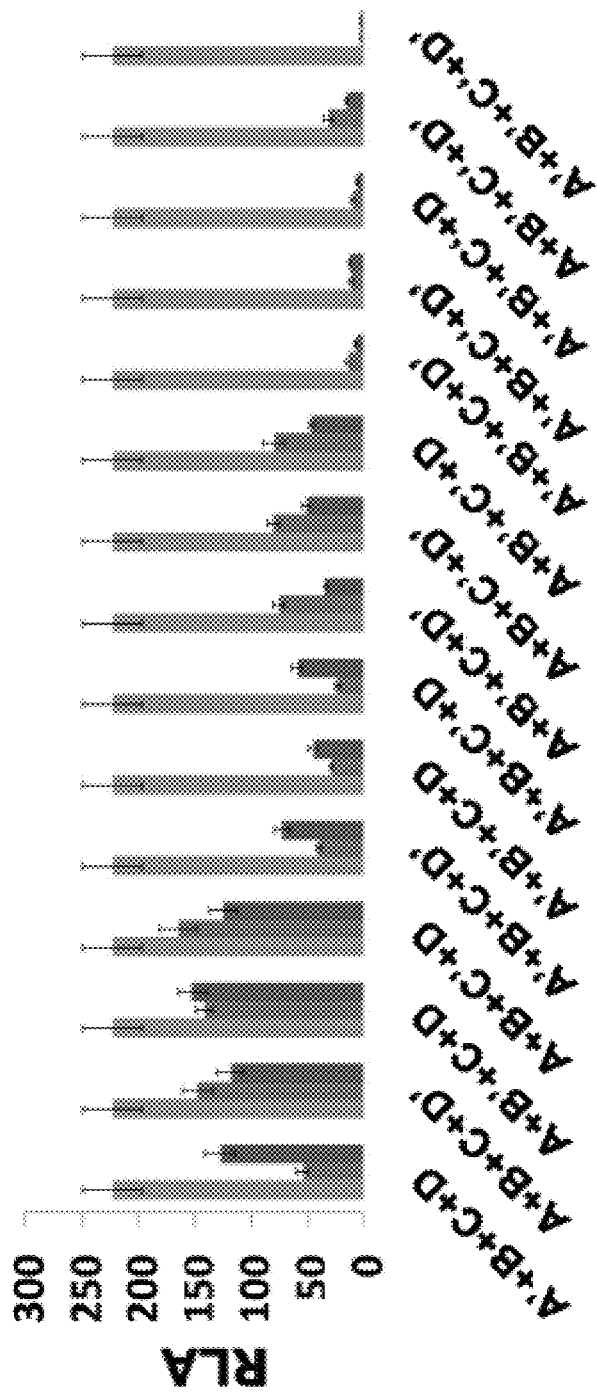
FIGS. 5A-5B show the requirement of transactivation domain for synergistic gene regulation.
Figure 5B:
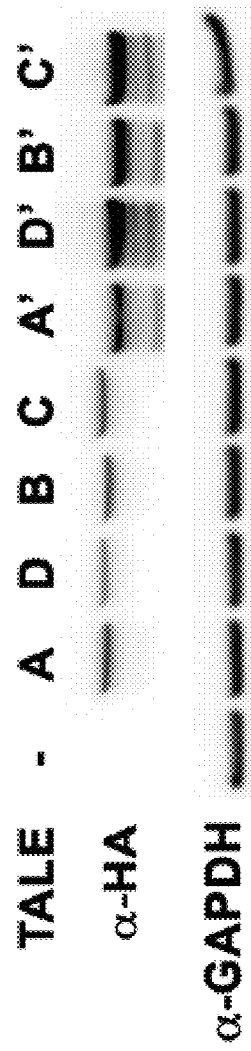

These results are consistent with a mechanism in which the VP64 acidic activation domain of multiple transcription factors is simultaneously interacting with and stabilizing components of the pre-initiation complex. This mechanism was confirmed by demonstrating that the VP64 domain, i.e., the transactivation domain, rather than nucleosome displacement by TALEs, was essential to achieving the synergistic effect on gene regulation (FIGS. 5A-5B). The VP64 transcriptional activation domain was removed from the TALE-TF destination expression plasmid and TALE A, B, C and D targeting the IL1RN gene were recloned and designated A', B', C' and D'. HEK293T cells were transfected with the IL1RN reporter vector and all combinations of four TALE-TFs in which one, two, three or four TALE-TFs were replaced with a TALE-TF lacking the VP64 domain. In FIG. 5A, the relative luciferase activities (RLAs) are shown in groups for each indicated combination (middle bar), the RLA for transfection of all four TALE-TFs with VP64 (left bar), and the RLA for transfection of only the one, two, or three TALE-TFs that contain VP64 (right bar). The total amount of transfected plasmid DNA was maintained constant with empty expression vector. The results indicate that removing the VP64 domain from one or more TALE-TFs is similar to not including that TALE-TF in the transfection, indicating that binding and stabilization of preinitiation complex components by VP64, and not simply DNA-binding by the TALE, is necessary for synergistic activation. HEK293T cells were transfected with TALE-TFs A, B, C, D and the corresponding TALE-TF variants lacking VP64 targeting IL1RN. The cell lysates were analyzed by Western blot with anti-HA and anti-GAPDH antibodies.

Figure 6:
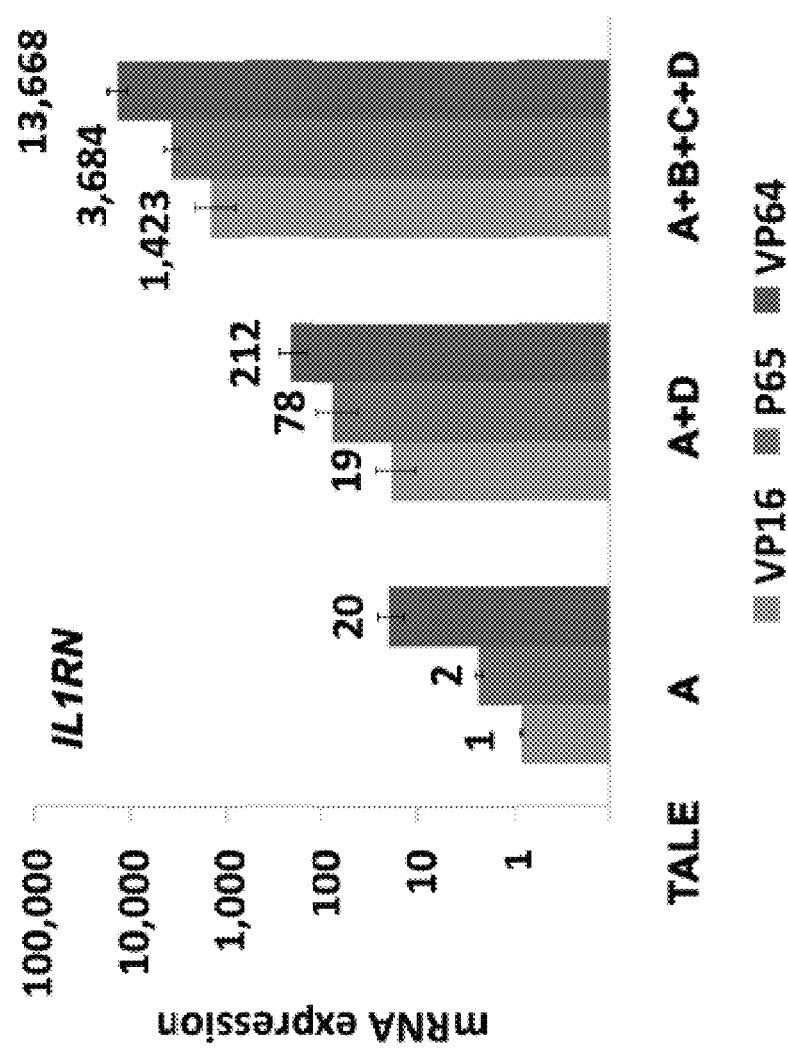
FIG. 6 shows the synergistic gene activation with multiple acidic activation domains as shown by quantitative RT-PCR to determine the levels of IL1RN transcripts.

Alternative acidic activation domains could also synergistically activate gene expression (FIG. 6). The VP64 transcriptional activation domain in the TALE-TF destination plasmid was replaced with two other well characterized acidic transcriptional activators: VP16 and P65. TALE-TFs A, B, C, and D targeting the IL1RN gene were recloned into these vectors. HEK293T cells were transfected with either TALE-TF A alone, TALE-TFs A and D, TALE-TFs A, B, C, and D together, or an empty vector as control. The RNA was analyzed using quantitative RT-PCR to determine the levels of IL1RN transcripts. The results are represented as relative levels of expression of IL1RN induced by each combination of TALE-TF with different activation domains normalized to GAPDH expression and control samples transfected with the empty vector only.

Example 3

Specificity of TALE-TFs

Figure 7:
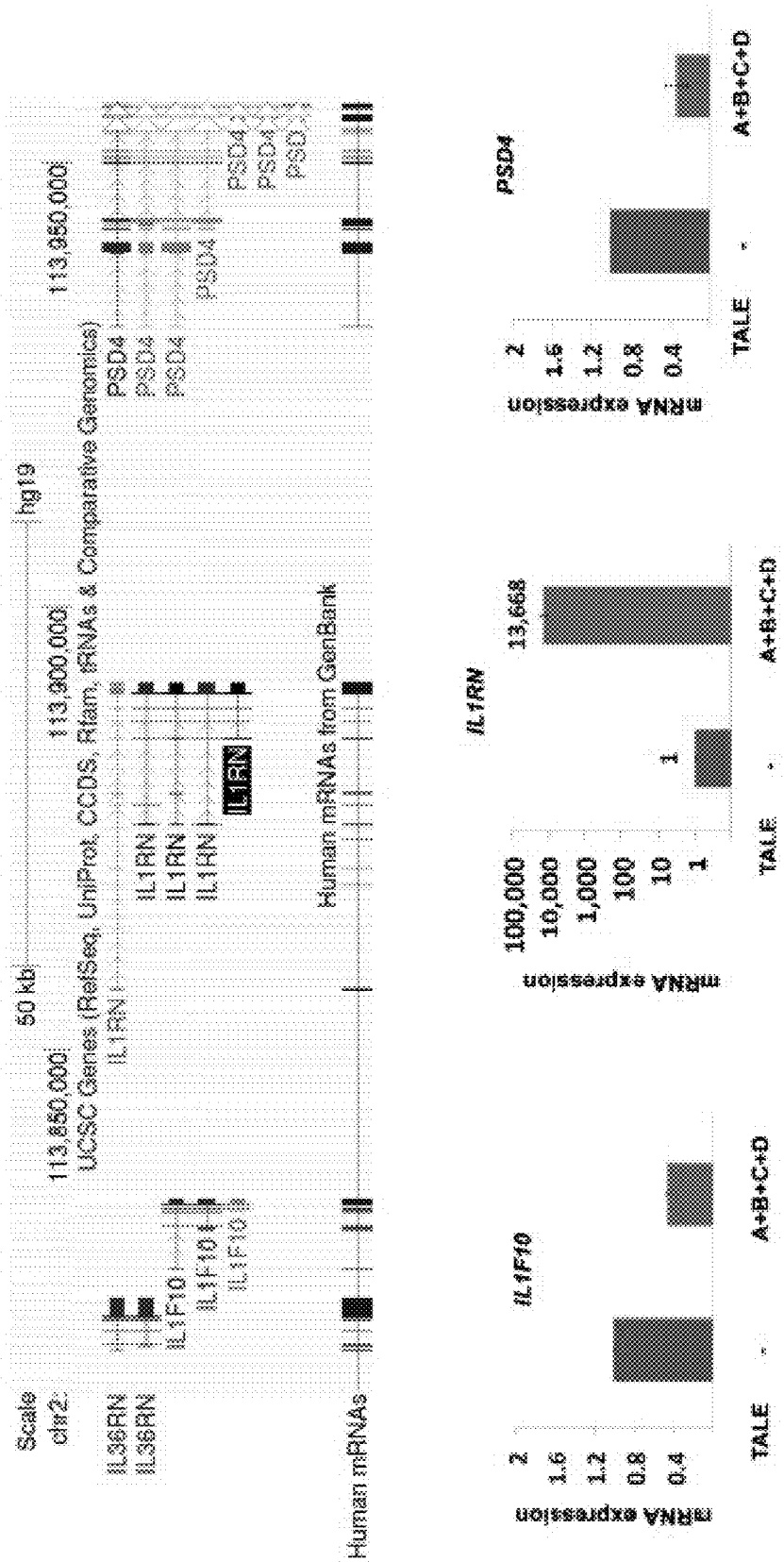
FIG. 7 shows the effect of synergistic gene activation by TALE-TFs on neighboring genes as shown by quantitative RT-PCR to determine the levels of IL1RN transcripts.

The expression of other genes near IL1RN did not increase, indicating that this large synergistic activation was specific to the target gene (FIG. 7). The IL1RN locus is flanked by genes ILIF10 and PSD4. To test whether transcriptional activation of the IL1RN gene caused changes in expression of nearby genes, quantitative RT-PCR was performed with cDNA prepared from cells transfected with TALE-TFs A, B, C, and D. The results are represented as levels of expression relative to GAPDH and normalized to samples transfected with an empty expression plasmid.

Figure 8:
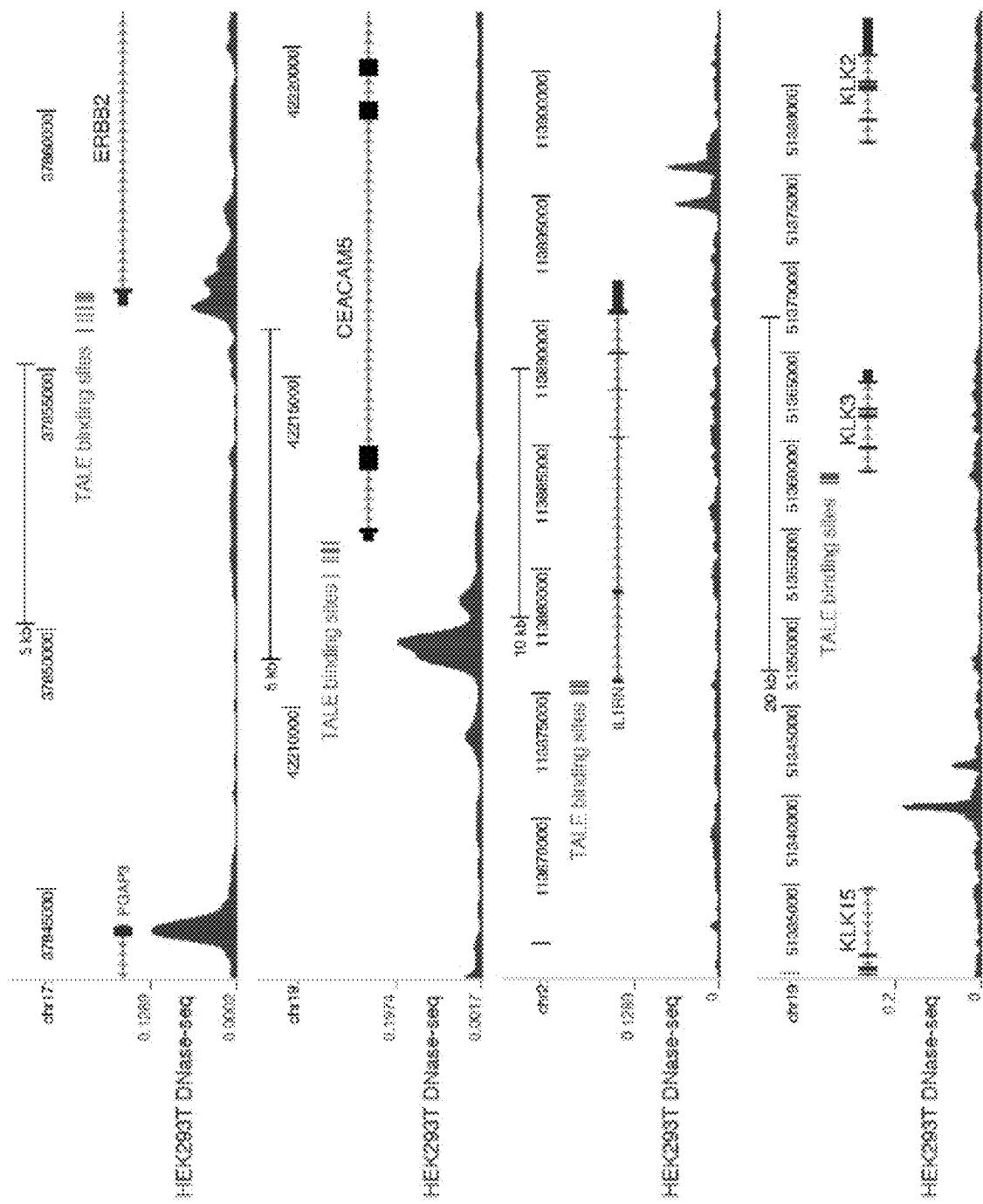
FIG. 8 shows the DNase hypersensitive regions of ERBB2, CEACAM5, IL1RN, and KLK3 genes.

The TALE-TFs were not specifically designed to target DNase-hypersensitive regions (FIG. 8). DNase-seq was performed in HEK293T cells to identify DNase hypersensitive regions as previously described (Song et al., *Genome Res* 21(10):1757 (2011); Song and Crawford, *Cold Spring Harbor Protocols* (2010)). The results show that open chromatin was not a requirement for gene activation by combinations of TALE-TFs. In fact, IL1RN, KLK3, and CEACAM5 are not expressed in HEK293T cells. Notably, targeting chromatin that is inaccessible to DNase did not prevent gene activation by the engineered TALE-TFs (FIGS. 1G-1I). These results suggest that targeting open chromatin may not be a prerequisite to successful TALE-TF engineering and that activation of silenced genes is possible in the absence of chromatin modifying drugs, particularly when using combinations of TALE-TFs. In contrast to these three genes, ERBB2 is moderately expressed in HEK293 cells and the TALE-TFs for ERBB2 regulation were targeted to open chromatin (FIG. 8). Combinations of these TALE-TFs also led to synergistic ERBB2 activation although the effect was not as substantial relative to the other genes as a result of higher levels of basal expression (FIGS. 1F, 1J, 1N).

Example 4

Combinatorial Regulation of Mammalian Genes by TALE-TFs

To comprehensively characterize the effects of combinatorial regulation of mammalian genes by engineered TALE- TFs, all 63 combinations of six TALE-TFs targeting three different genes with a corresponding luciferase reporter were co-transfected in HEK293T cells (FIGS. 2A-2C). Various combinations of TALE-TFs could be used to reproducibly achieve tunable levels of gene expression over a large dynamic range. Many TALE-TFs that did not activate the reporter when delivered alone contributed to synergistic activation of expression when combined with other TALE-TFs (Table 2). In some cases, the addition of a TALE-TF decreased gene expression. However, for all three genes there was an increase in the average gene expression with increasing numbers of TALE-TFs (FIG. 2D), and the average contribution of each additional TALE-TF decreased as the number of TALE-TFs increased (FIG. 2E).

TABLE 2

Relative Luciferase Activity for combinations of TALE-TFs.

| IL1RN | | | KLK3 | | | CEACAM5 | | |
|---|---|---|---|---|---|---|---|---|
| | RLA | SEM | | RLA | SEM | | RLA | SEM |
| E | 1.09 | 0.03 | C | 0.88 | 0.14 | A | 1.01 | 0.04 |
| F | 1.22 | 0.03 | B | 1.03 | 0.15 | E | 2.41 | 0.19 |
| D | 5.76 | 0.35 | E | 2.17 | 0.35 | C | 3.74 | 0.64 |
| C | 6.75 | 0.33 | F | 4.57 | 0.48 | D | 4.59 | 0.78 |
| B | 11.96 | 1.26 | A | 25.07 | 3.20 | F | 4.70 | 0.18 |
| A | 14.41 | 0.36 | D | 45.80 | 9.31 | B | 11.64 | 1.52 |
| E + F | 2.00 | 0.13 | C + B | 1.14 | 0.12 | A + E | 3.06 | 0.10 |
| C + F | 8.06 | 1.16 | C + E | 1.44 | 0.10 | A + C | 3.41 | 0.44 |
| D + F | 8.97 | 0.50 | B + E | 2.04 | 0.17 | A + D | 3.65 | 0.20 |
| A + E | 11.47 | 0.96 | F + B | 3.29 | 0.28 | A + F | 4.03 | 0.17 |
| E + C | 12.36 | 1.58 | C + F | 5.66 | 0.24 | C + E | 5.26 | 0.62 |
| D + E | 12.42 | 0.74 | F + E | 11.77 | 2.04 | F + E | 7.45 | 0.49 |
| A + F | 13.56 | 0.62 | A + C | 19.17 | 3.94 | F + D | 7.74 | 0.92 |
| B + F | 13.97 | 1.07 | A + B | 19.46 | 2.96 | D + E | 7.77 | 0.92 |
| E + B | 18.11 | 1.99 | B + D | 34.64 | 4.17 | C + B | 9.40 | 1.02 |
| A + C | 32.59 | 1.70 | C + D | 34.98 | 4.54 | A + B | 9.72 | 1.40 |
| D + C | 45.00 | 4.67 | A + F | 40.17 | 8.27 | B + E | 10.90 | 1.44 |
| A + D | 46.42 | 2.18 | A + E | 45.95 | 4.75 | C + F | 15.43 | 1.34 |
| A + B | 51.05 | 3.36 | D + E | 50.08 | 9.11 | F + B | 18.05 | 1.36 |
| D + B | 58.79 | 4.30 | F + D | 56.06 | 9.47 | C + D | 22.90 | 3.37 |
| B + C | 71.78 | 6.54 | A + D | 152.91 | 34.41 | B + D | 27.62 | 1.19 |
| D + E + F | 11.89 | 0.36 | C + B + E | 4.01 | 0.33 | A + C + E | 5.87 | 0.11 |
| E + C + F | 14.79 | 3.64 | C + F + B | 4.85 | 0.97 | A + D + E | 7.00 | 0.40 |
| A + E + F | 15.47 | 0.23 | C + F + E | 18.14 | 2.24 | A + F + D | 7.78 | 0.83 |
| E + B + F | 21.13 | 3.93 | F + B + E | 25.22 | 0.97 | A + F + E | 7.92 | 0.87 |
| A + D + E | 52.26 | 7.11 | A + B + E | 28.08 | 4.65 | A + C + F | 10.09 | 1.55 |
| A + C + F | 61.57 | 5.32 | A + C + B | 31.73 | 3.46 | A + B + E | 10.40 | 0.85 |
| A + D + F | 62.86 | 6.23 | A + C + E | 34.01 | 8.92 | A + C + B | 12.19 | 0.73 |
| D + E + B | 63.74 | 2.92 | A + C + F | 47.13 | 5.69 | C + F + E | 17.67 | 1.28 |
| D + C + F | 64.91 | 8.48 | A + F + B | 51.75 | 9.41 | C + B + E | 18.05 | 2.59 |
| A + E + C | 65.87 | 5.77 | C + B + D | 58.13 | 15.67 | A + F + B | 21.81 | 2.38 |
| D + B + F | 67.75 | 11.26 | C + F + D | 66.90 | 16.42 | C + F + B | 22.16 | 1.95 |
| B + C + F | 68.43 | 5.02 | B + D + E | 84.46 | 6.84 | A + B + D | 25.63 | 1.13 |
| D + E + C | 68.74 | 2.29 | C + D + E | 89.15 | 8.43 | F + D + E | 27.28 | 1.40 |
| E + B + C | 84.19 | 9.28 | A + F + E | 93.34 | 27.51 | A + C + D | 33.30 | 1.78 |
| A + E + B | 90.14 | 1.21 | F + B + D | 129.09 | 23.93 | F + B + E | 33.40 | 2.07 |
| A + B + F | 99.39 | 5.19 | A + B + D | 137.64 | 29.66 | C + F + D | 44.71 | 4.66 |
| A + B + C | 118.47 | 11.71 | A + D + E | 181.23 | 36.26 | C + B + D | 48.82 | 0.91 |
| A + D + B | 124.43 | 12.23 | A + F + D | 208.90 | 45.84 | C + D + E | 51.02 | 4.10 |
| D + B + C | 127.18 | 13.20 | F + D + E | 234.64 | 26.66 | B + D + E | 52.22 | 0.78 |
| A + D + C | 151.52 | 12.87 | A + C + D | 240.72 | 37.19 | F + B + D | 61.45 | 2.95 |
| A + D + E + F | 69.05 | 15.29 | C + F + B + E | 19.38 | 3.21 | A + C + B + E | 13.77 | 1.40 |
| D + E + B + F | 77.85 | 6.07 | A + C + B + E | 47.83 | 3.68 | A + C + F + E | 17.93 | 1.79 |
| A + E + C + F | 86.78 | 5.91 | A + C + F + B | 50.99 | 5.52 | A + C + F + B | 23.56 | 2.26 |
| D + E + C + F | 107.60 | 8.92 | C + B + D + E | 77.91 | 7.42 | A + F + D + E | 31.94 | 1.68 |
| E + B + C + F | 110.89 | 9.61 | C + F + B + D | 93.54 | 5.79 | C + F + B + E | 38.24 | 9.11 |
| A + D + C + F | 128.88 | 16.78 | A + C + F + E | 124.04 | 15.39 | A + C + B + D | 40.97 | 1.64 |
| A + D + B + F | 138.25 | 19.88 | A + F + B + E | 131.46 | 13.41 | A + F + B + E | 42.93 | 4.57 |
| A + B + C + F | 161.75 | 17.78 | C + F + D + E | 154.91 | 15.96 | A + C + F + D | 50.64 | 4.41 |
| A + E + B + F | 161.90 | 10.25 | A + C + B + D | 217.21 | 24.85 | A + C + D + E | 51.35 | 2.52 |
| D + E + B + C | 183.28 | 13.62 | F + B + D + E | 225.37 | 27.23 | A + B + D + E | 63.08 | 5.62 |
| D + B + C + F | 206.73 | 24.31 | A + B + D + E | 252.84 | 37.27 | C + B + D + E | 79.15 | 5.86 |
| A + D + E + C | 213.39 | 27.30 | A + C + F + D | 281.45 | 12.10 | C + F + B + D | 83.07 | 6.02 |
| A + D + B + C | 223.14 | 26.85 | A + C + D + E | 347.17 | 24.04 | A + F + B + D | 87.62 | 9.63 |
| A + D + E + B | 231.11 | 27.32 | A + F + B + D | 371.94 | 38.64 | C + F + D + E | 105.23 | 10.75 |

TABLE 2-continued

Relative Luciferase Activity for combinations of TALE-TFs.

| | IL1RN | | | KLK3 | | | CEACAM5 | |
|---|---|---|---|---|---|---|---|---|
| | RLA | SEM | | RLA | SEM | | RLA | SEM |
| A + E + B + C | 242.59 | 8.96 | A + F + D + E | 465.06 | 53.26 | F + B + D + E | 112.50 | 7.69 |
| A + D + E + C + F | 156.95 | 12.86 | A + C + F + B + E | 130.16 | 13.44 | A + C + F + B + E | 31.17 | 4.76 |
| A + D + E + B + F | 172.57 | 22.95 | C + F + B + D + E | 183.75 | 20.22 | A + C + B + D + E | 67.69 | 11.42 |
| D + E + B + C + F | 202.99 | 15.63 | A + C + F + B + D | 308.92 | 24.92 | A + F + B + D + E | 73.06 | 4.11 |
| A + D + E + B + C | 256.14 | 37.49 | A + C + B + D + E | 334.67 | 8.54 | A + C + F + B + D | 81.95 | 5.44 |
| A + D + B + C + F | 275.31 | 25.38 | A + C + F + D + E | 511.60 | 72.91 | C + F + B + D + E | 83.69 | 12.00 |
| A + E + B + C + F | 330.26 | 62.33 | A + F + B + D + E | 540.35 | 44.96 | A + C + F + D + E | 89.03 | 8.65 |
| A + D + E + B + C + F | 313.00 | 47.33 | A + C + F + B + D + E | 385.24 | 31.31 | A + C + F + B + D + E | 74.12 | 4.47 |

SEM = standard error of the mean.

To assign quantitative parameters to the relative contribution of each TALE-TF to the synergistic effect across the 63 data points in these experiments, polynomial model was applied to the data set of each gene of the form $$y_j = \left(\sum_{i=1}^{6} w_i x_{i,j}\right)^2$$

where $y_j$ is the relative luciferase activity for the jth combination of the six TALE-TFs. The value of $x_{i,j}$ is 0 if the ith TALE-TF is not included in the jth combination and it is 1 if it is included. The effect coefficient $w_i$ is a fit parameter that represents the relative contribution of the ith TALE-TF to the regulation of its target promoter in the context of all permutations of the six TALE-TFs. Multiple regression was used to solve for values of $w_i$ for all TALEs for each of the three target genes. These coefficients generate an excellent fit of the experimental data (FIGS. 2F-2H) and were highly significant ($P<2\times10^{-3}$) in accurately describing the relative contribution of each TALE-TF (Table 3).

In order to represent the contribution of each TALE-TF to the synergistic activation of gene expression, additive, multiplicative, and polynomial models of the form $$y_j = \sum_{i=1}^{6} w_i x_{i,j} \quad \text{additive}$$

$$y_j = 10^{\sum_{i=1}^{6} w_i x_{i,j}} \quad \text{multiplicative}$$

$$y_j = \left(\sum_{i=1}^{6} w_i x_{i,j}\right)^2 \quad \text{polynomial}$$

were tested for best fit of the data in FIGS. 2A-2C and Table 2, where $y_j$ is the relative luciferase activity for the $j^{th}$ combination of i TALE-TFs. The value of $x_{ij}$ is 0 if the $i^{th}$ TALE-TF is not included in the $j^{th}$ combination and is 1 if it is included. The effect coefficient $w_i$ is a fit parameter that represents the relative contribution of that particular TALE-TF to the regulation of its target promoter in the context of all permutations of the six TALE-TFs. Multiple regression was used to solve for values of $w_i$ for all TALEs for each

TABLE 3

Effect coefficients and corresponding P-values resulting from multiple regression of the polynomial model.

| | IL1RN | | KLK3 | | CEACAM5 | |
|---|---|---|---|---|---|---|
| | Effect coefficient | P-value | Effect coefficient | P-value | Effect coefficient | P-value |
| Intercept | −1.7 | 8.82e−5 | 2.4 | 3.02e−05 | −0.1 | 0.8 |
| TALE A | 4.4 | 6.15e−22 | 6.4 | 3.16e−23 | 0.0 | 1.0 |
| TALE B | 5.1 | 4.40e−2 | 0.7 | 0.1 | 2.4 | 1.67e−12 |
| TALE C | 4.4 | 4.59e−22 | 0.5 | 0.2 | 1.5 | 3.65e−07 |
| TALE D | 3.7 | 7.83e−19 | 8.8 | 6.00e−30 | 3.3 | 1.19e−17 |
| TALE E | 1.5 | 1.47e−06 | 3.0 | 3.21e−10 | 1.2 | 1.86e−05 |
| TALE F | 0.9 | 1.69e−03 | 3.5 | 1.27e−12 | 1.9 | 2.98e−09 | gene. The resulting fits for IL1RN (a-c), KLK3 (d-f) and CEACAM5 (g-i) are shown here, as well as x=y (solid line). The additive model does not account for synergy between TALE-TFs and therefore underestimates the data as the number of TALE-TFs and corresponding level of gene activation increases (a,d,g). The multiplicative model does not account for the diminishing effect of extra TALE-TFs as the number of TALE-TFs increases (FIG. 2E), and therefore overestimates the data as the number of TALE-TFs and corresponding level of gene activation increases (b,e,h). The polynomial model generally provides the best fit of the data (c,f,i), which mechanistically can be explained by its inclusion of second-order terms that account for interactions between TALE-TFs.

The polynomial model provided a stronger description of the data than the corresponding additive and multiplicative models (FIGS. 9A-9I). The additive model does not account for the synergy of TALE-TF activity (FIG. 2D) and the multiplicative model does not account for the diminishing contribution of each additional TALE-TF (FIG. 2E). The superior fit of the polynomial model relative to the additive model can be mathematically explained by the second-order terms that are the product of effect coefficients for different TALE-TFs. This suggests the presence of some form of cooperativity, but does not reveal the underlying mechanism. As discussed above, the simultaneous binding and stabilization of components of the pre-initiation complex by VP64 probably has a role, in addition to other secondary effects of VP64-mediated gene activation on local epigenetics and chromatin structure.

No clear correlation coefficient with TALE array length, composition, or distance to the TSS was found that was consistent for all genes (FIGS. 3A-3D). This suggests that these TALE-TF design parameters cannot be used independently to predict highly effective TALE-TFs. It is probable that other biological and structural components of these gene promoters, including genome folding and competition with endogenous regulatory factors, have a dominant role in determining the activity of single TALE-TFs and TALE-TF combinations.

The cooperative activity of TALE-TFs enables the control of gene expression without the need for small molecules used in conventional chemically regulated systems. The use of TALE-TF combinations that target endogenous promoters recapitulates the complexity of natural systems in a precise and controlled manner. This approach constitutes a powerful experimental system for elucidating the fundamental mechanisms of natural gene regulation. The capacity for combinatorial regulation also provides a new framework for engineering biocomputation systems that control endogenous genes in mammalian cells, similarly to recently developed genetic logic gates that control engineered transgenes. Precise control of gene expression with multiple tunable inputs may lead to greater potency, robustness and predictability in bioengineered systems in the context of cell-machine interfaces and gene and cell-based therapies.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

| TALE-TF SEQUENCES |
| --- |
| SEQ ID NO: 43: IL1RN TALE-A nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC |

TALE-TF SEQUENCES

AGCAACGGTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCCACGATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

GATGGCGGCAAGCAAGCGCTCGAAACGGTGCAGCGGCTGTTGCCGGTGCTGTGCCAGGACCATGGCCTGA

CTCCGGACCAAGTGGTGGCTATCGCCAGCAACGGTGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACGGTGGC

GGCAAGCAAGCGCTCGAAACGGTGCAGCGGCTGTTGCCGGTGCTGTGCCAGGACCAtggcCTGACCCCGG

ACCAAGTGGTGGCTATCGCCAGCAACAATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACATTGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCCACGATGGCGGCAAGCAAGCG

CTCGAAACGGTGCAGCGGCTGTTGCCGGTGCTGTGCCAGGACCATGGCCTGACCCCGGACCAAGTGGTGG ctatcgccagcAACGGTggcggcaagcaagcgctcgaaagcattgtggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA

SEQ ID NO: 44: IL1RN TALE-A polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASNNGGKQALETVQRLLPVLCQDHGLTPD

QVVAIASNNGGKQALETVQRLLPVLCQDHGLTPDQVVAIASNNGGKQALETVQRLLPVLCQDHGLTPDQV

VAIASHDGGKQALETVQRLLPVLCQDHGLTPDQVVAIASNGGGKQALETVQRLLPVLCQDHGLTPDQVVA

IASHDGGKQALETVQRLLPVLCQDHGLTPDQVVAIASHDGGKQALETVQRLLPVLCQDHGLTPDQVVAIA

SNGGGKQALETVQRLLPVLCQDHGLTPDQVVAIASHDGGKQALETVQRLLPVLCQDHGLTPDQVVAIASH

DGGKQALETVQRLLPVLCQDHGLTPDQVVAIASNGGGKQALETVQRLLPVLCQDHGLTPDQVVAIASNGG

GKQALETVQRLLPVLCQDHGLTPDQVVAIASNNGGKQALETVQRLLPVLCQDHGLTPDQVVAIASNGGGK

QALETVQRLLPVLCQDHGLTPDQVVAIASNIGGKQALETVQRLLPVLCQDHGLTPDQVVAIASHDGGKQA

LETVQRLLPVLCQDHGLTPDQVVAIASNGGGKQALESIVAQLSRPDPALAALTNDDHLVALACLGGRPAM

DAVKKGLPHAPELIRRVNRRIGERTSHRVAGSKASPKKKRKVGRADALDDFDLDMLGSDALDDFDLDMLG

SDALDDFDLDMLGSDALDDFDLDMLINYPYDVPDYAS

SEQ ID NO: 45: IL1RN TALE-B nucleotide
ATGGACTACAAAGACCATGACGGTGATTATAAAGATCATGACATCGATTACAAGGATGACGATGACAAGa tggccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt

TALE-TF SEQUENCES atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgccccctgAACCTGACCCCGGACCAAGTGGTGGCTATCGCCAGCAACAATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACAATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACATTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACGGTGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCCACGATGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACATTGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACATTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACAATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCAAC

GGTGGCGGCAAGCAAGCGCTCGAAACGGTGCAGCGGCTGTTGCCGGTGCTGTGCCAGGACCATGGCCTGA

CTCCGGACCAAGTGGTGGCTATCGCCAGCCACGATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACATTGGC

GGCAAGCAAGCGCTCGAAACGGTGCAGCGGCTGTTGCCGGTGCTGTGCCAGGACCAtggcCTGACCCCGG

ACCAAGTGGTGGCTATCGCCAGCAACAATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCCACGATGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCCACGATGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCAACATTGGCGGCAAGCAAGCG

CTCGAAACGGTGCAGCGGCTGTTGCCGGTGCTGTGCCAGGACCATGGCCTGACCCCGGACCAAGTGGTGG ctatcgccagcaacggtggcggcaagcaagcgctcgaaagcattgtggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA

SEQ ID NO: 46: IL1RN TALE-B polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASNNGGKQALETVQRLLPVLCQDHGLTPD

QVVAIASNNGGKQALETVQRLLPVLCQDHGLTPDQVVAIASHDGGKQALETVQRLLPVLCQDHGLTPDQV

| TALE-TF SEQUENCES |
| --- |
| VAIASNIGGKQALETVQRLLPVLCQDHGLTPDQVVAIASNGGGKQALETVQRLLPVLCQDHGLTPDQVVA IASHDGGKQALETVQRLLPVLCQDHGLTPDQVVAIASNIGGKQALETVQRLLPVLCQDHGLTPDQVVAIA SNIGGKQALETVQRLLPVLCQDHGLTPDQVVAIASNNGGKQALETVQRLLPVLCQDHGLTPDQVVAIASN GGGKQALETVQRLLPVLCQDHGLTPDQVVAIASHDGGKQALETVQRLLPVLCQDHGLTPDQVVAIASNIG GKQALETVQRLLPVLCQDHGLTPDQVVAIASNNGGKQALETVQRLLPVLCQDHGLTPDQVVAIASHDGGK QALETVQRLLPVLCQDHGLTPDQVVAIASHDGGKQALETVQRLLPVLCQDHGLTPDQVVAIASNIGGKQA LETVQRLLPVLCQDHGLTPDQVVAIASNGGGKQALESIVAQLSRPDPALAALTNDDHLVALACLGGRPAM DAVKKGLPHAPELIRRVNRRIGERTSHRVAGSKASPKKKRKVGRADALDDFDLDMLGSDALDDFDLDMLG SDALDDFDLDMLGSDALDDFDLDMLINYPYDVPDYAS

SEQ ID NO: 47: IL1RN TALE-C nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCAACATTGGCGG CAAGCAAGCGCTCGAAACGGTGCAGCGGCTGTTGCCGGTGCTGTGCCAGGACCATGGCCTGACCCCGGAC CAAGTGGTGGCTATCGCCAGCAACAATGGCGGCAAGCAAGCGCTCGAAACGGTGCAGCGGCTGTTGCCGG TGCTGTGCCAGGACCATGGCCTGACCCCGGACCAAGTGGTGGCTATCGCCAGCCACGATGGCGGCAAGCA AGCGCTCGAAACGGTGCAGCGGCTGTTGCCGGTGCTGTGCCAGGACCATGGCCTGACCCCGGACCAAGTG GTGGCTATCGCCAGCCACGATGGCGGCAAGCAAGCGCTCGAAACGGTGCAGCGGCTGTTGCCGGTGCTGT GCCAGGACCATGGCCTGACCCCGGACCAAGTGGTGGCTATCGCCAGCAACGGTGGCGGCAAGCAAGCGCT CGAAACGGTGCAGCGGCTGTTGCCGGTGCTGTGCCAGGACCATGGCCTGACCCCGGACCAAGTGGTGGCT ATCGCCAGCAACAATGGCGGCAAGCAAGCGCTCGAAACGGTGCAGCGGCTGTTGCCGGTGCTGTGCCAGG ACCATGGCCTGACCCCGGACCAAGTGGTGGCTATCGCCAGCAACATTGGCGGCAAGCAAGCGCTCGAAAC GGTGCAGCGGCTGTTGCCGGTGCTGTGCCAGGACCATGGCCTGACCCCGGACCAAGTGGTGGCTATCGCC AGCAACAATGGCGGCAAGCAAGCGCTCGAAACGGTGCAGCGGCTGTTGCCGGTGCTGTGCCAGGACCATG GCCTGACCCCGGACCAAGTGGTGGCTATCGCCAGCAACGGTGGCGGCAAGCAAGCGCTCGAAACGGTGCA GCGGCTGTTGCCGGTGCTGTGCCAGGACCATGGCCTGACCCCGGACCAAGTGGTGGCTATCGCCAGCCAC GATGGCGGCAAGCAAGCGCTCGAAACGGTGCAGCGGCTGTTGCCGGTGCTGTGCCAGGACCATGGCCTGA CCCCGGACCAAGTGGTGGCTATCGCCAGCAACATTGGCGGCAAGCAAGCGCTCGAAACGGTGCAGCGGCT GTTGCCGGTGCTGTGCCAGGACCATGGCCTGACTCCGGACCAAGTGGTGGCTATCGCCAGCCACGATGGC GGCAAGCAAGCGCTCGAAACGGTGCAGCGGCTGTTGCCGGTGCTGTGCCAGGACCATGGCCTGACCCCGG ACCAAGTGGTGGCTATCGCCAGCCACGATGGCGGCAAGCAAGCGCTCGAAACGGTGCAGCGGCTGTTGCC GGTGCTGTGCCAGGACCAtggcCTGACCCCGGACCAAGTGGTGGCTATCGCCAGCCACGATGGCGGCAAG CAAGCGCTCGAAACGGTGCAGCGGCTGTTGCCGGTGCTGTGCCAGGACCATGGCCTGACCCCGGACCAAG TGGTGGCTATCGCCAGCAACGGTGGCGGCAAGCAAGCGCTCGAAACGGTGCAGCGGCTGTTGCCGGTGCT |

| TALE-TF SEQUENCES |
| --- |
| GTGCCAGGACCATGGCCTGACCCCGGACCAAGTGGTGGCTATCGCCAGCCACGATGGCGGCAAGCAAGCG |
| CTCGAAACGGTGCAGCGGCTGTTGCCGGTGCTGTGCCAGGACCATGGCCTGACCCCGGACCAAGTGGTGG |
| CTATCGCCAGCCACGATGGCGGCAAGCAAGCGCTCGAAACGGTGCAGCGGCTGTTGCCGGTGCTGTGCCA |
| GGACCATGGCCTGACCCCGGACCAAGTGGTGGctatcgccagcaacggtggcggcaagcaagcgctcgaa |
| agcattgtggcccagctgagccggcctgatccggcgttggccgcgttgaccaacgacgaccacctcgtcg |
| ccttggcctgcctcggcggacgtcctgccatggatgcagtgaaaaagggattgccgcacgcgccggaatt |
| gatcagaagagtcaatcgccgtattggcgaacgcacgtcccatcgcgttgccGgatcCaAGGCTAGCCCG |
| AAAAAGAAACGCAAAGTTGGGCGCGCCGACGCGCTGGACGATTTCGATCTCGACATGCTGGGTTCTGATG |
| CCCTCGATGACTTTGACCTGGATATGTTGGGAAGCGACGCATTGGATGACTTTGATCTGGACATGCTCGG |
| CTCCGATGCTCTGGACGATTTCGATCTCGATATGTTAATTAACTACCCGTACGACGTTCCGGACTACGCT |
| TCTTGA |

SEQ ID NO: 48: IL1RN TALE-C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SNNGGKQALETVQRLLPVLCQDHGLTPDQVVAIASNGGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASHDG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASNGGGKQALETVQRLLPVLCQDHGLTPDQVVAIASHDGGKQA
LETVQRLLPVLCQDHGLTPDQVVAIASHDGGKQALETVQRLLPVLCQDHGLTPDQVVAIASNGGGKQALE
SIVAQLSRPDPALAALINDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 49: IL1RN TALE-D nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT

TALE-TF SEQUENCES

```
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACTCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCAtggcCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACAATGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtgcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA
```

SEQ ID NO: 50: IL1RN TALE-D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASHDGGKQALETVQRLLPVLCQDHGLTPDQVVAIASNNGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA
SNGGGKQALETVQRLLPVLCQDHGLTPDQVVAIASNIGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNGGGKQALE

TALE-TF SEQUENCES

SIVAQLSRPDPALAALINDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S

SEQ ID NO: 51: IL1RN TALE-E nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACAATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCT
GTTGCCGGTGCTGTGCCAGGACCATGGCCTGACTCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCAtggcCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACATTGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtggcccagctgagccggcctgatccggcgttggccgcgttgaccaacgacgaccacctcgtcg
ccttggcctgcctcggcggacgtcctgccatggatgcagtgaaaaagggattgccgcacgcgccggaatt

TALE-TF SEQUENCES

```
gatcagaagagtcaatcgccgtattggcgaacgcacgtcccatcgcgttgccGgatcCaAGGCTAGCCCG

AAAAAGAAACGCAAAGTTGGGCGCGCCGACGCGCTGGACGATTTCGATCTCGACATGCTGGGTTCTGATG

CCCTCGATGACTTTGACCTGGATATGTTGGGAAGCGACGCATTGGATGACTTTGATCTGGACATGCTCGG

CTCCGATGCTCTGGACGATTTCGATCTCGATATGTTAATTAACTACCCGTACGACGTTCCGGACTACGCT

TCTTGA
```

SEQ ID NO: 52: IL1RN TALE-E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASNGGGKQALETVQRLLPVLCQDHGLTPDVVAIASHDGGKQALETVQRLLPVLCQDHGLTPDQV
VAIASNGGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIA
SNGGGKQALETVQRLLPVLCQDHGLTPDQVVAIASNGGGKQALETVQRLLPVLCQDHGLTPDQVVAIASN
NGGKQALETVQRLLPVLCQDHGLTPDQVVAIASNGGGKQALETVQRLLPVLCQDHGLTPDQVVAIASNGG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNIGGKQALETVQRLLPVLCQDHGLTPDQVVAIASNGGGKQALE
SIVAQLSRPDPALAALINDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 53: IL1RN TALE-F nucleotide
ATGGACTACAAAGACCATGACGGTGATTATAAAGATCATGACATCGATTACAAGGATGACGATGACAAGa
tggccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACGGTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC

| TALE-TF SEQUENCES |
| --- |
| AGCCACGATGGCGGCAAGCAAGCGCTCGAAACGGTGCAGCGGCTGTTGCCGGTGCTGTGCCAGGACCATG |
| GCCTGACCCCGGACCAAGTGGTGGCTATCGCCAGCCACGATGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCCAC |
| GATGGCGGCAAGCAAGCGCTCGAAACGGTGCAGCGGCTGTTGCCGGTGCTGTGCCAGGACCATGGCCTGA |
| CCCCGGACCAAGTGGTGGCTATCGCCAGCAACGGTGGCGGCAAGCAAGCGCTCGAAACGGTGCAGCGGCT |
| GTTGCCGGTGCTGTGCCAGGACCATGGCCTGACCCCGGACCAAGTGGTGGCTATCGCCAGCCACGATGGC |
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCAACATTGGCGGCAAGCAAGCGCTCGAAACGGTGCAGCGGCTGTTGCC |
| GGTGCTGTGCCAGGACCATGGCCTGACTCCGGACCAAGTGGTGGCTATCGCCAGCAACATTGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCAACATTGGCGGCAAGCAAGCGCTCGAAACGGTGCAGCGGCTGTTGCCGGTGCT |
| GTGCCAGGACCAtggcCTGACCCCGGACCAAGTGGTGGCTATCGCCAGCAACATTGGCGGCAAGCAAGCG |
| CTCGAAACGGTGCAGCGGCTGTTGCCGGTGCTGTGCCAGGACCATGGCCTGACCCCGGACCAAGTGGTGG |
| CTATCGCCAGCAACAATGGCGGCAAGCAAGCGCTCGAAACGGTGCAGCGGCTGTTGCCGGTGCTGTGCCA |
| GGACCATGGCCTGACCCCGGACCAAGTGGTGGCTATCGCCAGCCACGATGGCGGCAAGCAAGCGCTCGAA |
| ACGGTGCAGCGGCTGTTGCCGGTGCTGTGCCAGGACCATGGCCTGACCCCGGACCAAGTGGTGGCTATCG |
| CCAGCAACATTGGCGGCAAGCAAGCGCTCGAAACGGTGCAGCGGCTGTTGCCGGTGCTGTGCCAGGACCA |
| TGGCCTGACCCCGGACCAAGTGGTGGctatcgccagcAACGGTggcggcaagcaagcgctcgaaagcatt |
| gtggcccagctgagccggcctgatccggcgttggccgcgttgaccaacgacgaccacctcgtcgccttgg |
| cctgcctcggcggacgtcctgccatggatgcagtgaaaaagggattgccgcacgcgccggaattgatcag |
| aagagtcaatcgccgtattggcgaacgcacgtcccatcgcgttgccGgatcCaAGGCTAGCCCGAAAAAG |
| AAACGCAAAGTTGGGCGCGCCGACGCGCTGGACGATTTCGATCTCGACATGCTGGGTTCTGATGCCCTCG |
| ATGACTTTGACCTGGATATGTTGGGAAGCGACGCATTGGATGACTTTGATCTGGACATGCTCGGCTCCGA |
| TGCTCTGGACGATTTCGATCTCGATATGTTAATTAACTACCCGTACGACGTTCCGGACTACGCTTCTTGA |

SEQ ID NO: 54: IL1RN TALE-F polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASHDGGKQALETVQRLLPVLCQDHGLTPDQVVAIASNGGGKQALETVQRLLPVLCQDHGLTPDQV

VAIASNIGGKQALETVQRLLPVLCQDHGLTPDQVVAIASNNGGKQALETVQRLLPVLCQDHGLTPDQVVA

IASNNGGKQALETVQRLLPVLCQDHGLTPDQVVAIASNGGGKQALETVQRLLPVLCQDHGLTPDQVVAIA

SHDGGKQALETVQRLLPVLCQDHGLTPDQVVAIASHDGGKQALETVQRLLPVLCQDHGLTPDQVVAIASH

DGGKQALETVQRLLPVLCQDHGLTPDQVVAIASNGGGKQALETVQRLLPVLCQDHGLTPDQVVAIASHDG

GKQALETVQRLLPVLCQDHGLTPDQVVAIASNIGGKQALETVQRLLPVLCQDHGLTPDQVVAIASNIGGK

QALETVQRLLPVLCQDHGLTPDQVVAIASNIGGKQALETVQRLLPVLCQDHGLTPDQVVAIASNIGGKQA

LETVQRLLPVLCQDHGLTPDQVVAIASNNGGKQALETVQRLLPVLCQDHGLTPDQVVAIASHDGGKQALE

TVQRLLPVLCQDHGLTPDQVVAIASNIGGKQALETVQRLLPVLCQDHGLTPDQVVAIASNGGGKQALESI

VAQLSRPDPALAALTNDDHLVALACLGGRPAMDAVKKGLPHAPELIRRVNRRIGERTSHRVAGSKASPKK

KRKVGRADALDDFDLDMLGSDALDDFDLDMLGSDALDDFDLDMLINYPYDVPDYAS

TALE-TF SEQUENCES

SEQ ID NO: 55: KLK3 TALE-A nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACATTGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCCACGATGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
ctatcgccagcaacggtggcggcaagcaagcgctcgaaagcattgtggcccagctgagccggcctgatcc
ggcgttggccgcgttgaccaacgacgaccacctcgtcgccttggcctgcctcggcggacgtcctgccatg
gatgcagtgaaaaagggattgccgcacgcgccggaattgatcagaagagtcaatcgccgtattggcgaac
gcacgtccatcgcgttgccGgatcCaAGGCTAGCCCGAAAAAGAAACGCAAAGTTGGGCGCGCCGACGC
GCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATA
TGTTAATTAACTACCCGTACGACGTTCCGGACTACGCTTCTTGA

TALE-TF SEQUENCES

SEQ ID NO: 56: KLK3 TALE-A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNIGGKQALETVQRLLPVLCQDHGLTPDQV
VAIASNNGGKQALETVQRLLPVLCQDHGLTPDQVVAIASHDGGKQALETVQRLLPVLCQDHGLTPDQVVA
IASHDGGKQALETVQRLLPVLCQDHGLTPDQVVAIASNGGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASHDG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 57: KLK3 TALE B nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccccctgAACCTGACCCCGGACCAAGTGGTGGCTATCGCCAGCAACATTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACGGTGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG -continued

TALE-TF SEQUENCES

ACCAAGTGGTGGCTATCGCCAGCCACGATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCCACGATGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACGGTGGCGGCAAGCAAGCGCTCGAAACGGTGCAGCGGCTGTTGCCGGTGCT

GTGCCAGGACCATGGCCTGACCCCGGACCAAGTGGTGGctatcgccagcaacggtggcggcaagcaagcg ctcgaaagcattgtggcccagctgagccggcctgatccggcgttggccgcgttgaccaacgacgaccacc tcgtcgcctggcctgcctcggcggacgtcctgccatggatgcagtgaaaaagggattgccgcacgcgcc ggaattgatcagaagagtcaatcgccgtattggcgaacgcacgtcccatcgcgttgccGgatcCaAGGCT

AGCCCGAAAAAGAAACGCAAAGTTGGGCGCGCCGACGCGCTGGACGATTTCGATCTCGACATGCTGGGTT

CTGATGCCCTCGATGACTTTGACCTGGATATGTTGGGAAGCGACGCATTGGATGACTTTGATCTGGACAT

GCTCGGCTCCGATGCTCTGGACGATTTCGATCTCGATATGTTAATTAACTACCCGTACGACGTTCCGGAC

TACGCTTCTTGA

SEQ ID NO: 58: KLK3 TALE B polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASNIGGKQALETVQRLLPVLCQDHGLTPD

QVVAIASNNGGKQALETVQRLLPVLCQDHGLTPDQVVAIASHDGGKQALETVQRLLPVLCQDHGLTPDQV

VAIASNGGGKQALETVQRLLPVLCQDHGLTPDQVVAIASHDGGKQALETVQRLLPVLCQDHGLTPDQVVA

IASNGGGKQALETVQRLLPVLCQDHGLTPDQVVAIASHDGGKQALETVQRLLPVLCQDHGLTPDQVVAIA

SHDGGKQALETVQRLLPVLCQDHGLTPDQVVAIASHDGGKQALETVQRLLPVLCQDHGLTPDQVVAIASN

GGGKQALETVQRLLPVLCQDHGLTPDQVVAIASHDGGKQALETVQRLLPVLCQDHGLTPDQVVAIASHDG

GKQALETVQRLLPVLCQDHGLTPDQVVAIASHDGGKQALETVQRLLPVLCQDHGLTPDQVVAIASHDGGK

QALETVQRLLPVLCQDHGLTPDQVVAIASNGGGKQALETVQRLLPVLCQDHGLTPDQVVAIASNGGGKQA

LESIVAQLSRPDPALAALINDDHLVALACLGGRPAMDAVKKGLPHAPELIRRVNRRIGERTSHRVAGSKA

SPKKKRKVGRADALDDFDLDMLGSDALDDFDLDMLGSDALDDFDLDMLGSDALDDFDLDMLINYPYDVPD

YAS

SEQ ID NO: 59: KLK3 TALE C nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcggggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

| TALE-TF SEQUENCES |
|---|
| GTGGCTATCGCCAGCCACGATGGCGGCAAGCAAGCGCTCGAAACGGTGCAGCGGCTGTTGCCGGTGCTGT |
| GCCAGGACCATGGCCTGACCCCGGACCAAGTGGTGGCTATCGCCAGCAACGGTGGCGGCAAGCAAGCGCT |
| CGAAACGGTGCAGCGGCTGTTGCCGGTGCTGTGCCAGGACCATGGCCTGACCCCGGACCAAGTGGTGGCT |
| ATCGCCAGCAACATTGGCGGCAAGCAAGCGCTCGAAACGGTGCAGCGGCTGTTGCCGGTGCTGTGCCAGG |
| ACCATGGCCTGACCCCGGACCAAGTGGTGGCTATCGCCAGCAACAATGGCGGCAAGCAAGCGCTCGAAAC |
| GGTGCAGCGGCTGTTGCCGGTGCTGTGCCAGGACCATGGCCTGACCCCGGACCAAGTGGTGGCTATCGCC |
| AGCAACATTGGCGGCAAGCAAGCGCTCGAAACGGTGCAGCGGCTGTTGCCGGTGCTGTGCCAGGACCATG |
| GCCTGACCCCGGACCAAGTGGTGGCTATCGCCAGCAACGGTGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCAAC |
| AATGGCGGCAAGCAAGCGCTCGAAACGGTGCAGCGGCTGTTGCCGGTGCTGTGCCAGGACCATGGCCTGA |
| CCCCGGACCAAGTGGTGGCTATCGCCAGCAACATTGGCGGCAAGCAAGCGCTCGAAACGGTGCAGCGGCT |
| GTTGCCGGTGCTGTGCCAGGACCATGGCCTGACCCCGGACCAAGTGGTGGCTATCGCCAGCAACATTGGC |
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCAACAATGGCGGCAAGCAAGCGCTCGAAACGGTGCAGCGGCTGTTGCC |
| GGTGCTGTGCCAGGACCATGGCCTGACCCCGGACCAAGTGGTGGCTATCGCCAGCAACGGTGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCCACGATGGCGGCAAGCAAGCGCTCGAAACGGTGCAGCGGCTGTTGCCGGTGCT |
| GTGCCAGGACCATGGCCTGACCCCGGACCAAGTGGTGGctatcgccagcaacggtggcggcaagcaagcg |
| ctcgaaagcattgtggcccagctgagccggcctgatccggcgttggccgcgttgaccaacgacgaccacc |
| tcgtcgccttggcctgcctcggcggacgtcctgccatggatgcagtgaaaaagggattgccgcacgcgcc |
| ggaattgatcagaagagtcaatcgccgtattggcgaacgcacgtcccatcgcgttgccGgatcCaAGGCT |
| AGCCCGAAAAAGAAACGCAAAGTTGGGCGCGCCGACGCGCTGGACGATTTCGATCTCGACATGCTGGGTT |
| CTGATGCCCTCGATGACTTTGACCTGGATATGTTGGGAAGCGACGCATTGGATGACTTTGATCTGGACAT |
| GCTCGGCTCCGATGCTCTGGACGATTTCGATCTCGATATGTTAATTAACTACCCGTACGACGTTCCGGAC |
| TACGCTTCTTGA |

SEQ ID NO: 60: KLK3 TALE C polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASHDGGKQALETVQRLLPVLCQDHGLTPDQVVAIASHDGGKQALETVQRLLPVLCQDHGLTPDQV

VAIASHDGGKQALETVQRLLPVLCQDHGLTPDQVVAIASNGGGKQALETVQRLLPVLCQDHGLTPDQVVA

IASNIGGKQALETVQRLLPVLCQDHGLTPDQVVAIASNNGGKQALETVQRLLPVLCQDHGLTPDQVVAIA

SNIGGKQALETVQRLLPVLCQDHGLTPDQVVAIASNGGGKQALETVQRLLPVLCQDHGLTPDQVVAIASN

NGGKQALETVQRLLPVLCQDHGLTPDQVVAIASNIGGKQALETVQRLLPVLCQDHGLTPDQVVAIASNIG

GKQALETVQRLLPVLCQDHGLTPDQVVAIASNNGGKQALETVQRLLPVLCQDHGLTPDQVVAIASNGGGK

QALETVQRLLPVLCQDHGLTPDQVVAIASHDGGKQALETVQRLLPVLCQDHGLTPDQVVAIASNGGGKQA

LESIVAQLSRPDPALAALINDDHLVALACLGGRPAMDAVKKGLPHAPELIRRVNRRIGERTSHRVAGSKA

SPKKKRKVGRADALDDFDLDMLGSDALDDFDLDMLGSDALDDFDLDMLGSDALDDFDLDMLINYPYDVPD

YAS

TALE-TF SEQUENCES

SEQ ID NO: 61: KLK3 TALE D nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCAACATTGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCCACGATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACATTGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCCACGATGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCCACGATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCCACGATGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCCACGATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

GATGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACGGTGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACAATGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACGGTGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACGGTGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCCACGATGGCGGCAAGCAAGCG

CTCGAAACGGTGCAGCGGCTGTTGCCGGTGCTGTGCCAGGACCATGGCCTGACCCCGGACCAAGTGGTGG

CTATCGCCAGCAACGGTGGCGGCAAGCAAGCGCTCGAAACGGTGCAGCGGCTGTTGCCGGTGCTGTGCCA

GGACCATGGCCTGACCCCGGACCAAGTGGTGGCTATCGCCAGCAACAATGGCGGCAAGCAAGCGCTCGAA

ACGGTGCAGCGGCTGTTGCCGGTGCTGTGCCAGGACCATGGCCTGACCCCGGACCAAGTGGTGGctatcg ccagcaacggtggcggcaagcaagcgctcgaaagcattgtgcccagctgagccggcctgatccggcgtt ggccgcgttgaccaacgacgaccacctcgtcgccttggcctgcctcggcggacgtcctgccatggatgca gtgaaaaagggattgccgcacgcgccggaattgatcagaagagtcaatcgccgtattggcgaacgcacgt cccatcgcgttgccGgatcCaAGGCTAGCCCGAAAAAGAAACGCAAAGTTGGGCGCGCCGACGCGCTGGA

| TALE-TF SEQUENCES |
| --- |
| CGATTTCGATCTCGACATGCTGGGTTCTGATGCCCTCGATGACTTTGACCTGGATATGTTGGGAAGCGAC |
| GCATTGGATGACTTTGATCTGGACATGCTCGGCTCCGATGCTCTGGACGATTTCGATCTCGATATGTTAA |
| TTAACTACCCGTACGACGTTCCGGACTACGCTTCTTGA |

SEQ ID NO: 62: KLK3 TALE D polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASNIGGKQALETVQRLLPVLCQDHGLTPD

QVVAIASHDGGKQALETVQRLLPVLCQDHGLTPDQVVAIASHDGGKQALETVQRLLPVLCQDHGLTPDQV

VAIASHDGGKQALETVQRLLPVLCQDHGLTPDQVVAIASNIGGKQALETVQRLLPVLCQDHGLTPDQVVA

IASHDGGKQALETVQRLLPVLCQDHGLTPDQVVAIASHDGGKQALETVQRLLPVLCQDHGLTPDQVVAIA

SHDGGKQALETVQRLLPVLCQDHGLTPDQVVAIASHDGGKQALETVQRLLPVLCQDHGLTPDQVVAIASH

DGGKQALETVQRLLPVLCQDHGLTPDQVVAIASNGGGKQALETVQRLLPVLCQDHGLTPDQVVAIASNNG

GKQALETVQRLLPVLCQDHGLTPDQVVAIASNGGGKQALETVQRLLPVLCQDHGLTPDQVVAIASNGGGK

QALETVQRLLPVLCQDHGLTPDQVVAIASNGGGKQALETVQRLLPVLCQDHGLTPDQVVAIASHDGGKQA

LETVQRLLPVLCQDHGLTPDQVVAIASNGGGKQALETVQRLLPVLCQDHGLTPDQVVAIASNNGGKQALE

TVQRLLPVLCQDHGLTPDQVVAIASNGGGKQALESIVAQLSRPDPALAALTNDDHLVALACLGGRPAMDA

VKKGLPHAPELIRRVNRRIGERTSHRVAGSKASPKKKRKVGRADALDDFDLDMLGSDALDDFDLDMLGSD

ALDDFDLDMLGSDALDDFDLDMLINYPYDVPDYAS

SEQ ID NO: 63: KLK3 TALE E nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgccccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACGGTGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACGGTGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACAATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACAATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACATTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACAATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACGGTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACAATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

TALE-TF SEQUENCES

```
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACAATGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacattggcggcaagcaagcg
ctcgaaagcattgtggcccagctgagccggcctgatccggcgttggccgcgttgaccaacgacgaccacc
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA
```

SEQ ID NO: 64: KLK3 TALE E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNIGGKQALETVQRLLPVLCQDHGLTPDQVVAIASNNGGKQALETVQRLLPVLCQDHGLTPDQVVAIA
SNGGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNNGGK
QALETVQRLLPVLCQDHGLTPDQVVAIASNNGGKQALETVQRLLPVLCQDHGLTPDQVVAIASNIGGKQA
LESIVAQLSRPDPALAALINDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS SEQ ID NO: 65: KLK3 TALE F nucleotide
```
ATGGACTACAAAGACCATGACGGTGATTATAAAGATCATGACATCGATTACAAGGATGACGATGACAAGa
tggccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
```

| TALE-TF SEQUENCES |
| --- |
| CAAGCAAGCGCTCGAAACGGTGCAGCGGCTGTTGCCGGTGCTGTGCCAGGACCATGGCCTGACCCCGGAC |
| CAAGTGGTGGCTATCGCCAGCAACGGTGGCGGCAAGCAAGCGCTCGAAACGGTGCAGCGGCTGTTGCCGG |
| TGCTGTGCCAGGACCATGGCCTGACCCCGGACCAAGTGGTGGCTATCGCCAGCAACGGTGGCGGCAAGCA |
| AGCGCTCGAAACGGTGCAGCGGCTGTTGCCGGTGCTGTGCCAGGACCATGGCCTGACCCCGGACCAAGTG |
| GTGGCTATCGCCAGCAACAATGGCGGCAAGCAAGCGCTCGAAACGGTGCAGCGGCTGTTGCCGGTGCTGT |
| GCCAGGACCATGGCCTGACCCCGGACCAAGTGGTGGCTATCGCCAGCAACAATGGCGGCAAGCAAGCGCT |
| CGAAACGGTGCAGCGGCTGTTGCCGGTGCTGTGCCAGGACCATGGCCTGACCCCGGACCAAGTGGTGGCT |
| ATCGCCAGCAACATTGGCGGCAAGCAAGCGCTCGAAACGGTGCAGCGGCTGTTGCCGGTGCTGTGCCAGG |
| ACCATGGCCTGACCCCGGACCAAGTGGTGGCTATCGCCAGCAACAATGGCGGCAAGCAAGCGCTCGAAAC |
| GGTGCAGCGGCTGTTGCCGGTGCTGTGCCAGGACCATGGCCTGACCCCGGACCAAGTGGTGGCTATCGCC |
| AGCAACGGTGGCGGCAAGCAAGCGCTCGAAACGGTGCAGCGGCTGTTGCCGGTGCTGTGCCAGGACCATG |
| GCCTGACCCCGGACCAAGTGGTGGCTATCGCCAGCAACAATGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCCAC |
| GATGGCGGCAAGCAAGCGCTCGAAACGGTGCAGCGGCTGTTGCCGGTGCTGTGCCAGGACCATGGCCTGA |
| CCCCGGACCAAGTGGTGGCTATCGCCAGCAACATTGGCGGCAAGCAAGCGCTCGAAACGGTGCAGCGGCT |
| GTTGCCGGTGCTGTGCCAGGACCATGGCCTGACCCCGGACCAAGTGGTGGCTATCGCCAGCAACATTGGC |
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCAACATTGGCGGCAAGCAAGCGCTCGAAACGGTGCAGCGGCTGTTGCC |
| GGTGCTGTGCCAGGACCATGGCCTGACCCCGGACCAAGTGGTGGCTATCGCCAGCAACAATGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCAACAATGGCGGCAAGCAAGCGCTCGAAACGGTGCAGCGGCTGTTGCCGGTGCT |
| GTGCCAGGACCATGGCCTGACCCCGGACCAAGTGGTGGctatcgccagcaacggtggcggcaagcaagcg |
| ctcgaaagcattgtggcccagctgagccggcctgatccggcgttggccgcgttgaccaacgacgaccacc |
| tcgtcgcctttggcctgcctcggcggacgtcctgccatggatgcagtgaaaaagggattgccgcacgcgcc |
| ggaattgatcagaagagtcaatcgccgtattggcgaacgcacgtcccatcgcgttgccGgatcCaAGGCT |
| AGCCCGAAAAAGAAACGCAAAGTTGGGCGCGCCGACGCGCTGGACGATTTCGATCTCGACATGCTGGGTT |
| CTGATGCCCTCGATGACTTTGACCTGGATATGTTGGGAAGCGACGCATTGGATGACTTTGATCTGGACAT |
| GCTCGGCTCCGATGCTCTGGACGATTTCGATCTCGATATGTTAATTAACTACCCGTACGACGTTCCGGAC |
| TACGCTTCTTGA |

SEQ ID NO: 66: KLK3 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNIGGKQALETVQRLLPVLCQDHGLTPDQVVAIASNNGGKQALETVQRLLPVLCQDHGLTPDQVVAIA
SNGGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNNGGK

| TALE-TF SEQUENCES |
| --- |
| QALETVQRLLPVLCQDHGLTPDQVVAIASNNGGKQALETVQRLLPVLCQDHGLTPDQVVAIASNGGGKQA
LESIVAQLSRPDPALAALINDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS

SEQ ID NO: 67: KLK3 TALE G nucleotide
ATGGACTACAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACAATGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtgggcccagctgagccggcctgatccgcgcgttggccgcgttgaccaacgacgaccac
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT |

| TALE-TF SEQUENCES |
| --- |
| CTGATGCCCTCGATGACTTTGACCTGGATATGTTGGGAAGCGACGCATTGGATGACTTTGATCTGGACAT |
| GCTCGGCTCCGATGCTCTGGACGATTTCGATCTCGATATGTTAATTAACTACCCGTACGACGTTCCGGAC |
| TACGCTTCTTGA |
| SEQ ID NO: 68: KLK3 TALE G polypeptide<br>MDYKDHDGDYKDHDIDYKDDDDKMAPKKKRKVGRSVDLRTLGYSQQQQEKIKPKVRSTVAQHHEALVGH |
| GFTHAHIVALSQHPAALGTVAVTYQHIITALPEATHEDIVGVGKQWSGARALEALLTDAGELRGPPLQLD |
| TGQLVKIAKRGGVTAMEAVHASRNALTGAPLNLTPDQVVAIASHDGGKQALETVQRLLPVLCQDHGLTPD |
| QVVAIASNGGGKQALETVQRLLPVLCQDHGLTPDQVVAIASNNGGKQALETVQRLLPVLCQDHGLTPDQV |
| VAIASNGGGKQALETVQRLLPVLCQDHGLTPDQVVAIASNNGGKQALETVQRLLPVLCQDHGLTPDQVVA |
| IASNNGGKQALETVQRLLPVLCQDHGLTPDQVVAIASNIGGKQALETVQRLLPVLCQDHGLTPDQVVAIA |
| SHDGGKQALETVQRLLPVLCQDHGLTPDQVVAIASHDGGKQALETVQRLLPVLCQDHGLTPDQVVAIASN |
| IGGKQALETVQRLLPVLCQDHGLTPDQVVAIASHDGGKQALETVQRLLPVLCQDHGLTPDQVVAIASNIG |
| GKQALETVQRLLPVLCQDHGLTPDQVVAIASNIGGKQALETVQRLLPVLCQDHGLTPDQVVAIASNNGGK |
| QALETVQRLLPVLCQDHGLTPDQVVAIASNIGGKQALETVQRLLPVLCQDHGLTPDQVVAIASNGGGKQA |
| LESIVAQLSRPDPALAALINDDHLVALACLGGRPAMDAVKKGLPHAPELIRRVNRRIGERTSHRVAGSKA |
| SPKKKRKVGRADALDDFDLDMLGSDALDDFDLDMLGSDALDDFDLDMLGSDALDDFDLDMLINYPYDVPD |
| YAS |
| SEQ ID NO: 69: CEACAM5 TALE A nucleotide<br>ATGGACTACAAAGACCATGACGGTGATTATAAAGATCATGACATCGATTACAAGGATGACGATGACAAGa |
| tggcccccaagaagaagaggaaggtgggccgcGgatcTgtggatctacgcacgctcggctacagtcagca |
| gcagcaagagaagatcaaaccgaaggtgcgttcgacagtggcgcagcaccacgaggcactggtgggccat |
| gggtttacacacgcgcacatcgttgcgctcagccaacacccggcagcgttagggaccgtcgctgtcacgt |
| atcagcacataatcacggcgttgccagaggcgacacacgaagacatcgttggcgtcggcaaacagtggtc |
| cggcgcacgcgccctggaggccttgctcacggatgcgggggagttgagaggtccgccgttacagttggac |
| acaggccaacttgtgaagattgcaaaacgtggcggcgtgaccgcaatggaggcagtgcatgcatcgcgca |
| atgcactgacgggtgccccctgAACCTGACCCCGGACCAAGTGGTGGCTATCGCCAGCAACATTGGCGG |
| CAAGCAAGCGCTCGAAACGGTGCAGCGGCTGTTGCCGGTGCTGTGCCAGGACCATGGCCTGACCCCGGAC |
| CAAGTGGTGGCTATCGCCAGCAACATTGGCGGCAAGCAAGCGCTCGAAACGGTGCAGCGGCTGTTGCCGG |
| TGCTGTGCCAGGACCATGGCCTGACCCCGGACCAAGTGGTGGCTATCGCCAGCAACATTGGCGGCAAGCA |
| AGCGCTCGAAACGGTGCAGCGGCTGTTGCCGGTGCTGTGCCAGGACCATGGCCTGACCCCGGACCAAGTG |
| GTGGCTATCGCCAGCAACAATGGCGGCAAGCAAGCGCTCGAAACGGTGCAGCGGCTGTTGCCGGTGCTGT |
| GCCAGGACCATGGCCTGACCCCGGACCAAGTGGTGGCTATCGCCAGCAACATTGGCGGCAAGCAAGCGCT |
| CGAAACGGTGCAGCGGCTGTTGCCGGTGCTGTGCCAGGACCATGGCCTGACCCCGGACCAAGTGGTGGCT |
| ATCGCCAGCCACGATGGCGGCAAGCAAGCGCTCGAAACGGTGCAGCGGCTGTTGCCGGTGCTGTGCCAGG |
| ACCATGGCCTGACCCCGGACCAAGTGGTGGCTATCGCCAGCCACGATGGCGGCAAGCAAGCGCTCGAAAC |
| GGTGCAGCGGCTGTTGCCGGTGCTGTGCCAGGACCATGGCCTGACCCCGGACCAAGTGGTGGCTATCGCC |
| AGCAACATTGGCGGCAAGCAAGCGCTCGAAACGGTGCAGCGGCTGTTGCCGGTGCTGTGCCAGGACCATG |
| GCCTGACCCCGGACCAAGTGGTGGCTATCGCCAGCCACGATGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCAAC |
| ATTGGCGGCAAGCAAGCGCTCGAAACGGTGCAGCGGCTGTTGCCGGTGCTGTGCCAGGACCATGGCCTGA |

| TALE-TF SEQUENCES |
| --- |
| CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACAATGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCAACATTGGCGGCAAGCAAGCGCTCGAAACGGTGCAGCGGCTGTTGCCGGTGCTGTGCCA
GGACCATGGCCTGACCCCGGACCAAGTGGTGGctatcgccagcCACGATggcggcaagcaagcgctcgaa
agcattgtgggcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA |

SEQ ID NO: 70: CEACAM5 TALE A polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNIGGKQALETVQRLLPVLCQDHGLTPD
QVVAIASNIGGKQALETVQRLLPVLCQDHGLTPDQVVAIASNIGGKQALETVQRLLPVLCQDHGLTPDQV
VAIASNNGGKQALETVQRLLPVLCQDHGLTPDQVVAIASNIGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SNIGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASHDGGKQALETVQRLLPVLCQDHGLTPDQVVAIASNIGGK
QALETVQRLLPVLCQDHGLTPDQVVAIASNGGGKQALETVQRLLPVLCQDHGLTPDQVVAIASNNGGKQA
LETVQRLLPVLCQDHGLTPDQVVAIASNIGGKQALETVQRLLPVLCQDHGLTPDQVVAIASHDGGKQALE
SIVAQLSRPDPALAALINDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S SEQ ID NO: 71: CEACAM5 TALE B nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc

TALE-TF SEQUENCES cggcgcacgcgccctggaggccttgctcacggatgcggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACGGTGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCAACAATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACATTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACATTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtgcccagctgagccggcctgatccggcgttggccgcgttgaccaacgacgaccacc
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA SEQ ID NO: 72: CEACAM5 TALE B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNNGGKQALETVQRLLPVLCQDHGLTPDQV
VAIASNIGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASNIGGKQALETVQRLLPVLCQDHGLTPDQVVAIA

TALE-TF SEQUENCES

SNIGGKQALETVQRLLPVLCQDHGLTPDQVVAIASHDGGKQALETVQRLLPVLCQDHGLTPDQVVAIASN

GGGKQALETVQRLLPVLCQDHGLTPDQVVAIASNNGGKQALETVQRLLPVLCQDHGLTPDQVVAIASNIG

GKQALETVQRLLPVLCQDHGLTPDQVVAIASNIGGKQALETVQRLLPVLCQDHGLTPDQVVAIASNIGGK

QALETVQRLLPVLCQDHGLTPDQVVAIASNIGGKQALETVQRLLPVLCQDHGLTPDQVVAIASNGGGKQA

LESIVAQLSRPDPALAALINDDHLVALACLGGRPAMDAVKKGLPHAPELIRRVNRRIGERTSHRVAGSKA

SPKKKRKVGRADALDDFDLDMLGSDALDDFDLDMLGSDALDDFDLDMLGSDALDDFDLDMLINYPYDVPD

YAS

SEQ ID NO: 73: CEACAM5 TALE C nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgccccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACATTGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCCACGATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCCACGATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACGGTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACGGTGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACAATGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCCACGATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

GATGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACAATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACATTGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACATTGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACATTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACATTGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCAACATTGGCGGCAAGCAAGCG

CTCGAAACGGTGCAGCGGCTGTTGCCGGTGCTGTGCCAGGACCATGGCCTGACCCCGGACCAAGTGGTGG

| TALE-TF SEQUENCES |
|---|
| CTATCGCCAGCAACAATGGCGGCAAGCAAGCGCTCGAAACGGTGCAGCGGCTGTTGCCGGTGCTGTGCCA |
| GGACCATGGCCTGACCCCGGACCAAGTGGTGGCTATCGCCAGCAACATTGGCGGCAAGCAAGCGCTCGAA |
| ACGGTGCAGCGGCTGTTGCCGGTGCTGTGCCAGGACCATGGCCTGACCCCGGACCAAGTGGTGGctatcg |
| ccagcaacggtggcggcaagcaagcgctcgaaagcattgtggcccagctgagccggcctgatccggcgtt |
| ggccgcgttgaccaacgacgaccacctcgtcgccttggcctgcctcggcggacgtcctgccatggatgca |
| gtgaaaaagggattgccgcacgcgccggaattgatcagaagagtcaatcgccgtattggcgaacgcacgt |
| cccatcgcgttgccGgatcCaAGGCTAGCCCGAAAAAGAAACGCAAAGTTGGGCGCGCCGACGCGCTGGA |
| CGATTTCGATCTCGACATGCTGGGTTCTGATGCCCTCGATGACTTTGACCTGGATATGTTGGGAAGCGAC |
| GCATTGGATGACTTTGATCTGGACATGCTCGGCTCCGATGCTCTGGACGATTTCGATCTCGATATGTTAA |
| TTAACTACCCGTACGACGTTCCGGACTACGCTTCTTGA |

SEQ ID NO: 74: CEACAM5 TALE C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASNIGGKQALETVQRLLPVLCQDHGLTPDQV
VAIASHDGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASNGGGKQALETVQRLLPVLCQDHGLTPDQVVAIA
SNNGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASNIGGKQALETVQRLLPVLCQDHGLTPDQVVAIASNIGGK
QALETVQRLLPVLCQDHGLTPDQVVAIASNIGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNIGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 75: CEACAM5 TALE D nucleotide
ATGGACTACAAAGACCATGACGGTGATTATAAAGATCATGACATCGATTACAAGGATGACGATGACAAGa
tggccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCAACGGTGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCAACAATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT

TALE-TF SEQUENCES

```
CGAAACGGTGCAGCGGCTGTTGCCGGTGCTGTGCCAGGACCATGGCCTGACCCCGGACCAAGTGGTGGCT
ATCGCCAGCCACGATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCCACGATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACAATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACAATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACATTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGctatcgccagcaacggtggcggcaagcaagcg
ctcgaaagcattgtggcccagctgagccggcctgatccggcgttggccgcgttgaccaacgacgaccacc
tcgtcgccttggcctgcctcggcggacgtcctgccatggatgcagtgaaaaagggattgccgcacgcgcc
ggaattgatcagaagagtcaatcgccgtattggcgaacgcacgtcccatcgcgttgccGgatcCaAGGCT
AGCCCGAAAAAGAAACGCAAAGTTGGGCGCGCCGACGCGCTGGACGATTTCGATCTCGACATGCTGGGTT
CTGATGCCCTCGATGACTTTGACCTGGATATGTTGGGAAGCGACGCATTGGATGACTTTGATCTGGACAT
GCTCGGCTCCGATGCTCTGGACGATTTCGATCTCGATATGTTAATTAACTACCCGTACGACGTTCCGGAC
TACGCTTCTTGA
```

SEQ ID NO: 76: CEACAM5 TALE D polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNGGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNGGGKQALETVQRLLPVLCQDHGLTPDQVVA
IASHDGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASNIGGKQALETVQRLLPVLCQDHGLTPDQVVAIASN
NGGKQALETVQRLLPVLCQDHGLTPDQVVAIASNNGGKQALETVQRLLPVLCQDHGLTPDQVVAIASNNG
GKQALETVQRLLPVLCQDHGLTPDQVVAIASNNGGKQALETVQRLLPVLCQDHGLTPDQVVAIASNIGGK
QALETVQRLLPVLCQDHGLTPDQVVAIASNGGGKQALETVQRLLPVLCQDHGLTPDQVVAIASNGGGKQA
LESIVAQLSRPDPALAALINDDHLVALACLGGRPAMDAVKKGLPHAPELIRRVNRRIGERTSHRVAGSKA
SPKKKRKVGRADALDDFDLDMLGSDALDDFDLDMLGSDALDDFDLDMLGSDALDDFDLDMLINYPYDVPD
YAS

TALE-TF SEQUENCES

SEQ ID NO: 77: CEACAM5 TALE E nucleotide
ATGGACTACAAAGACCATGACGGTGATTATAAAGATCATGACATCGATTACAAGGATGACGATGACAAGa tgccccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACGGTGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACAATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACGGTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCCACGATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACATTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCCACGATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACATTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACATTGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCAAC

ATTGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACAATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACAATGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACATTGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACATTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACATTGGCGGCAAGCAAGCGCTCGAAACGGTGCAGCGGCTGTTGCCGGTGCT

GTGCCAGGACCATGGCCTGACCCCGGACCAAGTGGTGGctatcgccagcaacattggcggcaagcaagcg ctcgaaagcattgtggcccagctgagccggcctgatccggcgttggccgcgttgaccaacgacgaccacc tcgtcgccttggcctgcctcggcggacgtcctgccatggatgcagtgaaaaagggattgccgcacgcgcc ggaattgatcagaagagtcaatcgccgtattggcgaacgcacgtcccatcgcgttgccGgatcCaAGGCT

AGCCCGAAAAAGAAACGCAAAGTTGGGCGCGCCGACGCGCTGGACGATTTCGATCTCGACATGCTGGGTT

CTGATGCCCTCGATGACTTTGACCTGGATATGTTGGGAAGCGACGCATTGGATGACTTTGATCTGGACAT

GCTCGGCTCCGATGCTCTGGACGATTTCGATCTCGATATGTTAATTAACTACCCGTACGACGTTCCGGAC

TACGCTTCTTGA

| TALE-TF SEQUENCES |
| --- |

SEQ ID NO: 78: CEACAM5 TALE E polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASNGGGKQALETVQRLLPVLCQDHGLTPDQVVAIASNNGGKQALETVQRLLPVLCQDHGLTPDQV

VAIASNGGGKQALETVQRLLPVLCQDHGLTPDQVVAIASHDGGKQALETVQRLLPVLCQDHGLTPDQVVA

IASNIGGKQALETVQRLLPVLCQDHGLTPDQVVAIASHDGGKQALETVQRLLPVLCQDHGLTPDQVVAIA

SNIGGKQALETVQRLLPVLCQDHGLTPDQVVAIASNIGGKQALETVQRLLPVLCQDHGLTPDQVVAIASN

IGGKQALETVQRLLPVLCQDHGLTPDQVVAIASNNGGKQALETVQRLLPVLCQDHGLTPDQVVAIASNNG

GKQALETVQRLLPVLCQDHGLTPDQVVAIASNIGGKQALETVQRLLPVLCQDHGLTPDQVVAIASNIGGK

QALETVQRLLPVLCQDHGLTPDQVVAIASNIGGKQALETVQRLLPVLCQDHGLTPDQVVAIASNIGGKQA

LESIVAQLSRPDPALAALINDDHLVALACLGGRPAMDAVKKGLPHAPELIRRVNRRIGERTSHRVAGSKA

SPKKKRKVGRADALDDFDLDMLGSDALDDFDLDMLGSDALDDFDLDMLGSDALDDFDLDMLINYPYDVPD

YAS

SEQ ID NO: 79: CEACAM5 TALE F nucleotide
ATGGACTACAAAGACCATGACGGTGATTATAAAGATCATGACATCGATTACAAGGATGACGATGACAAGa tggccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCAACAATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACGGTGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACGGTGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACAATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACAATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACAATGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCCACGATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACATTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACGGTGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

GATGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACATTGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACGGTGGC

| TALE-TF SEQUENCES |
|---|
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCCACGATGGCGGCAAGCAAGCGCTCGAAACGGTGCAGCGGCTGTTGCC |
| GGTGCTGTGCCAGGACCATGGCCTGACCCCGGACCAAGTGGTGGCTATCGCCAGCCACGATGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCCACGATGGCGGCAAGCAAGCGCTCGAAACGGTGCAGCGGCTGTTGCCGGTGCT |
| GTGCCAGGACCATGGCCTGACCCCGGACCAAGTGGTGGCTATCGCCAGCAACATTGGCGGCAAGCAAGCG |
| CTCGAAACGGTGCAGCGGCTGTTGCCGGTGCTGTGCCAGGACCATGGCCTGACCCCGGACCAAGTGGTGG |
| CTATCGCCAGCCACGATGGCGGCAAGCAAGCGCTCGAAACGGTGCAGCGGCTGTTGCCGGTGCTGTGCCA |
| GGACCATGGCCTGACCCCGGACCAAGTGGTGGCTATCGCCAGCCACGATGGCGGCAAGCAAGCGCTCGAA |
| ACGGTGCAGCGGCTGTTGCCGGTGCTGTGCCAGGACCATGGCCTGACCCCGGACCAAGTGGTGGctatcg |
| ccagcaacggtggcggcaagcaagcgctcgaaagcattgtggcccagctgagccggcctgatccggcgtt |
| ggccgcgttgaccaacgacgaccacctcgtcgccttggcctgcctcggcggacgtcctgccatggatgca |
| gtgaaaaagggattgccgcacgcgccggaattgatcagaagagtcaatcgccgtattggcgaacgcacgt |
| cccatcgcgttgccGgatcCaAGGCTAGCCCGAAAAAGAAACGCAAAGTTGGGCGCGCCGACGCGCTGGA |
| CGATTTCGATCTCGACATGCTGGGTTCTGATGCCCTCGATGACTTTGACCTGGATATGTTGGGAAGCGAC |
| GCATTGGATGACTTTGATCTGGACATGCTCGGCTCCGATGCTCTGGACGATTTCGATCTCGATATGTTAA |
| TTAACTACCCGTACGACGTTCCGGACTACGCTTCTTGA |

SEQ ID NO: 80: CEACAM5 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASNGGGKQALETVQRLLPVLCQDHGLTPDQVVAIASNGGGKQALETVQRLLPVLCQDHGLTPDQV
VAIASNNGGKQALETVQRLLPVLCQDHGLTPDQVVAIASNNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIA
SNIGGKQALETVQRLLPVLCQDHGLTPDQVVAIASNGGGKQALETVQRLLPVLCQDHGLTPDQVVAIASH
DGGKQALETVQRLLPVLCQDHGLTPDQVVAIASNIGGKQALETVQRLLPVLCQDHGLTPDQVVAIASNGG
GKQALETVQRLLPVLCQDHGLTPDQVVAIASHDGGKQALETVQRLLPVLCQDHGLTPDQVVAIASHDGGK
QALETVQRLLPVLCQDHGLTPDQVVAIASHDGGKQALETVQRLLPVLCQDHGLTPDQVVAIASNIGGKQA
LETVQRLLPVLCQDHGLTPDQVVAIASHDGGKQALETVQRLLPVLCQDHGLTPDQVVAIASHDGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 81: CEACAM5 TALE G nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacgcgatgcgggggagttgagaggtccgccgttacagttggac
acaggccaacttgtgaagattgcaaaacgtggcggcgtgaccgcaatggaggcagtgcatgcatcgcgca

TALE-TF SEQUENCES atgcactgacgggtgccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACGGTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCCACGATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCCACGATGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACATTGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCCACGATGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCCACGATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCAAC

ATTGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCCACGATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACATTGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACAATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCCACGATGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCCACGATGGCGGCAAGCAAGCG

CTCGAAACGGTGCAGCGGCTGTTGCCGGTGCTGTGCCAGGACCATGGCCTGACCCCGGACCAAGTGGTGG ctatcgccagcaacggtggcggcaagcaagcgctcgaaagcattgtggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA

SEQ ID NO: 82: CEACAM5 TALE G polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASHDGGKQALETVQRLLPVLCQDHGLTPDQVVAIASHDGGKQALETVQRLLPVLCQDHGLTPDQV

VAIASNGGGKQALETVQRLLPVLCQDHGLTPDQVVAIASHDGGKQALETVQRLLPVLCQDHGLTPDQVVA

IASHDGGKQALETVQRLLPVLCQDHGLTPDQVVAIASNIGGKQALETVQRLLPVLCQDHGLTPDQVVAIA

SHDGGKQALETVQRLLPVLCQDHGLTPDQVVAIASHDGGKQALETVQRLLPVLCQDHGLTPDQVVAIASN

TALE-TF SEQUENCES

IGGKQALETVQRLLPVLCQDHGLTPDQVVAIASHDGGKQALETVQRLLPVLCQDHGLTPDQVVAIASNIG

GKQALETVQRLLPVLCQDHGLTPDQVVAIASNNGGKQALETVQRLLPVLCQDHGLTPDQVVAIASNGGGK

QALETVQRLLPVLCQDHGLTPDQVVAIASHDGGKQALETVQRLLPVLCQDHGLTPDQVVAIASHDGGKQA

LETVQRLLPVLCQDHGLTPDQVVAIASNGGGKQALESIVAQLSRPDPALAALTNDDHLVALACLGGRPAM

DAVKKGLPHAPELIRRVNRRIGERTSHRVAGSKASPKKKRKVGRADALDDFDLDMLGSDALDDFDLDMLG

SDALDDFDLDMLGSDALDDFDLDMLINYPYDVPDYAS

SEQ ID NO: 83: ERBB2 TALE A nucleotide
ATGGACTACAAAGACCATGACGGTGATTATAAAGATCATGACATCGATTACAAGGATGACGATGACAAGa tgcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACAATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACAATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCCACGATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACGGTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACAATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACAATGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACATTGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCCAC

GATGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCCACGATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCCACGATGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACAATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACAATGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCCACGATGGCGGCAAGCAAGCGCTCGAAACGGTGCAGCGGCTGTTGCCGGTGCT

GTGCCAGGACCATGGCCTGACCCCGGACCAAGTGGTGGctatcgccagcaacggtggcggcaagcaagcg ctcgaaagcattgtggcccagctgagccggcctgatccggcgttggccgcgttgaccaacgacgaccacc tcgtcgccttggcctgcctcggcggacgtcctgccatggatgcagtgaaaaagggattgccgcacgcgcc

TALE-TF SEQUENCES ggaattgatcagaagagtcaatcgccgtattggcgaacgcacgtcccatcgcgttgccGgatcCaAGGCT

AGCCCGAAAAAGAAACGCAAAGTTGGGCGCGCCGACGCGCTGGACGATTTCGATCTCGACATGCTGGGTT

CTGATGCCCTCGATGACTTTGACCTGGATATGTTGGGAAGCGACGCATTGGATGACTTTGATCTGGACAT

GCTCGGCTCCGATGCTCTGGACGATTTCGATCTCGATATGTTAATTAACTACCCGTACGACGTTCCGGAC

TACGCTTCTTGA

SEQ ID NO: 84: ERBB2 TALE A polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASHDGGKQALETVQRLLPVLCQDHGLTPDQVVAIASNNGGKQALETVQRLLPVLCQDHGLTPDQV

VAIASNNGGKQALETVQRLLPVLCQDHGLTPDQVVAIASHDGGKQALETVQRLLPVLCQDHGLTPDQVVA

IASNGGGKQALETVQRLLPVLCQDHGLTPDQVVAIASNNGGKQALETVQRLLPVLCQDHGLTPDQVVAIA

SNNGGKQALETVQRLLPVLCQDHGLTPDQVVAIASNIGGKQALETVQRLLPVLCQDHGLTPDQVVAIASH

DGGKQALETVQRLLPVLCQDHGLTPDQVVAIASHDGGKQALETVQRLLPVLCQDHGLTPDQVVAIASHDG

GKQALETVQRLLPVLCQDHGLTPDQVVAIASNNGGKQALETVQRLLPVLCQDHGLTPDQVVAIASNNGGK

QALETVQRLLPVLCQDHGLTPDQVVAIASHDGGKQALETVQRLLPVLCQDHGLTPDQVVAIASNGGGKQA

LESIVAQLSRPDPALAALINDDHLVALACLGGRPAMDAVKKGLPHAPELIRRVNRRIGERTSHRVAGSKA

SPKKKRKVGRADALDDFDLDMLGSDALDDFDLDMLGSDALDDFDLDMLGSDALDDFDLDMLINYPYDVPD

YAS

SEQ ID NO: 85: ERBB2 TALE B nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACAATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACATTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACAATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCCACGATGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACATTGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCCACGATGGCGGCAAGCAAGCGCTCGAAACGGTGCAGCGGCTGTTGCCGGTGCTGTGCCAGGACCATG

| TALE-TF SEQUENCES |
|---|
| GCCTGACCCCGGACCAAGTGGTGGCTATCGCCAGCCACGATGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCCAC |
| GATGGCGGCAAGCAAGCGCTCGAAACGGTGCAGCGGCTGTTGCCGGTGCTGTGCCAGGACCATGGCCTGA |
| CCCCGGACCAAGTGGTGGCTATCGCCAGCCACGATGGCGGCAAGCAAGCGCTCGAAACGGTGCAGCGGCT |
| GTTGCCGGTGCTGTGCCAGGACCATGGCCTGACCCCGGACCAAGTGGTGGCTATCGCCAGCAACAATGGC |
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCCACGATGGCGGCAAGCAAGCGCTCGAAACGGTGCAGCGGCTGTTGCC |
| GGTGCTGTGCCAGGACCATGGCCTGACCCCGGACCAAGTGGTGGCTATCGCCAGCAACAATGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCCACGATGGCGGCAAGCAAGCGCTCGAAACGGTGCAGCGGCTGTTGCCGGTGCT |
| GTGCCAGGACCATGGCCTGACCCCGGACCAAGTGGTGGCTATCGCCAGCCACGATGGCGGCAAGCAAGCG |
| CTCGAAACGGTGCAGCGGCTGTTGCCGGTGCTGTGCCAGGACCATGGCCTGACCCCGGACCAAGTGGTGG |
| ctatcgccagcCACGATggcggcaagcaagcgctcgaaagcattgtggcccagctgagccggcctgatcc |
| ggcgttggccgcgttgaccaacgacgaccacctcgtcgccttggcctgcctcggcggacgtcctgccatg |
| gatgcagtgaaaaagggattgccgcacgcgccggaattgatcagaagagtcaatcgccgtattggcgaac |
| gcacgtcccatcgcgttgccGgatcCaAGGCTAGCCCGAAAAAGAAACGCAAAGTTGGGCGCCGACGC |
| GCTGGACGATTTCGATCTCGACATGCTGGGTTCTGATGCCCTCGATGACTTTGACCTGGATATGTTGGGA |
| AGCGACGCATTGGATGACTTTGATCTGGACATGCTCGGCTCCGATGCTCTGGACGATTTCGATCTCGATA |
| TGTTAATTAACTACCCGTACGACGTTCCGGACTACGCTTCTTGA |

SEQ ID NO: 86: ERBB2 TALE B polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNNGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASNNGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASH
DGGKQALETVQRLLPVLCQDHGLTPDQVVAIASHDGGKQALETVQRLLPVLCQDHGLTPDQVVAIASNNG
GKQALETVQRLLPVLCQDHGLTPDQVVAIASHDGGKQALETVQRLLPVLCQDHGLTPDQVVAIASNNGGK
QALETVQRLLPVLCQDHGLTPDQVVAIASHDGGKQALETVQRLLPVLCQDHGLTPDQVVAIASHDGGKQA
LETVQRLLPVLCQDHGLTPDQVVAIASHDGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 87: ERBB2 TALE C nucleotide
ATGGACTACAAAGACCATGACGGTGATTATAAAGATCATGACATCGATTACAAGGATGACGATGACAAGa
tggcccccaagaagaagaggaaggtggggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac

TALE-TF SEQUENCES

```
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACAATGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACAATGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCCAC
GATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCCACGATGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCAACGGTGGCGGCAAG
CAAGCGCTCGAAACGGTGCAGCGGCTGTTGCCGGTGCTGTGCCAGGACCATGGCCTGACCCCGGACCAAG
TGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACATTGGCGGCAAGCAAGCG
CTCGAAACGGTGCAGCGGCTGTTGCCGGTGCTGTGCCAGGACCATGGCCTGACCCCGGACCAAGTGGTGG
CTATCGCCAGCCACGATGGCGGCAAGCAAGCGCTCGAAACGGTGCAGCGGCTGTTGCCGGTGCTGTGCCA
GGACCATGGCCTGACCCCGGACCAAGTGGTGGctatcgccagcaacggtggcggcaagcaagcgctcgaa
agcattgtgcccagctgagccggcctgatccggcgttggccgcgttgaccaacgacgaccacctcgtcg
ccttggcctgcctcggcggacgtcctgccatggatgcagtgaaaaagggattgccgcacgcgccggaatt
gatcagaagagtcaatcgccgtattggcgaacgcacgtcccatcgcgttgccGgatcCaAGGCTAGCCCG
AAAAAGAAACGCAAAGTTGGGCGCGCCGACGCGCTGGACGATTTCGATCTCGACATGCTGGGTTCTGATG
CCCTCGATGACTTTGACCTGGATATGTTGGGAAGCGACGCATTGGATGACTTTGATCTGGACATGCTCGG
CTCCGATGCTCTGGACGATTTCGATCTCGATATGTTAATTAACTACCCGTACGACGTTCCGGACTACGCT
TCTTGA
```

SEQ ID NO: 88: ERBB2 TALE C polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV -continued

TALE-TF SEQUENCES

VAIASNIGGKQALETVQRLLPVLCQDHGLTPDQVVAIASHDGGKQALETVQRLLPVLCQDHGLTPDQVVA
IASNNGGKQALETVQRLLPVLCQDHGLTPDQVVAIASNNGGKQALETVQRLLPVLCQDHGLTPDQVVAIA
SNNGGKQALETVQRLLPVLCQDHGLTPDQVVAIASNNGGKQALETVQRLLPVLCQDHGLTPDQVVAIASH
DGGKQALETVQRLLPVLCQDHGLTPDQVVAIASHDGGKQALETVQRLLPVLCQDHGLTPDQVVAIASHDG
GKQALETVQRLLPVLCQDHGLTPDQVVAIASNGGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASNIGGKQA
LETVQRLLPVLCQDHGLTPDQVVAIASHDGGKQALETVQRLLPVLCQDHGLTPDQVVAIASNGGGKQALE
SIVAQLSRPDPALAALINDDHLVALACLGGRPAMDAVKKGLPHAPELIRRVNRRIGERTSHRVAGSKASP
KKKRKVGRADALDDFDLDMLGSDALDDFDLDMLGSDALDDFDLDMLGSDALDDFDLDMLINYPYDVPDYA
S

SEQ ID NO: 89: ERBB2 TALE D nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcgggggagttgagaggtccgccgttacagttggac
acaggccaacttgtgaagattgcaaaacgtggcggcgtgaccgcaatggaggcagtgcatgcatcgcgca
atgcactgacgggtgccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACGGTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
GGTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC
GGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCC
GGTGCTGTGCCAGGACCATGGCCTGACCCCGGACCAAGTGGTGGCTATCGCCAGCCACGATGGCGGCAAG
CAAGCGCTCGAAACGGTGCAGCGGCTGTTGCCGGTGCTGTGCCAGGACCATGGCCTGACCCCGGACCAAG

TALE-TF SEQUENCES

```
TGGTGGCTATCGCCAGCAACAATGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCAACAATGGCGGCAAGCAAGCG

CTCGAAACGGTGCAGCGGCTGTTGCCGGTGCTGTGCCAGGACCATGGCCTGACCCCGGACCAAGTGGTGG ctatcgccagcaacggtggcggcaagcaagcgctcgaaagcattgtggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtcccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA
```

SEQ ID NO: 90: ERBB2 TALE D polypeptide
```
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASHDGGKQALETVQRLLPVLCQDHGLTPDQVVAIASHDGGKQALETVQRLLPVLCQDHGLTPDQV

VAIASHDGGKQALETVQRLLPVLCQDHGLTPDQVVAIASNGGGKQALETVQRLLPVLCQDHGLTPDQVVA

IASNNGGKQALETVQRLLPVLCQDHGLTPDQVVAIASNNGGKQALETVQRLLPVLCQDHGLTPDQVVAIA

SNGGGKQALETVQRLLPVLCQDHGLTPDQVVAIASNGGGKQALETVQRLLPVLCQDHGLTPDQVVAIASN

GGGKQALETVQRLLPVLCQDHGLTPDQVVAIASHDGGKQALETVQRLLPVLCQDHGLTPDQVVAIASNGG

GKQALETVQRLLPVLCQDHGLTPDQVVAIASHDGGKQALETVQRLLPVLCQDHGLTPDQVVAIASHDGGK

QALETVQRLLPVLCQDHGLTPDQVVAIASNNGGKQALETVQRLLPVLCQDHGLTPDQVVAIASNNGGKQA

LETVQRLLPVLCQDHGLTPDQVVAIASNGGGKQALESIVAQLSRPDPALAALTNDDHLVALACLGGRPAM

DAVKKGLPHAPELIRRVNRRIGERTSHRVAGSKASPKKKRKVGRADALDDFDLDMLGSDALDDFDLDMLG

SDALDDFDLDMLGSDALDDFDLDMLINYPYDVPDYAS
```

SEQ ID NO: 91: ERBB2 TALE E nucleotide
```
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCAACAATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCCACGATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCCACGATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACATTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCCACGATGGCGGCAAGCAAGCGCT
```

| TALE-TF SEQUENCES |
| --- |
| CGAAACGGTGCAGCGGCTGTTGCCGGTGCTGTGCCAGGACCATGGCCTGACCCCGGACCAAGTGGTGGCT |
| ATCGCCAGCAACGGTGGCGGCAAGCAAGCGCTCGAAACGGTGCAGCGGCTGTTGCCGGTGCTGTGCCAGG |
| ACCATGGCCTGACCCCGGACCAAGTGGTGGCTATCGCCAGCCACGATGGCGGCAAGCAAGCGCTCGAAAC |
| GGTGCAGCGGCTGTTGCCGGTGCTGTGCCAGGACCATGGCCTGACCCCGGACCAAGTGGTGGCTATCGCC |
| AGCCACGATGGCGGCAAGCAAGCGCTCGAAACGGTGCAGCGGCTGTTGCCGGTGCTGTGCCAGGACCATG |
| GCCTGACCCCGGACCAAGTGGTGGCTATCGCCAGCCACGATGGCGGCAAGCAAGCGCTCGAAACGGTGCA |
| GCGGCTGTTGCCGGTGCTGTGCCAGGACCATGGCCTGACCCCGGACCAAGTGGTGGCTATCGCCAGCAAC |
| ATTGGCGGCAAGCAAGCGCTCGAAACGGTGCAGCGGCTGTTGCCGGTGCTGTGCCAGGACCATGGCCTGA |
| CCCCGGACCAAGTGGTGGCTATCGCCAGCAACAATGGCGGCAAGCAAGCGCTCGAAACGGTGCAGCGGCT |
| GTTGCCGGTGCTGTGCCAGGACCATGGCCTGACCCCGGACCAAGTGGTGGCTATCGCCAGCAACATTGGC |
| GGCAAGCAAGCGCTCGAAACGGTGCAGCGGCTGTTGCCGGTGCTGTGCCAGGACCATGGCCTGACCCCGG |
| ACCAAGTGGTGGCTATCGCCAGCCACGATGGCGGCAAGCAAGCGCTCGAAACGGTGCAGCGGCTGTTGCC |
| GGTGCTGTGCCAGGACCATGGCCTGACCCCGGACCAAGTGGTGGCTATCGCCAGCAACGGTGGCGGCAAG |
| CAAGCGCTCGAAACGGTGCAGCGGCTGTTGCCGGTGCTGTGCCAGGACCATGGCCTGACCCCGGACCAAG |
| TGGTGGCTATCGCCAGCAACGGTGGCGGCAAGCAAGCGCTCGAAACGGTGCAGCGGCTGTTGCCGGTGCT |
| GTGCCAGGACCATGGCCTGACCCCGGACCAAGTGGTGGCTATCGCCAGCAACAATGGCGGCAAGCAAGCG |
| CTCGAAACGGTGCAGCGGCTGTTGCCGGTGCTGTGCCAGGACCATGGCCTGACCCCGGACCAAGTGGTGG |
| ctatcgccagcaacggtggcggcaagcaagcgctcgaaagcattgtgcccagctgagccggcctgatcc |
| ggcgttggccgcgttgaccaacgacgaccacctcgtcgccttggcctgcctcggcggacgtcctgccatg |
| gatgcagtgaaaaagggattgccgcacgcgccggaattgatcagaagagtcaatcgccgtattggcgaac |
| gcacgtcccatcgcgttgccGgatcCaAGGCTAGCCCGAAAAAGAAACGCAAAGTTGGGCGCGCCGACGC |
| GCTGGACGATTTCGATCTCGACATGCTGGGTTCTGATGCCCTCGATGACTTTGACCTGGATATGTTGGGA |
| AGCGACGCATTGGATGACTTTGATCTGGACATGCTCGGCTCCGATGCTCTGGACGATTTCGATCTCGATA |
| TGTTAATTAACTACCCGTACGACGTTCCGGACTACGCTTCTTGA |

SEQ ID NO: 92: ERBB2 TALE E polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASNNGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASNIGGKQALETVQRLLPVLCQDHGLTPDQVVAIASHDGGKQALETVQRLLPVLCQDHGLTPDQVVA
IASNGGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASHDGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNIG
GKQALETVQRLLPVLCQDHGLTPDQVVAIASHDGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASNNGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS -continued

| TALE-TF SEQUENCES |
| --- |

SEQ ID NO: 93: ERBB2 TALE F nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacggatgcgggggagttgagaggtccgccgttacagttggac acaggccaacttgtgaagattgcaaaacgtggcggcgtgaccgcaatggaggcagtgcatgcatcgcgca atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACGGTGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACAATGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCCACGATGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACATTGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACGGTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACGGTGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACGGTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCAACATTGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCAAC

AATGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACAATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACAATGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACATTGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACGGTGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCCACGATGGCGGCAAGCAAGCG

CTCGAAACGGTGCAGCGGCTGTTGCCGGTGCTGTGCCAGGACCATGGCCTGACCCCGGACCAAGTGGTGG ctatcgccagcaacggtggcggcaagcaagcgctcgaaagcattgtggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA

TALE-TF SEQUENCES

SEQ ID NO: 94: ERBB2 TALE F polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASNGGGKQALETVQRLLPVLCQDHGLTPDQVVAIASNNGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNGGGKQALETVQRLLPVLCQDHGLTPDQVVAIASNGGGKQALETVQRLLPVLCQDHGLTPDQVVAIA
SNGGGKQALETVQRLLPVLCQDHGLTPDQVVAIASNIGGKQALETVQRLLPVLCQDHGLTPDQVVAIASN
NGGKQALETVQRLLPVLCQDHGLTPDQVVAIASNNGGKQALETVQRLLPVLCQDHGLTPDQVVAIASNNG
GKQALETVQRLLPVLCQDHGLTPDQVVAIASNIGGKQALETVQRLLPVLCQDHGLTPDQVVAIASNGGGK
QALETVQRLLPVLCQDHGLTPDQVVAIASNGGGKQALETVQRLLPVLCQDHGLTPDQVVAIASHDGGKQA
LETVQRLLPVLCQDHGLTPDQVVAIASNGGGKQALESIVAQLSRPDPALAALTNDDHLVALACLGGRPAM
DAVKKGLPHAPELIRRVNRRIGERTSHRVAGSKASPKKKRKVGRADALDDFDLDMLGSDALDDFDLDMLG
SDALDDFDLDMLGSDALDDFDLDMLINYPYDVPDYAS SEQ ID NO: 95: ERBB2 TALE G nucleotide
ATGGACTACAAAGACCATGACGGTGATTATAAAGATCATGACATCGATTACAAGGATGACGATGACAAGa
tggcccccaagaagaagaggaaggtgggccgcGgatcTgtggatctacgcacgctcggctacagtcagca
gcagcaagagaagatcaaaccgaaggtgcgttcgacagtggcgcagcaccacgaggcactggtgggccat
gggtttacacacgcgcacatcgttgcgctcagccaacacccggcagcgttagggaccgtcgctgtcacgt
atcagcacataatcacggcgttgccagaggcgacacacgaagacatcgttggcgtcggcaaacagtggtc
cggcgcacgcgccctggaggccttgctcacggatgcggggggagttgagaggtccgccgttacagttggac
acaggccaacttgtgaagattgcaaaacgtggcggcgtgaccgcaatggaggcagtgcatgcatcgcgca
atgcactgacgggtgcccccctgAACCTGACCCCGGACCAAGTGGTGGCTATCGCCAGCCACGATGGCGG
CAAGCAAGCGCTCGAAACGGTGCAGCGGCTGTTGCCGGTGCTGTGCCAGGACCATGGCCTGACCCCGGAC
CAAGTGGTGGCTATCGCCAGCCACGATGGCGGCAAGCAAGCGCTCGAAACGGTGCAGCGGCTGTTGCCGG
TGCTGTGCCAGGACCATGGCCTGACCCCGGACCAAGTGGTGGCTATCGCCAGCCACGATGGCGGCAAGCA
AGCGCTCGAAACGGTGCAGCGGCTGTTGCCGGTGCTGTGCCAGGACCATGGCCTGACCCCGGACCAAGTG
GTGGCTATCGCCAGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACCCCGGACCAAGTGGTGGCT
ATCGCCAGCAACAATGGCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCAAGCAAGCGCTCGAAAC
GGTGCAGCGGCTGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGTGCCAGGACCATG
GCCTGACCCCGGACCAAGTGGTGGCTATCGCCAGCAACATTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAAC
ATTGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCT
GTTGCCGGTGCTGTGCCAGGACCATGGCCTGACCCCGGACCAAGTGGTGGCTATCGCCAGCAACGGTGGC

TALE-TF SEQUENCES

```
GGCAAGCAAGCGCTCGAAACGGTGCAGCGGCTGTTGCCGGTGCTGTGCCAGGACCATGGCCTGACCCCGG

ACCAAGTGGTGGCTATCGCCAGCAACGGTGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCAACATTGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCAACATTGGCGGCAAGCAAGCG

CTCGAAACGGTGCAGCGGCTGTTGCCGGTGCTGTGCCAGGACCATGGCCTGACCCCGGACCAAGTGGTGG

CTATCGCCAGCAACAATGGCGGCAAGCAAGCGCTCGAAACGGTGCAGCGGCTGTTGCCGGTGCTGTGCCA

GGACCATGGCCTGACCCCGGACCAAGTGGTGGCTATCGCCAGCAACATTGGCGGCAAGCAAGCGCTCGAA

ACGGTGCAGCGGCTGTTGCCGGTGCTGTGCCAGGACCATGGCCTGACCCCGGACCAAGTGGTGGctatcg ccagcaacggtggcggcaagcaagcgctcgaaagcattgtgggcccagctgagccggcctgatccggcgtt ggccgcgttgaccaacgacgaccacctcgtcgccttggcctgctcggcggacgtcctgccatggatgca gtgaaaaagggattgccgcacgcgccggaattgatcagaagagtcaatcgccgtattggcgaacgcacgt cccatcgcgttgccGgatcCaAGGCTAGCCCGAAAAAGAAACGCAAAGTTGGGCGCGCCGACGCGCTGGA

CGATTTCGATCTCGACATGCTGGGTTCTGATGCCCTCGATGACTTTGACCTGGATATGTTGGGAAGCGAC

GCATTGGATGACTTTGATCTGGACATGCTCGGCTCCGATGCTCTGGACGATTTCGATCTCGATATGTTAA

TTAACTACCCGTACGACGTTCCGGACTACGCTTCTTGA
```

SEQ ID NO: 96: ERBB2 TALE G polypeptide
MDYKDHDGDYKDHDIDYKDDDDKMAPKKKRKVGRGSVDLRTLGYSQQQQEKIKPKVRSTVAQHHEALVGH
GFTHAHIVALSQHPAALGTVAVTYQHIITALPEATHEDIVGVGKQWSGARALEALLTDAGELRGPPLQLD
TGQLVKIAKRGGVTAMEAVHASRNALTGAPLNLTPDQVVAIASHDGGKQALETVQRLLPVLCQDHGLTPD
QVVAIASHDGGKQALETVQRLLPVLCQDHGLTPDQVVAIASHDGGKQALETVQRLLPVLCQDHGLTPDQV
VAIASHDGGKQALETVQRLLPVLCQDHGLTPDQVVAIASNIGGKQALETVQRLLPVLCQDHGLTPDQVVA
IASNNGGKQALETVQRLLPVLCQDHGLTPDQVVAIASNNGGKQALETVQRLLPVLCQDHGLTPDQVVAIA
SNIGGKQALETVQRLLPVLCQDHGLTPDQVVAIASNIGGKQALETVQRLLPVLCQDHGLTPDQVVAIASN
IGGKQALETVQRLLPVLCQDHGLTPDQVVAIASNNGGKQALETVQRLLPVLCQDHGLTPDQVVAIASNGG
GKQALETVQRLLPVLCQDHGLTPDQVVAIASNGGGKQALETVQRLLPVLCQDHGLTPDQVVAIASNGGGK
QALETVQRLLPVLCQDHGLTPDQVVAIASNIGGKQALETVQRLLPVLCQDHGLTPDQVVAIASNIGGKQA
LETVQRLLPVLCQDHGLTPDQVVAIASNNGGKQALETVQRLLPVLCQDHGLTPDQVVAIASNIGGKQALE
TVQRLLPVLCQDHGLTPDQVVAIASNGGGKQALESIVAQLSRPDPALAALTNDDHLVALACLGGRPAMDA
VKKGLPHAPELIRRVNRRIGERTSHRVAGSKASPKKKRKVGRADALDDFDLDMLGSDALDDFDLDMLGSD
ALDDFDLDMLGSDALDDFDLDMLINYPYDVPDYAS SEQ ID NO: 97: ERBB2 TALE H nucleotide
ATGGACTACAAAGACCATGACGGTGATTATAAAGATCATGACATCGATTACAAGGATGACGATGACAAGa tggcccccaagaagaagaggaaggtgggccgcGgatcTgtggatctacgcacgctcggctacagtcagca gcagcaagagaagatcaaaccgaaggtgcgttcgacagtggcgcagcaccacgaggcactggtgggccat gggtttacacacgcgcacatcgttgcgctcagccaacacccggcagcgttagggaccgtcgctgtcacgt atcagcacataatcacggcgttgccagaggcgacacacgaagacatcgttggcgtcggcaaacagtggtc cggcgcacgcgccctggaggccttgctcacgcgatgcgggggagttgagaggtccgccgttacagttggac acaggccaacttgtgaagattgcaaaacgtggcggcgtgaccgcaatggaggcagtgcatgcatcgcgca -continued

TALE-TF SEQUENCES atgcactgacgggtgcccccctgAACCTGACCCCGGACCAAGTGGTGGCTATCGCCAGCCACGATGGCGG

CAAGCAAGCGCTCGAAACGGTGCAGCGGCTGTTGCCGGTGCTGTGCCAGGACCATGGCCTGACCCCGGAC

CAAGTGGTGGCTATCGCCAGCAACAATGGCGGCAAGCAAGCGCTCGAAACGGTGCAGCGGCTGTTGCCGG

TGCTGTGCCAGGACCATGGCCTGACCCCGGACCAAGTGGTGGCTATCGCCAGCAACATTGGCGGCAAGCA

AGCGCTCGAAACGGTGCAGCGGCTGTTGCCGGTGCTGTGCCAGGACCATGGCCTGACCCCGGACCAAGTG

GTGGCTATCGCCAGCAACGGTGGCGGCAAGCAAGCGCTCGAAACGGTGCAGCGGCTGTTGCCGGTGCTGT

GCCAGGACCATGGCCTGACCCCGGACCAAGTGGTGGCTATCGCCAGCAACAATGGCGGCAAGCAAGCGCT

CGAAACGGTGCAGCGGCTGTTGCCGGTGCTGTGCCAGGACCATGGCCTGACCCCGGACCAAGTGGTGGCT

ATCGCCAGCAACGGTGGCGGCAAGCAAGCGCTCGAAACGGTGCAGCGGCTGTTGCCGGTGCTGTGCCAGG

ACCATGGCCTGACCCCGGACCAAGTGGTGGCTATCGCCAGCAACAATGGCGGCAAGCAAGCGCTCGAAAC

GGTGCAGCGGCTGTTGCCGGTGCTGTGCCAGGACCATGGCCTGACCCCGGACCAAGTGGTGGCTATCGCC

AGCAACATTGGCGGCAAGCAAGCGCTCGAAACGGTGCAGCGGCTGTTGCCGGTGCTGTGCCAGGACCATG

GCCTGACCCCGGACCAAGTGGTGGCTATCGCCAGCCACGATGGCGGCAAGCAAGCGCTCGAAACGGTGCA

GCGGCTGTTGCCGGTGCTGTGCCAGGACCATGGCCTGACCCCGGACCAAGTGGTGGCTATCGCCAGCAAC

GGTGGCGGCAAGCAAGCGCTCGAAACGGTGCAGCGGCTGTTGCCGGTGCTGTGCCAGGACCATGGCCTGA

CCCCGGACCAAGTGGTGGCTATCGCCAGCAACAATGGCGGCAAGCAAGCGCTCGAAACGGTGCAGCGGCT

GTTGCCGGTGCTGTGCCAGGACCATGGCCTGACCCCGGACCAAGTGGTGGCTATCGCCAGCAACGGTGGC

GGCAAGCAAGCGCTCGAAACGGTGCAGCGGCTGTTGCCGGTGCTGTGCCAGGACCATGGCCTGACCCCGG

ACCAAGTGGTGGCTATCGCCAGCCACGATGGCGGCAAGCAAGCGCTCGAAACGGTGCAGCGGCTGTTGCC

GGTGCTGTGCCAGGACCATGGCCTGACCCCGGACCAAGTGGTGGCTATCGCCAGCAACGGTGGCGGCAAG

CAAGCGCTCGAAACGGTGCAGCGGCTGTTGCCGGTGCTGTGCCAGGACCATGGCCTGACCCCGGACCAAG

TGGTGGCTATCGCCAGCCACGATGGCGGCAAGCAAGCGCTCGAAACGGTGCAGCGGCTGTTGCCGGTGCT

GTGCCAGGACCATGGCCTGACCCCGGACCAAGTGGTGGCTATCGCCAGCCACGATGGCGGCAAGCAAGCG

CTCGAAACGGTGCAGCGGCTGTTGCCGGTGCTGTGCCAGGACCATGGCCTGACCCCGGACCAAGTGGTGG ctatcgccagcaacggtggcggcaagcaagcgctcgaaagcattgtgggcccagctgagccggcctgatcc ggcgttggccgcgttgaccaacgacgaccacctcgtcgccttggcctgcctcggcggacgtcctgccatg gatgcagtgaaaaagggattgccgcacgcgccggaattgatcagaagagtcaatcgccgtattggcgaac gcacgtccatcgcgttgccGgatcCaAGGCTAGCCCGAAAAAGAAACGCAAAGTTGGGCGCGCCGACGC

GCTGGACGATTTCGATCTCGACATGCTGGGTTCTGATGCCCTCGATGACTTTGACCTGGATATGTTGGGA

AGCGACGCATTGGATGACTTTGATCTGGACATGCTCGGCTCCGATGCTCTGGACGATTTCGATCTCGATA

TGTTAATTAACTACCCGTACGACGTTCCGGACTACGCTTCTTGA

SEQ ID NO: 98: ERBB2 TALE H polypeptide
MDYKDHDGDYKDHDIDYKDDDDKMAPKKKRKVGRGSVDLRTLGYSQQQQEKIKPKVRSTVAQHHEALVGH

GFTHAHIVALSQHPAALGTVAVTYQHIITALPEATHEDIVGVGKQWSGARALEALLTDAGELRGPPLQLD

TGQLVKIAKRGGVTAMEAVHASRNALTGAPLNLTPDQVVAIASHDGGKQALETVQRLLPVLCQDHGLTPD

QVVAIASNNGGKQALETVQRLLPVLCQDHGLTPDQVVAIASNIGGKQALETVQRLLPVLCQDHGLTPDQV

VAIASNGGGKQALETVQRLLPVLCQDHGLTPDQVVAIASNNGGKQALETVQRLLPVLCQDHGLTPDQVVA

IASNGGGKQALETVQRLLPVLCQDHGLTPDQVVAIASNNGGKQALETVQRLLPVLCQDHGLTPDQVVAIA

SNIGGKQALETVQRLLPVLCQDHGLTPDQVVAIASHDGGKQALETVQRLLPVLCQDHGLTPDQVVAIASN

| TALE-TF SEQUENCES |
|---|
| GGGKQALETVQRLLPVLCQDHGLTPDQVVAIASNNGGKQALETVQRLLPVLCQDHGLTPDQVVAIASNGG |
| GKQALETVQRLLPVLCQDHGLTPDQVVAIASHDGGKQALETVQRLLPVLCQDHGLTPDQVVAIASNGGGK |
| QALETVQRLLPVLCQDHGLTPDQVVAIASHDGGKQALETVQRLLPVLCQDHGLTPDQVVAIASHDGGKQA |
| LETVQRLLPVLCQDHGLTPDQVVAIASNGGGKQALESIVAQLSRPDPALAALTNDDHLVALACLGGRPAM |
| DAVKKGLPHAPELIRRVNRRIGERTSHRVAGSKASPKKKRKVGRADALDDFDLDMLGSDALDDFDLDMLG |
| SDALDDFDLDMLGSDALDDFDLDMLINYPYDVPDYAS |

What is claimed is:

1. A method of increasing gene expression of a target gene in a mammalian cell, the method comprising administering to the mammalian cell in vitro two or more transcription activator-like effector transcription factors (TALE-TFs) that bind to at least a first target region and a second target region in the target gene,
- wherein at least one of the first target region and the second target region is within a non-open chromatin region,
- wherein the first target region or the second target region comprises the nucleotide sequence of one of SEQ ID NOs: 1-28, or the complement thereof,
- wherein each TALE-TF consists essentially of a repeat variable diresidue, a transcription activation domain, and a nuclear localization sequence,
- wherein gene expression is increased in the mammalian cell, and
- wherein the gene expression is increased in the mammalian cell without the use of a chromatin modifying drug.

2. A method of increasing gene expression of a target gene in a mammalian cell, the method comprising administering to the mammalian cell in vitro two or more transcription activator-like effector transcription factors (TALE-TFs) that bind to at least a first target region and a second target region in the target gene,
- wherein at least one of the first target region and the second target region is within a non-open chromatin region,
- wherein each TALE-TF consists essentially of a repeat variable diresidue region, a transcription activation domain, and a nuclear localization sequence,
- wherein gene expression is increased in the mammalian cell,
- wherein the target gene is IL1RN, KLK3, CEACAM5, or ERBB2, and
- wherein the first target region or the second target region comprises a polynucleotide having a nucleotide sequence selected from the group consisting of SEQ ID NOs: 1-28, or the complement thereof.

3. The method of claim 2, wherein the TALE-TFs bind to different target regions within the target gene.

4. The method of claim 2, wherein the gene expression is increased at least 1-fold.

5. The method of claim 2, wherein the TALE-TFs each comprise the same transcription activation domain.

6. The method of claim 2, wherein the TALE-TFs each comprise different transcription activation domains.

7. The method of claim 2, wherein the mammalian cell is a human cell.

8. The method of claim 2, wherein the gene expression is increased in the mammalian cell without the use of a chromatin modifying drug having an activity selected from the group consisting of histone acetyltransferase, histone deacetylase, histone methyltransferase, and histone kinase activity.

* * * * *